US008512995B2

(12) United States Patent
Machida et al.

(10) Patent No.: US 8,512,995 B2
(45) Date of Patent: Aug. 20, 2013

(54) DNA ENCODING POLYPEPTIDE INVOLVED IN BIOSYNTHESIS OF HERBOXIDIENE

(75) Inventors: Kazuhiro Machida, Shizuoka (JP); Kaoru Okayama, Shizuoka (JP); Masashi Itoh, Shizuoka (JP); Asako Toyoda, Shizuoka (JP)

(73) Assignees: Eisai R&D Management Co., Ltd., Tokyo (JP); Micro Biopharm Japan Co., Ltd., Tokyo (JP)

( * ) Notice: Subject to any disclaimer, the term of this patent is extended or adjusted under 35 U.S.C. 154(b) by 156 days.

(21) Appl. No.: 12/996,104

(22) PCT Filed: May 27, 2009

(86) PCT No.: PCT/JP2009/059708
§ 371 (c)(1),
(2), (4) Date: Dec. 3, 2010

(87) PCT Pub. No.: WO2009/147984
PCT Pub. Date: Dec. 10, 2009

(65) Prior Publication Data
US 2011/0295023 A1 Dec. 1, 2011

(30) Foreign Application Priority Data
Jun. 4, 2008 (JP) ................ P2008-146595

(51) Int. Cl.
*C12N 1/20* (2006.01)
*C12N 15/00* (2006.01)
*C07H 21/04* (2006.01)

(52) U.S. Cl.
USPC ..... 435/252.3; 536/23.2; 435/183; 435/320.1

(58) Field of Classification Search
USPC ........................................ 435/183; 536/23.2
See application file for complete search history.

(56) References Cited

U.S. PATENT DOCUMENTS

| | | | |
|---|---|---|---|
| 5,719,179 A | 2/1998 | Mizukami et al. | |
| 7,416,868 B2 * | 8/2008 | Zazopoulos et al. | 435/183 |
| 2009/0215134 A1 | 8/2009 | Machida et al. | |
| 2009/0269820 A1 | 10/2009 | Machida et al. | |

FOREIGN PATENT DOCUMENTS

| | | |
|---|---|---|
| EP | 1770165 | 4/2007 |
| JP | 6-022770 | 2/1994 |
| JP | 9-235283 | 9/1997 |
| WO | 93/13663 | 7/1993 |
| WO | WO00/53737 | 9/2000 |
| WO | WO01/59126 | 8/2001 |
| WO | WO2004/065401 | 8/2004 |
| WO | 2006/009276 | 1/2006 |
| WO | 2006/126723 | 11/2006 |

OTHER PUBLICATIONS

Barbara et al. [J. Org. Chem., (1992), 57: 7220-7226].*
International Preliminary Report on Patentability from PCT/JP2009/059708, Jan. 11, 2011.
Accession No. UNIPROT:A4FIQ4 (2007).
Extended European Office Action for App. Ser. No. 09758251.4, issued on Feb. 2, 2012.
Oliynyk, M. et al., "Complete genome sequence of the erythromycin-producing bacterium *Saccharopolyspora erythraea* NRRL23338," Nature Biotechnology (2007), 25(4):447-453.
Shao, L. et al., "Identification of the herboxidiene biosynthetic gene cluster in *Streptomyces chromofuscus* ATCC 49982," Applied and Environmental Microbiology, American Society for Microbiology, US (2012), AEM 06904-11:1-16.
Staunton, J. et al., "Polyketide biosynthesis: a millennium review," Nat. Prod. Rep., Royal Society of Chemistry (2001), 18(4):380-416.
Zhang, Y. et al., "Total Synthesis of Herboxidiene/GEX 1A," Organic Letters (2007), 9(16):3141-3143.
Donadio et al., "An erythromycin analog produced by reprogramming of polyketide synthesis", PNAS, USA 90:7119-7123 (1993).
Hopwood and Sherman, "Molecular Genetics of Polyketides and Its Comparison to Fatty Acid Biosynthesis", Annu. Rev. Genet. 24:37-66 (1990).
Katz and Donadio, "Polyketide Synthesis: Prospects for Hybrid Antibiotics", Annu. Rev. Microbiol. 47:875-912 (1993).
Machida et al., "Increase in Pladienolide D Production Rate Using a *Streptomcyes* Strain Overexpressing a Cytochrome P450 Gene", J. of Biosci. and Bioeng. 105(6):649-654 (2006).
Machida et al., "Organization of the Biosynthetic Gene Cluster for the Polyketide Antitumor Macrolide, Pladienolide, in *Streptomyces platensis* Mer-11107", Biosci. Biotechnol. Biochem., 72(11):2946-2952 (2008).
McDaniel et al., "Multiple genetic modification of the erythromycin polyketide synthase to produce a library of novel "unnatural" natural products", PNAS, USA 96:1846-1851 (1999).
Miller-Wideman et al., "Herboxidiene, A New Herbicidal Substance From *Streptomyces chromofuscus* A7847. Taxonomy, Fermentation, Isolation, Physico-Chemical and Biological Properties", J. of Antibiotics (Tokyo, Japan) 45(6):914-921 (1992).
Pfeifer et al., "Biosynthesis of Complex Polyketides in a Metabolically Engineered Strain of *E. coli*", Science 291:1790-1792 (2001).
Sakai et al., "GEX1 Compounds, Novel Antitumor Antibiotics Related to Herboxidiene, Produced by *Streptomyces* sp. II. The Effects on Cell Cycle Progression and Gene Expression", J. of Antibiotics 55(10):863-872 (2002).
Weber et al., "An Erythromycin Derivative Produced by Targeted Gene Disruption in *Saccharopolypspora erythraea*", Science 252:114-117 (2002).
Xue et al., "A gene cluster for macrolide antibiotic biosynthesis in *Streptomyces venezuela*: Architecture of metabolic diversity", PNAS, USA 95:12111-12116 (1998).
Communication under Rule 71(3) EPC dated Jun. 19, 2012 for European application No. 09758251.4.
Reply to Office Action submitted on Apr. 24, 2012 for European application No. 09758251.4.
Sakai et al. "GEX1 compounds, novel antitumor antibiotics related to herboxidiene, produced by *Streptomyces* sp. I. Taxonomy, production, isolation, physicochemical properties and biological activities." J Antibiot. (Tokyo), Oct. 2002, 55(10):855-62.
Search Report for European application No. 12188302.9, Dec. 6, 2012.

* cited by examiner

*Primary Examiner* — Tekchand Saidha
(74) *Attorney, Agent, or Firm* — Fish & Richardson P.C.

(57) ABSTRACT

The nucleotide sequence of a DNA involved in the biosynthesis of herboxidiene was determined. Utilizing this DNA, herboxidiene and analogues thereof can be efficiently produced.

27 Claims, 2 Drawing Sheets

DNA ENCODING POLYPEPTIDE INVOLVED IN BIOSYNTHESIS OF HERBOXIDIENE

TECHNICAL FIELD

The present invention relates to a polypeptide involved in the biosynthesis of herboxidiene, a DNA encoding the polypeptide, and a variant thereof. In addition, the present invention also relates to a transformant retaining a part or the entire of the DNA and the variant thereof, and a method for producing herboxidiene or an analogue thereof, using the transformant. Moreover, the present invention also relates to an analogue of herboxidiene.

BACKGROUND ART

Substances important as physiologically active substances have been found in various metabolites produced by actinomycetes. In particular, many compounds structurally having polyketide as a core structure (hereinafter referred to as polyketide compounds) have been found. For example, the following various compounds having a biological activity have been known: erythromycin, josamycin, tylosin, midecamycin and mycinamicin known as antibacterial substances; nystatin and amphotericin known as antifungal substances; milbemycin and avermectin known as insecticidal substances; tacrolimus and rapamycin known as immunosuppressive substances; and daunomycin, adriamycin, and aclacinomycin known as antitumor substances.

As one type of such compounds, there are a group of polyketide compounds having an excellent antitumor activity, named as herboxidiene. Herboxidiene is a compound represented by the formula (I) as shown below, which has been first discovered from a culture product of an actinomycete strain, *Streptomyces chromofuscus* A7847 (see Non Patent Literature 1). Thereafter, 5 or more types of analogues, including herboxidiene as a typical example, have been discovered from several actinomycete strains (see patent Literatures 1 and 2).

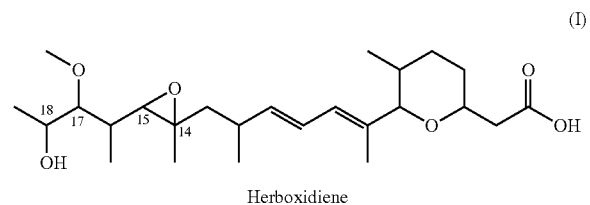 [SMILES: COC(C(C)O)C(C)C1OC1(C)CC(C)/C=C/C=C(\C)C1OC(CC(=O)O)CCC1C]

Herboxidiene

On the other hand, many facts have been known about the biosynthetic mechanism of such polyketide compounds. It has been said that the aforementioned variety of polyketide compounds share the same biosynthetic mechanism, and that the mechanism is extremely similar to the biosynthesis of fatty acid. That is to say, polyketide compounds are biosynthesized by steps of continuously condensing lower fatty acid such as acetic acid or propionic acid, and then subjecting the carbonyl group at position β of the extended acyl group to ketone reduction, dehydration, or enoyl reduction, according to the same method as fatty acid synthesis. It has been said that various repetitive steps of synthesizing these many polyketide compounds are regulated by the multifunctional enzyme complexes of polymers having different active sites (domains) necessary for individual reaction catalytic activities. A general reaction mode of polyketide biosynthesis is summarized, for example, in Non Patent Literatures 2 and 3.

It has been revealed that a DNA sequence encoding polyketide synthase generally encodes all activities necessary for the synthesis of polyketide skeletons, and that the DNA sequence is constituted with repeating units comprising a condensation step and a modification step after the condensation, namely, with modules. Each module participates in a specificity of a specific carboxylic acid constitutional unit contained in each condensation step and in a modification function after specific condensation. For example, Non Patent Literature 4 describes a gene encoding polyketide synthase involved in the biosynthesis of pikromycin by *Streptomyces venezuelae* ATCC15439. Patent Literature 3 describes the structure of a gene encoding erythromycin polyketide synthase of *Saccharopolyspora erythraea*. This gene is constituted with 6 modules, and each module conducts a single condensation step. That is, the precise sequence of acyl side chain elongation and the modification of the elongating chain are determined by gene information existing in each module.

Moreover, after the synthesis of polyketide skeletons by polyketide synthase, such variety of polyketide compounds are often modified by an enzyme catalyzing modification reactions such as hydroxylation, epoxidation or methylation (hereinafter referred to as a modifying enzyme, at times), so that they are converted to final metabolites. It has been revealed that a group of genes involved in these productions; namely, enzymes necessary for the biosynthesis of such final metabolites, and genes encoding regulatory factors necessary for the regulation of the productions (hereinafter, this gene group involved in biosynthesis may be generically referred to as solely "a biosynthetic gene", at times), are generally disposed in the genome of producing bacteria or in a DNA region on a plasmid, while forming a cluster.

If the information of the nucleotide sequence of a gene encoding polyketide synthase is determined, it becomes possible to modify a domain based on the obtained information, so as to change the size of a carbon chain and the functional group of the carbon at position β during a condensation process. For example, Non Patent Literature 5 describes that a novel derivative of erythromycin can be produced by selectively inactivating a specific domain in the polyketide synthase gene of erythromycin. Moreover, by replacing the domain of each module with another one, it becomes possible to produce a predictable, novel compound. For example, Non Patent Literature 6 describes that a variety of novel compounds can be produced by replacing several domains in the polyketide synthase gene of erythromycin with other domains.

Furthermore, if the nucleotide sequence of a biosynthetic gene cluster comprising a gene encoding a modifying enzyme (hereinafter referred to as a modifying enzyme gene, at times) is determined, it becomes possible to selectively modify the modifying enzyme gene based on the obtained information, so as to produce a predictable, novel compound. For example, Non Patent Literature 7 describes that a novel derivative, 6-deoxyerythronolide B, can be produced by deleting a hydroxylase gene eryF, existing in the neighborhood of the polyketide synthase gene of erythromycin.

Further, there is a case in which unnecessary by-products can be reduced and a single ingredient of interest can be produced by activating the expression of a modifying enzyme gene. In order to activate gene expression, there have been generally known methods, such as the activation of transcription by the substitution of a promoter, an increase in the number of gene copies using a multicopy vector, and the improvement of an enzyme activity by the introduction of a mutation into a gene. Moreover, there is a case in which productivity can be enhanced by activating or inactivating a regulatory gene by the same above methods.

Furthermore, there is also a case in which, using a different strain, a polyketide compound of interest can be produced by obtaining a gene encoding such biosynthetic gene cluster, and then by introducing the obtained gene into the different strain according to an adequate method. As a different strain used herein, microorganisms, and particularly, *Escherichia coli* that can be cultured in a short time, can be advantageously used. For example, Non Patent Literature 8 describes that a 6-deoxyerythronolide B of interest as an erythromycin precursor can be efficiently produced by incorporating a polyketide synthase gene into *Escherichia coli*.

Still further, Patent Literature 4 describes: a polypeptide involved in the biosynthesis of a macrolide compound, pladienolide, that is one type of polyketide compound; a DNA encoding the polypeptide and a variant thereof; a transformant retaining a part or the entire of the DNA or the variant thereof; and a method for producing the macrolide compound, pladienolide, using the transformant.

CITATION LIST

Patent Literature

[Patent Literature 1] Japanese Patent Application Laid-Open Publication No. 6-22770
[Patent Literature 2] Japanese Patent Application Laid-Open Publication No. 9-235283
[Patent Literature 3] International Publication WO1993/13663, pamphlet
[Patent Literature 4] International Publication WO2006/9276, pamphlet Non Patent Literature

[Non Patent Literature 1] J. Antibiot., 45 (1992) 914-921
[Non Patent Literature 2] Ann. Rev. Gen., 24 (1990) 37-66
[Non Patent Literature 3] Ann. Rev. Microbiol., 47 (1993) 874-912
[Non Patent Literature 4] Proc. Natl. Acad. Sci. USA 95 (1998) 12111-12116
[Non Patent Literature 5] Proc. Natl. Acad. Sci. USA 90 (1993) 7119-7123
[Non Patent Literature 6] Proc. Natl. Acad. Sci. USA 96 (1999) 1846-1851
[Non Patent Literature 7] Science 252 (1991) 114-116
[Non Patent Literature 8] Science 291 (2001) 1790-1792

SUMMARY OF THE INVENTION

Technical Problem

It is an object of the present invention to provide a polypeptide involved in the biosynthesis of herboxidiene, a DNA encoding the polypeptide, and a variant thereof. It is another object of the present invention to provide a transformant retaining a part or the entire of the DNA or the variant thereof, and a method for producing herboxidiene or an analogue thereof using the transformant. It is yet another object of the present invention to provide a herboxidiene analogue.

Solution to Problem

In order to solve the aforementioned problems, the present inventors have attempted to obtain a DNA of interest from *Streptomyces* sp. Mer-16208 (hereinafter referred to as Mer-16208, at times), which is a bacterium that produces herboxidiene and analogues thereof, according to a colony hybridization method, using a probe that had been prepared based on a sequence reportedly generally conserved in the keto synthase domain of polyketide synthase. However, a large number of cosmids were selected, and thus, the DNA of interest could not be promptly identified.

Hence, the inventors have focused on the fact that a modifying enzyme gene is highly likely to exist in the neighborhood of the polyketide synthase gene, and they have produced several primers based on the sequence of a pladienolide 18,19-epoxidase gene, pldD, existing in the neighborhood of a similar polyketide biosynthetic gene possessed by a known actinomycete *Streptomyces platensis* Mer-11107, and have then obtained a gene, hbdD, having a high identity to pldD, from the chromosomal DNA of Mer-16208. Using this gene as a probe, several cosmids comprising a DNA of interest were selected from a large number of cosmids obtained based on the sequence of a polyketide synthase domain, and finally, a nucleotide sequence (SEQ ID NO: 1) of approximately 65 kb comprising a DNA involved in the synthesis of herboxidiene was determined.

As a result of the analysis of the DNA of SEQ ID NO: 1, it became clear that seven open reading frames, hbdAI (nucleotides 8919-28295), hbdAII (nucleotides 28326-49892), hbdAIII (nucleotides 49892-55981), hbdD (nucleotides 56115-57545), hbdF (nucleotides 57575-58435), hbdE (nucleotides 58533-59798) and hbdR (nucleotides 6681-7706), are comprised in the DNA, and that such seven open reading frames are involved in the biosynthetic pathway of herboxidiene shown in FIG. 1. Specifically, hbdAI, hbdAII and hbdAIII are the polyketide synthase genes of herboxidiene; hbdD is the 14,15-epoxidase gene of herboxidiene; hbdF is the 17-O-methyl transferase gene of herboxidiene; hbdE is the 18-hydroxylase gene of herboxidiene; and hbdR is the transcription factor gene of herboxidiene. Moreover, Mer-16208 strains, in which these genes were disrupted, were produced, and herboxidiene and analogues thereof produced by each of the produced strains were then analyzed, so that the function of each gene was confirmed. Furthermore, the antitumor activities of the herboxidiene analogues were also confirmed.

Specifically, the present invention relates to the following [1] to [22].

[1] An isolated pure DNA comprising at least one region encoding a polypeptide involved in the biosynthesis of herboxidiene.
[2] The DNA according to [1] above, which comprises all regions encoding the polypeptide involved in the biosynthesis of herboxidiene.
[3] The DNA according to [1] or [2] above, wherein the polypeptide involved in the biosynthesis of herboxidiene is at least one selected from polyketide synthase, 18-hydroxylase, 14,15-epoxidase, 17-O-methyl transferase, and a transcription factor.
[4] The DNA according to any one of [1] to [3] above, which is derived from a microorganism belonging to genus *Streptomyces*.
[5] The DNA according to [1] above, which comprises at least one nucleotide sequence selected from the nucleotide sequences defined in the following (1) to (4):
(1) the nucleotide sequence defined in any one of the following (a) to (h):
(a) a nucleotide sequence consisting of contiguous nucleotides 6681 to 7706 of SEQ ID NO: 1;

(b) a nucleotide sequence consisting of contiguous nucleotides 8919 to 28295 of SEQ ID NO: 1;
(c) a nucleotide sequence consisting of contiguous nucleotides 28326 to 49892 of SEQ ID NO: 1;
(d) a nucleotide sequence consisting of contiguous nucleotides 49892 to 55981 of SEQ ID NO: 1;
(e) a nucleotide sequence consisting of contiguous nucleotides 56115 to 57545 of SEQ ID NO: 1;
(f) a nucleotide sequence consisting of contiguous nucleotides 57575 to 58435 of SEQ ID NO: 1;
(g) a nucleotide sequence consisting of contiguous nucleotides 58533 to 59798 of SEQ ID NO: 1; and
(h) a nucleotide sequence consisting of contiguous nucleotides 1 to 65360 of SEQ ID NO: 1,
(2) the nucleotide sequence of a DNA hybridizable under stringent conditions with a DNA comprising a sequence complementary to any one of the nucleotide sequences defined in (1) above,
(3) a nucleotide sequence having an identity of 85% or more to any one of the nucleotide sequences defined in (1) above, and
(4) a nucleotide sequence not hybridizable under stringent conditions with a DNA comprising a sequence complementary to the nucleotide sequences defined in (1) above due to the degeneration of the genetic code, but encoding an amino acid sequence identical to that of the nucleotide sequence defined in any one of (1) to (3) above.
[6] The DNA according to [1] above, which comprises at least one nucleotide sequence selected from the nucleotide sequences defined in the following (a) to (h):
(a) a nucleotide sequence consisting of contiguous nucleotides 6681 to 7706 of SEQ ID NO: 1;
(b) a nucleotide sequence consisting of contiguous nucleotides 8919 to 28295 of SEQ ID NO: 1;
(c) a nucleotide sequence consisting of contiguous nucleotides 28326 to 49892 of SEQ ID NO: 1;
(d) a nucleotide sequence consisting of contiguous nucleotides 49892 to 55981 of SEQ ID NO: 1;
(e) a nucleotide sequence consisting of contiguous nucleotides 56115 to 57545 of SEQ ID NO: 1;
(f) a nucleotide sequence consisting of contiguous nucleotides 57575 to 58435 of SEQ ID NO: 1;
(g) a nucleotide sequence consisting of contiguous nucleotides 58533 to 59798 of SEQ ID NO: 1; and
(h) a nucleotide sequence consisting of contiguous nucleotides 1 to 65360 of SEQ ID NO: 1.
[7] A polypeptide encoded by the DNA according to any one of [1] to [6] above.
[8] The polypeptide according to [7] above, having a polyketide synthase activity
[9] The polypeptide according to [8] above, having the amino acid sequence shown in SEQ ID NO: 2, 3 or 4, or a partial sequence thereof
[10] The polypeptide according to [7] above, having a 14,15-epoxidase activity
[11] The polypeptide according to [10] above, having the amino acid sequence shown in SEQ ID NO: 5 or a partial sequence thereof.
[12] The polypeptide according to [7] above, having a 17-O-methyl transferase activity.
[13] The polypeptide according to [12] above, having the amino acid sequence shown in SEQ ID NO: 6 or a partial sequence thereof.
[14] The polypeptide according to [7] above, having a 18-hydroxylase activity.

[15] The polypeptide according to [14] above, having the amino acid sequence shown in SEQ ID NO: 7 or a partial sequence thereof.
[16] The polypeptide according to [7] above, having a transcription factor activity.
[17] The polypeptide according to [16] above, having the amino acid sequence shown in SEQ ID NO: 8 or a partial sequence thereof.
[18] An autonomously or integratively replicating recombinant plasmid, carrying the DNA according to any one of [1] to [6] above.
[19] A transformant retaining the DNA according to any one of [1] to [6] above.
[20] A method for producing herboxidiene or an analogue thereof, comprising culturing the transformant according to [19] above in a medium and then collecting herboxidiene or an analogue thereof from the culture medium.
[21] A compound represented by the following formula (1):

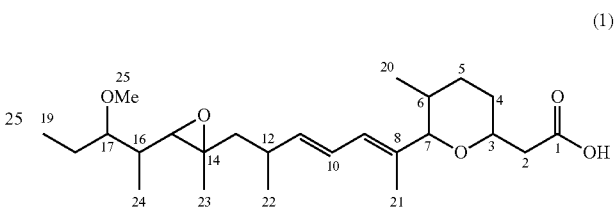

[22] A compound represented by the following formula (2):

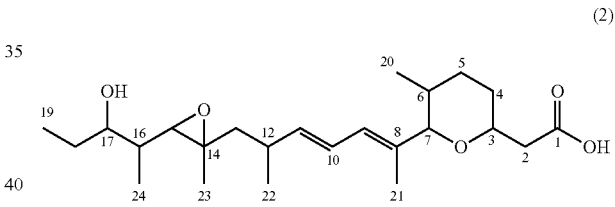

In the present specification, "DNA hybridizable under stringent conditions" means a DNA, which is obtained, for example, by using a DNA having the nucleotide sequence defined by any one of the above described items (a) to (h) as a probe, and applying a colony hybridization method, a plaque hybridization method, a Southern hybridization method or the like. Specifically, it is a DNA having a certain level or more of identity to the nucleotide sequence of the DNA used as a probe, and it is a DNA having an identity of, for example, 85% or more, preferably 90% or more, more preferably 93% or more, further preferably 95% or more, and most preferably 98% or more to the aforementioned nucleotide sequence. Conditions for hybridization may be selected, as appropriate, depending on the type of a DNA to be obtained, according to the descriptions of Sambrook et al., Molecular Cloning. A Laboratory Manual. 2nd ed., Cold Spring Harbor Laboratory Press (hereinafter abbreviated as Sambrook et al.). For example, when a DNA having an identity of 85% or more is obtained, there may be used conditions, in which hybridization is carried out at 56° C. to 59° C. in the presence of 0.5 M NaCl and 50% formamide, and the filter is then washed at 56° C. to 59° C. using a 0.1 to 2×SSC solution (wherein the composition of a 1×SSC solution consists of 150 mM sodium chloride and 15 mM sodium citrate). Moreover, when a DNA having an identity of 90% or more is obtained, there may be used conditions, in which hybridization is carried out at 61° C. to 64° C. in the presence of 0.5 M NaCl and 50% formamide, and the filter is then washed at 61° C. to 64° C. using a 0.1 to 2×SSC solution (wherein the composition of a 1×SSC solution consists of 150 mM sodium chloride and 15 mM sodium citrate).

"A variant of DNA" means a DNA modified by a deletion, conversion, addition, insertion or the like of a constitutional nucleotide(s), or a derivative thereof. "Identity" means the percentage of nucleotides shared by two sequences, when the two sequences are aligned in an optimal manner. That is to say, such identity can be calculated by the expression: identity=(the number of matched positions/the total number of positions)×100, and it can be calculated using a commercially available algorism. In addition, such algorism is integrated into the NBLAST and XBLAST programs described in Altschul et al., J. Mol. Biol. 215 (1990) 403-410. "Analogue" means a compound having a main skeleton characterized for its chemical structure, which is identical to that of a certain compound, but having a different modification or different structure of a side chain.

"A partial sequence of the amino acid sequence" may be an amino acid sequence having a domain essential for exhibiting a predetermined activity. Further, such partial sequence may comprise an amino acid sequence comprising a deletion, substitution, addition or insertion of one or multiple amino acid residues with respect to a certain amino acid sequence, and exhibiting a predetermined activity.

Advantages Effects of Invention

According to the present invention, it is possible to isolate a DNA encoding a polypeptide involved in the biosynthesis of herboxidiene and to determine the nucleotide sequence thereof. Further, it is also possible to produce a plasmid carrying the DNA and a transformant transformed with the plasmid, and to efficiently produce herboxidiene and analogues thereof, using the transformant. Still further, by modifying or changing the obtained DNA sequence, the type of carboxylic acid incorporated, a modification reaction after condensation, a modification reaction after skeleton formation, and all the combinations thereof are modified, and thereby, it becomes possible to produce a novel or specific herboxidiene analogue.

DESCRIPTION OF EMBODIMENTS

Figure 1:
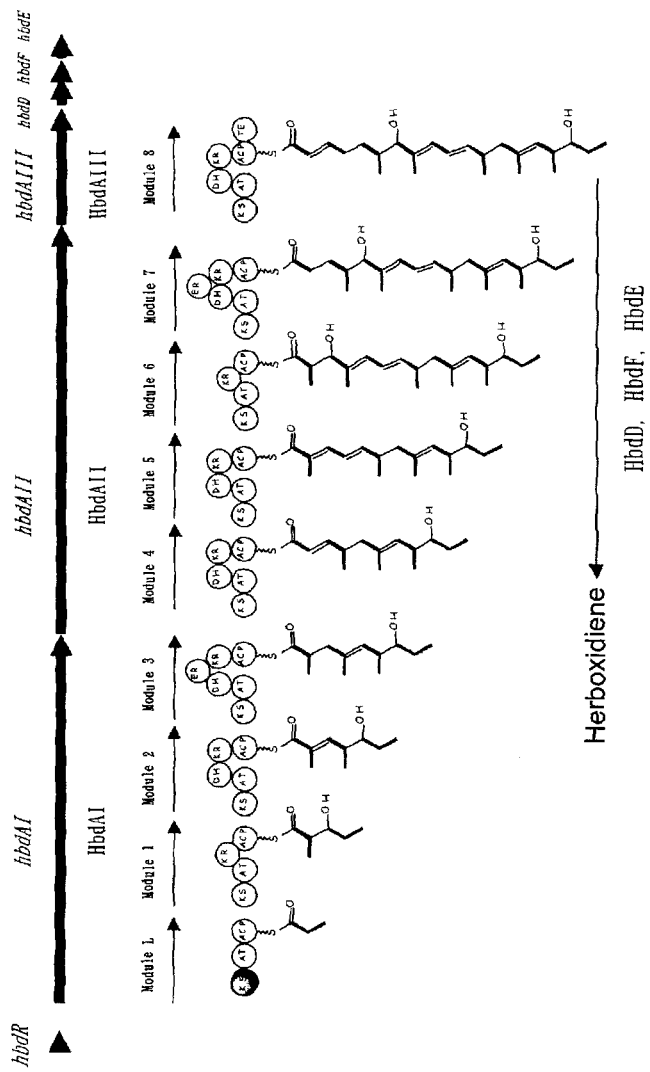
FIG. 1 is a view showing the biosynthetic pathway of herboxidiene in Mer-16208.

The embodiments of the present invention will be described in detail below.

In the present invention, a DNA partly or entirely encoding a polypeptide involved in the biosynthesis of herboxidiene can be isolated from cultured cells of microorganisms having an ability to produce herboxidiene, and the nucleotide sequence thereof can be determined. As such microorganisms, any microorganisms can be used regardless of species and the type of a strain, as long as they have an ability to produce herboxidiene. Preferred microorganisms include Streptomyces sp. Mer-16208 separated from the soil. The present cell strain was deposited as an international deposition with Patent Microorganisms Depositary, National Institute of Technology and Evaluation, an Independent Administrative Institution, 2-5-8, Kazusa Kamatari, Kisarazu-shi, Chiba-ken, Japan, under accession No. NITE BP-716 on Mar. 9, 2009.

The present inventors have attempted to obtain the DNA of the present invention from the above described microorganisms according to the colony hybridization method described in Sambrook et al. First, the genomic DNA of Mer-16208 which had been partially digested with a suitable restriction enzyme such as Sau3AI, was ligated to a cosmid vector capable of replicating in *Escherichia coli*, which had been digested with a restriction enzyme such as BamHI, and the thus obtained recombinant DNA was then incorporated into *Escherichia coli*, so as to obtain a transformed strain. On the other hand, using the DNA obtained from Mer-16208 as a template, and also using primers that had been designed with reference to the sequence information reportedly generally conserved in the keto synthase domain of polyketide synthase and the sequence information of the keto synthase domain of a pikromycin-producing bacterium (see Non Patent Literature 3), PCR was carried out, so that the amplified DNA was obtained. Using the DNA as a probe, the previously prepared transformed strain was screened. As a result, a large number of positive clones (cosmids) were obtained, and thus, a transformed strain having a DNA of interest could not be immediately identified.

Hence, the present inventors have focused on the fact that a modifying enzyme gene is highly likely to exist in the neighborhood of the polyketide synthase gene. The inventors have produced several primers based on the sequence of a pladienolide 18,19-epoxidase gene, pldD (which had been registered in accession No. AB435553 of Genbank) existing in the neighborhood of a similar polyketide biosynthetic gene possessed by a known actinomycete *Streptomyces* sp. Mer-11107 (which had been deposited as an international deposition with the International Patent Organism Depositary (IPOD), the National Institute of Advanced Industrial Science and Technology, an Independent Administrative Institution, Tsukuba Central 6, Higashi 1-1-1, Tsukuba-shi, Ibaraki-ken, Japan, under accession No. FERM BP-7812 on Nov. 27, 2001), and as a result, the inventors have obtained a gene, hbdD, having a high identity to pldD, from the chromosomal DNA of Mer-16208. Using this gene as a probe, several cosmids comprising a DNA of interest were selected from a large number of cosmids obtained based on the sequence of a polyketide synthase domain.

Since a part of the DNA involved in the biosynthesis of herboxidiene has been clarified, Southern hybridization was carried out using, as a probe, the gene hbdD that was likely to encode a 14,15-epoxidase involved in the biosynthesis of herboxidiene. Cosmids comprising a cluster of herboxidiene biosynthetic genes adjacent to hbdD were selected and aligned.

Next, the nucleotide sequence of a DNA fragment inserted into each cosmid was determined. First, after the isolation of each cosmid, it was cleaved into fragments with a size of approximately 1 kb for subcloning. Subsequently, the nucleotide sequence of each of the obtained subclones was determined, and an approximately 65-kb nucleotide sequence comprising the DNA involved in the synthesis of herboxidiene was then determined (see SEQ ID NO: 1).

The DNA shown in SEQ ID NO: 1 comprised seven open reading frames (ORF), hbdAI (nucleotides 8919-28295), hbdAII (nucleotides 28326-49892), hbdAIII (nucleotides 49892-55981), hbdD (nucleotides 56115-57545), hbdF (nucleotides 57575-58435), hbdE (nucleotides 58533-

59798) and hbdR (nucleotides 6681-7706). In addition, the amino acid sequences of polypeptides encoded by these sequences are as shown in SEQ ID NO: 2 to 8, respectively.

Among the thus obtained DNAs involved in the biosynthesis of herboxidiene of Mer-16208, hbdAI, hbdAII, and hbdAIII had several open reading frames each comprising one or more repeating units called modules, as with the already clarified other polyketide biosynthetic genes. As described later, each module encoded all or several domains selected from an acyl carrier protein (ACP) involved in the condensation reaction in polyketide synthesis, β-ketoacyl-ACP synthase (KS), acyl transferase (AT), ketoacyl reductase (KR) involved in a β-carbonyl group modification reaction, dehydratase (DH), and enoyl reductase (ER). A thioesterase (TE) domain that cleaves a polyketide chain from polyketide synthase exists in the last module.

The biosynthetic pathway of herboxidiene in Mer-16208 is shown in FIG. 1. Since a loading module (Module L) differs from other modules and the cysteine in the active center thereof is substituted with a glutamine, it is found that HbdAI is involved in the first reaction. In addition, it is also found that since module 8 has a thioesterase (TE) domain, HbdAIII is involved in the final reaction of polyketide. Thus, after the formation of the basic skeleton of polyketide, it is modified with a group of enzymes (HbdD, HbdF and HbdE) that are encoded by hbdD, hbdF and hbdE, so that herboxidiene seems to be biosynthesized. Moreover, hbdR has a high identity to a gene, lad, encoding a transcription factor, and thus, the hbdR seems to encode the transcription factor of the DNA involved in the biosynthesis of herboxidiene.

The thus clarified modules of the DNA involved in the biosynthesis of herboxidiene and the corresponding domains are as follows.

ORF hbdAI (nucleotides 8919-28295 of SEQ ID NO: 1) encodes a loading module, module 1, module 2 and module 3. The corresponding polypeptide is represented by the amino acid sequence shown in SEQ ID NO: 2.

Loading module (nucleotides 8919-12023)
KS0: nucleotides 8955-10217
AT0: nucleotides 10305-11360
ACP0: nucleotides 11790-11972
Module 1 (nucleotides 12024-16451)
KS1: nucleotides 12024-13262
AT1: nucleotides 13356-14441
KR1: nucleotides 15324-16196
ACP1: nucleotides 16218-16400
Module 2 (nucleotides 16452-21734)
KS2: nucleotides 16452-17711
AT2: nucleotides 17796-18860
DH2: nucleotides 19038-19739
KR2: nucleotides 20622-21461
ACP2: nucleotides 21483-21665
Module 3 (nucleotides 21735-28295)
KS3: nucleotides 21735-22991
AT3: nucleotides 23253-24305
DH3: nucleotides 24474-25169
ER3: nucleotides 26016-26936
KR3: nucleotides 26964-27812
ACP3: nucleotides 27834-28016

In addition, the amino acid sequence of the corresponding polypeptide is as follows.
KS0: amino acids 13-433
AT0: amino acids 463-814
ACP0: amino acids 958-1018
KS1: amino acids 1036-2511
AT1: amino acids 1480-1841
KR1: amino acids 2136-2426
ACP1: amino acids 2434-2494
KS2: amino acids 2512-2931
AT2: amino acids 2960-3314
DH2: amino acids 3374-3607
KR2: amino acids 3902-4181
ACP2: amino acids 4189-4249
KS3: amino acids 4273-4691
AT3: amino acids 4779-5129
DH3: amino acids 5186-5417
ER3: amino acids 5700-6006
KR3: amino acids 6016-6298
ACP3: amino acids 6306-6366

ORF hbdAII (nucleotides 28326-49892 of SEQ ID NO: 1) encodes module 4, module 5, module 6 and module 7, and the corresponding polypeptide is represented by the amino acid sequence shown in SEQ ID NO: 3.

Module 4 (nucleotides 28326-33644)
KS4: nucleotides 28419-29681
AT4: nucleotides 29751-30851
DH4: nucleotides 31017-31718
KR4: nucleotides 32526-33371
ACP4: nucleotides 33393-33575
Module 5 (nucleotides 33645-38873)
KS5: nucleotides 33645-34895
AT5: nucleotides 34974-36047
DH5: nucleotides 36231-36938
KR5: nucleotides 37722-38606
ACP5: nucleotides 38628-38810
Module 6 (nucleotides 38874-43532)
KS6: nucleotides 38874-40133
AT6: nucleotides 40203-41267
KR6: nucleotides 42405-43247
ACP6: nucleotides 43269-43451
Module 7 (nucleotides 43533-49892)
KS7: nucleotides 43533-44792
AT7: nucleotides 44865-45962
DH7: nucleotides 46137-46847
ER7: nucleotides 47724-48641
KR7: nucleotides 48669-49520
ACP7: nucleotides 49542-49724

Moreover, the amino acid sequence of the corresponding polypeptide is as follows.
KS4: amino acids 32-452
AT4: amino acids 476-842
DH4: amino acids 898-1131
KR4: amino acids 1401-1682
ACP4: amino acids 1690-1750
KS5: amino acids 1774-2190
AT5: amino acids 2217-2574
DH5: amino acids 2636-2871
KR5: amino acids 3133-3427
ACP5 amino acids 3435-3495
KS6: amino acids 3517-3936
AT6: amino acids 3960-4314
KR6: amino acids 4694-4974
ACP6: amino acids 4982-5042
KS7: amino acids 5070-5489
AT7: amino acids 55145879
DH7: amino acids 5938-6174
ER7: amino acids 6467-6772
KR7: amino acids 6782-7065
ACP7: amino acids 7073-7133

ORF hbdAIII (nucleotides 49892-55981 of SEQ ID NO: 1) encodes module 8, and the corresponding polypeptide is represented by the amino acid sequence shown in SEQ ID NO: 4.

Module 8 (nucleotides 49892-55981)
KS8: nucleotides 49892-51271

AT8: nucleotides 51341-52420
DH8: nucleotides 52589-53278
KR8: nucleotides 54083-54940
ACP8: nucleotides 54962-55144
TE8: nucleotides 55163-55981

Furthermore, the amino acid sequence of the corresponding polypeptide is as follows.
KS8: amino acids 41-460
AT8: amino acids 484-843
DH8: amino acids 900-1129
KR8: amino acids 1398-1683
ACP8: amino acids 1691-1751
TE8: amino acids 1758-2030

ORF hbdD (nucleotides 56115-57545 of SEQ ID NO: 1) encodes 14,15-epoxidase involved in the biosynthesis of herboxidiene, and the corresponding polypeptide is represented by the amino acid sequence shown in SEQ ID NO: 5. ORF hbdF (nucleotides 57575-58435 of SEQ ID NO: 1) encodes 17-O-methyl transferase involved in the biosynthesis of herboxidiene, and the corresponding polypeptide is represented by the amino acid sequence shown in SEQ ID NO: 6. ORF hbdE (nucleotides 58533-59798 of SEQ ID NO: 1) encodes 18-hydroxylase involved in the biosynthesis of herboxidiene, and the corresponding polypeptide is represented by the amino acid sequence shown in SEQ ID NO: 7. ORF hbdR (nucleotides 6681-7706 of SEQ ID NO: 1) encodes a transcription factor involved in the biosynthesis of herboxidiene, and the corresponding polypeptide is represented by the amino acid sequence shown in SEQ ID NO: 8.

Thus, if a nucleotide sequence is once determined, the DNA involved in the biosynthesis of herboxidiene of the present invention can be obtained by a known method based on the information of the determined nucleotide sequence.

For example, the DNA having the nucleotide sequence shown in SEQ ID NO: 1 is digested with a suitable restriction enzyme, and the digested DNA is then separated and recovered by the method described in Sambrook et al., so as to prepare an oligonucleotide used as a probe or a primer. When the obtained oligonucleotide is used as a probe, the obtained DNA fragment is preferably labeled with digoxigenin or the like. DIG Labeling & Detection Kit (Roche Diagnostics) or the like is preferably used for such labeling with digoxigenin.

Subsequently, a library is produced from a cell body of microorganisms having an ability to produce herboxidiene according to the genome cloning method or cDNA cloning method described in Sambrook et al., etc. Clones (colonies) to be hybridized with the previously prepared probe are selected from the obtained library, and plasmids are then extracted from the selected clones according to the method described in Sambrook et al. A DNA of interest involved in the biosynthesis of herboxidiene can be obtained from the obtained plasmids.

In this case, when the extracted plasmids comprise only a partial fragment of the DNA involved in the biosynthesis of herboxidiene, the extracted plasmids are digested with a suitable restriction enzyme such as BamHI, so that the restriction map of these plasmids is produced according to the conventional method. Thereafter, restriction fragments existing in common in several clones are discovered from the restriction map, and the cloned segments are connected with one another at overlapped portions, so as to obtain a DNA comprising the entire DNA involved in the biosynthesis of herboxidiene.

Otherwise, the DNA involved in the biosynthesis of herboxidiene can also be obtained by directly performing a PCR using the above-mentioned library and primer, so as to directly amplify the DNA of interest.

The nucleotide sequence of the DNA encoding a polypeptide involved in the biosynthesis of herboxidiene can be determined by analyzing by a commonly used nucleotide sequence analysis method such as a dideoxy method [Proc. Natl. Acad. Sci. USA, 74, 5463 (1977)], or using a nucleotide sequence analyzer such as a 373A DNA sequencer (manufactured by PerkinElmer). Specifically, a double-stranded plasmid DNA is directly used as a template in a cycle sequence reaction, in which various sequence-specific oligonucleotide primers are used, or, alternatively, a DNA fragment is segmented, and the DNA fragments are introduced into bacteriophage M13, randomly, using a library or a plasmid vector in which the fragments are partially overlapped, so as to produce an overlapping library, hr which a deletion has been successively introduced from the terminal portion of the DNA fragment. Subsequently, the sequence of each recombinant DNA fragment can be determined using an oligonucleotide primer specific to the vector sequence.

Moreover, based on the determined nucleotide sequence of the DNA, a DNA of interest can be prepared by performing a chemical synthesis using a DNA synthesizer such as DNA Synthesizer Type 8905 (manufactured by PerSeptive Biosystems). The arrangement, edition and analysis of the obtained nucleotide sequence data can be carried out using the existing software such as Genetyx™ manufactured by Genetyx Corporation.

Furthermore, the polypeptide of the present invention can be produced by expressing the DNA of the present invention in host cells, applying the methods described, for example, in Sambrook et al. and Ausubel et al., Current Protocols in Molecular Biology, John Wiley & Sons, Inc. A site, into which the DNA of the present invention or a variant thereof is to be incorporated, may be either on the plasmid or on the chromosome of a host microorganism. Such plasmid may comprise an autonomous replicating sequence, a promoter sequence, a terminator sequence, a drug resistance gene, etc. as well as the aforementioned DNA or a variant thereof. Further, the plasmid may be an integration-type plasmid having a sequence homologous to a given region of the genome of a host to be used.

Thus, a host and a plasmid-vector system for expressing a polypeptide encoded by the DNA of the present invention are not particularly limited, as long as the DNA is stably retained and expressed therein. For example, if actinomycetes originally having an ability to produce herboxidiene or an analogue strain thereof is used as a host, an autonomous replicating vector pIJ6021 [Gene 166, 133-137 (1995)], a chromosome-integration-type vector KC515 [The bacteria, vol. 9, Antibiotic-producing *Streptomyces* (ed: Queener, S. E. and Day, L. E.). p. 119-158. Academic Press, Orlando, Fgla], and the like can be used.

As a method for isolating and purifying a polypeptide produced by the transformant of the present invention, a conventional enzyme isolation purification method can be applied. For example, when the polypeptide of the present invention is expressed in cells in a dissolved state, after completion of a culture, the cells are recovered by centrifugation, and are then suspended in an aqueous buffer. Thereafter, the cells are disrupted using a sonicator, a French press, a homogenizer, a Dyno mill, etc., so as to obtain a cell-free extract. A purified sample can be obtained by applying a conventional enzyme isolation purification method to a supernatant obtained by centrifuging the obtained cell-free extract.

Moreover, based on the information of the amino acid sequence of the previously obtained polypeptide, a chemical synthesis method such as a fluorenylmethyloxycarbonyl method (Fmoc method) or a t-butoxycarbonyl method (t-Boc method) is applied, so as to produce the polypeptide of the present invention.

Furthermore, a transformant containing the previously obtained herboxidiene biosynthetic gene is cultured in a medium, so that herboxidiene or an analogue thereof is generated and accumulated in the culture. Thereafter, the herboxidiene or the analogue thereof can be produced by collecting it from the culture. Culture conditions are not particularly limited, and the culture is carried out under conventional host culture conditions.

Further, the size of the carbon chain of a basic polyketide skeleton and the functional group of a β-carbon during a condensation process can be changed by modifying modules, based on the nucleotide sequence information of the DNA involved in the biosynthesis of herboxidiene. Still further, by selectively inactivating a modifying enzyme after the formation of polyketide, the specific component of a predictable herboxidiene analogue can be preferentially produced. For example, by deleting the hbdE of Mer-16208 that is a strain mainly producing herboxidiene, a strain that mainly produces the 18-deoxy product of herboxidiene can be obtained. As a method for deleting such hbdE, a method of conducting a substitution or conversion by homologous recombination according to the conventional method described in Sambrook et al. may be applied.

Using the thus obtained strain capable of preferentially producing a specific herboxidiene analogue, the specific herboxidiene analogue can be produced in accordance with the method for producing herboxidiene.

EXAMPLES

The present invention will be specifically described in the following examples. However, the present invention is not limited at all by these examples. In addition, in the following descriptions, the concentration is indicated as % by weight, unless otherwise specified.

Example 1

Identification of Nucleotide Sequences of hbdD and Peripheral Region Thereof (1): Culture of Mer-16208 and Obtainment of Genomic DNA The hypha of Mer-16208 was inoculated into 50 ml of Tryptic Soy Broth (hereinafter referred to as TSB, at times), and it was then subjected to a shaking culture at 28° C. for 3 days. Thereafter, the obtained culture media was centrifuged at 3000 rpm for 10 minutes to collect a cell body. A chromosomal DNA was prepared from the cell body, using Blood & Cell Culture kit (QIAGEN).

(2): Cloning of Partial Sequence of DNA Encoding Protein (HbdD) Possibly Having 14,15-Epoxidation Activity With reference to the sequence of pldD, a pladienolide 18,19-epoxidase gene, possessed by an actinomycete *Streptomyces* sp. Mer-11107 that produces pladienolide as a secondary metabolite having an epoxy portion similar to that of herboxidiene, the following primers (PLDDF and PLDDR) were designed and produced (see SEQ ID NOS: 9 and 10 in the sequence listing).

```
PLDDF:   5'-CCGATCGAGGACGGACGCTGG-3'

PLDDR:   5'-GGCGGCCACCGACATGCCGTGCCCGTA-3'
```

Subsequently, using these two types of primers (PLDDF and PLDDR), and also using the chromosomal DNA of Mer-16208 obtained in the above section (1) as a template, PCR was carried out. In the PCR, Takara LA Taq (Takara Bio Inc.) and a PCR amplifier (T Gradient by Biometra GmbH) were used, and a three-staged reaction consisting of a denaturation at 98° C. for 20 seconds, an annealing at 50° C. for 2 minutes, and an elongation at 68° C. for 2 minutes was repeated 35 times. As a result, a DNA fragment with a size of approximately 290 bp (hereinafter referred to as DNA fragment-A1) was amplified. It was highly likely that this DNA fragment-A1 was a portion of a DNA encoding a protein having a epoxidation activity. The DNA fragment-A1 amplified by the PCR was recovered from the reaction mixture, using Wizard SV Gel and PCR Clean-Up System (Promega).

Subsequently, in order to obtain the DNA fragment-A1 in an amount sufficient for analyzing the nucleotide sequence of the thus obtained DNA fragment-A1, the DNA fragment-A1 was ligated to a plasmid vector pT7Blue T (Novagen), using DNA Ligation kit ver. 2 (Takara Bio Inc.), and *Escherichia coli* JM109 was then transformed with the ligated product. Thereafter, the transformed *Escherichia coli* was selected using an L-Broth agar medium (1.0% Bactotrypton, 0.5% yeast extract, 0.5% NaCl, and 1.5% agar) containing ampicillin (50 μg/mL), X-gal (5-bromo-4-chloro-3-indolyl-β-D-galactoside; 40 μg/mL), and IPTG (isopropyl-(3-D-thiogalactopyranoside; 100 μM). The thus separated, transformed *Escherichia coli* colony was cultured in an L-Broth liquid medium (1% Bactotrypton, 0.5% yeast extract and 0.5% NaCl) containing ampicillin (50 μg/mL). Thereafter, a plasmid DNA was separated and purified from the cell body of the proliferated transformed *Escherichia coli*, using a plasmid purification kit (Labo Pass Mini, Hokkaido System Science Co., Ltd.), so as to obtain a certain amount of the DNA fragment-A1.

(3): Analysis of Nucleotide Sequence of Cloned DNA Fragment-A1

The nucleotide sequence of the DNA fragment-A 1 obtained in the above section (2) was analyzed by a dye terminator cycle sequencing method using a DNA nucleotide sequence analyzer (ABI PRISM (registered trademark) 310 Genetic Analyzer; Applied Biosystems). As a result of the analysis of the nucleotide sequence, the DNA fragment-A1 amplified by the PCR was measured to be approximately 290 bp by electrophoresis. As a result of the sequencing of the nucleotide sequence, the size of the DNA fragment-A1 was found to be exactly 288 bp (see nucleotides 56832-57119 of SEQ ID NO: 1). At both ends of the above described, cloned 288-bp DNA sequence, DNA sequences corresponding to the two types of primers used in the above described PCR were found. Thus, it became clear that the DNA fragment-A1 had been specifically amplified by these two types of primers (PLDDF and PLDDR) in the above described PCR.

(4): Analysis of Peripheral Region of DNA Fragment-A1

As described above, the partial sequence of the DNA encoding the protein (HbdD) possibly having a 14,15-epoxidation activity derived from Mer-16208 had been determined. Hence, the nucleotide sequence of a peripheral region ranging from the upstream region to downstream region of the cloned fragment was amplified by an inverse PCR method, and cloning, and sequence analysis were then carried out. Specifically, the chromosomal DNA of Mer-16208 (see the section (1)) was digested with a restriction enzyme SalI in an H buffer (50 mM Tris-HCl, pH 7.5, 10 mM $MgCl_2$, 1 mM dithiothreitol, and 100 mM NaCl). The obtained restriction enzyme-digested DNA fragment was self-cyclized using DNA Ligation Kit ver. 2 (Takara Bio Inc.).

On the other band, the following primers (HbdDin-1F and HbdDin-1R) were designed and produced from the nucleotide sequence of the DNA fragment-A1 (see SEQ ID NOS: 11 and 12 in the sequence listing).

```
HbdDin-1F:  5'-GCCCTCGGGGACGCGCTGGCCGCGTTCAAC-3'

HbdDin-1R:  5'-CTGCGCGGGCCTCAGGCCCGTCAGGGTGAC-3'
```

Subsequently, using these two types of primers (HbdDin-1F and HbdDin-1R), and also using the above self-cyclized chromosomal DNA of Mer-16208 as a template, a PCR was carried out. In the PCR, Takara LA Taq (Takara Bio Inc.) and a PCR amplifier (T Gradient by Biometra GmbH) were used, and a two-staged reaction consisting of a denaturation at 98° C. for 20 seconds, and annealing and elongation at 68° C. for 7 minutes, was repeated 30 times.

As a result, DNA fragments each having a size of approximately 2.5 kbp (DNA fragment-B1) were amplified. It was highly likely that these DNA fragments-B1 were a DNA encoding a protein having a 14,15-epoxidation activity and a DNA having a DNA sequence comprising the upstream and downstream regions thereof.

The DNA fragments-B1 were recovered from the PCR amplification reaction mixture, using Wizard SV Gel and PCR Clean-Up System (Promega). Thereafter, in order to obtain the DNA fragments-B1 in amounts sufficient for analyzing the nucleotide sequences of the thus obtained DNA fragments, in the same manner as that described in the above section (2), a certain amount of each DNA fragment was obtained using a plasmid vector pT7Blue T (Novagen), DNA Ligation kit ver. 2 (Takata Bio Inc.), *Escherichia coli* JM109, and a plasmid purification kit (Labo Pass Mini, Hokkaido System Science Co., Ltd.)

(5): Analysis of Nucleotide Sequence of DNA Fragment-B1 (with Size of Approximately 2.5 kbp)

The nucleotide sequence of the DNA fragment-B1 obtained in the above section (4) was analyzed by a dye terminator cycle sequencing method using a DNA nucleotide sequence analyzer (ABI PRISM (registered trademark) 310 Genetic Analyzer; Applied Biosystems). Thus, the nucleotide sequence was analyzed, and as a result, the information of the 2712-bp nucleotide sequence of the DNA fragment-B1 was obtained (see nucleotides 56703-59414 of SEQ ID NO: 1).

As a result of searching the open reading frame (ORF) in this 2712-bp sequence, it was found that 3 types of proteins were encoded. As a result of searching the amino acid sequences of the proteins using BLAST search, it was found that a partial sequence of an ORF (hbdD) encoding a protein having a high identity to an epoxidase was present in nucleotides 56703-57545 of SEQ ID NO: 1. The protein HbdD encoded by the hbdD had the highest identity to the amino acid sequence of the protein PldD having a high identity to the pladienolide 18,19-epoxidase of *Streptomyces* sp. Mer-11107 (57% identity). This result suggested that the hbdD was highly likely to be a gene encoding the 14,15-epoxidase involved in the biosynthesis of herboxidiene. Herein, "identity of amino acid sequences" means the percentage of polypeptides shared by two sequences, when the two sequences are aligned in an optimal manner. That is to say, such identity can be calculated by the expression: identity=(the number of matched positions/the total number of positions)×100, and it can be calculated using a commercially available algorism. In addition, such algorism is integrated into the PBLAST program described in Altschul et al., J. Mol. Biol. 215 (1990) 403-410.

Moreover, in a region immediately downstream of the hbdD (nucleotides 57575-58435 of SEQ ID NO: 1), an ORF (hbdF) encoding a protein having a high identity to a methyl transferase existed. The protein HbdF encoded by the hbdF consisted of 287 amino acids, and it had the highest identity to the amino acid sequence of the methyl transferase MitM of *Streptomyces lavendulae* (61% identity). This result suggested that the hbdF was highly likely to be a gene encoding the 17-O-methyl transferase involved in the biosynthesis of herboxidiene.

Furthermore, in a region immediately downstream of the hbdF (nucleotides 58533-59414 of SEQ ID NO: 1), a partial sequence of an ORF (hbdE) encoding a protein having a high identity to a cytochrome P-450 hydroxylase existed. The protein HbdE encoded by the hbdE had the highest identity to the amino acid sequence of the cytochrome P-450 hydroxylase PikC of *Streptomyces venezuelae* (60% identity). This result suggested that the hbdE was highly likely to be a gene encoding the 18-hydroxylase involved in the biosynthesis of herboxidiene.

Example 2

Obtainment of Cosmid Clone Comprising Biosynthetic Gene Cluster Sequence Adjacent to hbdD, E and F (1): Preparation of Genomic Library of Mer-16208

160 μl of sterilized purified water, 200 μl of genomic DNA solution of Mer-16208 (1 mg/ml), 40 μl of 10×M buffer [100 mM Tris-HCl (pH 7.5), 100 mM MgCl$_2$, 10 mM dithiothreitol, and 500 mM NaCl], and 1 μl of restriction enzyme Sau3AI (1 unit/μl) were mixed. The obtained mixture was incubated at 37° C. for 6 minutes. Thereafter, the reaction mixture was extracted with 400 μl of phenol-chloroform mixed solution (phenol:chloroform:isoamyl alcohol=25:24:1, volume ratio), and the aqueous phase was then recovered. It was further extracted with 400 μl of chloroform, and the aqueous phase was recovered again. Thereafter, 50 μl of 3 M sodium acetate (pH 6.0) and 1 ml of ethanol were added to this solution, and the obtained mixture was then left at −80° C. for 30 minutes. The resultant was centrifuged, and the precipitated DNA was then recovered. The recovered DNA was washed with 70% ethanol, and was then dissolved in 50 μl of sterilized purified water. Thereafter, 10 μl of 10×BAP buffer [500 mM Tris-HCl (pH 9.0) and 10 mM MgCl$_2$] and 2 μl of calf intestinal alkaline phosphatase (Takara Shuzo Co., Ltd.) were added to the above obtained solution, and the obtained mixture was then incubated at 37° C. for 1 hour. This reaction mixture was extracted with 100 μl of phenol-chloroform mixed solution (phenol:chloroform:isoamyl alcohol=25:24:1, volume ratio), and the aqueous phase was recovered. It was further extracted with 100 μl of chloroform, and the aqueous phase was recovered again. Thereafter, 10 μl of 3 M sodium acetate (pH 6.0) and 300 μl of ethanol were added to this solution, and the obtained mixture was then left at −80° C. for 30 minutes. The resultant was centrifuged, and the precipitated DNA was then recovered. The recovered DNA was washed with 70% ethanol, and was then dissolved in 20 μl of TE buffer [10 mM Tris-HCl (pH 8.0) and 1 mM EDTA].

On the other hand, 10 μg of SuperCos cosmid vector (Stratagene) was digested with a restriction enzyme XbaI in accordance with the manual provided by Stratagene, and the DNA terminus was then dephosphorylated by calf intestinal alkaline phosphatase (Takara Shuzo Co., Ltd.). It was further digested with a restriction enzyme BamHI, followed by purification, and the resultant was then dissolved in 10 µl of TE buffer.

2.5 µl of solution of the Sau3AI partial digest of the aforementioned Mer-16208 genomic DNA was added to 1 µl of the obtained cosmid DNA solution. Further, 1.5 µl of sterilized purified water, 5 µl of Solution II of DNA Ligation Kit (Takara Shuzo Co., Ltd.), and 10 µl of Solution I thereof were successively added to the solution. The mixture was incubated at 23° C. for 14 hours. Thereafter, 4 µl of the reaction mixture was packaged into a lambda phage, using Gigapack III XL Kit (Stratagene). A transduction test was carried out on the obtained packaging solution (total amount: 500 µl), and its ability to form colonies was examined. As a result, the colony formation ability was found to be 192 cfu (colony forming unit)/µl.

(2) Preparation of Probe Containing hbdD, E and F

Based on the information of the 2712-bp nucleotide sequence containing the partial sequences of hbdD, hbdF and hbdE, obtained in Example 1(5), two types of primers, Hbd-Din-3F and hbdEin-1R, consisting of the following sequences, were synthesized (see SEQ ID NOS: 13 and 14 in the sequence listing).

```
HbdDin-3F:  5'-CCCGCCCTTCACGGAGCGGGAGCGCGCGCT-3'

HbdEin-1R:  5'-GAGCAGTTCGCAGATCACCGCGATGGGCAG-3'
```

Using these primers, PCR was carried out under the following conditions.

(Composition of PCR Reaction Mixture)

| | |
|---|---|
| Sterilized purified water | 31 µl |
| 2x GC buffer II | 50 µl |
| dNTP mixed solution | 16 µl |
| (dATP, dGTP, dTTP and dCTP; 2.5 mM each) | |
| HbdDin-3F (100 pmol/µl) | 0.5 µl |
| HbdEin-1R (100 pmol/µl) | 0.5 µl |
| Mer-16208 total DNA (100 ng/µl) | 1 µl |
| LA Taq polymerase (5 U/µl, Takara Shuzo Co., Ltd.) | 1 µl |

(Reaction Temperature Conditions)
95° C., 3 minutes
(98° C., 20 seconds; 63° C., 30 seconds; 68° C., 2 minutes) 30 cycles
68° C., 3 minutes A 1.5-kb DNA fragment amplified as a result of this reaction was electrophoresed on 0.8% agarose gel, and the separated 1.5-kb DNA fragment was cut out. Thereafter, the DNA was recovered and purified using Wizard SV Gel and PCR Clean-Up System (Promega). The obtained 50 µl of TE solution was defined as a probe solution containing hbdD, E and F.

(3): Screening Using Probe Containing hbdD, E and F

Using the packaging solution of the genomic DNA library of Mer-16208 prepared in the above section (1), *Escherichia coli* XL-1 Blue MR (Stratagene) used as a host was transfected in accordance with the manual provided by Stratagene. The cell suspension obtained after the transfection operation was poured and spread onto each of 10 Petri dishes (each having an internal diameter of 90 mm and a height of 15 mm) each containing LB-50 µg/ml ampicillin-1.5% agar medium, and it was then cultured at 37° C. for 18 hours. Colonies growing in each Petri dish were transferred to a Hybond N+ filter (Amersham Biosciences), and thereafter, an alkali treatment and a neutralization treatment were carried out under conditions described in the manual included with the Hybond N+ filter. Thereafter, the resultant was dried at 80° C. for 2 hours, so that a DNA derived from the colonies was immobilized on the filter.

Using 100 ng of the 1.5-kb DNA fragment containing hbdD, E, and F prepared in the above section (2) as a probe, the genomic DNA library was screened by a colony hybridization method, employing AlkPhos Direct System (Amersham Biosciences). The hybridization was carried out in NaCl with a salt concentration of 0.5 M at 68° C. for 1 hour. Conditions for the labeling of the probe DNA, hybridization, and detection were determined in accordance with the manual included with AlkPhos Direct System. Among the examined approximately 2,200 colonies, two colonies which had strongly hybridized with the alkaline phosphatase-labeled probe were separated. Cosmids (pHb635 and pHb197) were extracted and purified from *Escherichia coli* clones derived from these colonies.

(4): Preparation of Probe Containing Terminal Sequence of pHb635

The terminal sequences of DNA fragments inserted into the cosmids pHb635 and pHb197 obtained in the above section (3) were analyzed by a dye terminator cycle sequencing method using a DNA nucleotide sequence analyzer (ABI PRISM (registered trademark) 310 Genetic Analyzer, Applied Biosystems). As a result, it was found that the pHb635 possessed the area ranging from a region in the midcourse of a gene encoding polyketide synthase (nucleotide 22595 of SEQ ID NO: 1) to a region in the midcourse of hbdE (nucleotide 58958 of SEQ ID NO: 1), and that the pHb197 possessed the area ranging from a region in the midcourse of hbdD (nucleotide 57359 of SEQ ID NO: 1) to a region downstream of hbdE. Hence, in order to obtain a cosmid clone containing a sequence upstream of the terminal sequence of pHb635, a probe containing the terminal sequence of pHb635 was prepared. Based on the information of a 537-bp nucleotide sequence containing the terminal sequence of pHb635 (nucleotides 22595-23131 of SEQ ID NO: 1), two types of primers, 635-1F and 635-1R, consisting of the following sequences, were synthesized (see SEQ ID NOS: 15 and 16 in the sequence listing).

```
635-1F:   5'-GGTCGAGGGGCACGGTACGGGACGACGCT-3'

635-1R:   5'-CCCTGCACCGTGGCCGGGCCCTGCTCGGT-3'
```

Using these primers, PCR was carried out under the following conditions.

(Composition of PCR Reaction Mixture)

| | |
|---|---|
| Sterilized purified water | 31 µl |
| 2x GC buffer II | 50 µl |
| dNTP mixed solution | 16 µl |
| (dATP, dGTP, dTTP and dCTP; 2.5 mM each) | |
| 635-1F (100 pmol/µl) | 0.5 µl |
| 635-1R (100 pmol/µl) | 0.5 µl |
| pHb635 cosmid DNA (50 ng/µl) | 1 µl |
| LA Taq polymerase (5 u/µl, Takara Shuzo Co., Ltd.) | 1 µl |

(Reaction Temperature Conditions)
95° C., 6 minutes
(98° C., 20 seconds; 65° C., 30 seconds; 68° C., 1 minute) 30 cycles
68° C., 2 minutes A 486-bp DNA fragment amplified as a result of this reaction was electrophoresed on 0.8% agarose gel, and the separated 486-bp DNA fragment was cut out. Thereafter, a DNA was recovered and purified using Wizard SV Gel and PCR Clean-Up System (Promega). The obtained 50 µl of TE solution was defined as a probe solution containing the terminal sequence of pHb635.

(5): Screening Using Probe Containing Terminal Sequence of pHb635

Using the packaging solution of the genomic DNA library of Mer-16208 prepared in the section (1) above, *Escherichia coli* XL-1 Blue MR (Stratagene) used as a host was transfected in accordance with the manual provided by Stratagene. The cell suspension obtained after the transfection operation was poured and spread onto each of 10 Petri dishes (each having an internal diameter of 90 mm and a height of 15 mm) each containing LB-50 µg/ml ampicillin-1.5% agar medium, and it was then cultured at 37° C. for 18 hours. Colonies growing in each Petri dish were transferred to a Hybond N+ filter (Amersham Biosciences), and thereafter, an alkali treatment and a neutralization treatment were carried out under conditions described in the manual included with the Hybond N+ filter. Thereafter the resultant was dried at 80° C. for 2 hours, so that a DNA derived from the colonies was immobilized on the filter. Using 100 ng of the 486-bp DNA fragment containing the terminal sequence of pHb635 prepared in the above section (4) as a probe, the genomic DNA library was screened by a colony hybridization method, employing AlkPhos Direct System (Amersham Biosciences). The hybridization was carried out in NaCl with a salt concentration of 0.5 M at 70° C. for 1 hour. Conditions for the labeling of the probe DNA, hybridization, and detection were determined in accordance with the manual included with AlkPhos Direct System. Among the examined approximately 1,900 colonies, one colony which had strongly hybridized with the alkaline phosphatase-labeled probe was separated. A cosmid (pHb8221) was extracted and purified from an *Escherichia coli* clone derived from this colony.

Example 3

Determination of Nucleotide Sequence of Herboxidiene Biosynthetic Gene Cluster

The terminal sequence of a DNA fragment inserted into the cosmid pHb8221 obtained in the above Example 2(5) was analyzed by a dye terminator cycle sequencing method using a DNA nucleotide sequence analyzer (ABI PRISM (registered trademark) 310 Genetic Analyzer, Applied Biosystems). As a result, it was found that the pHb8221 possessed the area ranging from a region in the midcourse of a gene encoding polyketide synthase (nucleotide 37955 of SEQ ID NO: 1) to an upstream region containing the terminal sequence o pHb635. From the above results, pHb197, pHb635, and pHb8221 were selected as cosmids each containing a herboxidiene biosynthetic gene, and the nucleotide sequences of DNA fragments inserted into these cosmids were then determined.

Each cosmid was isolated using QIAGEN Large-Construct Kit (QIAGEN), and it was then sheared to a size of approximately 1 kb using HydroShear (Genomic Solutions), followed by subcloning using BKL Kit (Takara Shuzo Co., Ltd.).

The obtained subclone was analyzed by a dye terminator cycle sequencing method using a DNA nucleotide sequence analyzer (ABI PRISM (registered trademark) 310 Genetic Analyzer; Applied Biosystems). As a result, an approximately 65-kb nucleotide sequence containing the DNA involved in the synthesis of herboxidiene was determined (see SEQ ID NO: 1).

This DNA shown in SEQ ID NO: 1 comprised seven open reading frames (ORFs), hbdAI (nucleotides 8919-28295), hbdAII (nucleotides 28326-49892), hbdAIII (nucleotides 49892-55981), hbdD (nucleotides 56115-57545), hbdF (nucleotides 57575-58435), hbdE (nucleotides 58533-59798) and hbdR (nucleotides 6681-7706). In addition, the amino acid sequences of polypeptides encoded by these sequences are as shown in SEQ ID NOS: 2 to 8, respectively. Among the thus obtained DNAs involved in the biosynthesis of herboxidiene of Mer-16208, the functions of hbdAI, hbdAII and hbdAIII were analyzed based on the descriptions of Omura et al., Macrolide Antibiotics: Chemistry, Biology, and Practice, Second Edition, Academic Press. As a result, they had eleven open reading frames each comprising one or more repeating units called modules, as with the already clarified other polyketide biosynthetic genes. As described later, it was identified from the amino acid sequence conserved in each domain that each module encoded all or several domains selected from an acyl carrier protein (ACP) involved in the condensation reaction in polyketide synthesis, β-ketoacyl-ACP synthase (KS), acyl transferase (AT), ketoacyl reductase (KR) involved in a β-carbonyl group modification reaction, dehydratase (DH), and enoyl reductase (ER), and that a thioesterase (TE) domain that cleaves a polyketide chain from polyketide synthase existed in the last module (a GFDSL motif containing a pantotheine-binding serine residue in the ACP domain, a conserved active motif TVDTGC-SSSLV in the KS domain, motifs GHSXG and AXHs involved in the activity of the AT domain; an NADP(H)-binding site motif GXGXXAXXXA in the KR domain; an active site motif HXXXG(D)XXXXP in the DH domain; an NADP(H)-binding site motif LXHXAXGGVG in the ER domain; and GXSXG and GDH motifs in the TE domain).

It was found that a loading module (Module L) differs from other modules and the cysteine in the active center thereof is substituted with a glutamine, and thus that HbdAI is involved in the first reaction. In addition, it was also found that since module 8 has a thioesterase (TE) domain, HbdAIII is involved in the final reaction of polyketide. Thus, it was thought that, after the formation of the basic skeleton of polyketide, it is modified with a group of enzymes (HbdD, HbdF and HbdE) that are encoded by hbdD, hbdF and hbdE, so that herboxidiene seems to be biosynthesized. Moreover, hbdR had a high identity to a gene, lacI, encoding a transcription factor, and thus, the hbdR seemed to encode the transcription factor of the DNA involved in the biosynthesis of herboxidiene.

The thus clarified modules of the DNA involved in the biosynthesis of herboxidiene and the corresponding domains were as follows.

ORF hbdAI (nucleotides 8919-28295 of SEQ ID NO: 1) encoded a loading module, module 1, module 2 and module 3. The corresponding polypeptide was represented by the amino acid sequence shown in SEQ ID NO: 2.

Loading module (nucleotides 8919-12023)
KS0: nucleotides 8955-10217
AT0: nucleotides 10305-11360
ACP0: nucleotides 11790-11972
Module 1 (nucleotides 12024-16451)
KS1: nucleotides 12024-13262
AT1: nucleotides 13356-14441
KR1: nucleotides 15324-16196
ACP1: nucleotides 16218-16400
Module 2 (nucleotides 16452-21734)

KS2: nucleotides 16452-17711
AT2: nucleotides 17796-18860
DH2: nucleotides 19038-19739
KR2: nucleotides 20622-21461
ACP2: nucleotides 21483-21665
Module 3 (nucleotides 21735-28295)
KS3: nucleotides 21735-22991
AT3: nucleotides 23253-24305
DH3: nucleotides 24474-25169
ER3: nucleotides 26016-26936
KR3: nucleotides 26964-27812
ACP3: nucleotides 27834-28016

In addition, the amino acid sequence of the corresponding polypeptide was as follows.
KS0: amino acids 13-433
AT0: amino acids 463-814
ACP0: amino acids 958-1018
KS1: amino acids 1036-2511
AT1: amino acids 1480-1841
KR1: amino acids 2136-2426
ACP1: amino acids 2434-2494
KS2: amino acids 2512-2931
AT2: amino acids 2960-3314
DH2: amino acids 3374-3607
KR2: amino acids 3902-4181
ACP2: amino acids 4189-4249
KS3: amino acids 4273-4691
AT3: amino acids 4779-5129
DH3: amino acids 5186-5417
ER3: amino acids 5700-6006
KR3: amino acids 6016-6298
ACP3: amino acids 6306-6366

ORF hbdAII (nucleotides 28326-49892 of SEQ ID NO: 1) encoded module 4, module 5, module 6 and module 7, and the corresponding polypeptide was represented by the amino acid sequence shown in SEQ ID NO: 3.
Module 4 (nucleotides 28326-33644)
KS4: nucleotides 28419-29681
AT4: nucleotides 29751-30851
DH4: nucleotides 31017-31718
KR4: nucleotides 32526-33371
ACP4: nucleotides 33393-33575
Module 5 (nucleotides 33645-38873)
KS5: nucleotides 33645-34895
AT5: nucleotides 34974-36047
DH5: nucleotides 36231-36938
KR5: nucleotides 37722-38606
ACP5: nucleotides 38628-38810
Module 6 (nucleotides 38874-43532)
KS6: nucleotides 38874-40133
AT6: nucleotides 40203-41267
KR6: nucleotides 42405-43247
ACP6: nucleotides 43269-43451
Module 7 (nucleotides 43533-49892)
KS7: nucleotides 43533-44792
AT7: nucleotides 44865-45962
DH7: nucleotides 46137-46847
ER7: nucleotides 47724-48641
KR7: nucleotides 48669-49520
ACP7: nucleotides 49542-49724

Moreover, the amino acid sequence of the corresponding polypeptide was as follows.
KS4: amino acids 32-452
AT4: amino acids 476-842
DH4: amino acids 898-1131
KR4: amino acids 1401-1682
ACP4: amino acids 1690-1750
KS5: amino acids 1774-2190
AT5: amino acids 2217-2574
DH5: amino acids 2636-2871
KR5: amino acids 3133-3427
ACP5: amino acids 3435-3495
KS6: amino acids 3517-3936
AT6: amino acids 3960-4314
KR6: amino acids 4694-4974
ACP6: amino acids 4982-5042
KS7: amino acids 5070-5489
AT7: amino acids 5514-5879
DH7: amino acids 5938-6174
ER7: amino acids 6467-6772
KR7: amino acids 6782-7065
ACP7: amino acids 7073-7133

ORF hbdAIII (nucleotides 49892-55981 of SEQ ID NO: 1) encoded module 8, and the corresponding polypeptide was represented by the amino acid sequence shown in SEQ ID NO: 4.
Module 8 (nucleotides 49892-55981)
KS8: nucleotides 49892-51271
AT8: nucleotides 51341-52420
DH8: nucleotides 52589-53278
KR8: nucleotides 54083-54940
ACP8: nucleotides 54962-55144
TE8: nucleotides 55163-55981

Furthermore, the amino acid sequence of the corresponding polypeptide was as follows.
KS8: amino acids 41-460
AT8: amino acids 484-843
DH8: amino acids 900-1129
KR8: amino acids 1398-1683
ACP8: amino acids 1691-1751
TE8: amino acids 1758-2030

Moreover, AT0, AT1, AT2, AT3, AT5 and AT6 have an amino acid sequence characteristic for an AT domain that incorporates methylmalonic acid (GHSQG, VDYASH, etc. of a motif involved in activity), and AT4, AT7 and AT8 have an amino acid sequence characteristic for an AT domain that incorporates malonic acid (GHSV(I)G, HAFHS, etc. of a motif involved in activity). From these results, it has become clear that each AT domain has appropriate substrate specificity.

As described above, the protein HbdD encoded by ORF hbdD (nucleotides 56115-57545 of SEQ ID NO: 1) had the highest identity to the amino acid sequence of the protein PldD having a high identity to the pladienolide 18,19-epoxidase of *Streptomyces* sp. Mer-11107 (57% identity). This result suggested that the hbdD was highly likely to be a gene encoding the 14,15-epoxidase involved in the biosynthesis of herboxidiene. The corresponding polypeptide HbdD was represented by the amino acid sequence shown in SEQ ID NO: 5.

As described above, the protein HbdF encoded by ORF hbdF (nucleotides 57575-58435 of SEQ ID NO: 1) had the highest identity to the amino acid sequence of the methyl transferase MitM of *Streptomyces lavendulae* (61% identity). This result suggested that the hbdF was highly likely to be a gene encoding the 17-O-methyl transferase involved in the biosynthesis of herboxidiene. The corresponding polypeptide HbdF was represented by the amino acid sequence shown in SEQ ID NO: 6.

As described above, the protein HbdE encoded by ORF hbdE (nucleotides 58533-59798 of SEQ ID NO: 1) had the highest identity to the amino acid sequence of the cytochrome P-450 hydroxylase PikC of *Streptomyces venezuelae* (60% identity). This result suggested that the hbdE was highly likely to be a gene encoding the 18-hydroxylase involved in the biosynthesis of herboxidiene. The corresponding polypeptide HbdE was represented by the amino acid sequence shown in SEQ ID NO: 7.

Figure 2:
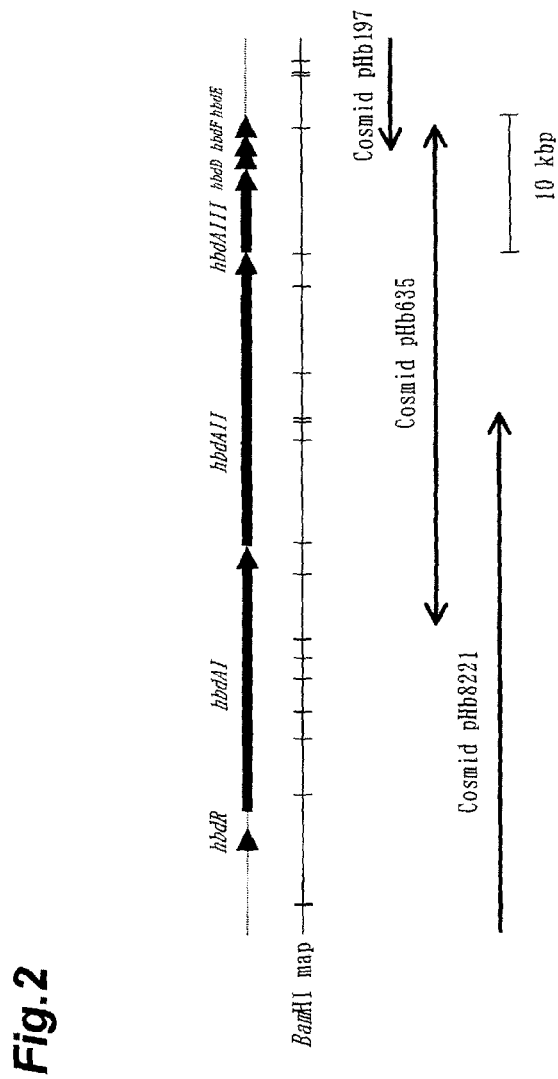
FIG. 2 is a view showing the correlation between each ORF of a DNA involved in the biosynthesis of herboxidiene in Mer-16208 and a cosmid.

A protein HbdR encoded by ORF hbdR (nucleotides 6681-7706) had the highest identity to the amino acid sequence of the transcription factor SACE_4536 of *Saccharopolyspora erythraea* (57% identity). This result suggested that the hbdR was highly likely to be a gene encoding the transcription factor of the biosynthetic gene of herboxidiene. The corresponding polypeptide HbdR was represented by the amino acid sequence shown in SEQ ID NO: 8. FIG. 1 shows the biosynthetic pathway of herboxidiene in Mer-16208. In addition, FIG. 2 shows the correlation between each ORF and a cosmid.

Example 4

Construction of Herboxidiene 18-Hydroxylase Gene (hbdE)-Deficient Strain

Based on the approximately 65-kb nucleotide sequence containing the DNA involved in the biosynthesis of herboxidiene determined in Example 3 (see SEQ ID NO: 1), it became clear that herboxidiene is biosynthesized in the biosynthetic pathway shown in FIG. 1. Thus, it was considered that a strain producing only the 18-deoxy product of herboxidiene could be obtained by disrupting only the cytochrome P-450 gene hbdE thereof. Such hbdE-deficient strain was constructed by the following method.

(1) Preparation of Shuttle Vector pMKOSCPR

A shuttle vector pMKOSCPR capable of replicating in a herboxidiene-producing strain, *Streptomyces* sp. Mer-16208, and in *Escherichia coli*, was produced. Based on the nucleotide sequence of a SuperCos1 cosmid vector (Stratagene), two types of primers, NP2-SN2F and CE1-NXHR, consisting of the following sequences, were synthesized (see SEQ ID NOS: 17 and 18 in the sequence listing).

```
NP2-SN2F:   5'-GGGCATATGACTAGTCTGATCAAGAGACAGGATG-3'

CE1-NXHR:   5'-GGGCATATGTCTAGAAGCTTGGTAACTGTCAGACCA
            AGT-3'
```

Based on the nucleotide sequence of a conjugal gene oriT (J. Bacteriol., 169, 5320-5323, 1987) derived from *Escherichia coli* plasmid RP4, two types of primers, OT-SF and OT-SR, consisting of the following sequences, were synthesized (see SEQ ID NOS: 19 and 20 in the sequence listing).

```
OT-SF:   5'-GGGCCCGGGCTCGGTCTTGCCTTGCTCGT-3'

OT-SR:   5'-GGGCCCGGGGCGCTTTTCCGCTGCATAAC-3'
```

Based on the nucleotide sequence of a plasmid SCP2 (J. Gen. Microbiol., 126, 427-442, 1981) derived from an actinomycete *Streptomyces coelicolor* A3(2) (NBRC151732), two types of primers, SCPR-AF and SCPR-SR, consisting of the following sequences, were synthesized (see SEQ ID NOS: 21 and 22 in the sequence listing).

```
SCPR-AF:   5'-GGGCCTAGGTCGACGGCCTCGGTCACGGCGC
           T-3'

SCPR-SR:   5'-CCCACTAGTCCTCGAATTCTTCGAGCAATGG
           ATCCATC-3'
```

Using these primers, PCR was carried out under the following conditions.

(Composition of PCR Reaction Mixture)

| | |
|---|---|
| Sterilized purified water | 31.5 μl |
| 10x KOD buffer | 5 μl |
| dNTP mixed solution | 5 μl |
| (dATP, dGTP, dTTP and dCTP; 2.5 mM each) | |
| MgSO₄ solution | 3 μl |
| Dimethyl sulfoxide | 2.5 μl |
| NP2-SN2F or OT-SF or SCPR-AF (50 pmol/μl) | 0.5 μl |
| CE1-NXHR or OT-SR or SCPR-SR (50 pmol/μl) | 0.5 μl |
| SuperCos1 or RP4 or SCP2 (100 ng/μl) | 1 μl |
| KOD-plus-polymerase (1 u/μl, Toyobo Co., Ltd.) | 1 μl |

(Reaction Temperature Conditions)
95° C., 6 minutes
(98° C., 20 seconds; 60° C., 30 seconds; 68° C., 6 minutes) 30 cycles
68° C., 7 minutes As a result of this reaction, a 3.2-kb DNA fragment (DNA fragment AC1) comprising an aminoglycoside resistance gene aphII (Gene, 19(3), 327-336, 1982) and an *Escherichia coli* plasmid replicating origin ColE1 (Gene, 33(1), 103-119, 1985) was amplified by a reaction using NP2-SN2F, CE1-NXHR and SuperCos1. A 0.8-kb DNA fragment (DNA fragment OT1) comprising the conjugal gene oriT was amplified by a reaction using OT-SF, OT-SR and RP4. A 5.8-kb DNA fragment (DNA fragment SR1) comprising the replication region of the plasmid SCP2 of Actinomycetes was amplified by a reaction using SCPR-AF, SCPR-SR and SCP2. The DNA fragments AC1, OT1 and SR1 were purified using Wizard SV Gel and PCR Clean-Up System (Promega). The DNA fragment AC1 was digested with a restriction enzyme NdeI, and it was then self-cyclized using DNA Ligation Kit ver. 2.1 (Takara Bio Inc.). The obtained cyclized DNA AC1 and the DNA fragment OT1 were each digested with a restriction enzyme SmaI, and they were then ligated to each other using DNA Ligation Kit ver. 2.1 (Takara Bio Inc.). Thus, *Escherichia coli* plasmid pMKO1 having an aminoglycoside resistance gene aphII and the conjugal gene oriT were obtained. In addition, the DNA fragment SR1 was digested with restriction enzymes SpeI and AvrII, and using DNA Ligation Kit ver. 2.1 (Takara Bio Inc.), the thus digested DNA fragment was then ligated to a plasmid pMKO1 that had been digested with a restriction enzyme SpeI. Hence, a shuttle vector pMKOSCPR, in which the replication region of the plasmid SCP2 of actinomycetes had been inserted into pMKO1, was constructed.

(2) Preparation of hbdE-Deficient Plasmid pMKOSCPR-EU-tsr-ED

Based on the nucleotide sequence shown in SEQ ID NO: 1, four types of primers, dEU-AHEF, dEU-NXR, dED-XF and dED-EHR, consisting of the following sequences, were synthesized (see SEQ ID NOS: 23, 24, 25 and 26 in the sequence listing).

```
dEU-AHEF:   5'-CCCATTAATAAGCTTGAATTCACGGGAACGGGTCC
            TCAT-3' dEU-NXR:    5'-CCCTCTAGACATATGGTCGTCCTCCGGGAGACG-3' dED-XF:     5'-CCCTCTAGAGCCCGGAGTCAGAGGTGGT-3' dED-EHR:    5'-CCCAAGCTTGAATTCGCCGATGGCGGAGCGCAT-3'
```

Based on the nucleotide sequence of a thiostrepton resistance gene tsr (Mol. Gen. Genet., 199(1), 26-36, 1985) derived from *Streptomyces azureus* NBRC12744, two types of primers, TR-AF and TR-XR, consisting of the following sequences, were synthesized (see SEQ ID NOS: 27 and 28 in the sequence listing).

```
TR-AF:   5'-CCCATTAATCGGCATCGCGTGGCGGGCCCGATT-3'

TR-XR:   5'-CGGTCTAGATTATCGGTTGGCCGCGAGATT-3'
```

Using these primers, PCR was carried out under the following conditions.

(Composition of PCR Reaction Mixture)

| | |
|---|---|
| Sterilized purified water | 31.5 µl |
| 10x KOD buffer | 5 µl |
| dNTP mixed solution | 5 µl |
| (dATP, dGTP, dTTP and dCTP; 2.5 mM each) | |
| MgSO$_4$ solution | 3 µl |
| Dimethyl sulfoxide | 2.5 µl |
| dEU-AHEF or dED-XF or TR-AF (50 pmol/µl) | 0.5 µl |
| dEU-NXR or dED-EHR or TR-XR (50 pmol/µl) | 0.5 µl |
| Mer-16208 chromosomal DNA or *S. azureus* NBRC12744 chromosomal DNA (100 ng/µl) | 1 µl |
| KOD-plus-polymerase (1 u/µl, Toyobo Co., Ltd.) | 1 µl |

(Reaction Temperature Conditions)
95° C., 6 minutes
(98° C., 20 seconds; 60° C., 30 seconds; 68° C., 3 minutes) 30 cycles
68° C., 4 minutes As a result of this reaction, a 2.1-kb DNA fragment (DNA fragment EU1) comprising nucleotides 56477-58529 of SEQ ID NO: 1 was amplified by a reaction using dEU-AHEF, a dEU-NXR and Mer-16208 chromosomal DNA. A 2.1-kb DNA fragment (DNA fragment ED1) comprising nucleotides 59808-61863 of SEQ ID NO: 1 was amplified by a reaction using dED-XF, a dED-EHR and Mer-16208 chromosomal DNA. A 1.2-kb DNA fragment (DNA fragment TR1) comprising a thiostrepton resistance gene tsr was amplified by a reaction using TR-AF, TR-XR and *S. azureus* NBRC12744 chromosomal DNA. The DNA fragments EU1, ED1 and TR1 were purified using Wizard SV Gel and PCR Clean-Up System (Promega).

Total four DNA fragments, namely, the DNA fragment EU1 digested with restriction enzymes NdeI and HindIII, the DNA fragment ED1 digested with restriction enzymes XbaI and HindIII, the DNA fragment TR1 digested with restriction enzymes XbaI and NdeI, and the shuttle vector pMKOSCPR digested with a restriction enzyme HindIII were ligated to one another, using DNA Ligation Kit ver. 2.1 (Takara Bio Inc.). Thus, there was constructed an approximately 15.1-kb plasmid pMKOSCPR-EU-tsr-ED, in which an approximately 5.3-kb DNA fragment in which the thiostrepton resistance gene tsr had been inserted between the DNA fragments EU1 and ED1 was inserted into pMKOSCPR.

(3) Preparation of hbdE-Deficient Strain Using pMKOSCPR-EU-tsr-ED

Conjugal *Escherichia coli* S17-1 (ATCC47055) was transformed with the obtained pMKOSCPR-EU-tsr-ED by an electroporation method, so as to obtain an S17-1/pMKOSCPR-EU-tsr-ED strain. The obtained S17-1/pMKOSCPR-EU-tsr-ED strain was inoculated into 12 ml of LB medium (1% Bactotrypton, 0.5% yeast extract and 0.5% NaCl) containing 25 µg/ml kanamycin, followed by a shaking culture at 30° C. for 3 hours. Thereafter, the cells were collected, were then washed with 10 ml of LB medium twice, and were then suspended in 2 ml of LB medium. The obtained suspension was defined as a donor cell suspension.

At the same time of the preparation of the donor cell suspension, Mer-16208 was applied to an ISP4 medium (Becton, Dickinson and Company), and it was then cultured at 30° C. for 1 week. Thereafter, the spores were collected, and were then suspended in 1 ml of saline. The obtained suspension was defined as a receptor cell suspension.

500 µl of the obtained S17-1/pMKOSCPR-EU-tsr-ED strain donor cell suspension was mixed with 10 µl of Mer-16208 receptor cell suspension, and the obtained mixture was then applied to an ISP4 medium (Becton, Dickinson and Company). The mixture was cultured at 30° C. for 18 hours, and 2.5 ml of SNA (0.8% nutritive medium: Becton, Dickinson and Company, 0.4% agar) containing 2 mg/ml ribostamycin was laminated on the culture. The resultant was cultured at 30° C. for 7 days, so as to obtain a pMKOSCPR-EU-tsr-ED transformed strain resistant to ribostamycin.

The obtained pMKOSCPR-EU-tsr-ED transformed strain was inoculated into 25 ml of TSB medium that did not contain ribostamycin, and the obtained mixture was then subjected to a shaking culture at 30° C. for 2 weeks. It is to be noted that the plasmid vector pMKOSCPR had a low replication efficiency in Mer-16208, and that, if it is cultured in a medium containing no drug resistance marker (ribostamycin), Mer-16208 cannot retain the pMKOSCPR. The culture solution of the pMKOSCPR-EU-tsr-ED transformed strain was collected, and it was then washed with 10 ml of sterilized water twice and suspended in 10 ml of sterilized water. The appropriately diluted suspension was applied to a YMS agar medium (0.4% yeast extract 1% malt extract, 0.4% soluble starch, 2% agar and 10 mM calcium chloride) containing 25 µg/ml thiostrepton, and it was then cultured at 30° C. for 4 days. A single colony growing on the YMS medium containing thiostrepton was transferred to a YMS agar medium containing 25 µg/ml thiostrepton and a YMS agar medium containing 200 µg/ml ribostamycin, followed by a culture at 30° C. for 2 days.

After completion of the culture, a strain which was resistant to thiostrepton and was sensitive for ribostamycin was selected. The obtained strain was an hbdE-deficient strain, in which 1278 bp (nucleotides 58530-59807 of SEQ ID NO: 1) was deleted from the hbdE gene in the genome and a thiostrepton resistance gene was inserted into the deleted site, and this strain was defined as an Mer-16208 hbdE::tsr strain.

Example 5

Construction of Herboxidiene 17-O-methyl Transferase Gene (hbdF)-Deficient Strain Based on the approximately 65-kb nucleotide sequence containing the DNA involved in the biosynthesis of herboxidiene determined in Example 3 (see SEQ ID NO: 1), it became clear that herboxidiene is biosynthesized in the biosynthetic pathway shown in FIG. 1. Thus, it was considered that a strain producing only the 17-demethyl product of herboxidiene could be obtained by disrupting only the methyl transferase gene hbdF thereof. Such hbdF-deficient strain was constructed by the following method.

(1) Preparation of Plasmid pMKOSCPR-FU-tsr-FD Used for Disrupting hbdF

Based on the nucleotide sequence shown in SEQ ID NO: 1, four types of primers, dFU-AHEF, dFU-NXR, dFD-XF and dFD-EHR, consisting of the following sequences, were synthesized (see SEQ ID NOS: 29, 30, 31 and 32 in the sequence listing).

```
dFU-AHEF:   5'-CCCATTAATAAGCTTGAATTCCTCCACGCCGAGACG
            GTA-3' dFU-NXR:    5'-CCCTCTAGACATATGGCTGTCCTTCCGGTCGCC-3' dFD-XF:     5'-CCCTCTAGAGTGCCGCTGACCGCCCGA-3' dFD-EHR:    5'-CCCAAGCTTGAATTCCGAGCGGTACGTCGCGTT-3'
```

Using these primers, PCR was carried out under the following conditions.
(Composition of PCR Reaction Mixture)

| | |
|---|---|
| Sterilized purified water | 31.5 µl |
| 10x KOD buffer | 5 µl |
| dNTP mixed solution (dATP, dGTP, dTTP and dCTP; 2.5 mM each) | 5 µl |
| MgSO$_4$ solution | 3 µl |
| Dimethyl sulfoxide | 2.5 µl |
| dFU-AHEF or dFD-XF (50 pmol/µl) | 0.5 µl |
| dFU-NXR or dFD-EHR (50 pmol/µl) | 0.5 µl |
| Mer-16208 chromosomal DNA (100 ng/µl) | 1 µl |
| KOD-plus-polymerase (1 u/µl, Toyobo Co., Ltd.) | 1 µl |

(Reaction Temperature Conditions)
95° C., 6 minutes
(98° C., 20 seconds; 60° C., 30 seconds; 68° C., 3 minutes) 30 cycles
68° C., 4 minutes As a result of this reaction, a 2.1-kb DNA fragment (DNA fragment FU1) comprising nucleotides 55517-57571 of SEQ ID NO: 1 was amplified by a reaction using dFU-AHEF and dFU-NXR, and a 2.1-kb DNA fragment (DNA fragment FD1) comprising nucleotides 58445-60523 of SEQ ID NO: 1 was amplified by a reaction using dFD-XF and dFD-EHR. The DNA fragments FU1 and FD1 were purified using Wizard SV Gel and PCR Clean-Up System (Promega).

Total four DNA fragments, namely, the DNA fragment FU1 digested with restriction enzymes NdeI and HindIII, the DNA fragment FD1 digested with restriction enzymes XbaI and HindIII, the DNA fragment TR1 digested with restriction enzymes XbaI and NdeI, which was obtained in Example 4(2), and the shuttle vector pMKOSCPR digested with a restriction enzyme HindIII, which was obtained in Example 4(1), were ligated to one another, using DNA Ligation Kit ver. 2.1 (Takara Bio Inc.). Thus, there was constructed an approximately 15.1-kb plasmid pMKOSCPR-FU-tsr-FD, in which an approximately 5.3-kb DNA fragment in which the thiostrepton resistance gene tsr had been inserted between the DNA fragments FU1 and FD1 was inserted into pMKOSCPR.

(2) Preparation of hbdF-Deficient Strain Using pMKOSCPR-FU-tsr-FD

Conjugal *Escherichia coli* S17-1 (ATCC47055) was transformed with the obtained pMKOSCPR-FU-tsr-FD by an electroporation method, so as to obtain an S17-1/pMKOSCPR-FU-tsr-FD strain. The obtained S17-1/pMKOSCPR-FU-tsr-FD strain was inoculated into 12 ml of LB medium (1% Bactotrypton, 0.5% yeast extract and 0.5% NaCl) containing 25 µg/ml kanamycin, followed by a shaking culture at 30° C. for 3 hours. Thereafter, the cells were collected, were then washed with 10 ml of LB medium twice, and were then suspended in 2 ml of LB medium. The obtained suspension was defined as a donor cell suspension.

At the same time of the preparation of the donor cell suspension, Mer-16208 was applied to an ISP4 medium (Becton, Dickinson and Company), and it was then cultured at 30° C. for 1 week. Thereafter, the spores were collected, and were then suspended in 1 ml of saline. The obtained suspension was defined as a receptor cell suspension.

500 µl of the obtained S17-1/pMKOSCPR-FU-tsr-FD strain donor cell suspension was mixed with 10 µl of Mer-16208 receptor cell suspension, and the obtained mixture was then applied to an ISP4 medium (Becton, Dickinson and Company). The mixture was cultured at 30° C. for 18 hours, and 2.5 ml of SNA (0.8% nutritive medium: Becton, Dickinson and Company, 0.4% agar) containing 2 mg/ml ribostamycin was laminated on the culture. The resultant was cultured at 30° C. for 7 days, so as to obtain a pMKOSCPR-FU-tsr-FD transformed strain resistant to ribostamycin.

The obtained pMKOSCPR-FU-tsr-FD transformed strain was inoculated into 25 ml of TSB medium that did not contain ribostamycin, and the obtained mixture was then subjected to a shaking culture at 30° C. for 2 weeks. The culture solution of the pMKOSCPR-FU-tsr-FD transformed strain was collected, and it was then washed with 10 ml of sterilized water twice and suspended in 10 ml of sterilized water. The appropriately diluted suspension was applied to a YMS agar medium (0.4% yeast extract, 1% malt extract, 0.4% soluble starch, 2% agar and 10 mM calcium chloride) containing 25 µg/ml thiostrepton, and it was then cultured at 30° C. for 4 days. A single colony growing on the YMS medium containing thiostrepton was transferred to a YMS agar medium containing 25 µg/ml thiostrepton and a YMS agar medium containing 200 µg/ml ribostamycin, followed by a culture at 30° C. for 2 days.

After completion of the culture, a strain which was resistant to thiostrepton and was sensitive for ribostamycin was selected. The obtained strain was an hbdF-deficient strain, in which 873 bp (nucleotides 57572-58141 of SEQ ID NO: 1) was deleted from the hbdF gene in the genome and a thiostrepton resistance gene was inserted into the deleted site, and this strain was defined as an Mer-16208 hbdF::tsr strain.

Example 6

Construction of Herboxidiene 14,15-Epoxidase Gene (hbdD)-Deficient Strain

Based on the approximately 65-kb nucleotide sequence containing the DNA involved in the biosynthesis of herboxidiene determined in Example 3 (see SEQ ID NO: 1), it became clear that herboxidiene is biosynthesized in the biosynthetic pathway shown in FIG. 1. Thus, it was considered that a strain producing only the 14,15-olefin product of herboxidiene could be obtained by disrupting only the 14,15-epoxidase gene hbdD thereof. Such hbdD-deficient strain was constructed by the following method.

(1) Preparation of Plasmid pMKOSCPR-DU-tsr-DD Used for Disrupting hbdD

Based on the nucleotide sequence shown in SEQ ID NO: 1, four types of primers, dDU-AHEF, dDU-NXR, dDD-XF and dDD-EHR, consisting of the following sequences, were synthesized (see SEQ ID NOS: 33, 34, 35 and 36 in the sequence listing).

dDU-AHEF: 5'-CCCATTAATAAGCTTGAATTCCCGTACCGTCACCACGGA-3' dDU-NXR: 5'-CCCTCTAGACATATGCGTGACGTTCCTTCCTCG-3' dDD-XF: 5'-CCCTCTAGAGCGACCGGAAGGACAGCG-3' dDD-EHR: 5'-CCCAAGCTTGAATTCGAGATGGCCCTCGTTCTT-3'

Using these primers, PCR was carried out under the following conditions.

(Composition of PCR Reaction Mixture)

| Sterilized purified water | 31.5 µl |
|---|---|
| 10x KOD buffer | 5 µl |
| dNTP mixed solution | 5 µl |
| (dATP, dGTP, dTTP and dCTP; 2.5 mM each) | |
| MgSO₄ solution | 3 µl |
| Dimethyl sulfoxide | 2.5 µl |
| dDU-AHEF or dDD-XF (50 pmol/µl) | 0.5 µl |
| dDU-NXR or dDD-EHR (50 pmol/µl) | 0.5 µl |
| Mer-16208 chromosomal DNA (100 ng/µl) | 1 µl |
| KOD-plus-polymerase (1 u/µl, Toyobo Co., Ltd.) | 1 µl |

(Reaction Temperature Conditions)
95° C., 6 minutes
(98° C., 20 seconds; 60° C., 30 seconds; 68° C., 3 minutes) 30 cycles
68° C., 4 minutes As a result of this reaction, a 2.1-kb DNA fragment (DNA fragment DU1) comprising nucleotides 54058-56111 of SEQ ID NO: 1 was amplified by a reaction using dDU-AHEF and dDU-NXR, and a 2.1-kb DNA fragment (DNA fragment DD1) comprising nucleotides 57555-59606 of SEQ ID NO: 1 was amplified by a reaction using dDD-XF and dDD-EHR. The DNA fragments DU1 and DD1 were purified using Wizard SV Gel and PCR Clean-Up System (Promega).

Total four DNA fragments, namely, the DNA fragment DU1 digested with restriction enzymes NdeI and HindIII, the DNA fragment DD1 digested with restriction enzymes XbaI and HindIII, the DNA fragment TR1 digested with restriction enzymes XbaI and NdeI, which was obtained in Example 4(2), and the shuttle vector pMKOSCPR digested with a restriction enzyme HindIII, which was obtained in Example 4(1), were ligated to one another, using DNA Ligation Kit vet 2.1 (Takara Bio Inc.). Thus, there was constructed an approximately 15.1-kb plasmid pMKOSCPR-DU-tsr-DD, in which an approximately 5.3-kb DNA fragment in which the thiostrepton resistance gene tsr had been inserted between the DNA fragments DU1 and DD1 was inserted into pMKOSCPR.

(2) Preparation of hbdD-Deficient Strain Using pMKOSCPR-DU-tsr-DD

Conjugal *Escherichia coli* S17-1 (ATCC47055) was transformed with the obtained pMKOSCPR-DU-tsr-DD by an electroporation method, so as to obtain an S17-1/pMKOSCPR-DU-tsr-DD strain. The obtained S17-1/pMKOSCPR-DU-tsr-DD strain was inoculated into 12 ml of LB medium (1% Bactotrypton, 0.5% yeast extract and 0.5% NaCl) containing 25 µg/ml kanamycin, followed by a shaking culture at 30° C. for 3 hours. Thereafter, the cells were collected, were then washed with 10 ml of LB medium twice, and were then suspended in 2 ml of LB medium. The obtained suspension was defined as a donor cell suspension.

At the same time of the preparation of the donor cell suspension, Mer-16208 was applied to an ISP4 medium (Becton, Dickinson and Company), and it was then cultured at 30° C. for 1 week. Thereafter, the spores were collected, and were then suspended in 1 ml of saline. The obtained suspension was defined as a receptor cell suspension.

500 µl of the obtained S17-1/pMKOSCPR-DU-tsr-DD strain donor cell suspension was mixed with 10 µl of Mer-16208 receptor cell suspension, and the obtained mixture was then applied to an ISP4 medium (Becton, Dickinson and Company). The mixture was cultured at 30° C. for 18 hours, and 2.5 ml of SNA (0.8% nutritive medium: Becton, Dickinson and Company, 0.4% agar) containing 2 mg/ml ribostamycin was laminated on the culture. The resultant was cultured at 30° C. for 7 days, so as to obtain a pMKOSCPR-DU-tsr-DD transformed strain resistant to ribostamycin.

The obtained pMKOSCPR-DU-tsr-DD transformed strain was inoculated into 25 ml of TSB medium that did not contain ribostamycin, and the obtained mixture was then subjected to a shaking culture at 30° C. for 2 weeks. The culture solution of the pMKOSCPR-DU-tsr-DD transformed strain was collected, and it was then washed with 10 ml of sterilized water twice and suspended in 10 ml of sterilized water. The appropriately diluted suspension was applied to a YMS agar medium (0.4% yeast extract, 1% malt extract, 0.4% soluble starch, 2% agar and 10 mM calcium chloride) containing 25 µg/ml thiostrepton, and it was then cultured at 30° C. for 4 days. A single colony growing on the YMS medium containing thiostrepton was transferred to a YMS agar medium containing 25 µg/ml thiostrepton and a YMS agar medium containing 200 µg/ml ribostamycin, followed by a culture at 30° C. for 2 days.

After completion of the culture, a strain which was resistant to thiostrepton and was sensitive for ribostamycin was selected. The obtained strain was an hbdD-deficient strain, in which 1443 bp (nucleotides 56112-57554 of SEQ ID NO: 1) was deleted from the hbdD gene in the genome and a thiostrepton resistance gene was inserted into the deleted site, and this strain was defined as an Mer-16208 hbdD::tsr strain.

Example 7

Construction of Herboxidiene Polyketide Synthase Gene (hbdAIII)-Deficient Strain Based on the approximately 65-kb nucleotide sequence containing the DNA involved in the biosynthesis of herboxidiene determined in Example 3 (see SEQ ID NO: 1), it became clear that herboxidiene is biosynthesized in the biosynthetic pathway shown in FIG. 1. Since a protein HbdAIII encoded by hbdAIII thereof had the highest identity to the amino acid sequence of the polyketide synthase Orf17 of *Streptomyces aizunensis* (54% identity), the hbdAIII was considered to be a polyketide synthase gene, which constitutes the basic skeleton of herboxidiene, together with hbdAI and hbdAII. Thus, in order to confirm that a strain that does not produce herboxidiene can be produced by disrupting the hbdAIII, a hbdAIII-deficient strain was constructed by the following method.

(1) Preparation of Plasmid pMKOSCPR-A3U-tsr-A3D Used for Disrupting hbdAIII

Based on the nucleotide sequence shown in SEQ ID NO: 1, four types of primers, dA3U-AHFE, dA3U-NXR, dA3D-XF and dA3D-EHR, consisting of the following sequences, were synthesized (see SEQ ID NOS: 37, 38, 39 and 40 in the sequence listing).

```
dA3U-AHEF:  5'-CCCATTAATAAGCTTGAATTCCGTCAACTTCCGCG
            ATGT-3' dA3U-NXR:   5'-CCCTCTAGACATATGGGTCATGACATCTCCAAG-3' dA3D-XF:    5'-CCCTCTAGATACCGACGTACCCACCGA-3' dA3D-EHR:   5'-CCCAAGCTTGAATTCCCATGTGCATGATCGATT-3'
```

Using these primers, PCR was carried out under the following conditions.
(Composition of PCR Reaction Mixture)

| | |
|---|---|
| Sterilized purified water | 31.5 µl |
| 10x KOD buffer | 5 µl |
| dNTP mixed solution | 5 µl |
| (dATP, dGTP, dTTP and dCTP; 2.5 mM each) | |
| MgSO$_4$ solution | 3 µl |
| Dimethyl sulfoxide | 2.5 µl |
| dA3U-AHEF or dA3D-XF (50 pmol/µl) | 0.5 µl |
| dA3U-NXR or dA3D-EHR (50 pmol/µl) | 0.5 µl |
| Mer-16208 chromosomal DNA (100 ng/µl) | 1 µl |
| KOD-plus-polymerase (1 u/µl, Toyobo Co., Ltd.) | 1 µl |

(Reaction Temperature Conditions)
95° C., 6 minutes
(98° C., 20 seconds; 60° C., 30 seconds; 68° C., 3 minutes) 30 cycles
68° C., 4 minutes As a result of this reaction, a 2.1-kb DNA fragment (DNA fragment A3U1) comprising nucleotides 47816-49897 of SEQ ID NO: 1 was amplified by a reaction using dA3U-AHEF and dA3U-NXR, and a 2.0-kb DNA fragment (DNA fragment A3D1) comprising nucleotides 55991-58022 of SEQ ID NO: 1 was amplified by a reaction using dA3D-XF and dA3D-EHR. The DNA fragments A3U1 and A3D1 were purified using Wizard SV Gel and PCR Clean-Up System (Promega).

Total four DNA fragments, namely, the DNA fragment A3U1 digested with restriction enzymes NdeI and HindIII, the DNA fragment A3D1 digested with restriction enzymes XbaI and the DNA fragment TR1 digested with restriction enzymes XbaI and NdeI, which was obtained in Example 4(2), and the shuttle vector pMKOSCPR digested with a restriction enzyme HindIII, which was obtained in Example 4(1), were ligated to one another, using DNA Ligation Kit vet 2.1 (Takara Bio Inc.). Thus, there was constructed an approximately 15.1-kb plasmid pMKOSCPR-A3U-tsr-A3D, in which an approximately 5.3-kb DNA fragment in which the thiostrepton resistance gene tsr had been inserted between the DNA fragments A3U1 and A3D1 was inserted into pMKOSCPR.

(2) Preparation of hbdAIII-Deficient Strain Using pMKOSCPR-A3U-tsr-A3D

Conjugal *Escherichia coli* S17-1 (ATCC47055) was transformed with the obtained pMKOSCPR-A3U-tsr-A3D by an electroporation method, so as to obtain an S17-1/pMKOSCPR-A3U-Ar-A3D strain. The obtained S17-1/pMKOSCPR-A3U-tsr-A3D strain was inoculated into 12 ml of LB medium (1% Bactotrypton, 0.5% yeast extract and 0.5% NaCl) containing 25 µg/ml kanamycin, followed by a shaking culture at 30° C. for 3 hours. Thereafter, the cells were collected, were then washed with 10 ml of LB medium twice, and were then suspended in 2 ml of LB medium. The obtained suspension was defined as a donor cell suspension.

At the same time of the preparation of the donor cell suspension, Mer-16208 was applied to an ISP4 medium (Becton, Dickinson and Company), and it was then cultured at 30° C. for 1 week. Thereafter, the spores were collected, and were then suspended in 1 ml of saline. The obtained suspension was defined as a receptor cell suspension.

500 µl of the obtained S17-1/pMKOSCPR-A3U-tsr-A3D strain donor cell suspension was mixed with 10 µl of Mer-16208 receptor cell suspension, and the obtained mixture was then applied to an ISP4 medium (Becton, Dickinson and Company). The mixture was cultured at 30° C. for 18 hours, and 2.5 ml of SNA (0.8% nutritive medium: Becton, Dickinson and Company, 0.4% agar) containing 2 mg/ml ribostamycin was laminated on the culture. The resultant was cultured at 30° C. for 7 days, so as to obtain a pMKOSCPR-A3U-tsr-A3D transformed strain resistant to ribostamycin.

The obtained pMKOSCPR-A3U-tsr-A3D transformed strain was inoculated into 25 ml of TSB medium that did not contain ribostamycin, and the obtained mixture was then subjected to a shaking culture at 30° C. for 2 weeks. The culture solution of the pMKOSCPR-A3U-tsr-A3D transformed strain was collected, and it was then washed with 10 ml of sterilized water twice and suspended in 10 ml of sterilized water. The appropriately diluted suspension was applied to a YMS agar medium (0.4% yeast extract, 1% malt extract, 0.4% soluble starch, 2% agar and 10 mM calcium chloride) containing 25 µg/ml thiostrepton, and it was then cultured at 30° C. for 4 days. A single colony growing on the YMS medium containing thiostrepton was transferred to a YMS agar medium containing 25 µg/ml thiostrepton and a YMS agar medium containing 200 µg/ml ribostamycin, followed by a culture at 30° C. for 2 days.

After completion of the culture, a strain which was resistant to thiostrepton and was sensitive for ribostamycin was selected. The obtained strain was an hbdA/H-deficient strain, in which 6093 bp (nucleotides 49898-55990 of SEQ ID NO: 1) was deleted from the hbdAIII gene in the genome and a thiostrepton resistance gene was inserted into the deleted site, and this strain was defined as an Mer-16208 hbdAIII::tsr strain.

Example 8

Production of Herboxidiene Transcription Factor Gene (hbdR)-Deficient Strain

Based on the approximately 65-kb nucleotide sequence containing the DNA involved in the biosynthesis of herboxidiene determined in Example 3 (see SEQ ID NO: 1), it became clear that herboxidiene is biosynthesized in the biosynthetic pathway shown in FIG. 1. Since a protein HbdR encoded by hbdR thereof had the highest identity to the amino acid sequence of the transcription factor SACE_4536 of *Saccharopolyspora erythraea* (57% identity), the hbdR was considered to be a gene encoding the transcription factor of the herboxidiene biosynthetic gene. Thus, in order to confirm that a strain whose herboxidiene productivity is changed can be produced by disrupting the hbdR, a hbdR-deficient strain was constructed by the following method.

(1) Preparation of Plasmid pMKOSCPR-RU-tsr-RD Used for Disrupting hbdR

Based on the nucleotide sequence shown in SEQ ID NO: 1, four types of primers, dRU-AHEF, dRU-NXR, dRD-XF and dRD-EHR, consisting of the following sequences, were synthesized (see SEQ ID NOS: 41, 42, 43 and 44 in the sequence listing).

dRU-AHEF: 5'-CCCATTAATAAGCTTGAATTCGGTGGTGACGGACTCGAT-3' dRU-NXR: 5'-CCCTCTAGACATATGTGGCCTCCTCGGTAGACA-3' dRD-XF: 5'-CCCTCTAGAGGACCCGAGCTGGGGCTA-3' dRD-EHR: 5'-CCCAAGCTTGAATTCGTTGATGACGCAGTGGAC-3'

Using these primers, PCR was carried out under the following conditions.

(Composition of PCR Reaction Mixture)

| | |
|---|---|
| Sterilized purified water | 31.5 µl |
| 10x KOD buffer | 5 µl |
| dNTP mixed solution | 5 µl |
| (dATP, dGTP, dTTP and dCTP; 2.5 mM each) | |
| MgSO₄ solution | 3 µl |
| Dimethyl sulfoxide | 2.5 µl |
| dRU-AHEF or dRD-XF (50 pmol/µl) | 0.5 µl |
| dRU-NXR or dRD-EHR (50 pmol/µl) | 0.5 µl |
| Mer-16208 chromosomal DNA (100 ng/µl) | 1 µl |
| KOD-plus-polymerase (1 u/µl, Toyobo Co., Ltd.) | 1 µl |

(Reaction Temperature Conditions)
95° C., 6 minutes
(98° C., 20 seconds; 60° C., 30 seconds; 68° C., 3 minutes) 30 cycles
68° C., 4 minutes As a result of this reaction, a 2.0-kb DNA fragment (DNA fragment RU1) comprising nucleotides 4658-6677 of SEQ ID NO: 1 was amplified by a reaction using dRU-AHEF and dRU-NXR, and a 2.0-kb DNA fragment (DNA fragment RD1) comprising nucleotides 7716-9740 of SEQ ID NO: 1 was amplified by a reaction using dRD-XF and dRD-EHR. The DNA fragments RU1 and RD1 were purified using Wizard SV Gel and PCR Clean-Up System (Promega).

Total four DNA fragments, namely, the DNA fragment RU1 digested with restriction enzymes NdeI and HindIII, the DNA fragment RD1 digested with restriction enzymes XbaI and HindIII, the DNA fragment TR1 digested with restriction enzymes XbaI and NdeI, which was obtained in Example 5(2), and the shuttle vector pMKOSCPR digested with a restriction enzyme HindIII, which was obtained in Example 5(1), were ligated to one another, using DNA Ligation Kit vet 2.1 (Takara Bio Inc.). Thus, there was constructed an approximately 15.0-kb plasmid pMKOSCPR-RU-tsr-RD, in which an approximately 5.3-kb DNA fragment in which the thiostrepton resistance gene tsr had been inserted between the DNA fragments RU1 and RD1 was inserted into pMKOSCPR.

(2) Preparation of hbdR-Deficient Strain Using pMKOSCPR-RU-tsr-RD

Conjugal *Escherichia coli* S17-1 (ATCC47055) was transformed with the obtained pMKOSCPR-RU-tsr-RD by an electroporation method, so as to obtain an S17-1/pMKOSCPR-RU-tsr-RD strain. The obtained 517-1/pMKOSCPR-RU-tsr-RD strain was inoculated into 12 ml of LB medium (1% Bactotrypton, 0.5% yeast extract and 0.5% NaCl) containing 25 µg/ml kanamycin, followed by a shaking culture at 30° C. for 3 hours. Thereafter, the cells were collected, were then washed with 10 ml of LB medium twice, and were then suspended in 2 ml of LB medium. The obtained suspension was defined as a donor cell suspension.

At the same time of the preparation of the donor cell suspension, Mer-16208 was applied to an ISP4 medium (Becton, Dickinson and Company), and it was then cultured at 30° C. for 1 week. Thereafter, the spores were collected, and were then suspended in 1 ml of saline. The obtained suspension was defined as a receptor cell suspension.

500 µl of the obtained S17-1/pMKOSCPR-RU-tsr-RD strain donor cell suspension was mixed with 10 µl of Mer-16208 receptor cell suspension, and the obtained mixture was then applied to an ISP4 medium (Becton, Dickinson and Company). The mixture was cultured at 30° C. for 18 hours, and 25 ml of SNA (0.8% nutritive medium: Becton, Dickinson and Company, 0.4% agar) containing 2 mg/ml ribostamycin was laminated on the culture. The resultant was cultured at 30° C. for 7 days, so as to obtain a pMKOSCPR-RU-tsr-RD transformed strain resistant to ribostamycin.

The obtained pMKOSCPR-RU-tsr-RD transformed strain was inoculated into 25 ml of TSB medium that did not contain ribostamycin, and the obtained mixture was then subjected to a shaking culture at 30° C. for 2 weeks. The culture solution of the pMKOSCPR-RU-tsr-RD transformed strain was collected, and it was then washed with 10 ml of sterilized water twice and suspended in 10 ml of sterilized water. The appropriately diluted suspension was applied to a YMS agar medium (0.4% yeast extract, 1% malt extract, 0.4% soluble starch, 2% agar and 10 mM calcium chloride) containing 25 µg/ml thiostrepton, and it was then cultured at 30° C. for 4 days. A single colony growing on the YMS medium containing thiostrepton was transferred to a YMS agar medium containing 25 µg/ml thiostrepton and a YMS agar medium containing 200 µg/ml ribostamycin, followed by a culture at 30° C. for 2 days.

After completion of the culture, a strain which was resistant to thiostrepton and was sensitive for ribostamycin was selected. The obtained strain was an hbdR-deficient strain, in which 1038 bp (nucleotides 6678-7715 of SEQ ID NO: 1) was deleted from the hbdR gene in the genome and a thiostrepton resistance gene was inserted into the deleted site, and this strain was defined as an Mer-16208 hbdR::tsr strain.

Example 9

Test Regarding Productivity of Herboxidiene and Analogue Thereof by Herboxidiene Biosynthetic Gene hbdE-Deficient Strain 250 µl of the frozen stock of the Mer-16208 hbdE::tsr strain obtained in Example 4 was inoculated into 25 ml of a seed culture medium (2% potato starch, 2% glucose, 2% soybean powder (Honen SoyPro (registered trademark); manufactured by J-OIL MILLS Inc.), 0.5% yeast extract, 0.25% NaCl, 0.32% CaCO₃, 0.0005% CuSO₄, 0.0005% ZnSO₄.7H₂O, 0.0005% MnCl₂.4H₂O, pH7.4), and it was then cultured at 28° C. for 3 days.

4 ml of the obtained seed culture solution was inoculated into 400 ml of a main culture medium (2% potato starch, 2% glucose, 2% soybean powder, 0.5% yeast extract, 0.25% NaCl, 0.32% CaCO₃, 0.0005% CuSO₄, 0.0005% ZnSO₄.7H₂O, 0.0005% MnCl₂.4H₂O, pH7.4), and it was then cultured at 28° C. for 7 days.

After completion of the culture, to 600 µl of the obtained culture solution, acetonitrile was added in an equal amount, for extraction. A supernatant obtained by centrifuging the extract was subjected to high performance liquid chromatography (HPLC) under the conditions as shown below, so as to measure the amounts of herboxidiene and analogues thereof. The measurement results are shown in Table 1.

Example 10

Test Regarding Productivity of Herboxidiene and Analogue Thereof by Herboxidiene Biosynthetic Gene hbdF-Deficient Strain 250 µl of the frozen stock of the Mer-16208 hbdF::tsr strain obtained in Example 5 was inoculated into 25 ml of a seed culture medium (2% potato starch, 2% glucose, 2% soybean powder, 0.5% yeast extract, 0.25% NaCl, 0.32% $CaCO_3$, 0.0005% $CuSO_4$, 0.0005% $ZnSO_4.7H_2O$, 0.0005% $MnCl_2.4H_2O$, pH7.4), and it was then cultured at 28° C. for 3 days.

1 ml of the obtained seed culture solution was inoculated into 100 ml of a main culture medium (2% potato starch, 2% glucose, 2% soybean powder, 0.5% yeast extract, 0.25% NaCl, 0.32% $CaCO_3$, 0.0005% $CuSO_4$, 0.0005% $ZnSO_4.7H_2O$, 0.0005% $MnCl_2.4H_2O$, pH7.4), and it was then cultured at 28° C. for 3 days.

After completion of the culture, to 600 µl of the obtained culture solution, acetonitrile was added in an equal amount, for extraction. A supernatant obtained by centrifuging the extract was subjected to HPLC under the conditions as shown below, so as to measure the amounts of herboxidiene and analogues thereof. The measurement results are shown in Table 1.

Example 11

Test Regarding Productivity of Herboxidiene and Analogue Thereof by Herboxidiene Biosynthetic Gene hbdD-Deficient Strain 250 µl of the frozen stock of the Mer-16208 hbdD::tsr strain obtained in Example 6 was inoculated into 25 ml of a seed culture medium (2% potato starch, 2% glucose, 2% soybean powder, 0.5% yeast extract, 0.25% NaCl, 0.32% $CaCO_3$, 0.0005% $CuSO_4$, 0.0005% $ThSO_4.7H_2O$, 0.0005% $MnCl_2.4H_2O$, pH7.4), and it was then cultured at 28° C. for 3 days.

2 ml of the obtained seed culture solution was inoculated into 200 ml of a main culture medium (2% potato starch, 2% glucose, 2% soybean powder, 0.5% yeast extract, 0.25% NaCl, 0.32% $CaCO_3$, 0.0005% $CuSO_4$, 0.0005% $ZnSO_4.7H_2O$, 0.0005% $MnCl_2.4H_2O$, 2% β-cyclodextrin, pH7.4), and it was then cultured at 28° C. for 3 days.

After completion of the culture, to 600 µl of the obtained culture solution, acetonitrile was added in an equal amount, for extraction. A supernatant obtained by centrifuging the extract was subjected to HPLC under the conditions as shown below, so as to measure the amounts of herboxidiene and analogues thereof. The measurement results are shown in Table 1.

Example 12

Test Regarding Productivity of Herboxidiene and Analogue Thereof by Herboxidiene Biosynthetic Gene hbdAIII-Deficient Strain 250 µl of the frozen stock of the Mer-16208 hbdAIII::tsr strain obtained in Example 7 was inoculated into 25 ml of a seed culture medium (2% potato starch, 2% glucose, 2% soybean powder, 0.5% yeast extract, 0.25% NaCl, 0.32% $CaCO_3$, 0.0005% $CuSO_4$, 0.0005% $ZnSa_4.7H_2O$, 0.0005% $MnCl_2.4H_2O$, pH7.4), and it was then cultured at 28° C. for 3 days.

600 µl of the obtained seed culture solution was inoculated into 60 ml of a main culture medium (2% potato starch, 2% glucose, 2% soybean powder, 0.5% yeast extract, 0.25% NaCl, 0.32% $CaCO_3$, 0.0005% $CuSO_4$, 0.0005% $ZnSO_4.7H_2O$, 0.0005% $MnCl_2.4H_2O$, pH7.4), and it was then cultured at 28° C. for 3 days.

After completion of the culture, to 600 µl of the obtained culture solution, acetonitrile was added in an equal amount, for extraction. A supernatant obtained by centrifuging the extract was subjected to HPLC under the conditions as shown below, so as to measure the amounts of herboxidiene and analogues thereof. The measurement results are shown in Table 1.

Example 13

Test Regarding Productivity of Herboxidiene and Analogue Thereof by Herboxidiene Biosynthetic Gene hbdR-Deficient Strain 250 µl of the frozen stock of the Mer-16208 hbdR tsr strain obtained in Example 8 was inoculated into 25 ml of a seed culture medium (2% potato starch, 2% glucose, 2% soybean powder, 0.5% yeast extract, 0.25% NaCl, 0.32% $CaCO_3$, 0.0005% $CuSO_4$, 0.0005% $ZnSO_4.7H_2O$, 0.0005% $MnCl_2.4H_2O$, pH7.4), and it was then cultured at 28° C. for 3 days.

600 µl of the obtained seed culture solution was inoculated into 60 ml of a main culture medium (2% potato starch, 2% glucose, 2% soybean powder, 0.5% yeast extract 0.25% NaCl, 0.32% $CaCO_3$, 0.0005% $CuSO_4$, 0.0005% $ZnSO_4.7H_2O$, 0.0005% $MnCl_2.4H_2O$, pH7.4), and it was then cultured at 28° C. for 3 days.

After completion of the culture, to 600 µl of the obtained culture solution, acetonitrile was added in an equal amount, for extraction. A supernatant obtained by centrifuging the extract was subjected to HPLC under the conditions as shown below, so as to measure the amounts of herboxidiene and analogues thereof. The measurement results are shown in Table 1.

Example 14

Test Regarding Productivity of Herboxidiene and Analogue Thereof by Herboxidiene-Producing Strain, Mer-16208

250 µl of the frozen stock of Mer-16208 was inoculated into 25 ml of a seed culture medium (2% potato starch, 2% glucose, 2% soybean powder, 0.5% yeast extract, 0.25% NaCl, 0.32% $CaCO_3$, 0.0005% $CuSO_4$, 0.0005% $ZnSO_4.7H_2O$, 0.0005% $MnCl_2.4H_2O$, pH7.4), and it was then cultured at 28° C. for 3 days.

600 µl of the obtained seed culture solution was inoculated into 60 ml of a main culture medium (2% potato starch, 2% glucose, 2% soybean powder, 0.5% yeast extract, 0.25% NaCl, 0.32% $CaCO_3$, 0.0005% $CuSO_4$, 0.0005% $ZnSO_4.7H_2O$, 0.0005% $MnCl_2.4H_2O$, pH7.4), and it was then cultured at 28° C. for 3 days.

After completion of the culture, to 600 µl of each of the obtained culture solutions, acetonitrile was added in an equal amount, for extraction. A supernatant obtained by centrifuging the extract was subjected to HPLC under the conditions as shown below, so as to measure the amounts of herboxidiene and analogues thereof. The measurement results are shown in Table 1.

HPLC conditions applied in Examples 9-14
Analyzer: Agilent 1100 series
Column: Unison UK-C18 (4.6 mm×50 mm, 3 μm)
Mobile phase A: water/acetonitrile/formic acid=1000/10/1
Mobile phase B: acetonitrile/water/formic acid=1000/10/1
Gradient: 30%-70% mobile phase B (0 to 4 minutes)
　　70%-100% mobile phase B (4 to 4.5 minutes)
　　100% mobile phase B (4.5 to 6 minutes)
　　100%-30% mobile phase B (6 to 6.01 minutes)
　　30% mobile phase B (6.01 to 7 minutes)
Flow rate: 2.0 mL/min
Detection: UV 254 nm
Injection volume: 10 μl
Column temperature: 30° C.
Analysis time: 7 minutes
Retention time: herboxidiene, 3.33 minutes; HX354, 4.94 minutes; HX355, 3.83 minutes; HX356, 2.78 minutes; MW392, 4.91 minutes

TABLE 1

|  | HX356 (mg/L) | Herboxidiene (mg/L) | HX355 (mg/L) | MW392 (mg/L) | HX354 (mg/L) |
|---|---|---|---|---|---|
| Mer-16208 hbdE::tsr strain | 0.00 | 0.00 | 9.40 | 0.00 | 23.26 |
| Mer-16208 hbdF::tsr strain | 90.63 | 0.00 | 5.87 | 0.00 | 0.00 |
| Mer-16208 hbdD::tsr strain | 0.00 | 0.00 | 0.00 | 35.82 | 0.00 |
| Mer-16208 hbdAIII::tsr strain | 0.00 | 0.00 | 0.00 | 0.00 | 0.00 |
| Mer-16208 hbdR::tsr strain | 0.00 | 0.60 | 0.65 | 0.00 | 0.00 |
| Mer-16208 | 0.00 | 78.64 | 0.65 | 0.00 | 0.00 |

It was confirmed that the Mer-16208 hbdAIII::tsr strain as an hbdAIII-deficient strain did not produce herboxidiene and analogues thereof. In addition, it was confirmed that the amount of herboxidiene produced by the Mer-16208 hbdR::tsr strain as an hbdR-deficient strain was significantly smaller than that produced by Mer-16208.

Example 15

Isolation and Purification of HX354 and HX355, and Confirmation of Structures Thereof 80 g of salt was added to a supernatant obtained by centrifuging 400 ml of the cell suspension obtained in Example 9, and the pH of the suspension was then adjusted to pH 2-3 by addition of 2 mol/L hydrochloric acid. Thereafter, 400 ml of ethyl acetate was added to the suspension, and the mixture was then intensively stirred and was extracted. Centrifugation was carried out. Anhydrous sodium sulfate was added to the obtained ethyl acetate layer to remove water from the ethyl acetate layer. Filtration was carried out, and the filtrate was washed with an adequate amount of ethyl acetate. Thereafter, the resultant was subjected to an evaporator, and ethyl acetate was distilled away. The obtained dry solid was dissolved in 1.5 ml of methanol, and the peaks of HX354 and HX355 were then fractionated by preparative HPLC. The solvent was distilled away from these fraction samples, so as to obtain 5 mg of HX354 and 2 mg of HX355.

(Preparative HPLC Conditions)
Preparatory device: Agilent 1100 series, preparatory autosampler
Column: Zorbax RX-C18 (9.4 mm×250 mm, 5 μm)
Mobile phase A: water
Mobile phase B: acetonitrile
Gradient: 20% mobile phase B (0 to 1 minute)
　　20%-100% mobile phase B (1 to 8 minutes)
　　100% mobile phase B (8 to 14 minutes)
　　100%-20% mobile phase B (14 to 15 minutes)
　　20% mobile phase B (15 to 18 minutes)
Flow rate: 3.0 ml/min
Detection: UV 254 nm
Injection volume: 50 μl
Column temperature: 40° C.
Analysis time: 18 minutes
Retention time: HX354, 11.6 minutes; HX355, 10.3 minutes

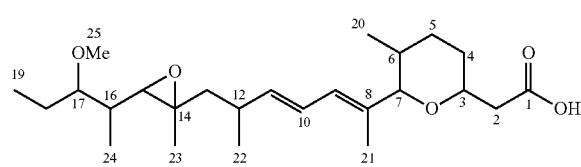

(1)

Physical Values of HX354 (1)
$^1$H-NMR (500 MHz, CD$_3$OD) δ (ppm): 6.32 (dd, 1H, J=15, 11 Hz, H10), 5.94 (d, 1H, J=11 Hz, H9), 5.49 (dd, 1H, J=15, 9 Hz, H11), 3.79 (m, 1H, H3), 3.39 (s, 3H, H25), 3.37 (d, 1H, J=10 Hz, H7), 3.13 (m, 1H, H17), 2.64 (d, 1H, J=10 Hz, H15), 2.48 (dd, 1H, J=16, 8 Hz, H2a), 2.47 (overlap, 1H, H12), 2.41 (dd, 1H, J=16, 6 Hz, H2b), 1.91 (dd, 1H, J=13, 4 Hz, H13a), 1.88 (m, 1H, H5a), 1.74 (m, 1H, H4a), 1.71 (s, 3H, H21), 1.62 (m, 1H, H18a), 1.56 (m, 1H, H18b), 1.56 (m, 1H, H6), 1.44 (m, 1H, H16), 1.36 (m, 1H, H4b), 1.32 (m, 1H, H5b), 1.29 (s, 3H, H23), 1.19 (dd, 1H, J=13, 11 Hz, H13b), 1.07 (d, 3H, J=7, H22), 0.90 (t, 3H, J=8, H19), 0.84 (d, 3H, J=7, H24), 0.71 (d, 3H, J=7, H20)
$^{13}$C-NMR (125 MHz, CD$_3$OD) δ (ppm): 175.19 (C1), 140.76 (C11), 136.17 (C8), 129.66 (C9), 126.54 (C10), 92.19 (C7), 85.72 (C17), 75.48 (C3), 67.78 (C15), 61.85 (C14), 58.45 (C25), 48.13 (C13), 42.28 (C2), 37.52 (C16), 36.56 (C12), 33.50 (C5), 33.40 (C6), 32.81 (C4), 24.90 (C18), 22.71 (C22), 18.09 (C20), 16.84 (C23), 12.07 (C21), 11.80 (C24), 10.13 (C19)
ESI-MS: m/z=421 [M-H]$^-$

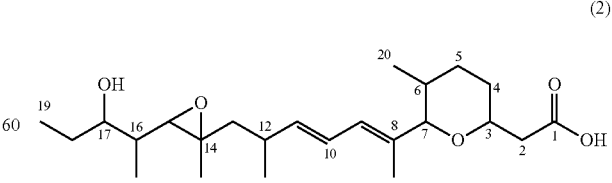

(2)

Physical Values of HX355 (2)
$^1$H-NMR (500 MHz, CD$_3$OD) δ (ppm): 6.30 (dd, 1H, J=15, 11 Hz, H10), 5.91 (d, 1H, J=11 Hz, H9), 5.48 (dd, 1H, J=15, 9 Hz, H11), 3.76 (m, 1H, H3), 3.44 (m, 1H, H17), 334 (d, 1H, J=10 Hz, H7), 2.63 (d, 1H, J=9 Hz, H15), 2.46 (dd, 1H, J=16, 7 Hz, H2a), 2.46 (overlap, 1H, H12), 2.38 (dd, 1H, J=16, 6 Hz, H2b), 1.90 (dd, 1H, J=13, 5 Hz, H13a), 1.86 (m, 1H, H5a), 1.71 (m, 1H, H4a), 1.69 (s, 3H, H21), 1.53 (m, 2H, H6 and H18a), 1.44 (m, 1H, H18b), 133 (m, 2H, H4b and H16), 1.27 (s, 3H, H23), 1.27 (m, 1H, H5b), 1.17 (dd, 1H, J=13, 11 Hz, H13b), 1.04 (d, 3H, J=7, H22), 0.93 (t, 3H, J=8, H19), 0.84 (d, 3H, J=7, H24), 0.69 (d, 3H, J=7, H20)

$^{13}$C-NMR (125 MHz, CD$_3$OD) δ (ppm): 175.19 (C1), 140.73 (C11), 136.16 (C8), 129.67 (C9), 126.51 (C10), 92.20 (C7), 75.80 (C17), 75.52 (C3), 68.05 (C15), 61.74 (C14), 48.12 (C13), 42.33 (C2), 39.79 (C16), 36.49 (C12), 33.48 (C5), 33.42 (C6), 32.82 (C4), 28.83 (C18), 22.65 (C22), 18.11 (C20), 16.83 (C23), 12.11 (C21), 11.57 (C24), 10.80 (C19)

ESI-MS: m/z=407 [M-H]$^-$

As a result, it was confirmed that the Mer-16208 hbdE::tsr strain as an hbdE-deficient strain did not produce herboxidiene, but it produced HX354 as a 18-deoxy product of herboxidiene and HX355 as a 18-deoxy, 17-O-demethyl product of herboxidiene.

Example 16

Isolation and Purification of HX356 and Confirmation of Structure Thereof 20 g of salt was added to a supernatant obtained by centrifuging 100 ml of the cell suspension obtained in Example 10, and the pH of the suspension was then adjusted to pH 2-3 by addition of 2 mol/L hydrochloric acid. Thereafter, 100 ml of ethyl acetate was added to the suspension, and the mixture was then intensively stirred and was extracted. Centrifugation was carried out Anhydrous sodium sulfate was added to the obtained ethyl acetate layer to remove water from the ethyl acetate layer. Filtration was carried out, and the filtrate was washed with an adequate amount of ethyl acetate. Thereafter, the resultant was subjected to an evaporator, and the ethyl acetate was distilled away. The obtained dry solid was dissolved in 1.5 ml of methanol, and the peak of HX356 was then fractionated by preparative HPLC. The solvent was distilled away from this fraction sample, so as to obtain 4.5 mg of HX356.

(Preparative HPLC Conditions)
Preparatory device: Agilent 1100 series, preparatory autosampler
Column: Zorbax RX-C18 (9.4 mm×250 mm, 5 µm)
Mobile phase A: water
Mobile phase B: acetonitrile
Gradient: 20% mobile phase B (0 to 1 minute)
 20%-100% mobile phase B (1 to 8 minutes)
 100% mobile phase B (8 to 14 minutes)
 100%-20% mobile phase B (14 to 15 minutes)
 20% mobile phase B (15 to 18 minutes)
Flow rate: 3.0 ml/min
Detection: UV 254 nm
Injection volume: 50 µl
Column temperature: 40° C.

Analysis time: 18 minutes
Retention time: HX356, 9.0 minutes

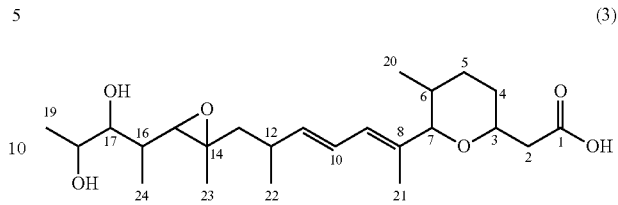

(3)

Physical Values of HX356 (3)

$^1$H-NMR (500 MHz, CD$_3$OD) δ (ppm): 6.30 (dd, 1H, J=15, 11 Hz, H10), 5.91 (d, 1H, J=11 Hz, H9), 5.48 (dd, 1H, J=15, 9 Hz, H11), 3.77 (m, 2H, H18 and H3), 3.34 (d, 1H, J=10 Hz, 1H, H7), 327 (t, 1H, J=6 Hz, H17), 2.66 (d, 1H, J=5 Hz, H15), 2.46 (overlap, 1H, H12), 2.46 (dd, 1H, J=15, 8 Hz, H2a), 2.38 (dd, 1H, J=15, 6 Hz, H2b), 1.92 (dd, 1H, J=14, 5 Hz, H13a), 1.85 (m, 1H, H5a), 1.71 (m, 1H, H4a), 1.64 (s, 3H, H21), 1.54 (m, 1H, H6), 1.46 (m, 1H, H16), 1.33 (m, 1H, H4b), 1.30 (s, 3H, H23), 1.25 (m, 1H, H5b), 1.17 (dd, 1H, J=14, 11 Hz, H13b), 1.12 (d, 3H, J=7, H19), 1.04 (d, 3H, J=7, H22), 0.87 (d, 3H, J=7, H24), 0.69 (d, 3H, J=7, H20)

$^{13}$C-NMR (125 MHz, CD$_3$OD) δ (ppm): 175.36 (C1), 140.70 (C11), 136.19 (C8), 129.66 (C9), 126.54 (C10), 92.19 (C7), 78.24 (C17), 75.55 (C3), 69.59 (C18), 67.83 (C15), 62.23 (C14), 48.09 (C13), 42.42 (C2), 37.12 (C16), 36.50 (C12), 33.48 (C5), 33.43 (C6), 32.82 (C4), 22.66 (C22), 19.63 (C19), 18.11 (C20), 16.80 (C23), 12.12 (C21), 11.90 (C24)

ESI-MS: m/z=423 [M-H]$^-$

As a result, it was confirmed that the Mer-16208 hbdF::tsr strain as an hbdF-deficient strain did not produce herboxidiene, but it produced HX356 as a 17-O-demethyl product of herboxidiene and HX355 as a 18-deoxy, 17-O-demethyl product of herboxidiene.

Example 17

Isolation and Purification of MW392 and Confirmation of Structure Thereof 40 g of salt was added to a supernatant obtained by centrifuging 200 ml of the cell suspension obtained in Example 11, and the pH of the suspension was then adjusted to pH 2-3 by addition of 2 mol/L hydrochloric acid. Thereafter, 200 ml of ethyl acetate was added to the suspension, and the mixture was then intensively stirred and was extracted. Centrifugation was carried out. Anhydrous sodium sulfate was added to the obtained ethyl acetate layer to remove water from the ethyl acetate layer. Filtration was carried out, and the filtrate was washed with an adequate amount of ethyl acetate. Thereafter, the resultant was subjected to an evaporator, and the ethyl acetate was distilled away. The obtained dry solid was dissolved in 1.5 ml of methanol, and the peak of MW392 was then fractionated by preparative HPLC. The solvent was distilled away from this fraction sample, so as to obtain 4.5 mg of MW392.

(Preparative HPLC Conditions)
Preparatory device: Agilent 1100 series, preparatory autosampler
Column: Zorbax RX-C18 (9.4 mm×250 mm, 5 µm)
Mobile phase A: water
Mobile phase B: acetonitrile Gradient: 20% mobile phase B (0 to 1 minute)
  20%-100% mobile phase B (1 to 8 minutes)
  100% mobile phase B (8 to 14 minutes)
  100%-20% mobile phase B (14 to 15 minutes)
  20% mobile phase B (15 to 18 minutes)
Flow rate: 3.0 ml/min
Detection: UV 254 nm
Injection volume: 50 μl
Column temperature: 40° C.
Analysis time: 18 minutes
Retention time: MW392, 11.3 minutes

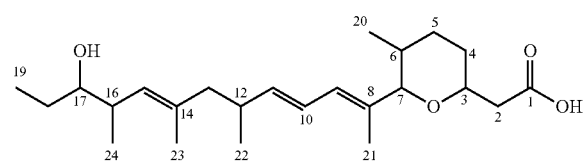

(4)

Physical Values of MW392 (4)

$^1$H-NMR (500 MHz, CD$_3$OD) δ (ppm): 6.20 (dd, 1H, J=15, 11 Hz, H10), 5.89 (d, 1H, J=11 Hz, H9), 5.33 (dd, 1H, J=15, 8 Hz, H11), 4.93 (d, 1H, J=11 Hz, H15), 3.76 (m, 1H, H3), 3.31 (overlap, 1H, H7), 3.12 (td, 1H, J=9, 3 Hz, H17), 2.46 (dd, 1H, J=16, 8 Hz, H2a), 2.38 (overlap, 1H, H12), 2.38 (dd, 1H, J=16, 6 Hz, H2b), 2.30 (m, 1H, H16), 1.97 (dd, 2H, J=7, 4 Hz, H13ab), 1.85 (m, 1H, H5a), 1.68 (m, 1H, H4a), 1.68 (s, 3H, H21), 1.60 (s, 3H, H23), 1.52 (m, 2H, H6 and H18a), 126 (m, 3H, H4b, H5b and H18b), 0.98 (d, 31-1, J=7, H22), 0.92 (d, 3H, J=7, H24), 0.91 (t, 3H, J=7, H19), 0.68 (d, 31-1, J=7, H20)

$^{13}$C-NMR (125 MHz, CD$_3$OD) δ (ppm): 175.21 (C1), 141.67 (C11), 135.26 (C8), 133.94 (C14), 131.44 (C15), 129.82 (C9), 12531 (C10), 92.18 (C7), 78.57 (C17), 7551 (C3), 49.88 (C13), 42.29 (C2), 40.02 (C16), 36.72 (C12), 33.50 (C5), 33.46 (C6), 32.84 (C4), 28.94 (C18), 20.84 (C22), 18.04 (C20), 17.70 (C19), 16.71 (C23), 12.20 (C21), 10.65 (C24)

ESI-MS: m/z=391 [M-H]$^-$

As a result, it was confirmed that the Mer-16208 hbdD::tsr strain as an hbdD-deficient strain did not produce herboxidiene, but it produced MW392 as a 14,15-olefin, 17-O-demethyl and 18-deoxy product of herboxidiene.

Test Example

Proliferation Inhibitory Action on WiDr Human Colon Cancer Cells

WiDr human colon cancer cells, which had been cultured in an RPMI1640 medium (manufactured by SIGMA) containing 10% fetal bovine serum, penicillin (100 units/mL) and streptomycin (100 μg/mL), were dispersed on a 96-well plate in an amount of 2×10$^3$ cells/90 μl/well. The cells were cultured in a CO$_2$ incubator overnight. Thereafter, 10 μl of the aforementioned culture solution containing the compound HX354 or HX355 of 3-fold dilution series used in the aforementioned examples was added to the culture, and the mixture was then cultured. Three days later, 50 μl of CellTiter-Glo Luminescent Cell Viability Assay (Promega) was added to the culture, the mixture was then shaken for 2 minutes, and it was then left at rest for 15 minutes. Thereafter, luciferase luminescence was measured with a luminometer, and the measured luminescence was used as an indicator for the number of living cells The concentrations (IC$_{50}$ values) of HX354 and HX355, where the proliferation of the WiDr human colon cancer cells was inhibited by were obtained. The results are shown in the following table.

TABLE 2

| Compound No. | IC$_{50}$(nM) |
|---|---|
| HX354 | 91 |
| HX355 | 168 |

The invention claimed is:

1. An isolated DNA comprising a nucleotide sequence consisting of:
   contiguous nucleotides 8919 to 28295 of SEQ ID NO:1;
   contiguous nucleotides 28326 to 49892 of SEQ ID NO:1; or
   contiguous nucleotides 49892 to 55981 of SEQ ID NO:1.

2. The isolated DNA of claim 1, wherein the nucleotide sequence consists of contiguous nucleotides 8919 to 28295 of SEQ ID NO:1.

3. The isolated DNA of claim 1, wherein the nucleotide sequence consists of contiguous nucleotides 28326 to 49892 of SEQ ID NO:1.

4. The isolated DNA of claim 1, wherein the nucleotide sequence consists of contiguous nucleotides 49892 to 55981 of SEQ ID NO:1.

5. An isolated DNA comprising a nucleotide sequence encoding a polypeptide comprising the amino acid sequence of SEQ ID NO:2, SEQ ID NO:3, or SEQ ID NO:4.

6. The isolated DNA of claim 5, wherein the nucleotide sequence encodes a polypeptide comprising the amino acid sequence of SEQ ID NO:2.

7. The isolated DNA of claim 5, wherein the nucleotide sequence encodes a polypeptide comprising the amino acid sequence of SEQ ID NO:3.

8. The isolated DNA of claim 5, wherein the nucleotide sequence encodes a polypeptide comprising the amino acid sequence of SEQ ID NO:4.

9. An isolated DNA comprising a nucleotide sequence encoding a polypeptide exhibiting polyketide synthase activity, wherein the nucleotide sequence hybridizes, under conditions of hybridization at 61° C. to 64° C. in the presence of 0.5 M NaCl and 50% formamide and washing at 61° C. to 64° C. using a 0.1 to 2×SSC solution, to a polynucleotide sequence fully complementary to:
   contiguous nucleotides 8919 to 28295 of SEQ ID NO:1;
   contiguous nucleotides 28326 to 49892 of SEQ ID NO:1; or
   contiguous nucleotides 49892 to 55981 of SEQ ID NO:1.

10. The isolated DNA of claim 9, wherein the nucleotide sequence hybridizes, under conditions of hybridization at 61° C. to 64° C. in the presence of 0.5 M NaCl and 50% formamide and washing at 61° C. to 64° C. using a 0.1 to 2×SSC solution, to a polynucleotide sequence fully complementary to contiguous nucleotides 8919 to 28295 of SEQ ID NO:1.

11. The isolated DNA of claim 9, wherein the nucleotide sequence hybridizes, under conditions of hybridization at 61° C. to 64° C. in the presence of 0.5 M NaCl and 50% formamide and washing at 61° C. to 64° C. using a 0.1 to 2×SSC solution, to a polynucleotide sequence fully complementary to contiguous nucleotides 28326 to 49892 of SEQ ID NO:1.

12. The isolated DNA of claim 9, wherein the nucleotide sequence hybridizes, under conditions of hybridization at 61° C. to 64° C. in the presence of 0.5 M NaCl and 50% formamide and washing at 61° C. to 64° C. using a 0.1 to 2×SSC solution, to a polynucleotide sequence fully complementary to contiguous nucleotides 49892 to 55981 of SEQ ID NO:1.

13. An isolated DNA comprising a nucleotide sequence encoding a polypeptide exhibiting polyketide synthase activity, wherein the nucleotide sequence is at least 90% identical to a polynucleotide consisting of:
   contiguous nucleotides 8919 to 28295 of SEQ ID NO:1;
   contiguous nucleotides 28326 to 49892 of SEQ ID NO:1; or
   contiguous nucleotides 49892 to 55981 of SEQ ID NO:1.

14. The isolated DNA of claim 13, wherein the nucleotide sequence is at least 90% identical to a polynucleotide consisting of contiguous nucleotides 8919 to 28295 of SEQ ID NO:1.

15. The isolated DNA of claim 13, wherein the nucleotide sequence is at least 90% identical to a polynucleotide consisting of contiguous nucleotides 28326 to 49892 of SEQ ID NO:1.

16. The isolated DNA of claim 13, wherein the nucleotide sequence is at least 90% identical to a polynucleotide consisting of contiguous nucleotides 49892 to 55981 of SEQ ID NO:1.

17. The isolated DNA of claim 13, wherein the nucleotide sequence is at least 95% identical to a polynucleotide consisting of contiguous nucleotides 8919 to 28295 of SEQ ID NO:1.

18. The isolated DNA of claim 13, wherein the nucleotide sequence is at least 95% identical to a polynucleotide consisting of contiguous nucleotides 28326 to 49892 of SEQ ID NO:1.

19. The isolated DNA of claim 13, wherein the nucleotide sequence is at least 95% identical to a polynucleotide consisting of contiguous nucleotides 49892 to 55981 of SEQ ID NO:1.

20. An autonomously or integratively replicating recombinant plasmid, comprising the DNA of claim 1.

21. A transformant comprising the DNA of claim 1.

22. An autonomously or integratively replicating recombinant plasmid, comprising the DNA of claim 5.

23. A transformant comprising the DNA of claim 5.

24. An autonomously or integratively replicating recombinant plasmid, comprising the DNA of claim 9.

25. A transformant comprising the DNA of claim 9.

26. An autonomously or integratively replicating recombinant plasmid, comprising the DNA of claim 13.

27. A transformant comprising the DNA of claim 13.

* * * * *

SEQUENCE LISTING

```
<160> NUMBER OF SEQ ID NOS: 44

<210> SEQ ID NO 1
<211> LENGTH: 65360
<212> TYPE: DNA
<213> ORGANISM: Streptomyces sp. Mer-16208

<400> SEQUENCE: 1
gcgtggcgga ggaggacggg cagccgtcgc aactgcccag cagccgcagc cgtacggccc      60
cgtccgccgt gacgccgagc agctccacgt caccgccgtg cgagccgaga tacggccgga     120
cgctctccag cgcgttctcg acccgcgtct ccacgctgta cgggtgcagt ccgtgcacca     180
gcagcacgct ggccaccaga tcgtcgtcgg cgagggcggc caggaccttg tcgtccagcc     240
cgccgtgctc gtggacgagg tcgagcagcc gctccaggcc ggccccgtag aagtcggtga     300
ccagccggac cagctcctcg ccgcgctcgc gcgccgccgg gccgcccgcc gcgccggccg     360
```

```
agatcagtgc gtcgatgcgt tccccggtcg cccgccagac ctcggacggc gcgggctcgt    420
gcgtctgccg ctccgccatg tcactcactg cccgcggact gcgtgggcga gtgcagcaat    480
tccagcttct tgccctcacc gagatacatg tggacgccgc aggggagaca ggggtcgaag    540
ctgcgtaccg tacgcatgat gtcgatgccc ttgaagttct cccggtcgtt ctcctcgaag    600
atgggctggc cctgcaccgc gtcctcgtac ggtccgggcg tcccgtagga gtcacgcggg    660
ctcgcgttcc acggggtcgg cgggtacggg tggtagttgg cgatcttgcc gtccctgatc    720
accatgtggt gcgagagcac cccgcgcacg gcctccgtga agccgcagcc gacgccctcc    780
tccggcacct cgaacttctc ccaggtcttg gtgcggccgg cccggatctc cccgagcgcc    840
ttctccgcga agtgcagcgc gcaggccgcc gcgtacgcct ggaagtaggt gcgcgcccgg    900
ttgcgctcga tggtgttgct ccagcgcggg acgtgccact cgaactcgac cgggcccttg    960
gtggcggtct tggggaggtt gatccgcaca ctcttgccgg tggccttgat gtagccgatg   1020
tcgaccaggc ccgccagcgc ggtggtccac agccgggcga gcgtccgcc gccggtgtcg   1080 agcgcgaggt agtccgtgcc gtcgaaccag cgcggcgaca tcacccaact gtacttgtca   1140
cccaggtcgc gcttctgggg ctgcgggttg gtgtgctggt tccacggatg ccgccggtcg   1200
accgggttgc cgagcgggtc gtgggtcacg aacatctcct gctcctccca gtcgttgtag   1260
tacgacgagc cgagcaggat gcggataccg aggttgatct tcaccaggtc ggtggtgacg   1320
agcttgccgt ccacgacgac accgggggtc acatacatct tccggcccca ggcggtcatg   1380
tcccggtact cgaagttgca gtgctccggg tcctggaagg agcccagca gcccagcagg   1440 atacggcggt tgcccacctg ttcgtagccg ggcagcgcct cgtagaagaa gtcgaagagg   1500
tcgtcgtgga gcgtacgac cttcttcatg aactccacgt agcgctggag acgggtgatg   1560
tagtccgtca tgagctggat ggtcgccacc gtgcccacgc caccggggta gagcgtggag   1620
gggtgcacgt ggcggccctc catcagacag aacatctcgc gggtcatgcg gctgacctgg   1680
agggcctcgc ggtagaactc gccggtgaac gggttcagcg cgcgcatgat gtcgccgatg   1740
gtccggtgcc cgtgggcgtc ggcgtgcggc gaggggggtgc gattggcctg ttcgaggacg   1800
ccgggattgg tctcggcgac catcttctcg cagtagtcga ccccgaccag attctcctgg   1860
aagatgttgt ggtcgaacat gtactcggcg gcctcgccga ggttcacgat ccactcgccg   1920
atgtgcgggg gcttcacgcc gtacgccatg ttctgcgcgt aacaggaaca ggtggcgtgg   1980
ttgtcaccgc agatcccgca gatccggctg gtgatgaagt gggcgtcgcg cggatccttg   2040
cccttcatga agaccgagta gccgcggaag atcgagctgg tgctgtggca ctcggcgacg   2100
accttctgct tgaagtcgat cttcgtgtag atgcccagac tcccgacgat acgggtgatg   2160
ggatcccacg ccatctccac cagctcgtct ttaccctggc tcgtcgtcgt catgatgagg   2220
ccgcctcttt ttccttttcg gtgcgttacc aggtgcgggt ggcgccggtg gtcagtttct   2280
tgccgcgggt acgccacttg ggctcgcggt cgagggtgtg cgtggtgatg ttccgcagcc   2340
gccgcatcgt cgagccgtac agcccgacgg cattcgtgga gagctttccg ccgggaggct   2400
cgtccatgaa cggcatgaat ttgtcgggga atcccggcat ggtgcagccg atgcagattc   2460
cgccgacgtt ggggcagccg ccgataccgt tcatccagcc gcgcttgggc acattgcatt   2520
tcacggtggg gccccagcaa cccagcttga cgatgcactc gggctggccg tactcggtcg   2580
cgaagtcgcc ctgctcgtag tagccggccc ggtcgcaccc ctcgtgcacc gtacggccga   2640
acagccaggt cggacggagc gactcgtcga ggggatcat cggggcctgg tcggtggcca   2700
tgtagagcag ataggtgagc gtctccgaca ggttgtccgg ctggatgggg cagccgggga   2760
```

```
cgcacacgat cgggatacco gccttggact tccactccca gcccaggtag tccggcacgc   2820
ccatggcgcc ggtggggttg ccogccatgg cgtggatgcc gccgtacgtg gcgcacgtac   2880
cgaccgcgac gaccgccgtg gccttgggcg cgagccggtc gagccactcg ctggtggtca   2940
tcggctgccc ggtcgccggg tcgttgccga acccgcacca gtaccctcc tcgtgcagtt    3000 tctcgttggg gatcgacccc tcgaccacca ggacgaacgg ttccagttcg ccccggtcgg   3060
ccttgaagaa ccattcgagg aaatcgtcgg cgccgccggt ggggccgcac tcgaagtcga   3120
tgagcggcca gtgcacgcg atctgcggca gaccgggcag cgcgccgagc gcgatttcct    3180
cgatgctggg ctgcgtggcg gcggtgagtg ccaccgaatc cccgtcgcaa ctcagtcccg   3240
cattgatcca caggacatgg atgagagtgt tctccgcttt taccgctgct tctgtcggca   3300
tagcccgctg ccttccggga tgggaccgcc cgataccagt gagggtggcg acactcacct   3360
tgctaccatc tagaatccgc ccggttgttc tgtcaacacg agattgttcc gggtgaccat   3420
ccattagccc cggttcggcc ggggccgaat gggtgagcga gggaaagctg gccattgatg   3480
catgaattgt caatcaccca gagcgtggtc gacgcggtgt gcgagcgtgc cgcgggaaga   3540
cccgtgcgta ccgtccggct ccgggtgggg gcgctgaccg cggtggtgcc cgacgcgatg   3600
cggttctgct tcgatctgac caccgcgggc acggtcgccg aaggcgccct cctggagatc   3660
gaccagcccc ccggaacggc gcactgccgg gcgtgtgagc gggacttcac cctgaccgat   3720
cttgtattgc tgtgtccgtg cggcagcgcc gacgtgaata tcacgtcggg gcgggagctg   3780
cagatcgtct cgatgagagt gggctgaccc catgtgcggt acttgcggtt gcgtcggcgg   3840
aagcggtgag ggcggcgggg cgaggatcgc cgtaccgcac gcccaccogc acgaccacga   3900 ccacgttcac gccggccacg gccctgacca caccggcgta cggaccacc cgtcggccga    3960 ccgggggagt accggggacg gcgagaccat caccctcgaa cagaaggtcc tcgtcaagaa   4020
cgacgacctg gccgtccgta accgcgcctg gctcgcggaa cggggcatcg tggccgtgaa   4080
catgatgagt tcgcccgggg ccggcaagac caccctcctc gaacgcaccc tcagggactt   4140
cgccggccgc cgcccggtcg ccgtcatcga gggcgaccag gagacggcgc tcgacgcgga   4200
gcggatcagg cgggcgggcg gcaccgtcgt ccagatcaac accggcgccg gctgccacct   4260
cgacgcggag atggtgcggg gcgcgctcac ggccctggaa ccggagccgg gctcgctgat   4320
cctggtcgag aacgtgggca atctggtctg tcccgcgctc ttcgacctcg gggagcgcag   4380
ccgggccgtg atcatctcgg tcaccgaggg gacggacaag ccgctcaagt acccgtacat   4440
gttcgccgcc gccgacctcg tgatcatcaa caagatcgac ctgctcccgt acgtcgactt   4500
cgacgtcgag cagtgcgaga agtacgcccg gtcggtcaat ccggagctgc gggtactgac   4560
cgtctcggcg accaccggcg aggggatggc ggcctggtac gactgggtcg cgcaccoctg   4620 atcactgcgc cggccgctcc acccggaccg ggccgccggt ggtgacggac tcgatcgcgg   4680
cgagggcgat ggccagcgcg gcgcggcgt cctcgccggt gaccgcgggg gcgcgcccgg    4740
cgcggacgca gtcggtgaag tcggcgagtt cggcgacgta ggcgtcgcgg aacaggtcct   4800
ggtcgtagct gacgctctcg gcactgacac cgtccgggcc gtaggacgtg agatgggtac   4860
ggcgcacctc gcccatggtg agcatgcccg ccgagccgaa gacctcgccg cgtacgtcgt   4920
agccgtacac ggcctggaag ttggcctcgg cggtggcgag ggcgccgttg tcgaagcgga   4980
tggtgacgac ggcggtgtcg agcaggccgc ggtccttgaa gtcggggcgg accagggcgt   5040
cggccagggc gaagacctcg acggcctcgg caccgggggtt gaggaagcgc agggtgtcga   5100
agtcgtggat cagcgtctcc aggaagatcg tccacggcgg gatgggcgcg gggtcggcca   5160
```

```
gcttcgggtc gcgggtcagc gagcgcagga gctgcggggt gccgatggag ccggcggcga      5220
ccttgtcgtg ggcggcgcgg aaaccggcgt cgtagcggcg gttgaaaccc acctggaggg      5280
ccacacccgc ctctcgggcc gcggagacgg cgcggtcggc gtccgcgagg gtgacggcca      5340
tgggcttctc gcagtaaacc gccttgcccg cccgcgccgc cgcctcgacg agatcggcgt      5400
gggtgcgggc cggggtggcg atgaccacgg cgtcgatctc cgggtcggcg aggaacgcgg      5460
cgatgtccgt gtaggccacg ggggcgtcca gatggtccgc gaggcgccgc gccgcgtccg      5520
gtacggggtc ggcgaccgcg gcgagacgga caccggggat acgccgggcg agggtggtgg      5580
cgtggaagga acccatccgt ccggcgccga tcaggccgac ggcgaggggt ggctgagagg      5640
gcatgcggaa tctccgtatc tccgtacgta cgccgtgacc gggcgaggcc ggtccatggc      5700
cgggggagtg tgttcaggtg gtgtgaaggc ggtacggaag cgctccatgg ccaggtcgct      5760
gtcggtggag gcccatgcct ccatggccac ggtgccctgg tagccgaggt ccgtgagggc      5820
gcgggcgacg gccgggtagt ggatctcgcc ggtcccgggc tcacaacggc cggggacgtc      5880
cgcgacctgg atctcgccga tcagccccag gccgtgggcc cgccggacca gttcgacgag      5940
gttcccctcg ccgatctgcg cgtggtacag gtcgaggttc atccgcaggc ccggccggtc      6000
caccgcggcg accagggcca gggtgtcggc ggcccgggcg aacggcaccc cgggatggtc      6060
gaccgcggtg ttgagattct ccagggtgaa gaccactccg cgcgctctcg ccagctccgc      6120
gatcctgtca agggtccgca gggcggccgg ccacagggga ccggtgtcct cgtcggcgac      6180
cggcaccacc ggcaggcccg cgccgtccag gccggtgccc tgcaggttca gccgcgggca      6240
gcccagtcgt tcggcggcct tgaccgactc ctcggccgtg cgcagcagct ccgccgcccc      6300
gtcctcgtcg gtcagggtgc gcggagata gccggtcatc gaggagagga cggccggggt      6360
cctggccagc gcgtcgaggt cgtgccggct ccagtcccag atctcgacct ggaagccggc      6420
gtcgtggata cgccgggccc gctcctggat cggaaggtcc cggaagacca tctcggcgca      6480
gatcgccaac gtgtacatcc gccacccgcc tcacttcttc tataacgttc tagtcggggt      6540
tgcagtacgc cagtcggcca ccctggctgt caagggccgg gaacgcccgg actggaacgt      6600
tgcagtagcg cggggaggcg gccgtaccac ctggtctacg atcggcggcc cggggggagtt      6660
gtctaccgag gaggccagac gtgccaccga tctccgcggc gggggaccgg aaacggccca      6720
ccctcgccga tgtcgcggcg cgcgcgggcg tctccacggc gctcgtctcc gtcgtgatgc      6780
gcggggccaa gggcgccggc gccgccaccc gtgagcgggt cctcgaagcc gcgcgggaga      6840
tcggctaccg gcccgacacc cgggcgcgcc tgctgcgcag cagccgttcc cgtctgctcg      6900
gggtgcagtt cggactccag cacccctccc acgccgacct ggtggaaggg gtctacggtg      6960
cggccgagtc cgccgggtac caggtcgcgc tgagcgcggt cgcgcccagc cgcggcgaac      7020
agcacgccct ggagacgctg ctcgccgacc gctgcgaggc gctgatcctg ctcggtcccg      7080
agctccccgc cgcacggctg acggaactcg ccggccagat gccggtcgtc ccgtcgcca      7140
ggagactccg gcagccgtcc ggagccgtcg aggtggtacg gaccgccgac gacgaggggg      7200
cccgccaggc cgtggaccac ttggtcgggc tcggccaccg ggccgtcgcc cacatcgacg      7260
gcggccgggc ccccgcgcg gccgaccggc gccgcggcta ccgcaccgcc atgaaccgcc      7320
acgggctggc ccggcacgcg tacgtcctgc ccggcggtcc gaccgaggag gacggcgcgg      7380
cggccgcccg tacgctgctg gccggcccgg cccgtccac cgccgtactg gccttcaacg      7440
accgttgtgc cacgggcgtc ctcgacacct tcctgcgcgc cggtgtcccc gtccccggcg      7500
aggtctccgt cgtcggcttc gacgacagcc ggctcgcgcg cctggcccac atcgacctca      7560
```

```
ccaccgtcgg ccaggacgtc gcccgcctca cccgggaggc cgtcgcacgg gtcgtgggac    7620
ggctcgacgg cgatccggtc cccgaccggg agaccgtggt ggccccgtgc ctcgtcatcc    7680
gcaccaccac ggcggcgcca cccgggtagc cccggggacc cgagctgggg ctacccgggt    7740
gggcctgaac cggggggccg ccgggccggc cccttacaga acatcggctc tgtcactacg    7800
tttttccgga cagatccacg gcaatggtgg ccggtttgtg ctggattacc ggttctctcc    7860
acctcctgga ccgaagcggc ggactcaatt ccggccaggg cgcggtgaca tggtcctgtg    7920
ccgaccgctt ccgtacgaga cgggcggtct cgcccgtgtt cggcaggtcg gcacggtcga    7980
tgaccgattg tcgccggtct ccgccgccgg tctccgcgga gccgccccg ggtggccggg      8040 tggtggcagg cggcaccggt cactcccgta caccaggccc cgtgatcctc gtgggccctg    8100
gcgtacggga cctggcctgc gcggttcgcg ccgtcgcggc ccggcggagc cgggcggccg    8160
gagtccggag gggagcgcgg gggcgcgtct cctccgtatc ctgttggccc cgaatccatg    8220
aagcaatatg cccacgtcaa tttcccatga tccggctgga aagatctaat tccttgatcc    8280
tcggcgtccc gctcgtttcg acggtcacgc cgacccggcc ggacgttcat gacacgcggg    8340 acgtcgggc tgtccagttt tcgccccttc agatttctcg ccgcgggctc gtatggtctg    8400
cagtgagaaa tcgaatgact gatggcgggg agggcgtaag tgcgtggtga actcctggcg    8460
cgcagacgca cgcgatgttc ttcgggacca ggggaaaag gcgttcttcc cctgatcggc     8520
gagatccgct acgtttcttc agccgtcggc ccgccggctc cggggggagcc ttcgcggacc    8580 ggtccgttct ccgtcatcgg cgactgagga cgggacggcg ccgggcatga acccgcgggt    8640 caccctacg cctccgggac cggaccggcg ctcctcgttc cgaggtcgga gcggtgcggg     8700
agccttccgg cattccggcg acgaagcccc gatgacggat atcgatccgc cgaagcgtaa    8760
tcgagagttt tccggaactt cataaatccg ggagagctgc cggatcacgc gcgggcgaag    8820
tgagagtccg gtgcgccgca ccgatgatgt gtgctgcttg caatccctga tgaaaacggg    8880
cgagaaacgg tggtgggcgc gtgaggacgg ctggggacgt gactgattca acaattgagg    8940
gccatggtca taaaggccct gttgccattg tcggactgtc ctgccgtctt ccgaaggccg    9000
ccgacaggca cgcgttctgg acgatgctgg ccgacggagc ccacggcgtg acggacgtcc    9060
ccgcggaccg gtgggaccac gccgagtact tcgacgagga ccccggcgca ccggggaagg    9120
tcaacacccg caggggcgcc ttcctggacc aggtcgaccg gttcgacccc gccttcttcg    9180
ggatctcgcc gcgcgaggcc accgccatgg acccgcagca gcgcctcgcg ctcgaactga    9240
gctgggaggc gatcgaggac gcgcggatcg tccccggcag cctcgcgtcc accaggaccg    9300
gcgtgttcat gggagcgatg aacgacgagt acgccaccct cacccgcgg gccgggctgc     9360 gccaggtcga ccagcacacc ttcaccggag tgcagcgcag cctgatcgcc aaccgggtct    9420
cctacttcct cggcgtgcgc gggcccagcg tgaccatgga caccgacag tcgtcctccc     9480 tggtcgcggt gcacctggcc gtacagagcc tgcggaccgg agaagccgac atcgccctgg    9540
ccggcggcgt gaacctcacg ctcaccccg agggcgccgt cggcgcggcc aagctcggcg     9600
cgctctcccc cgacggccgc tgctacacct tcgacgcccg ggccaacggc ttcgtccgcg    9660
gcgagggcgg cggtgtcgtg gtgctgaaac ccctggccgc cgcgctcgcc gacggggacc    9720
gtgtccactg cgtcatcaac ggcagcgccg tcaacaacga cggtggcggt gacgggctga    9780
cggtgcccag cggccccgcg caggaagagg tgctgcgcct cgcgtacgag cgggcggggg    9840 tggacccgc ctcggtccag tacgtggagc tgcacggcac cggtacccgg ctcggcgacc     9900
cgatcgaggc cgcggccctc ggcgccgtac tgggcgcggc gcgcggcacg gcggccccgc    9960
```

```
tccaggtggg ttcggtcaag accaacgttg gccacctgga gtccgccgcc ggtgtcaccg    10020
ggctcatcaa gaccgcgctg gcgatacggc accggctgct gccgccgagc ctcggcttca    10080
ccacaccgaa cccgcggatc ccgctggccg acctgaacct cgacgtccgc gtcacgcacg    10140
gcgaatggcc cgcgccggac cggccgttgg tcgccggggt cagctcgttc ggggtcggcg    10200
ggaccaactg ccacgtcgtc ctctccgagg tctcggccgc ggctgacgtg gcggtcgagg    10260
acgcatgcga gccctcggcc gggccggggg cggtggggc ccctgggtg gtctccggcc     10320 ggacggtggc ggcggtacgg gaacaggccg cgcgcctccg cgcgcaggtc gcggaccacc    10380
cggagacgga cctgtccgac ctgggccgct ccctcgccac gaccaggacc gccttccgcc    10440
accgggccgc cgtgaccgcc accgatcggg ccggataccct ggccggactc gacgccctcg   10500
cctccggcga cgcggccccg ggctggtcc agggcacggc cgacgccccg ggcggcaccg     10560
tcttcgtctt tcccggtcag ggttcccagt gggtggggat ggccgtggag ttgatggggt    10620
cctcgggggt gttcgcggcg cggatggggg agtgtgcgca ggcgctgtcg ccgtacgtgg    10680
actggtcgtt gtccgaagta ctggacgacg gtgaggcgtt ggggcgggtg gatgtggtgc    10740
agccggcgtt gtgggcggtg atggtgtcgt tggcggaggt gtggcgttcg tacggtgtgg    10800
agccggtggc ggtggtgggg cacagccagg gggagatcgc cgcggcgtgt gtggcggggg   10860
cgttgtcgct ggaggacggt gcgcgcgtgg tcgccctgcg cagccaggcc ctcgtctccc    10920
tctccggacg cggcacgatg gcctccgtcg ccctgcccgc cggtgaactg accctgggcg    10980
cctccctgtc ggtggccgcc gtcaacggac gcgctccac ggtggtcgcc ggagacgaga     11040
gcgcgatcga cgcgctggtg gcggagttga ccaccggggg cgtcagggcc gccgtatcg     11100 ccgtcgacta cgcctcgcac tcggcccacg tcgaggcgat ccgcgaccgg ctgcacaccg    11160
cgctggcccc gatcacacca cggaccgcct cggtcccctt cttctcgacg ctgaccgggc    11220
agtggctcga cgccggtgcg acggacgccg actactggta ccggaacctc gcggcacccg    11280
tccgcttcga ggaggcggtc cgcgggctgc tcgcagcggg ccaccgggcg ttcatcgagg    11340
tgagcccgca ccccgtactg gtgatgggcg tccaggagac cgccgaggcc atgggcgtac    11400
ccgtggtcgt cgtgccctcg tccggcgggg acgacggcac gcgggcccgt gtgatggcct    11460
cgctcgccga actgtccgtg cacggggccg gtatcgactg gacggcggtc ttccgggcg     11520 gacgccgcgt cgagctgccc acctatccct tccagcgaca gcgctactgg atcgccccgg    11580
cgcccgaagc ggcagcgtac gaaggcgagt cggcggatgc cggtgacccg gtgggcgcga    11640
gggagccgac gggcgcgggc gcgttggcgg acaacggcgc gggcgtgccg gtggacgacg    11700
ggcgaccggc gtacgaggac accccgtcg gggcggacgt cctcgacgcc ggccgggtgc     11760
ggcagctcgt ccgggcccac gccgccgccg tcctcggcca caccacccg gccgcggtcg     11820 agacggacct gcccttcaag gacctcggct tcgactccca gatgaccgtc gcactgcgcg    11880
accgcctcag cggcgcgctc ggccggcggc tgccgtccgc cctgctcttc gaccatccga    11940
cgccggacgc gctcatcgcc catctctccg gcggccccgc ctctcgcccc gccgccgca     12000 acgacggctc cgccaccggc ggcgaccga tcgcgatcgt cgggatgagc tgccgctttc     12060
ccggcggcgt acggagcccg gaggacctgt gggacctggt ggtctccggc gcggacgcga    12120
tctcggcgtt ccccgccgac cggggctggg acctcgacgc gctcgccgcg accagccaca    12180
cccggcatgg cggattcctg cacgacgcg ccgagttcga cgggcgttc ttcggcatca      12240 gcccgcgcga ggcgctcgcg accgaccccc agcagcggct gctgctggag atctcctggg    12300
aggcgctgga acgcgccggt ctcgacccgg ccacgctgcg cgacagcgac accggtgtgt    12360
```

```
tcgtcgggc gatggcccag gactatgtgc cacgcctgca cgaggcgccg gacgggttcg   12420
ccgggtacgg gctcaccggc tccaccggct ccgccgcctc cggccgcatc tcgtacgtcc   12480
tggggctgcg cggcccggcg ctgaccgtgg acacggcgtg ctcctcctcg ctggtcgccc   12540
agcaccttgc ggcacaggcc ctgcggcgcg gcgagtgctc cctggtgctg gccggcgggg   12600
tgacggtgat ggccaacccc ggcatgttcg tcgagttctc ccggcagggc ggactggcgc   12660
cggacggccg gtgcaaggcg ttcggcgcgg gcgccgacgg tacggggtgg gccgagggcg   12720
ccgggatgct cgtcctggaa cggctctccg acgcccggcg caacggacac ccggtactgg   12780
cgctcctccg tggctccgcc gtcaaccagg acggcgcctc caacggcctg accgcgccca   12840
acggcccctc ccagcaggag gtgatccggc gcgcgctcgc cgacgccgga ctcgcaccgt   12900
ccgacgtgga cgcggtggag gcacacggta cgggcaccac cctgggcgac ccgatcgagg   12960
ccgaggcact gctcgccacg tacgacagg accgtgaaca cccgctgtgg ctcggttcgt    13020
tgaagtccaa catcggccac acccaagccg ccgccggggt cggcggggtg atcaagacgg   13080
tcctggccct gcaccacggg atcgtcccca ggaccctgca cgcggacgag gtctcgcccc   13140
aggtggactg gtcggcgggg caggtcgcgc ccgtcaccgc gaacgtggcc tggccggaga   13200
ccggacgccc gcgccgggcc gccgtgtcgt cgttcggtgt cagcggtacc aacgcgcaca   13260
ccatcatcga acaggccccg ccggaagatg agttggcgcc ggagctcctt cccggctcat   13320
cgcctgccgc agccgtgggc cagggccccc tcccgtggca gctctccggc cgtacgcccc   13380
aggcgctcca ggcccaggcg cggcgcctcg ccatccatct cgacgccagg cccggtctcg   13440
gcgccgccga catcgggcgc tccctcgccg ccacccggtc cgccttcgag caccgcgccg   13500
tactgctcgg ccgcgaccgc gacgaactgc gcgggctgct caccgcactg gccgacgggc   13560
ggaccgaccc ccggctggcc cggggcagcg ccgacaccac cggacgcgtc gtcttcgtct   13620
tccccggcca gggctcccag tgggccggga tggccgtcga actgctcgcc accgagccgg   13680
tgttcgccgc gcgcatggcc gactgcgccc gcgccctcgc cccgcatgtg acgtggtcgc   13740
tgtccgaagt gctctccgac gccgaggcgt tggagcgggt cgacgtggtg cagcccgcgc   13800
tgttcgcggt gctggtgtcg ctggccgcgc tgtggcgctc gtacggtgtg gagcccgccg   13860
ccgtgctcgg gcacagccag ggcgagatcg ccgctgcctg cgtcgcgggc gccctcaccc   13920
tggaggacgc cgcccgggtg agcgccctgc gcgccaagct gatcctcgcc gaactcgccg   13980
ggccgggcgg catggcctcg gtcgcgctgg cccccagga gctgctgccg cgcctcgaag   14040
cctgggacgg acggctctcg ttggccgcgt ccaacgggcc tacggcgtcc gtcgtctccg   14100
gcacaccgga ggcgctggac gaactgctgg ccgcgctcga cgccgagcag gtcagggtcc   14160
gcaggatccc ggtggactac gcctcgcact ccccgcaggt cgaagaggtc cgcgacgccc   14220
tcctggacgc cctcgccacc gtacggccgc gcaccgcccc cggcaccgct cccgtccgtt   14280
tcttctccac cgtcaccggc ggaccgctcg acaccgccgc cctggacgcc gcgtactggt   14340
acaccaacct gcgcaccacc gtccgcttcg agcaggccac ccgggccgcg ctcgaccagg   14400
ggtacgacct gttcatcgag gtcagcccgc atccggtgac cgtccccagc ctccaggaga   14460
ccatcgaggc caccgaggca cacgccgtgg ccctcgggtc gctgcgccgc gacgacgggg   14520
ggcaggaacg attcctcacc tcggtcgcga cggcccacac ccaggcggc accccggact   14580 ggaccggcct cctcggcacg ggaccccggg tcgagctgcc cacgtacgcc ttccagcgcg   14640
aacggtactg gctgctgccc gagccggtga gccgggctgt gagcggaccg gacgactggc   14700
gctaccgcgt cacctggcgc cccgtcaccc cccggcccgc accgccactg gccgggcagt   14760
```

```
ggctgctgct cgccccgcc gagggcatcg gcgcacccct cgtcgcgcgg tgtgaacggg    14820
cgctggcgga agcgggagcc gaggtcgtcc ggccggccgc cggcgacccg gcggcgctca    14880
ccgacctgct cacggccggg aaaacacccg ccggggtcct ctccctgctc gccctggacg    14940
agcgccgcgc accggacggc tccgcgccgc acggactcct cgacaccgtc gcgctggccc    15000
aggccctctc cgggcgggag ataccgctgt ggctcgccac ccggggcgcc gtcgccgtcg    15060
accccgacga ccggctcgac gaccccgaac aggcggccgt ctggggcctg gccgggccc    15120 tcgccctcga atcaccgcgg gaccggggcg gactggtgga cctccccgcc cacctcgacg    15180
acaccgcggc ggccctgctc gccgccgcgc tcaccggcga cagcgacgag gaccaggtgg    15240
ccgtacgccc cgccggtctc ttcgtacggc gactggtgcg ggccgcgctc ccgccggcca    15300
cggccgcccc ctggcggccc cgcgacaccg cgctgatcac cggcggcacc ggcgcactcg    15360
gcgcgcgggt ggcccgctgg ctcgccgccg ccggggccgg acacctcgtc ctggcgagcc    15420
gcagcggccc cgaggcaccg ggagccgccg cgctgcgcgc cgaactcacc gcgctcggcc    15480
cctcggtgga gatcgtcgcc tgcgacaccg cccgccgcga ggaactggcc gcgctgctgg    15540
actccgtacc cgaggaccgc ccgctgcgca cggtcgtgca caccgccggg gtcctggtcg    15600
agtccaccgt gcgcaccctc accacggaag aactcgaaca gaccttgcgc gccaagaccg    15660
agaccgcccg ccatctccac gaactcaccg gagaactcga cgcgttcgtg ctcttctcct    15720
ccggcgccgg tgtctggggc agcggcggac agggcgcgta cggcgcggcc aacgcctacc    15780
tcgacgcgct cgccccggcac cgccgcgacc acgggctgcc cgccacggcc gtctcctggg    15840
gcgcgtgggg cggcggcggg atgggcgccg tcgacggcgc cgaggacgtc tggcggcgcc    15900
tcggcgtcct cccgatggac ccccgatccg ccgtcaccgc gctccaacga gccctggacg    15960
ccggggagaa caccctcacc gtcgccgaca tcgactggcg ccgcttcgcc ccggccttcg    16020
cgtccgccgg gccccggccg ctcctcgccg acctgcccga ggcgcggcgc gccctgaacg    16080
ggcccgccga tgacaccacc acggacccgg ccgccgcgac ccccggcgg cccgaacgga    16140 tccggaagct ggagggcctg cccgaggccc ggcgcgccga cgccctgctc gaactcgtcc    16200
gcgccgaggc cgccgccgta ctcggccacc ccgacccgcg cgccgtacgg ccgggacggc    16260
ccttcaagga gagcggcttc gactcgctga cctccgtcga actccgcgac aggctggtcg    16320
ccgccgtcgg ccaccggctc cccacagagcc tcgtcttcga ccggccgaca ccgacggcgc    16380
tcgcccgcca cctcgacacc ctgctgttcg gcgccgccac caccgggacc gggaccacgg    16440
gggcctccga cgaacccgtc gcgatcatcg ccatggcctg ccgctacccg gcggcgtca    16500 gctcccccga ggagctgtgg gagctggtcg ccgccggtac ggacgcggtg tccgagttcc    16560
ccgccgaccg gggctggaac gtggagtccc tgtacgacgc cgaccccgac cggccgggta    16620
cctcccatgt gcggcacggc ggattcctgt acgacgccgc cgagttcgac gccgaactct    16680
tcgggatgag cccccgcgag gcacgggcca ccgaccccca gcagcggctg ctgctggaga    16740
cggcctggga gacgttcgag cgcgcgggca tcgaccccg gtcgctggcg ggctccccga    16800
ccggggtgtt cgtcggcgcg atgtcccagg actacgggcc ccggatgcac gaggcaccgc    16860
aggagctgga ggggtatctg ctcaccggca acatcggcag tgtggcctcc ggccgcgtct    16920 cgtacaccttt cggcctcgaa ggcccggcga tgaccgtcga caccggttgc tccgcctccc    16980
tcgtcgcact ccacctcgcc gcgcagtccc tgcggcgcgg cgagagctcg atggcgctcg    17040
cgggcggggt gaccgtgatg tccacccccg gtgtgttcat cgagttctcc cggcagcgcg    17100
gactcgccct cgacggccgg tgcaaggcgt tcggggcggg cgccgacggc accggctggt    17160
```

```
cggaaggcgt gggcctgctc ctgctggagc ggctctccga cgccgaacgc aacggccacg   17220
agatcctcgc cgtcgtccgg ggcagcgccg tcaaccagga cggcgcgtcc aacgggctga   17280
ccgcacccaa cggcccctcg caggagcgcg tcatccggcg cgccctggcc gacgccggac   17340
tcaccccggc cgaggtcgac gcggtcgagg gacacggtac gggcaccaca ctcggcgacc   17400
cgatcgaggc cgaggcgctg ctcgcgacgt acgggcagaa ccgtgaacgc ccctgtggc    17460 tcggctcgtt gaagtccaac atcggccaca cccagaccgc ggccggggtc ggcggtgtga   17520
tcaagatggt gcaggcgatg cggcacggcg tcctgccgag gaccctgcac gccgatgagc   17580
cctcgccccg gatcgactgg tcggcgggcg ccgtgtcact gctcacggag gagcgggcct   17640
ggcccgacga gggccgtccg cgccgcgcgg gcgtctccgg attcggggtg ggcgggacca   17700
acgcccatgt catcgtcgaa cagggcccgc cgcccgcccc cgtcaccctg tccgccccg    17760 tcaccccgcc cgccgatgcc cccggcgcgc tgccctggct gctgtcgggc cgtaccgaac   17820
aggccctgcg cgaccaggcg cggaagctct ccgcacacct cgccgcgcac ccggacacga   17880
ccccgctcga cgtggcgtac accctggcca ccggccggac cgcgctcgac caccgggccg   17940
tcgtggtcgc ggccgaccgc gccggattcg ccgccgcact cgacgcgctg gccaccggcg   18000
acgacgtatg cgcccggggc atcgccgacg aggaccccgg aaccgtcttc gtctttcccg   18060
gtcagggttc ccagtgggtg gggatggctg tggagttgat ggggtcctcg ggggtgttcg   18120
cggcgcggat gggggagtgt gcgcaggcgc tgtcgccgta cgtggactgg tcgttgtccg   18180
aagtactgga cgacggtgag gcgttgggc gggtggatgt ggtgcagccg gcgttgtggg    18240
cggtgatggt gtcgttggcg gaggtgtggc gttcgtacgg tgtggagccg gtggcggtgg   18300
tggggcacag tcaggggag atcgccgcgg cgtgtgtggc cggtgcgttg tcgctggagg    18360
acggcgcacg ggtcgtcgcc ctgcgcagcc aggccctccg ggagctctcc ggcggtggcg   18420
cgatggcggc gctgctgctc gcacccgatg aggtcgcccg gctgatcgaa ccctgggacg   18480
gccggctcac catcgccgcg tacaacggcc cgaactccac caccgtcgcc ggggaccccg   18540
aggccgtcga agcgctgcac gcccactgcg agcgcgaacg gatccagtcc cgccgcgtcg   18600
ccgtcgacta cgcctcccac tcgccgcagg tcgaggagat acgcgaccgg ctgctcgccg   18660
acctggcccc gatcacccg cgcccggccg gcataccgtt ccactccacc gtcaccggcg    18720
caccgctcga caccaccgga ctggacgccg cgtactggta caccaacctg cgtaggcccg   18780
tcctcttcga accgaccgta cgggcccctga tcgacgccgg acacggcatc ttcatcgagc   18840
cgagcgccca ccccgtcctc accaccgccg tccaggacac cgccgagcgg gccgggcgac   18900
ccgtcgccgc gttcggcacc ctgcgcaggg agggcgggc ggccggccgc tggctggcct    18960
ccctcgccga ggcgcatgtc cacggcgccc ccgtcgactg gtccgggctc ctcaccgggg   19020
gccgcaggac cgatctgccc acctacgcct tccagcgcga cggtactggg ctggaccccgg  19080 tcaccgcgtc cgggcgcgcc gtcgcggagg gcgcggcggg cctcgggctc agctccgcgg   19140 cccaccgct gctcggcgcc gccgtggagt tggccggcac ggacgagtac gtcctcaccg    19200
gacgggtgtc cctccgcacc cacccctggc tcgccgacca cgccgtgtcc ggcaccgtac   19260
tgctgccggg caccgcgttc gtcgaactcg cgctgcgcgc cggggacgag gtgcgctgcg   19320
accggatcga cgaactgacc ctgagcgcac ccctgttgat cgacgcgag gtgaccctcc    19380 aggttctcgt cggggccgcc gacgccgacg ggcggcgaac agtggcggtg cactcccgta   19440
cgtcccaggg cgcgtcctgg acccggcacg ccgacgcgc gctgtacgcc ggaggagcgc    19500
cgggaccgtc cccgaccggg gaggagatgg cctggccgcc gcccggggcg cgtcccgtgg   19560
```

```
cacaggcggg cctctacccg gcgctcgccg cgaccggcta cgactacggc cccgccttcc   19620
agggcctgcg cgccgtatgg caggacggcg acgaccttct cgccgaagtg gcgctcccgg   19680
acggcgagtc ggccgacggg ttcgcgctcc accccgcgct gctggacgcc tgcctccatc   19740
cgctggggct cggaaagggg cccggatcgg gccttggaac gggcctcggt tccgagccgg   19800
gcgacgggga cgggacccgg ctgccgttcg cctggaccgg ggtccgactg cacgcggtgg   19860
gcgccacatc cgtacgcgta cggatctccc cgtccggcgg tgacgcggtc tccgtgacgg   19920
tcagcgaccc ggcgggcgca ccggtcgcca cggtggaggg cctggtcctg cggcccctgg   19980
ccgccgggca gctcaccgcc gcacgccacg acgaccacga cgcgctgttc cggctggtct   20040
ggaacccgct caccgacccg gctccggtcc cgtcccgat tccggccggg cccgcccagg   20100
ggatccccct catgggtacg gcggcgctgg acacggccct cgcggagggc gtgccgctgc   20160
ccgccgttgt cgccgtacgg cccgacgcgc cggccgggga cgacctggcc gcccgcgtcc   20220
acggggcgac cgcgcggctg ctggagctgt tgcgcgcctg gctggccgac gagcggcgcg   20280
ccgccacccg gctggtgatc ctcacccggg gcgccgtcgc cgtccgggcg gacgaggaga   20340
tcctcgacct cgcgcaggcg ccgctgtggg ggctcgtccg cgcggcgcag accgagaacc   20400
ccgaccggtt cctgctcctc gacacggata cgggcagtga tacggatacg gccccgggcg   20460
gtgctggcga tgtggatacg gacccgggtg tcgacgcggc cgtcgccgcc gtgctcgcgg   20520
ccggagagcc gcaggccgcg ctgcgcggcg gcgccgtact ggtgccacgg cttgcccggc   20580
cggcagccac ccgtctcccc gtcccgcgc tcgaccgga cggcgccgta ctgatcaccg   20640
gaggcaccgg caccctcggc ggcctcgtcg cccggcacct cgtcaccacc cacggggtcg   20700
cccacctcgt actgatcggc cgccggggcc cggacgcgcc cggcgccgcc gagctgagcg   20760
ccgaactcac cgccctcggc gccgaggtga ccgtcgccgc gtgcgacgcc gccgaccggg   20820
acgcgctcgc cgcgctgctg gcggacctcc ccgtccggct gacggcggtc gtgcacacgg   20880
cgggcgccgt ggacgacggc gtcctggaat cactcacccc cgaccggctc gccccgtcc   20940 tgcggcccaa ggtcgacgcc gccctcaacc tgcatgaact caccgacggt ctggacgcgt   21000
tcatactgtt ctcctcggcg tcggccacct tcggcaccgc gggacaggcc acctactgcg   21060
ccgccaacgc gttcctcgac gcgcttgccc accaccgccg tacggccgga ctccccgccg   21120
tctccctggc ctggggctac tgggagcaga ccagcgagct gacccgtggc ctcggcgccg   21180
gtgacatcgc ccggctggaa cgctcggggg tgctcccgct caccaccggg cgcggactcg   21240
cgctcttcga cgcggcgcgg ggcctggcgg aaccccttcgc ggtcacggcg cggctcgaca   21300
ccgcaccccg ggcccaggtc cccgccctgc tgcgcgacct cgtcagggca cccgcccggc   21360
gcgccgccga gggcccccgcc gtcaccccccg gcgggaccgc gctgtcggac cggctcaccg   21420
ggctctccgt accggagcgc gcacagctcc tcctcgccga ggtgctgcgc cacgccgccg   21480
ccgtcctcgg ccgtaccgga tccaccggac tgctgccggg acgtcccttc cgtgacaacg   21540
ggttcgactc gctgaccgcc gtcgaactgc ggaaccggct caccaccctg accgggctgc   21600 ggctgccgc cacctggtc ttcgaccacc ccaccccccct cgcgctcgcc gacgacctgg   21660 cgcggcgct gaccgttacc accaccaccg gcgccgccgc accgcccgcc gccccggccc   21720
ccgtccccgg cgacgagccc atcgcgatcg tcgcgatggc ctgccgctac ccgggcgggg   21780
tcacctcgcc cgaggagctg tgggagctgg tcgctgccgg tacgacgcc gtgtccgact   21840 tccccgccga ccggggctgg gacgtcgagg cgctgtacga cccggacccc gccacgaccg   21900
gcacgtcgta cacccggagc ggcgcgttcc tccacgacgc ggcggacttc gaccacgaac   21960
```

```
tgttcgggat gagccccgc gagtccctgg ccaccgatcc acagcagcgg ctgctcctgg   22020
agaccacctg ggaggtcttc gaacgggcgg gcatcgaccc gctgtcggtg aagggcagca   22080
gcaccggggt gttcgtcggc gcgatgtaca cgactacgc ctcccgcatc caccaggccc    22140
cggccaccgt cgaaggacaa ctgctcaccg gcagcgcggg cagtgtcgcc tccgggcggc   22200
tggcctacgt cttcggtctc gaaggccgg cgatcaccgt cgacaccgcg tgctcctcct    22260
cgctcgtcgc cctgcacctg gccgccaggt cgctgcgcca gggcgagagt tcgctggcgg   22320
tggcgggcgg ggtgacactg atggcaggac cgaccctgtt cgtggagttc tcccggcagc   22380
gcggactctc cgccgacggc cgctgcaagg cgttcggcgc gggggccgac ggcaccggct   22440
ggggcgaggg ggtcggcgtc ctgctgctgg aacggctctc ggacgcggaa cgcaacggcc   22500
acgaggtcct cgccctgctg cgcggcaccg ccgtgaacca ggacgcgcg tccaacggcc    22560 tgaccgcgcc caacggtccc gctcaacagc gcgtgatccg gggggccctg gacgacgcgg   22620
ggctgaccgc ccaggacatc gacgtggtcg aggggcacgg tacggggacg acgctgggcg   22680
acccgatcga ggcgcaggcc gtactggcga cgtacgggca ggaccgtgaa cgcccggtgt   22740
ggctgggctc gttgaagtcg aacatcgggc acacccaggc cgccgccggg gtcggcggcg   22800
tcatcaagat ggtcgaggcg atgcgccacg gcaccctccc gaggaccctg cacgccgacg   22860
agccctcgcc cgaagtggac tgggagcgcg gcgcggtgga gctgctgacc gaggcccggc   22920
cgtggcccgg cgggacaccc cggcgcgccg gggtctcctc cttcggcgcg ggcggcacca   22980
acgcccacgt catcatcgaa cagggcccga tcgcagagca gggtcccatc atcgaacagg   23040
gtccggccac ggagcagggt ccgatcaccg agccgggccc ggccaccgag cagggcccgg   23100
ccaccgagca gggcccggcc acggtgcagg gccctgccac ggagcaggac ccgatcaccg   23160
agcgggaccc gatcgccgaa caggacccgc cgccgaagc gccgccgtt cccgccgcca    23220 cgacctccgc cggggaaacc gccccgctgc cctgggtgct ctccgccagg agcgagccgg   23280
cgctacgggc ccaggccgcc cggctgctct ccttcctggc gtcccacgac gacctcggtc   23340
ccgccgaggt cggccactcc ctggtcacca cccgcgcctc tctggaccac cgtgcggtcc   23400
tcgtggccgc cgaccgcccc gagttcctgg cgcacctcac cgcactcgcc gagggcggcg   23460
gacccgccgt cgtcggcagc gccggcggcc acggccgtac ggtcttcgtc ttccccggcc   23520
agggctccca gtgggccgga atggccctcg gactaatgga gtcctcgccg gtgttcgcgg   23580
cgcggatggc ggagtgtgag gacgcgctgt cgccgtacac ggactggtcg ttgtccgaag   23640
tgctgggcga cggcgaggcg ttggagcggg tggatgtggt gcagcccgcg ctgttcgcgg   23700
tgatggtgtc cttggccgcg ctgtggcgct cgtacggtgt ggaacccgcc gccgtgctcg   23760
ggcacagcca gggggagatc gccgccgcct gtgtcgccgg cgcgctctcc ctggccgacg   23820
ccgcccgggt ggtcgtgctc cgaagtcagg cgctgaccga gctgtccggg cgcggcgcca   23880
tggcctcggt ggcgctcggc agggacgcgc tggggccccg gctctccgag cggctgtcgg   23940
tcgccgccgt caacgggccc gcgtccaccg tggtctccgg agaccccctc gcccttgacg   24000
cgctcctcga caccctcacc gccgaggggg tacgacccgg tcgtatcgcg gtggactacg   24060
cctcccactc cggccatgtg gaggccgtac aggcccggtt gctcgacgac ctcgccccga   24120
tcaccccccg taccccgcgc atccccttct tctcgaccgt ctccgcgagc tggctcaccg   24180
agcccgtcga cgccggctac tggtaccgga acctgcgggg gaccgtcgag ttcgaggccg   24240
ccaccccgcg gctcgtcgcg gaggggtacg gcgtcttcgt cgaggcgagc ccgcaccccg   24300
tcctcaccgt cgccgatccag gagagcgccg aggacgccgt cgtcgtcggc tcgctgcgcc   24360
```

```
gcgacgagga cgggccgcgc cgcttcctca cctccctcgc cgaggcccac gtccggggcg   24420
tcgacgtcac ctggacgccc gcgttccccg gtacgcaccg ccgggtcggc ctgcccacct   24480
acgccttcca gcgcgaacgg ttctggctgg agcagagccc cggaggcccc gccgatgtca   24540
cctcggccgg gctccacccc gccgaacacc ccctgctggg cgcgaccgtg ccctgcccg    24600 gatcgggcgg ccacctcgcc acgggacggc tctcccggga cgaccacccc tggctcgcgg   24660
accacggcgt gctcggcacg gtcctgctcc cgggcgccgc gctggccgaa ctcgccgtcc   24720
gggccgggga ccagatcggc tgccccgacc tggaagaact cgtcctccac gcgccgctcg   24780
cgctgcccgc gagcggcggc gtaccggtac agctcgaact cggcgggccc gacgcgtcgg   24840
gccggcgcac cctgagcgtg cacgcgtacg gccccgacgg ccaggacacc tggacgcggc   24900
acgccaccgg tgtcctggcc cccgcccgg aacaggcggg cgaagcgctc accgcgtggc    24960
cgcccaccgg cgcgacccc ctcgacctcg gcgccttcta ccccgggctc gccgctcgcg     25020
gctacggcta cgggccgcc ttccaggggc tccgcgccgc ctggcgcgac ggcgaggaca     25080
tcgtcgccga ggtcgccctg cccgaggaac accacgcgca ggccgcgctg ttcgggctgc   25140
accccgccct cttcgacgcg gccctgcaca ccgtcgggct cggcaaggcc ctggacgggc   25200
acgaccggcc gctgctgccg ttctcctggc aggggggtgag cctgcacgcg gtcggcgccg   25260
cggcgctgcg ggtccgtacc cgcttcaccg gccccgacac cgtctcgctc accctggcgg   25320
gacccgacgg ggcgccggtg ccacggtcg cctccctcac ggtgcggccc ctcgccccgg     25380 agcggccccgc cgccgcaccc gccgtacgcg acgcgctgtt ccacgtcgca tggcgcgagc   25440
agccccgaac ggccccgcac ggcgccgtcg agggcccgct cctcgtgctc ggcgcggacg   25500
gcctcgggat gcgcgccgcg ctggagacgg ccggcgtatc ggtggcggtg tgccaggacg   25560
tggccgactg gaacccccgcc ggggacgcac ccgttcccct gtcggtggtc accggcgacc   25620
tgccgggacg caccccgcgc gaggccgtac gccgagccct cgccctggta cggagctggc   25680
tcgccgacga ccggttcgcc gcctcgcgcc tggtactcgt gacccgcggc gcggtcgcca   25740
cccaccacga cgaggacatc acctcccctcg cgcaggccgc cgtgtggggc ttcgtccgta   25800
cggcgcaggc ggagcacccc ggccggttcg ccctgctcga cctcggcgcg ggggagccgc   25860
ccctcgccgg gctgcccgcc gcgctggcgt cgggcgaacc ccaactcgcc ctgcgctccg   25920
gcggcttcct cgtcccgcgc ctggacaggc tcgaccggag cggcacccctg ctgccacccc   25980 tggacggggc gtggcggctc gacgtcacca gccccggcac cctggagaac ctggcgttcc   26040
tgcccgcgcc ggaagccgaa gcgcccctgg gcgagggcga gatacgggtc gccgtacggg   26100
ccgccgggct gaacttccgc gatgtcctca tcgcgctggg catgtatccg ggcgcgggca   26160
tcatgggcag cgagggcgcc ggaaccgtac tcgaaaccgg tcctggagtc accggactcg   26220
ccgtcggcga cgccgtgttc ggcctgttcc tcgcccggatc cttcggcccc cgcgtggtgg   26280
ccgaccggcg gctggtcgcg aaggtccgg ccggctggtc cctcaccgac gccgcctccg     26340
tccccgtcac cttcctcacc gcctaccacg ccctggtcga cctggcgggg ctgcgcccccg   26400 gcgagtcggt gctcgtgcac gcagcgaccg gcggtgtcgg tacggccgcc gtccaactcg   26460
cccggcacct cggcgcggag gtcttcgcga cggcgggccc cggcaaatgg cacgcgctgc   26520
gcgccctcgg cctggacgag gaccacatcg cctcctcccg cgacctcgac ttcgaggagc   26580
gtttccgcga cgccaccggc ggacgtggcg tcgacgtcgt cctcaactcc ctggcccgcg   26640
cgttcacgga cgcctcccctg cggctgctgg ccgagggcgg ccggttcgcc gagatggcaa   26700
agacggacct ccgcgacccc gacgaggtcg ccgcgcggta tccgggcgtg acctaccggg   26760
```

```
cgttcgagct gatggacgcg ggacccgacc gggtccgcgc gatcctcgcc gagctgctga  26820
cgctcttcga acgcggcgtc ctcgccccgg cgcccgtgac cacctgggac atccgcaggg  26880
cgccggacgc cgtacgcttc ctcagccagg ccaaacacct cggcaagctc gtcctcaccc  26940
tgcccgcccc gctcgacccg gacggaacgg tcctggtcac cggcgcgtcc gggaccctgg  27000
gcggcgccgt cgcccgccat ctcgtgaccc ggcacggtgt acgccacctg gtgctcgcct  27060
cccggagcgg cccctccgcc gaactgtgcg ccgaactcac cgcgcacggc gccacggtga  27120
ccgccgccgc ctgcgacatc gccgaccgca cggcgctggc ccgcctcctg gacgcggttc  27180
ccggccccca tccgctcacc ggggtggtcc acgcggccgg ggtcctcgac gacggagtgg  27240
tcgactcgct gaccccggaa cgtatcgaca cggtcctgcg gcccaaggtc gacggcgcgg  27300
cccatctcca cgaactgacc cgccacctgg acctgtcggc gttcgtcctc ttctcctccg  27360
ccgccgcgac gctcggcagc gcgggccagg cggcgtacgc ggcggccaac gcctatctgg  27420
acgccctcgc ccagcaccgc cgcgcgacg gcctgccccgc cacctcgctg gcctggggcc  27480
tgtgggccga gcgcagtgcg atgaccgggc atctggacga caacgacctg gcccgcatgg  27540
gtcgttcggg catcgcgccg ctcaccaccg aggacgcct cgcgctcttc gacgcgggcc  27600
gctccgccgc cgaggccgcc gtcgtaccgc tgcggctgga cctcgcggcg ctccggtcgc  27660
acgccgggga cccggcgttc ccgccgctgt tccacggtct cgtccgggcc ccggcgcccc  27720
gggcggccga ggcaccaccg gcctccgagg gggtacgtga ccggttcgcc gccctgcgcg  27780
gggccgaccg ggagcgcgcg ctgcgcgaac tggtctgcga ccacgcggcg accgtcctcg  27840
gacacggcga cagcgcctcc gtcacaccgg gacggccgtt caaggagctc gggttcgact  27900
cgctgacggc cgtggaactc cgtaaccggc tgggcggcgc caccgggctg cggctctccg  27960
cgaccctcgt cttcgaccac ccgacgcccc tcgccctcgc cgaacacctg cgcgccgaac  28020
tcttcgccga cgaggaaccg gcgggcgcct ccccggcggc cgagctggaa cggctcgaag  28080
cggcgctcgc cctggccgcc cccgacacgt tcgaccggac ccaggtcacc acccggctgc  28140
gcgcgctcct caagcgcgtc gagcgggccg agcgggccga gcgggctgaa cgggccgaac  28200
cgaacgggca ggccgggccc gacggcgcac tcgacctctc ctcggccacg cacgacgaga  28260
tcttcgccct catcgacggg cagcacgacg acgtctgagg ctcccccccac ccgctaggag  28320 acaccgtggc gaccgaacag gaactcttcg cctacctcaa gaaagccacc agcgatcttc  28380
agcaggcccg gcgccgggtc cgtgaactgg agtcgccgga gcccgtcgcc atcgtcgcga  28440
tggcctgccg ttacccccggc gcggtgcgct cgcccgagga cctgtgggag ctggtcgcct  28500
ccggcaccga cgccgtgacg cccttccccg acgaccgcgg ctgggacctc gacgggctct  28560
acgacccgga tccggatgtg cccggcacgt cctacggcag ggagggcggc ttcgtcgccg  28620
gcgccgccga cttcgacgcg ccgttcttcg gcatctcgcc gcgcgaggcg ctggccatgg  28680
acccccagca gcggttgctg ctggagacgt cgtgggaggt cctggagcgg gcgggcatca  28740
acccggccac gctgcgtgcc ggcaggaccg gtgtcttcac cgggatcagc caccaggact  28800
acgcgctggg cctgagcacc tccgccgagg tctccgaggg acacctcatg acgggcaacg  28860
ccgtcagtgt gatgtccggc cgcgtcgcgt acaccttcgg cttcgagggg cccgcggtca  28920
ccgtcgacac cgcctgctcg tcgtcgctgg tcgccctgca cctcgccgtg cagtcgctgc  28980
gtacggggga gtgcacccctc gcgctcgcgg gcggggccac cgtgatggcc accccgaacg  29040
ccttcacccg gttcagccgg gagcgcgac tggcccccga cggccggtgc aaggcgttcg  29100
gcgcgggcgc cgacggcacc gggttcagcg acggcgtcgg cgtcctgctg ctggaacggc  29160
```

```
tctcggacgc cgagcgcaac ggccaccgga tactggcggt cgtccggggc agcgcggtca   29220
accaggacgg cgcgtccaac gggctgaccg cccccaacgg ccccgcccag cagcgcgtca   29280
tccgggaggc gctggccgcc gccgggctcg acccgtccga ggtcgacgcc gtcgaggcgc   29340
acggtacggg gaccacgctc ggcgacccga tcgaggcgca ggcgctcctc gcgacgtacg   29400
ggcagaaccg ggaccgcccg ctgtggctcg gctcgctgaa gtccaacatc gggcacaccc   29460
aggccgccgc gggcgtcggc ggcgtcatca agatggtcga ggcgatgcgc cacggcaccc   29520
tgccgaggac cctgcacgcc gacgagccct cgcccgggt ggactggtcg ccggggcgg    29580 tggaaccgct caccgaggcg cggccgtggg agccggcgc cggaggcgtc cgcagggccg    29640
gcgtctcctc cttcgggatc agcggcacca acgcccatgt cgtcctggag gagccgcccg   29700
cgcgccagga gacccccggg cgccggggc gggcccggc cgcgacgccc tgggtgctct    29760
ccgccaggag cgcgcccgcc ctgcgggccc aggccgaggc gctgctcgcc ttcctggacc   29820
cgcgccgaga ccaccacgcc gacatcggtg ctgccgtcac cgacaccgac ctcgccttct   29880
ccctggcgac cacgcgggcc gcgctcgaac accgcgccac ggccgtcgcc ggggaccggg   29940
agggcctgct ggccacggtg cggaccatcg ccgacggatc ggcggccacc accgtggccg   30000
gcgccgaccc caaggtggcg ttcctcttcg cgggccaggg ctcccagcgc gtcggaatgg   30060
gccgggaact cgccgcgcgc ttccccggtgt cgccgccgc gctcgacacg gtgtgcgggg   30120
ccctcgaccc gtatctcgac cgggcgctgc gcgatgtcat cgacggtgac gcgccgaccc   30180
tggactccac cgaccacgcc cagcccgcgc tgttcgcgct ggaagtggcg ctccaccggc   30240
tgctggagtc gtggggtgtc cggcccgacg cggtcgccgg gcactcggtc ggggagatcg   30300
ccgccgcgca catcgccggg gtgctgacgc tcgacgacgc cgcactgctg gtgagtgccc   30360
ggggccggct gatgcggcgc ctgcccgagg cggcgcgat ggtggcgatc gaggccccgg    30420
aggccgaagt cctcccgctc gtcgccccgt tcaccggacc gttcaccggc gccggggcat   30480
ccgtcgccgc cgtcaacacc gcgacgtcca ccgtcgtctc gggtgacgag agcgccgtac   30540
gggagatcgc cgcgcacttc gaggagcgag gcgtccgcac caaacggctg cgggtgagcc   30600
acgccttcca ctccccgctg atggagccca tgctcgccga gttcgccgcg gtcgtcgagg   30660
gcctgtcgtt cgccccgccc gagctcacct tcgtctccac cgtcaccggc cgggccatga   30720
ccgatgaagt ggccaccccc gcctactggg tccgtcacgc gcgggacgcc gtccggttcg   30780
cggacgccgt caccgaactg gcctccctcg gtgtcaccgc gctcgtggaa ctgggcccgg   30840
acgcgaccct ctccgccctg gcggcgggcg ccgccccggt ggtcctgccg gtgctgcgca   30900
aggaccggga cgaggagcgt tccgccgccg ccgcgctgac cggcctgtgg gcgcacggcg   30960
taccggtggc gtggcccgcg tacttcaccg gcaccgaccc gcgccccgcc gacctgccca   31020
cctacgcctt ccagcgggag cggtactggc tcgaccccgt cacctccgcg cccgccgggg   31080
cgagcgccct cgggctcggc gcggcggacc atccgctgct cggcgccgtc accaccctcg   31140
cggcgggcga cgggctgctg ttcaccggcc ggctcgccac cgcgacccac cggtggctcg   31200
ccgaccacgc cgtcgacggc accgtcctgc tgccggcac cgccttcgtg gaactcgccg   31260
tacgcgccgg ggacgaggcg gggtgcgacc gcgtcgacga actcaccctg ctcgccccgc   31320
tcgtgctgcc cacgcacgac ggcgtacgcc tccagatcgc ggtgggcgcg cccgaccgg    31380 cgggccggcg cgccgtcacc ctgcactccc ggcccgaggc gtacggcgcg gacgaaccgt   31440
ggacgctgca cgcgagcggt ctcctcgccc cgtccaccac cccgccaccg gacgacctcg   31500
cggtctggcc gcccgagggc gccacggcgc tgccggtcga cgggtctac gcccgcctgg    31560
```

```
ccgaacgggg ttacggatac gggcccgcgt tccaggggct gcgcgctgcc tggacccgcg    31620
gcgacgaggt cttctccgag gtcgccctcg atccggtggg gcagcgggac gccgcggcgt    31680
tcggcctcca tccggcgctg ctggacgccg ccctgcacgc caccgccgta cggaccctcg    31740
gcgacggggg agcgcggctg ctgccgttct cctggaacgg tgtgtcgctg tacgcctcgg    31800
gcgcgaccgc gctgcgcgtg cgggtcgccc cggcggacga cggcgcgctc tccgtgctcg    31860
tgacggacga cgaggggcgc cccgtcgcct cggtcgacgc gctgaccgta cgggcggccg    31920
gcgccgacga cgtcactgcg gccggagggg cgacgacgc gctgttccgg ctcgactgga    31980
ccgaactccc gcccgccgac gcgccggaac gggggcccgg gagcctggtg gtgctcggcg    32040
gcgacggcct cggactcgac ctcgatcccg gtgccggccc cgccgtgcgc gtccacgccg    32100
cactcgcggg gctggacacc gtgccggaca ccgtcctcgc gccgttcctc accccggtg     32160 cgggcggcac ggacctcgcg ggcgccgccc acaccgccac ccggcgggcg ctcgcgctcg    32220
tacgggagtg gctcgccgac gagcggttcg cggcgtcccg gctggtcttc ctcacccgtg    32280
gcgcactcac cgccgacctg gcgaacgcgc cggtctgggg cctcgtacgc gccgcgcagt    32340
cggagcaccc cggccggttc accctgctcg acctggacga gatcaccccc gagggcgtcc    32400
gcgcggggct cgccgccgat cattcccaac tcagggtgac cgagggacgg ttgcgggtgc    32460
cccggctcgc ccgggtgggc gccgccgccg gtggcgcgga gcgccccgcc ccctggtccc    32520
cgtccggaac cgtactgatc accggcggta cgggcggact cgggagcctg gtcgcccgcc    32580
atctcgtcac cgagcacggg gtgcgccgcc tcgtcctcgc cgggaggcgc gggcccgagg    32640
cccccggcgc ggccgaactc tccgccgaat tgggcgcgtt gggtgccgag gtgaccgtcg    32700
tggcctgcga cgccgccgac cgggacgccc tggccgccct gctggccgcg cacccgccga    32760
acgccgtcgt gcacacggcg ggcgtgctgg acgacggcgt catcgcctcg ctgacacccg    32820
agcgtctcga cgccgtcctg cggcccaagg tggacgccgc cgtcaacctg cacgaactca    32880
cctcggaact cgaagcgttc gtcctcttct cctcggcgtc cgggctgctc ggcggcgcgg    32940
gacaggccaa ctacgccgcc gccaacgcct ttctcgacgc cctcgctacc gcccgtaccg    33000
cacagggcct gcccgcgctc tccctcgcct ggggagcctg ggccggtgac cacggcatga    33060
ccggcaccct ggacgaggcc gacacccggc ggatggcgcg cggcggagtg ctgccgctcg    33120
gcgcggagcg cggactcggc ctcttcgacc gggcgttggc ggctgaccgg ccgctgctcg    33180
tcccgatgct gctggacacc gccgccgtac ggaactccgg cgagcccgtg cccgaactcc    33240
tgcgcggcct catccggccg ccccgccggc gcggcgcgg gggcggcgcc ggggacggcg    33300
gtggcaccgc cctggcgcgg aggctggccg cgctcgaccc ggccgaccgc gcggccgaac    33360
tgctcaccct cgtccgtacc gaggtcgccc tcgccctcgg atacgccgac ccggggacca    33420
tcgaggccga caaggcgttc aaggacctgg gcttcgactc gctgaccgcc gtggagctgc    33480
gcaacgcgct gcacacccgg accgggctcc ggctgcccgc caccctcctg ttcgacgcgc    33540
ccaccccgct ggtcctcgcc ggccggctcg ccgccgaact cgccgggacc ggcggaccgg    33600
gcgccgcagc cccggccgcc caggcacgcg cccgtaccga ccaggagccg atcgccatcg    33660
tcgcgatggg ctgccacttc cccgcggggg tgcgctcgcc cgaggagctg tggtccctcg    33720
tcaccggccg cgtcgacgcc gtctccgcct tcccggacga ccggggctgg acgtggacg     33780 cgctgtacga cacggacccc gaccggccgg gcacctcgta cacccggcac ggcggattcc    33840 tgcgggcgc aagcctgttc gacccggcct tcttcgggat gagcccccgc gaggcgctgg    33900
ccaccgaccc gcagcagcgg ctgctgctgg agaccacctg ggaggtgttc gaacgcgccg    33960
```

```
gtatcgaccc ggcgacggtg aagggcaccc cgaccggtgt cttcgtcgga gtcatgtaca   34020
acgactacgc acagtgcctg gcggagagcc tggaagggca catcgccggc ggcagcgccg   34080
ccagcgtggc atccgggcgc ctctcgtaca ccttcggcct cgaaggcccc gccgtcaccg   34140
tggacacggc gtgctcctcc tcgctggtcg ccgtgcacct cgccgcccag tcgctgcggc   34200
agggcgagtg caccctggcg ctcgcgggcg gtgtcaccgt catgtccacc cccaccacct   34260
tcgtcgagtt ctcccggcag cggggcctct cgcccgacgg ccggtgcaag gcgtacggcg   34320
cggacgcgga cggcaccggc tggtccgagg gcgtcggcct gctcctgctg aacggctct   34380 ccgacgccga acgcaacggc cacgagatcc tcgccgtcgt ccggggcagc gccgtcaacc   34440 aggacgcgc gtccaacgga ctgaccgccc ccaacggccc cgcccagcag cgcgtcatcc   34500
gccaggccct cgccaacgcc gggctcggcg ccgccgacat cgaggccgtg aaggacacg   34560 gtacggggac gaccctgggc gacccgatcg aggcgcaggc cctgctcgcc acgtacggac   34620
aggaccggga ccgcccgctg tggctgggct cgctgaagtc caacatcggg cacacgcagg   34680
ccgccgcggg cgtcggcggc atcatcaaga tggtgcaggc catccggcac ggcgtcctgc   34740
cccgcaccct gcacgcggac gagccgtcgc cgcacgtgga ctggtccgcg ggcgccgtct   34800
cgctgctcca cgagaacctg ccgtggcccg ggacgggacg gccgcgccgc gccggcgtct   34860
cctcgttcgg ggtgagcggc accaacgcgc acaccctcct cgaagaggcc ccgcgcccgg   34920
ccgccccgcc ccggccccgc gaggtgccgc ccccgccgac ggagccggtg ccctgggtcc   34980
tctccgcgaa gaccccgcag gccctgcgcg cacaggccgc ccggctcgcc cggcacctgg   35040
acgacgaccc ggaggtctcc ggcgccaccg ccgccgatgt cgggctgtcc ctggcgacca   35100
cccggtccgc cttcgaccac cgggccgtcc tcgtcggcca cgaccgggc gaattccgcg   35160 ccctgctggc cgagttggcg accgacaccg tatccgcgcg gatcgtacga ggcaccgcgc   35220
gccccccggg caagaccgtc ttcgtcttcc ccggccaggg ctcccagtgg cccggcatgg   35280
ccgtcgacct gctcgcacac ccggtgttcc gggcccggat ggaggagtgc gccgccgcgc   35340
tcgcacccca tgtggaatgg tccctgtggg acgtcctggg cgacgccgag gcgctgcgtc   35400
gcgtggacgt cgtccagccc gcgctcttcg ccgtgatggt ctcgctcgcc gcactgtggc   35460
gctcgtacgg tgtggagccc gccgccgtcg tcggacactc ccagggcgag atcgccgccg   35520
cctgcgtcgc gggcggcctc accctgcccg acgcggccaa ggtcgtcgcc ctgcgcagcc   35580
gggcgatcct ggaactggcc ggacgcggcg gcatggtgtc gctgcccctc tccgccgccg   35640
aggcggccgg gcgtctcgac ggccgggacg gcctgtcggt cgccgcggtc aacggacccc   35700
gctccgtcgt ggtggcaggc gacgaccagg ccctcgacgc gctgctggcc tcctgcgagg   35760
ccgacggcat ccgcgcccgc cgggtccccg tcgactacgc ctcccactcc gcgcacgtcg   35820
aggccgtcca ggaggagctg cgtaccatcc tggacggcat cacaccacgc ccagggcccg   35880
tcgccttcta ctcggccgtc accggcgccc tcctcgacac caccgcactc gaccccgcct   35940
actggtaccg caacctccgc gagaccgtac ggttcgacga ggccaccgg gcgctggccg   36000 gcagcggcca ccaccgcttc atcgagatgg accgcaccc cgtcctcgcc gtggggatcc   36060
gcgagaccct ggaagagttc ggccgccacg gccaggtcct cggctcgctg cgccgcgacg   36120
acggcggccc cgagcgcctg ctgctctccc tcgccgaagc acacgccgga ggccaacggc   36180
tcgactggca ggcggtgttc gccgggctcg gcgcgcgccg cgtcccgctg ccgacgtacc   36240
cgttccaggc cgagcggtac tggcccgccc cgcgcgccgg acggcgcggc gacctcaccg   36300
ccctcggact gagcgcgagc ggccatccgc tgttcggcgc cggggtcccg atggccgagg   36360
```

```
gcgacggcgt actcctcgtc ggcgcgctct ccctggccac ccacccgtgg ctggccgacc    36420
acgccgtggg ggacacggtc ctcctgcccg gcacggcctt cgtggaactc gcgctgcgcg    36480
ccggggacca catcggctgc gccggactcg ccgaactcac cctccaggca ccgctgatcc    36540
tgcccgcccg gggcaccgta cgcctccagc tcacggtggg ggagccggac gaacagggca    36600
ggcggccgat cacggccggc tcccggcaga cgacgacgg gccatggacc cggcacgcca    36660
ccggcgtact cgaaccgacg gccgccgcgc cgggaacggg ccccgacgcc acggacttca    36720
ccgcgtggcc gccgcccggc gccaccccg tcgcggtcga cgacctctac gaccggctgc    36780
ccggcatcgg gctgcggtac gggcccgcct tccagggcgt ccgcgcgctc tggcggcgcg    36840
gcgacgacct gttcgccgag gtacggctcg cccccgaaca gcgcgacgag gcagggctgt    36900
tcggggtgca ccccgccctg ctggacgcgg cgctccaccc gttcctgacc ggcgtcctgg    36960
acgccgacac acacgacgga caggtggcgc tgcccttcgc gtggaccggg gtggccctcc    37020
acgcgacggg cgcgagcgcg ctacgggtcc ggctcgcccc gggaggccgc gtcgaggccg    37080
ccgacgaaag gggcgcgccg gtggcgaccg tgggcgccct ctcctcccgg cctgtccccg    37140
tcgccggact cgccgcacac ggcccgctct accggatcgt ctggcagccg ctcgccccgg    37200
acccggccgg tgacgcgggc ggtacgggcg gggtgatcct gggcgaggac atcctcggcc    37260
tcggactgcc cgcgtacccc gacctcgaca cgctcgccgc cgcccgccg gcggccggc     37320 cggtgttcgc caccctgtcg ggcgggccgg gggcggacgc cgtccacacc gccacgcacg    37380
aggcgctggc cctggcccgg gcatggaccg gcgacgaacg cttcgacgga tcccgtctgg    37440
tcgtggtggg ccggggcgcg gtcgcgacgg ccggggacga ggacgtgccc gacctggccg    37500
cggcggccgc acacgggctg ctgcgctcga cgcagtcgga acaccccgac cggatcgtcc    37560
tggtcgacat cggccacgcc ggggattcca cggccctgct gtatgccgcg cgtcctgcg    37620 acgagcccaa cgtcgccgta cgcgatggcg agttgcgcgt accgcgactg gagcgcgtac    37680
cggcggacgc cgatgagccg accggatcgt gggatccgga cggtacggtg ctgatcaccg    37740
gcggcaccgg agtgctgggc ggcctggtcg cccggcatct cgccgccacg cacgggtac    37800 ggcgtctcct gctgaccagc aggcgcggct ccgattcccc gggcgccacc gaactcgccg    37860
cggagctggc ggcgttgggc gccgaggtga ccgtcgcggc ctgcgacgcc gccgaccggg    37920
acgccctggc ggccctgctg gccggccacc ggatcacctc cgtcgtgcac accgccggtg    37980
tactggacga cggggtcatc ggcgccctca ccccgaacg cgtcgacacc gtcctgcggc    38040
ccaaggccga cgcggcactc cacctccatg aactcaccca cgatctcgac gcgttcgtgc    38100
tgttctcctc ggccgccgcc gcgttcggc ccccgg gaca gggcaactac gcggcgggca    38160
acgccttcct cgacgcgctc gcccagcacc gcagggcccg cgggctgccc gccgtatcgc    38220
tcgcctgggg cctgtgggag cagtccagcg cgatgaccgg ccacctcggc gcggacgacc    38280
tcgcccggca gcgcgcgacc ggggccctcg cgctcccgtc ggcggagggg ctacggctct    38340
tcgacgcggc gacggccacg cgcggcgcg accggtgac cggcgcgggc tcgacggcgg    38400
ttcagggtgc ggcacttctc ctgccgctgc ggctcgacct cgcccggctg cgcgcctccg    38460
ccgcccccgt cccccgcgctg ctgcgcggac tcgtcaggac cgccgcgcgc ccaccgccg    38520 gtacggccac caccgacggc tcgggctcg cccaccggct gaccgccctc ccgtcgagc     38580 agcagcaccg cgaactcctc gacctggtac ggggccacgc cgctgccgta ctcggccacc    38640
cgggaccgga ggcgatcgac ccggacacgg ccacccgcga cctcggcttc gactcgctca    38700
ccgccgtggc gctccgcaat cagctcgccg aggccaccgg gctgcggctg cccgccaccc    38760
```

```
tcgtcttcga ccacccgacc ccggccgcgc tcgccaccac cctgcgcacc cggctgaccg    38820
gcatctccga ggcaccggcc gcaccggtcg ccgggaccgt cgtaccgtcc gacgacccga    38880
tcgccgtcgt cgggatggcc tgccgctacc cgggcggggt gcgctcgccc gaggacctgt    38940
gggaactggt ggcggcgggc ggcgacgcga tcgccgcgat gcccggcgac cggggctggg    39000
acatcgacgg gctctacgac cccgaccagg accgcaccgg caccttcgcc acccgcgagg    39060
gcggattcct ctacgacgcc gccgagttcg accggcgtt cttcgggatc tccccgcgcg     39120
aggccctggc catggacccg cagcaacggc tgctgctgga cctcgtgg caggcgttcg      39180 agcgggccgg tatcgacccc gcgacggcgc gcggcagcag gaccggtgtg ttcgtcggcg    39240
tcatgtacca cgactacggc gccggggcgg acgccgtacc cgaggacgtc gagggtatc     39300 tcggcggcgg tacggcgggc agtgtcgcct ccggccgcgt ctcctacacc ctcggactcg    39360
aaggcccggc ggtcaccgtc gacaccgcct gctcctcctc actggtcacc ctgcacctcg    39420
ccgcgcaggc actgcgggcc ggcgactgca cgatggcgct cgcgggcggc gccacggtga    39480
tgtcgacgcc cggcaccttc gtcgagttct cccggcagcg cggcctcgcc gccgacggcc    39540
gctgcaagtc cttcgccgcg ggcgccgacg gcaccggctg gggcgagggc gccggaatgc    39600
tcctcctgga acggctctcc gacgccgaac gcaacggcca cgacgtgctc gcggtcgtcc    39660
gctccaccgc gatcaaccag gacggcgcct ccaacgcct ctccgcgccc aacgccccg      39720 cccagcaacg ggtgatccgc caggccctgg ccaacgcccg gctctcctcc gccgatgtcg    39780
acgtggtcga ggggcacggt acggggacca cgctcggtga cccgatcgag gcggacgcgc    39840
tcctggcgac ctacgggcag gaccgtgaac accgctctg gctcggctcg ttgaagtcga     39900
acatcggcca cacccaggcc gcagccgggg tcgcgggcgt catcaagatg gtgcaggcgc    39960
tgcgacacgg cctgctgccc cgcaccctgc acgtggacca accgagcccg cacatcgact    40020
ggacggcggg agcggtacgg ctgctcaccg acgcccggcc gtggcccgac acgggacggc    40080
cgcgccgcgc cggtgtctcc tcgttcgggg tgagcggcac caacgcgcac gccatcctcg    40140
aacaggcccc cgaggcgccc gtacccgacc atcgggactc cccggcccc ggtgcggtgc     40200 cgtgggtgct gtcggcgaag accgccgaag cgctgcgcgc ccaggccggg cggctggccg    40260
cgcgggcgac ggaccggccg ccgggcgatg tcggcctgtc cctcgcgacc acccgtaccc    40320
gattcgagcg ccgggcggtg gtgatcggcg cggacggcgc cgcgcttctc gcgggcacgg    40380
acgccctggc gcacggcgag cccagggccg atgtcgtcga gggcgtcgcg gacctgcgcg    40440
gccgtaccgt cttcgtcttc cccggccagg gctcccaatg ggtcggtatg gcaggcgagt    40500
tgatggagtc ctcgccggtg ttcgcggccc ggatggcgga gtgtgccgag gcgctggcgc    40560
cgtacacgga ctggtcgttg tccgatgtgc tgggcgacgg cgcggcgttg gggcgggtgg    40620
aggtggtgca gcccgcgctg ttcgcggtga tggtgtcctt ggccgcgctc tggcgttcgt    40680
acggtgtgga acccgcggcg gtcgtcgggc acagccaggg ggagatcgcc gccgcctgtg    40740
tcgccggggc gctctccctg gccgacgccg ccaggatcgt agccctgcgc agccgggcca    40800
tcgccgcgac cctggccggt cacggcggca tgatgtcgct ggcgctctcc gtcgccgagg    40860
ccgagagcca actcgcgcac cgggacggcc ggatcaccct cgccgcgtc aacggccccc     40920 gctccgtggt cgtggcgggg gagccggccg ccctggagga gctgcgggcc gccgtcgagg    40980
agagcggccg gcgggcccgg cggatccccg tcgactacgc ctcgcacacc gcccacgtcg    41040
aggcggtcga ggccgaactc ctcgccaccc tggccgatgt ggcgccgagg tccgcgaccg    41100
tgccgttctt ctccacggtc accgcaggat ggctcgacgg cacccgactc gacgccgcgt    41160
```

```
actggtaccg caatctgcgc gaaccggtcc gcttcgagga ggccgtccgg gaactcgcca   41220
cgcacggctt cgacttcttc gtcgagacga gcggccatcc ggtgctgacc gtcggcgtac   41280
gcgagaccct cgacgccctc gactcgcccc cgtcaccct gggttcgctg cgccgcgacg    41340
acggcggacc cgatcgcttc ctgcggtcac tggcggaggg acatgttcgc gggctgtccg   41400
tcgactggac gcccgcgttc ccgggggcac gccgtaccgc cctgcccacc tacgccttcc   41460
agcgcgagcg ctactggctg gagtccggca ggcagcgcgc gaccgctccg cgggacgcga   41520
cggaccgcgc gttctgggcc gccgtcgagc gcgcggacct ggccgagctg accggcaccc   41580
tcgccctgac cggggacgaa cccctcagcg ccgtactgcc cgcgctctcc tcctggcggc   41640
ggcgccaccg ggaacgctcc cgtacggacg gctggcgcta ccggatcacc tggcagcccg   41700
tcgccgccac gcgccggccg gccgccggca cccgcctggt cctgctgccc gccaccggcg   41760
acggggccgc gtgggccgac gcgctcggcg accccaccgt acggatcgtg gtggacgccg   41820
acgacccggc caccctcgcg gcccggctgc gcgcggtacg ggacgcgctg cccgacggcg   41880
gccggatcac gggcgtggtc tcgctgctgg ccctggacgg acgcgccggg ccggccggga   41940
ccgccgtgcc cgtgggtacg gccgcgaccc tcaccctggt ccaggccctc ggcgacgccg   42000
acgtggacgc cccgctgtgg ctgctcaccc agggcgccgt cgcggtcggc cccgagcggc   42060
tcgcgcgggt gccccaggcg cagatctggg ggctcggccg ggtcgtcgcc ctggagcacc   42120
cggaacgctg gggcggcctg atcgacctgc cggagtcgcc cgacggggcc gcgacggagc   42180
ggctggccgg ggcgctgacc cgtaccgacg acgaggacca actcgcgatc cgcgcctccg   42240
gtgtgtacgt caggcgcctc acccgagcgc ccgagacgtc acccacgtcg tcgtccacgt   42300
cgtcccccac gtcgtcgtcc gcggcggtcc ggacgctgc ggtcccggac gcgacctggc    42360
gcccgtccgg gacctggcgc ccgtccggga cctggcgccc gtccgggacc gtcctggtca   42420
ccggcggtac cggcgccctc ggcgcgcggg ccgcccgctg gctggcggcg tccggggcgg   42480
gccacctcgt cctcaccagc aggcgcggcc ccgaggcgcc cggcgcggcc gaactcaccg   42540
ccgaactgcg cgcattgggc gccgaggtga ccgtcgccgc ctgcgacgcc gccgaccgtg   42600
acgcgatggg acggctgctg gccgagcacc cgccgaccgc ggtcgtccac accgcgggcg   42660
tgctggacga cggcgtcctc gaccacctcg acaccggcag gctggcgacg gtgttcggcc   42720
ccaagacggc cgccgcgacc gtcctcgacg cgctgacccg cgacctcggc ctcgacctct   42780
cggcgttcgt cctgttctcc tcggccgccg gagtgctggg cagcgccgga caggccaact   42840
acgccgccgc caacgcccat ctcgacgccc tcgccgaaca gcgccgtgcc gacggcctgc   42900
ccgccacctc cgtggcctgg ggcgcctggg cggacagcgg gctcgccatg gacgcgggcg   42960
tcgtggagcg gcggctccag cagggcggcg tcctgccgat ggccccgac ctcgccctcg    43020
gtgcgctcca acaggccctg gaccagggcg atacggcggt gatggtcgcc gacatcgact   43080
ggcagcgctt caccggcgcg ggcgcggggcc ggacccgccc ctggctcggc cggctcgccg   43140
gcgccccgac cgcccccgac gggaccgcgc cggacgcggc accggacctc ctccggcaac   43200
tccggggcca gggcgccgcc cagcgcgccc gcaccctgcg gacgctcgtc cggacccagg   43260
ccgccgtcgt cctcggccac gcggcccccg catccgtcga gcgggacgg gcgttccgcg    43320
acctcggcct cgactccctc accgccgtcg aactgcgcaa ccggctcggc gcggccaccg   43380
gactgaaact gcccaccacc ttggtcttcg accatccgac ggccgccctc ctcgcggacc   43440
acctggagca cgaactcttc ggcgccgacg aggcgctcgc cccgggcgac gagctctccc   43500
cggacgccgc gccgctcgcc gcgaccgaca gcgacccat cgtgatcgtc gccatgagct    43560
```

```
gccggttccc cggtggcgta cggaacccgg acgacctgtg ggagctgctg gccgccgggc   43620
gcgacgccgt cggcgcgttc ccggacgacc gcggctggga cctcgacgcg ctccaccacc   43680
ccgacccgga ccaccggggc acgacgtaca cccggcacgg cgccttcctc cacgacgcgc   43740
ccgacttcga cgccgacctg ttcgggatat cgccgcgcga ggccctggcc atggacccgc   43800
agcagcgggt gctcctggag acggcctggg aggcgttcga gggtgcgggc atcgacccgg   43860
ccaccctgcg gggcagccgg gccggcgtct tcgtcggcac caacgggcag gactacgcgg   43920
gcggtcccgg cgacgcgccc gaaggcaccg agggctatct gctggcgggc aacgcggcca   43980
gcgtcgtgtc cggacgcatc gcctacacct tcggcctgga gggcccggcc gtcaccgtgg   44040
acaccgcctg ctcctccgcg ctggtcgccc tgcactgggc ggcccaggcc ctgcgccagg   44100
gcgagtgcac actcgccctg gccggcgggg tgtcggtgat gtcgacccCg gccgcgttcg   44160
tggagttctc ccggcagcgc ggcctcgccc ccgacggccg gtgcaaggcg ttcgccgact   44220
ccgccgacgg tacgggctgg ggcgagggcg ccgggctggt cgtgctggaa cggctctccg   44280
acgccgaacg ccacggccat ccggtactgg cgctcgtgcg cggcagcgcc gtcaaccagg   44340
acggcgcctc caacggactg accgcgccca acggccccgc ccagcagcgg gtgatccgcc   44400
aggccctcgc ccatgcccgg ctcgccccgg ccgacatcga cgccgtcgag gcacacggca   44460
ccggcaccac cctgggtgac ccgatcgagg cgcaggccct gctcgccacg tacgggcagg   44520
accgcgaacg cccgctgtgg ctcggctcgg tcaagtccaa cctcggccac acccaggccg   44580
cggcgggcat ggcgggggtg ctgaaaatgg tgcaggccat gcggcacgcg accctgccca   44640
ggaccctcca tgtggacgcg ccgacctccc aggtcgactg gtcggcgggc gcggtgtccc   44700
tgctgaccga ggagcggccc tgggaagcgg gcgaacggcc gcgccgcgcg ggggtgtcat   44760
ccttcggcgt gagcggtacg aacgcccacg tcatcctcga acagggaccg gcggccccgt   44820
cccgccccgt accccccgcc gcacccgacc ccctgcccct gccggtcgtc ctgtccgggc   44880
ggaccgaacc ggccctgcgc gcccaggcgt cgaggctgcg cgcgcatctg gccgcgcgcc   44940
cggacgacac gctcctggac ctcgcgttct cgctggccac cacccgctcc gcgctcgacc   45000
ggcgcgccgt ggtgctcgcc ggctcccgcg acacgctgcg gagcggactc gacgcgctcg   45060
ccgagggccg gagcgccgcc ggagtcgtca ccggcgccgc caggaccggg cggagcgtcg   45120
cgttcctgtt ctccgggcag ggctcgcagc gtgcgggcat ggggcgcgaa ctgtacgacg   45180
cgtaccccgt gttcgcccgc gcgctcgacg agatctgcgc ggaactcgac ccgctcctcg   45240 accccccggct cggcgggtcc ctgcgtacgg ccatgttcca cggccccgcc caggacagcg   45300 acccctcga ccgcaccgag ctgacccagc ccgccctctt cgccctggag atcgccctcc   45360
accggctgct ggaccactgg ggcatcaccc cggagtacgt ggcgggccac tccgtcgcgg   45420
agatcgccgc cgcgcaggtc gcgggcgtcc tgtcgctgcc cgacgcagcc gccctggtgg   45480
tggcgcgtgg acggctgatg caggcactgc ccggcggcgg cgcgatgctc gccgtgaacg   45540 ccccccgaggc ggccgtcctc cccctgctgg cggagcacga gggccgcgtg gccgtcgccg   45600
ccgtcaacgg gccggcctcc gtggtcgtcg ccggtgacga ggaccggtc acccggatcg   45660 gtgaactcct caccgcatcc ggggtacgga ccaggcggct gcgggtcagc cacgccttcc   45720
attcgccgca catggacggg atgctgacgg agttccgccg gatcgccgac ggattgacgt   45780
acggcacgcc ccgtatcccc gtcgtgtcgg cgctggccgg ccggagcgtc accgacgaga   45840
tgggcacggc ggagtactgg acccggcacg cccgcgacgc cgtccggttc cacgacgccg   45900
tcgggaccct gcgggaccct ggcgtcaccg tcttcgtcga actcggcccg gcagcgccc   45960
```

```
tcaccccgat ggtggtggaa tccctcggcg acggggcgag cgccctcccc gtactgcgcg   46020
gggaccggac ggagaccgac ggcgcgctcg acgcgctggc ccggctgcac gtcgccgggg   46080
tgagccccga ctgggccgcc ttccacgccg gttccggcgc ggcgcgcgtc ccctcccct    46140 cgtacgcctt ccagcggtgc cggtactgga tggagcgccc cgcacccgcc gccgacctcg   46200
gctccgccgg gctcaccgtc tccgggcatc cgctgctcgg cgccggggtg ccgctcgcgc   46260
acggcccggg cgcgctcttc accggctcgc tctcggtacg gacccacccc tggctggccg   46320
accacacggt ctccgcgtg accgtcctgc ccggcacggc cttcgtggaa ctcgcggtgc    46380
acgccgggga ccaggtcggc tgcgccaccg tggaagaact caccatcgag gcaccccgg    46440 tgctcccgga gcgcggcgcc gtccaggtcc agctctgggt cgacggaccc gacgcctcgg   46500
gacgccgcgc actgaccctg tacgacgggc ccggcagcga cgaccggac gcgccggccg    46560 cgtggacccg gcacgccggc ggagtcctcg cgcggggcgc caccgcgccg ggggacgccc   46620
tcacggcgtg gccgccctcc ggcgccgagc cggtgccggt cgacgacctg taccgtacgg   46680
tcgccgacgc cgggttcggc tacggaccgg tcttccgcgg gctgcgcgcc gcgtggcgcc   46740
ggggcgacga ggtgtacgcc gaggtcgccc tccccgagga gaacggggcg ccgacgagg    46800 cccgccggtt cggcctgcac cccgccctgc tcgacgcggc gctgcacacc gtcgcgctct   46860
cccgggccgg ccaggacggc atcggacgga tgccgttcgc ctggtccggg gtggccctgc   46920
acgcctcggg cgccgccgcg ttgcgcgtac ggctcaccgc caccgggacg gacacggtcg   46980
ccctgaccgt cgccgacccg gccggggcga gcgtcgccac cgtggagtcg ctgaaactcc   47040
gcccggtcgc cgccgggctc ggcgcggccc ccgccaggac cgacgccctc cacacggtgg   47100
agtggacccc gctggagacg cgcccgtcg acaccccgt cgacaccccc gacaactccg     47160
tcgcacctgt cgtacctgtg gcgcccgtcg tacggatcgc cacggccgcc gatctcgccg   47220
cgctggacga ggtaccccggt ctcgtcgccg tggccctgcc ccgcacggcg ggcacggcgg  47280
ccgaccaggc ccgcggtgcc gtgcaccgga cggtggagct gcttcaggca tggctcgcgg   47340 accccggtg cgccggatcc cgtctcgcct tcctgaccag cgccgctgcg gggcccgaca    47400
gccccgacgg tcccggcacc ttcggcgccg gtagccccga cagtccgtac ggcgccgaca   47460
cgctcgacgg cctcggtcag gcgcccgtct ggggcgcggt gcgctcggcg cgcgccgaac   47520
acccgggccg cttcctcctc gtggacgccg acgacccggc cgcctgcctc gccctgctgc   47580
cctccctcgc cacgctggac gaacccgaac tggccgtacg cgccggggcg gtcaccgtgc   47640
cccggctgac ccggctctcc tccgacgacg cgctcgtacc ccccgccggg accgccgcct   47700
ggcggctcga catccccgtc cagggcaccc cggacaacct gcgcctggtc ggggaaccgg   47760
ccgccgccgc accgctggac gaccacgaga tccgggtcgc gatccgcgcg gcgggcgtca   47820
acttccgcga tgtcctcacc accctgggcg cctaccccgg ccccgccgtc atcggcatcg   47880
agggcgccgg catcgtcacc gggaccggcg ccggggtggc cgacctggcg cccggcgacc   47940
gggtcgcggg catcttctcc ggcgcgttcg gaccgatcgc cgtcaccgac caccggatgg   48000
tcgcgcgact ccccgaggac tggtccttcg aacaggcggc gtcggtcccc gtcgcgttcc   48060
tgaccgcgta ctacgccctc accgacctcg ccggcctcaa ggagggcgag tccgtcctcg   48120
tccacgccgc ggcggcgggg gtcggcatgg ccgccgtaca actcgcccgg catctgggcg   48180
ccgaggtgta cggcacggcg agcccggcca aatgggacac cctcaccggg gcggggctgc   48240
ccgccgaccg cgtcgcctcc tcccgtacga ccgacttcgc cggccagttc ctgaccgcca   48300
cgcacggccg cggcgtcgac gtcgtcctca acgcgctcac cggcgagttc atcgacgcct   48360
```

```
cgctgcggct gctgcccogg ggaggccgct tcctggagat gggcaaggcg gagatcagga   48420
ccgccgacgc ggtgggcacc ggccatccgg gcgtcgccta ccgggcgttc gacctcatgg   48480
aggcggggcc cgcgcgcatc cgggagatgc tcaccgacat cctcggcctg ttcgcgtccg   48540
gcgcgctgac cccgctgccc gtcaggacct gggacgtgcg ccgcgcccgg gaggcgttcc   48600
gccacctcgg ccaggcccgg cacatcggca aggtcgtcct caccgtgccc cgcccgctcg   48660
acccgtccgg caccgtcctg atcaccggcg cgaacggcgc cctcggctca cacatcgccc   48720
gccacctcgt caccgcacac ggcgcccgca ccctgctcct cgtcggccgc ggcggcgccg   48780
acgacctgcg cgacgaactg ctcgcgctcg gcgccgacgc gacctccgcg gcctgcgacg   48840
tcaccgaccg cgacgccctg gcccggctgc tctccggggt ctccctgacc gccgtcgtcc   48900
actgcgcggg cgtcctcgac gacggcgtgg tcaccgcgct gaccccgac cggatcgaca   48960 ccgtcctgcg ccccaaggtg gacgccgcgc tccatctgca cgaactgacc gcccaccacg   49020
acctcgccgc gttcgtgctg ttctcctcgg ccgccgccgt cttcggcagc ccggggcagg   49080
ccgcctacgc cgcggggaac accttcctcg acgccctggc ccggcggcgg cgtgccgccg   49140
gactgcccgc ccagtcgctc gcctgggccc cctgggcccc ggacgacggc atgaccagcc   49200
acctcacctc caccgacctc acccgcgtcg cccgcggcgg catggcctcc ctgacaccgg   49260
cccagggcct ggcgctgtac gacgcggccg gcgccgccga ccaggccctc gtcgtccccg   49320
tactcctgga cctcgccgcg ctgcgcaccc cggcggcggg caccgaaggg cccgcggccc   49380
tgctccgcgg cctcgtcacc cgcgccggcc ggcgggcggc gtccccggcc ggaacggcgg   49440
cctccgcgac cgcacccgag tggccgcgcc ggctcgccgc cctgaccgcc gccgaacgcg   49500
accaggtcct cggtgaactc gtcaggaccg aggccgccgc cgtcctcggc catgccacgg   49560
ccgacgccat cgaccccgac cggggcttcc tcgacctggg cttcgactcg ctgacggcgc   49620
tggaactgcg caaccggatg aacgccgcca ccgcgctccg cctccccgcc accctcgtct   49680
tcgaccaccc gaccccgctc gccctcgtcc ggcacctgcg cgacgcactg gccccggacc   49740
ccgggacgga tccggcgggt cccaccgcca ccgccaccgc cggcagcacc gacaccgcgg   49800 gaccccgcc ggagaacccc atcgactcca tggagctcga cggactgctt gagctggcgt   49860
acgagaacgc cgactcggac ttggagatgt catgaccggc accggcgccc ccaccggaac   49920
cgagcagagg atcgtcgacg cgctccgggc gtccctcaag gccaacgaga gactgcggcg   49980
gcagaacgac gaactcaccg ccgcctccgt agagccgctg gcgatcgtgg gcatgagctg   50040
ccgcttcccc ggcggggtcg ccaccccga cgcgctgtgg gagctgatct ccgccgggcg   50100
ggacgcgctc accccgttcc ccgcggaccg cgactgggac ctggcggcgc tgtacgaccc   50160
cgacccggac cgggccggca cctcgtacgt ccgcgtcggc ggcttcctcc acgacgcggc   50220
cgagttcgac ggggccttct tcggcatctc gccccgcgag gccgccgcga tggacccgca   50280
gcagcgcctc tccctggaga ccgcctggga ggtgttcgag cacgccggga tcgacccggc   50340
gaccctccgc tccagccgga ccggtgtctt cgtcggcgcc gccgaccagg ggtacggcac   50400
ccggctgcgc ccccgcccg aggacctgga gggatatctg ctgaccggca cgccgcctc   50460 cgtcatctcg gggcggatcg cctacacact cggcctggag ggcccggcgc tcaccgtcga   50520
cacggcgtgc tcctcgtcgc tggtcgccct ccacctcgcc ggacaggcgc tgcgccgcgg   50580
cgagtgctcg ctcgccctgg cgggcggggt gtccgtcatg gtgaccccg gcaccttcgt   50640 cgagttcagc aggcagcgcg ggctcgccgc cgacggccgc tgcaagtcct tcgccgccgc   50700
cgccgacggc accggctggg gcgagggcgc ggtcatggtg ctgctggaaa ggctctcgga   50760
```

```
cgccgaacgg agcggacacc ccgtgctggc cgtcgtacgc ggcagcgccg tcaaccagga    50820
cggcgccagc agcggcctga ccgcccccaa cggccccgcg cagcagcgcg tcatccgcga    50880
ggcgctgggc gccgcccggc tcaccccggc cgatgtggac gccgtcgagg cgcacggcac    50940
cggcaccgcc ctgggcgacc cgatcgaggc gcaggcgctg ctcgccacgt acgggcagga    51000
ccgcgaacac ccgctctggc tcggctcggt caagtccaac atcggccaca ctcaggccgc    51060
ctccgggctg gcgggcgtgg tcaagacggt gctggcgctg cgccacggcg tactgccgag    51120
gacgctgcac gtcgacgcgc cgaccccgcg cgtggactgg aagcgggcg ccgtgtcgct    51180 gctgaccgag gcgcggccct gggtacgca cgggcgcccc cggcgggccg gggtgtcctc    51240
gttcggcgtc agcggcacca acgcccacgt cgtcctggag aagcgccgg tcgcaccggc    51300 cgttcccgaa accgccgtac cgcgcccgg cgtcctgccc tgggtcctgt cggccaggag    51360
cgaggaggcg ctgcgcgccc aggcggcgcg gctggccgcc cacctcacca ccaggtccgg    51420
cgacagcctc gccgacatcg gctactccct cgccaccacc cgctccgcct tcccgcacag    51480
ggcggccgtg gtcgccgccg accgcgattc gttcctgcgc ggcctggacg cgctcgccac    51540
cggcgcgccc ggcccggtca ggggcaccgc gcgccccac tccaggacgg cctggctctt    51600
ctcgggacag ggcgcccaac ggcccggcat gggacgggac ctggccgacg ccttccccgc    51660
cttcgcggac gccctggacg aggtgtgcgc gcagctcgac ccgcgactgc cccgcccgct    51720
gcgggaggtc atgttcgccg ccgagggaac accggaggcg gcgctcctgg accgtacgga    51780
gttcacccag cccgcgctgt cgccttcga ggtggccctg ttccggctgt tcacgtcgtg    51840
ggggctcacc cctgacctgc tgctcggcca ctccatcggc gagatcgccg ccgcgcacgc    51900
cgccggtgtg ctgtccctcc cggacgcgtg cgcgctggtc gcggcccggg gccggctgat    51960
gcaggcactg cccgagggcg gcgccgtcgt atcggtcagg gccgaggagg acgaggtcgc    52020
cgcctcgctg gccggccgga ccggccggct gggcgtcgcc gccgtcaacg ggcccgcctc    52080
cacggtcatc gccggggacg aggaggccgt catggaggcc gcccggtact gggaggcgcg    52140
ggggcgcagg acacggcggc tgcgcgtgag ccacgccttc cactcgccgc tgatggaacc    52200
gatgctcgcc gagctgcgga ccgtcgtcgc gggcctcacc ttctccgcgc cgcgtatccc    52260
ggtcgtctcg accctcaccg gcgagcccgc gaccccctg gacgaaccgg agtactgggt    52320
acggcaggcc agggagcccg tacggttccg cgacggcgtc cgcgccctgg aacggctcgg    52380
cgcccgcacc tatctggaga tcggccccga cgcggtcctc accccgatgg ccgagacctg    52440
cctgaccgga ccggcggccc tggtcgcggc cgtccgcagg accggcggcg gaccgctcgg    52500
cgcgcacacc gcgctggccg aactcttcgc ggacggcgcg cccgtggact ggcccgccgt    52560
gttccccgga gccgggcgcg tggacctgcc cacgtacgcg ttccgccgcc gccgcttctg    52620
ggcgagcgcg ggaccgtcgg ccgatgtcgg cgccgccggg ctcacccgg cgggacaccc    52680 gctgctcggc gccaccctgg agcccgccgc cggggaggc cccgtcttca ccggacggct    52740
ctcgctgcgc tcccacccct ggctcgccta ccacgccgtc ggcggtacgg tcctcttccc    52800
cggcaccggc ttcctcgaac tggccttcca gcgggggcg tacgtcggct gcggacgcgt    52860
cgacgaactc ctcgtcgagg cgcccctcgt cctcggcgca gagggcgcgg cccgggtcca    52920
ggtcaccgta ggcgaacccg gcgagcacgg cacccgtacc gtctccgtcc acgccaggcc    52980
cgacggcgcc gacctgccgt ggacgctcca cgcgagcgg gtgctcgcac cggacaccga    53040 accgccggc ttcgacctca ccgcgtggcc gccgacggg gccaccccgc tggaggtcga    53100
cgggctctac gcctccgtcg cggacctcgg ctacgactac ggctccgcgt tccagggcgt    53160
```

```
acggcgtgcc tggcggcgcg gcgcggagac cttcgccgag gtccgcctcc ccggcgaaca   53220
gcgcgagacg gcgggcgcct tcggcgtgca cccggcgctg ctggacgcct gtctgcacgt   53280
gctgggcctg tcggcggcg acgaggaccg gggcgccgcc tcgcaccggc tcgtcttctc    53340
ctggaacggc gtacggctcc acgggagcgg ccccgccgag ctgcgcgtac gcatgacgtc   53400
caccgggccc gactccgtca ccctggacgc ggccgacgcc accggccgcc ccgtggtgtc   53460
catcggctcc cttgccctgc ggagtgtcgc cgccgaccgg ctcagggccg cgacaggggc   53520
cgtccgcgac gccctgttcc gtatcaccct ggccgaactg ccccggcgg gagaggagtt    53580 ccgggccctg cggctggtgg cgctggagga cggggacgg accgcgtacg ggcgcccgg     53640 caccgcctcg tacgccggtc tcgaagccct caccaaggcg atcgacgacg gcctgcgcgt   53700
ccccgacgcg gtcgtcgtgc cctgcctgtc gggccgggac gcccacgggg ccacccaccg   53760
ggcgctcgac ctcgtaaggg aatggctcgc cgacgaccgg ttcgccccgt cccggctggt   53820
cttcctcacc agcggcgcgg tggggagggc gtcaccgac ctggtgcacg cgcccctgtg    53880
gggcctggtc aggtcggccg cgagcgaaca cccggaccgc ttcgccctgg tggacctcga   53940
cgacccggcg gaccggcacc gtacgctgcc cgccgccctc gcccacgcg agaccgaggt    54000 gatcgtccgg gccgggaccc cgtacgcgcc ccgcctcgcg cggctcgccg cctccggccg   54060
taccgtcacc acggacccgg cgggcaccgt cctcgtcacg ggcgccaccg gggcgctcgg   54120
cggcctggtc gcccggcacc tcgtgcgcgc acacggcgta cggaggctgc tgctgctcag   54180
ccgcagtgga gccgccgccg agggcgcgga ccatctcctc gccgacctgc gggagttggg   54240
cgcggaggcc gagttcgccg cctgcgacac ggccgaccgc gcggccctcg ccgacgtgct   54300
gggacgcgtg ccggccggcc gtccgctgac cgccgtggtg cacacggcgg gcgtcctcga   54360
cgactccgtc gtcaccgaac tcaccccgg ccggctcgac cgggtgctgc gccccaaggt    54420
cgacggcgcg ctcaacctcc acgaactgac cgccggcgcc gacctctcgg ccttcgtgct   54480
cttctcctcg gtcgcgggca tcgtcggcac ccccggccag gccaactacg ccgccgccaa   54540
cgccttcctg gacgccctcg ccggccaccg gcgcgcggcc gggctgcccg ccacctcgct   54600
ggcctggggg ctctgggcac cggcggcgg catgaccggc accctggacg actccgaccg    54660
ggccaggatc gcgcgctccg ggatgcgggc cctgtccgcc gaggacggac tcgccctgtt   54720
cgatctcggc tgggcccagg acgaggcggt cgtcgtcccc gcggcgttcg acctcgcggg   54780
gctgcgggga cgcgccccgca ccggcggcgt cccgcgccg ctgcgggccc tggtgccccc    54840
gccgccccgc cgggccggga cacccgccga cgccccctcg ctcgcccggc gctggccgg    54900 cctcccgag gacgagcggg acggcgcggt actcgaactg gtccggggtc tcgcggccga    54960
ggtgctcggc cacgggtcac cggacgcggt cggccccgaa caggacttca tcgagatggg   55020
gttcgactcg ctgaccaccg tggaactgcg caactgcctc gcggaggccg tcggttcacc   55080
cctcccggcc actctgctct tcgagtgcac gacgccccgc gccctcgccg cccggctgcg   55140
ctccgcggtg gcggtacccg aacaggccgc cggaccacgg ccgtcggccg agtccggggc   55200
gggcctgagc gccctgttcc gcgcggcgtg cgacgacggc cggttcgagg cgttcgtcca   55260
tctgctgggc gacgccgcct cgttccggcc caccttcacc gacggtacgg gccggcgcc    55320 gaggccgctg cggctcgcga cggggagga cccccggg ctcttctgct tccctcgtt      55380 cctggccatc gccggacccc agcagtacgc gcggttcgcc gccgccttcc gcggcgtacg   55440
cgaggtgacg gtgctccccg aaccgggctt cacggacggg ggtcccctcc cggccgacgt   55500
gggcgcgctc gtcgcactcc acgccgagac ggtacggcgc cacgcgggcc ccgccccgta   55560
```

```
cgccctgctg ggccactcct cgggcgcgat gatcgcgtac gccgtcgccg cccgtctgga   55620
agaactcggc gccgcgccgc gggccgtggt gctcctggac gtcgtcccga cggacgtgca   55680
cgcgctcccc ggcttccagt ccgatctggc ggccggtctg cgggagcggg acggggacgc   55740
cgcctcgctc gacgaccaac gcctcaccgc catgggcggc tacgtccggg ccttcgcgac   55800
ctgggagccc gcggagatct ccgtacccac cctgctggtg cgggcggggg agaaccactg   55860
gtcctcggcc tggccgcacc cgcacacggc cgtggacgcg cccggggacc acttcacgat   55920
gctggagacc cacgcggggg agacggcccg cctggtccag gagtggctgt ccggcctctc   55980
ctgacccacg taccgacgta cccaccgact cacgtaccca ccgactcacg tacacaccga   56040
ctcacctacg agccacctca cgtacgcacc acctcacgtc cccccggttc acacgaggaa   56100
ggaacgtcac ggcgatggca gcacgagcga cccacgcggt ggtcctgggc ggtggtctgg   56160
ccggcaccct ggccgccgcc gcactggcgg gccacgcgga ccacatcacc ctggtcgaac   56220
gcgaccggat gcccgccggc ccccaggagc gcacaggcgt gccgcaggcg cgccacgcgc   56280
acatgctgat gtccagcggc gcggaggcga tcgacgcgct cgtccccggc gtcaccaaga   56340
acctctacgc cgccggggcg caccgcgtca gcgtacggaa gggcctcgtc tcctccaccg   56400
cccagggctg ggtgccgagg tccgcggacc tccagtacgt catcacctgc gggcgggccc   56460
tgctggactg gaccgtacgg gaacgggtcc tcatggaccc gcgcgtgacc ctgctccagg   56520
gcacggacgt caccgggctc gacggcgaca gccgccgcgt caccgccgtc cgggtccgcg   56580
accgcgccac cggcgaggcg tcgctgatcg gggcggacct cgtcgtcgac gcgaccggcc   56640
gcggctcggc cgcgcgcacc tggctggagg agctggggat accccgggta cgggaggaga   56700
ccgtcgacac cggactcgcc tactccaccc ggctgttccg ggtgccgccc ggtgcggagc   56760
gggacttccc ggccgtgacc gtgatgccga gccccgccga cccggtcccc ggccgctcgg   56820
gcaccctgct gccgatcgag gacggccggt ggctggtcac cctgacgggc ctgaggcccg   56880
cgcagccgcc gacggacgac gcgggcttcc tgccgttcgc ccgcaccctg cgcaccccccg   56940 tcatcggcga cctcatcgag gcggcgcagc cgctcggccc ggtgtgcggc tcccgcagca   57000
cggccaaccg ccgccggtac tacgaggaac tctccctctg gcccgacggg ttcgtggccc   57060
tcggggacgc gctggccgcg ttcaacccccg tgtacgggca cggcatgtcc gtggcggcga   57120
aggccgcgac cgcgctccgt acggacctgg aacggtacgg atacctaccg gagcgctcgc   57180
ggcacgtcca gcgcgccgtc gcggccaccg tgaacgacgc ctgggccctc gccgtcggcc   57240
aggacgtcca gtacccggac gtcatcggcc cccggcccgg cgccgcggcg aagctgatgc   57300
ggcgctactc cgcccgcgcc gcgcgggcct ccgccaccccg gcccgccgtc gccgccgcga   57360
tcgccgacat cttcacactg tcggcgccgg tgtcccgcct gctggcaccg agggcggtgc   57420
tcggcgccct gcggggcccc ggcgccccgc ccctgacggc cccgcccttc acggagcggg   57480
agcgcgcgct cttctcccgc gaaccgcggg agcccacacg gaaaacggaa caggacacca   57540
cgcagtgatc accggcgacc ggaaggacag cgagatgagc cgaagcaccg aggagaccct   57600
gtggacgacg aggaggtcg gccaccgcta cgaccggctg tcgcgggtgc ccgaactgct   57660
ggcgttcggt gagagcctgc acttcgggta ctgggaggac cccgaggacg agggcggtct   57720
ctccgacgcg atgggacgcc tcaccgatct ggtcatcggc gggctggacg ccggaccccg   57780 cagccggggtg ctcgacctcg ggtgcggggt cggcggcccc gccgtcaagc tcgcctccgc   57840
caccggcgcc gaggtcgtcg gcgtcaccgt cagccgggaa cagatcacga aggccaccgg   57900
cctcgcccgg gccgagggcc tgacggggca ggtggtgttc cagtacgccg acgccatgga   57960
```

```
cctgccgttc gaggaggggg agttcgacgc ggtcttcggc ctggaatcga tcatgcacat   58020
ggaccggccc gccgtgctcg cgcagatcgc gagggtgctg cggcccggcg gccggctcgt   58080
cctgaccgac gaggtcctcc gcgcgccgat ccccgccgac cgcgccgagg acgacgagac   58140
cgtcgccggc tatctgcgcg ccaacatgat caggtccctg gccacaccgg aggcgtaccc   58200
ggagctgctg acgggcgccg gtctcgatcc cgaggcgatc acggacatca ccgaccggac   58260
cgtccgcccc acgttccgta ccctctggcg tcaggcgaac gaccgtctcg acacgatcct   58320
caacgacctg ggatcgcccc cggcggccgt ggcggaggag ctgcgcggct ggcaacgcct   58380
cgcggagatc cccgagttcg gctacctcct gatcagcgcc caccgcccgg ccgctgact   58440 gcctgtgccg ctgaccgccc gaaccgccta ccgctcgagc cgctgaccgg ccgcccgccg   58500
cggccgacga acgtctcccg gaggacgaca ccatgaccga gacctgcccc gcccacgccg   58560
tctacacccc cgcgtacttc aaggacccct accccgcgct gacccggctc agggacgccg   58620
gccccgtaca ccgcgtcgaa cgcccgacg ggctcgtcgt ctggctgatc acccgttacg   58680
ccgaggcaca ggcggcgctc ggcgaccccc gcctctccat ggacggcgag gtcgtccaga   58740
aggcgctggg ggccttcgcg tacgctacc tcgaccgga gaacgaggcg ccgcacaccc   58800
tgctgtcgag cgacccgccc gaccacaccc ggctgcgcag actggtcaac cggaccttca   58860
ccgcccgccg gatccaggcc ctgcgccccc gggtgcagga gctgatggac ggactgctcg   58920
acgcgctcgg accggacgcc gcgcacgccg acctgatcga ggcggtggcc gcgccgctgc   58980
ccatcgcggt gatctgcgaa ctgctcgggg tgccccgga ggactacgac agcttcaagc   59040
tgtggacgac gacgatgttc gtgctccccg ccgacgtcgg ggacggcatg tcaccgaccg   59100
acgccatgcg caacctgcgc cgctacctca gcgacctcat cgccgccaaa cgcgccgagc   59160
ggccggagac cggtcagggc gcggcgggcg ccgaggagtc cggggatctg ctctccgcgc   59220
tgatcgcggt ccgggacacc gacgaaggca ggctctccga gcacgagttg gtgagcatgg   59280
ccgtacaact gctcatcgcc ggacacgaga ccacggtcaa cggcatcggc aacgccgtgc   59340
tcaacctcct gcgccacccg gagcagctcg cggcgctccg ggcggaaccg gccctgctgc   59400
cccgggccgt cgacgaactg ctgcgcttcg aaggcccgtt ggagacggcg attctgcgcg   59460
tcgcgaccga gccgatcccg ctgggcgacc aggtcgtccc ggccggcgcc ctggtcaagg   59520
tggtcctcgc cgccgccaac cgggacccgg accggttcgc cgcgcccgac accctcgaca   59580
tcacacggaa gaacgagggc catctccagt tcggccacgg catccacaac tgtctgggcg   59640
ccttcctcgc ccgatggag accgagatcg cgatcagctc actgctgcgc cggtacccgg   59700
ggctctccct cggggtgccg gaggacgaga tccgctggcg ggagatcgcg atcatgcgcg   59760
ccctggcgga acttcccgtc acgctcaccg ggccggtctg aggggacgcc cggagtcaga   59820
ggtggtcgaa cggctccgcg agccggaagg tgccccgtgg cgcctcccgg tacgtggaca   59880
gcgtacggac ctggaagtac gcgccccacg acggctccgg cggcacgatc ccgtactccg   59940
tgctggtccg gaagccgtat ctgccgtagt acgcggggtc gcccagcagc gcgacgagcg   60000
gttcgccgag ggcgtccgcc gcgccgagca cggagtggac gagcgccagc ccgacgccgc   60060
gccgctgatg gccggggtgc acgccgagcg gagcgagcag cagcgccggg gcgccgtcga   60120
cccgcccacg tgtgcacgcc acatgcccga cgacctgccc ctcctcccg cccggtcgc   60180 cgacggcgac gagcgacagc gccggcagcc agtcgtcaca ggcgcgcagc gcgtcgagga   60240 gcgggggcctc cacgggctcc ggcctctccg gtgtcgcgaa ggcggccgtg gtgacggccc   60300
gtacggcggc atggtctgcg ggggtctcgc gtcggatcag caccggcaca gtctggaacg   60360
```

```
gcgccgcgcc tcggggcaaa gggattactc cgccggcgcc ccaccccgcg cctccccgaa   60420
gatcgtggcg agcaccgagg agagcggcgg accgccgagg acgtcccgca gctccgccac   60480
gccgtggcgc agctccgccg gggtgaacgc gacgtaccgc tcgatccgct cgttgagcgt   60540
gcgccggaac cgtgcgtaga gcgtgtcgtc ggtacggacc cgggcggcga tctccacgag   60600
ggccgcggtc ccggcgacgt cgtcctcggg tatccggtgc cgcggcagca catccgcgaa   60660
ccgcccggcc gaccgtccga agagcgtgga gccgagccgc cgtacggtga agacgtgcgc   60720
gtagtgctgc tcgtgcagcc cgagcggcag ccggccgagc gccagcgcct cgtgagcgcg   60780
cgtgagcccc ggcgccagca gttggtgcgg gacggtcgcg acctgccgca gcagtgcccg   60840
ctgcggcagg aaacggcagt cggcccgccc cccggcgatc tcgtggctcc gttcgcggtg   60900
tgcgccgtac gggccgccgc agaccaggac acgccgaaac cggggccagt cgcgcagcag   60960
atcgggaatc caccggtcga gcaggcgcag gtagtcgttg ttgacgtcga agtccagcag   61020
gaagttcttg aacccgccga cgttgatcag caggtcgtac tccggtgcgc cgccgcgcgg   61080
tacgtcgcgc accccggcga ggtcgatgac cggcccggac agatgggtca ccgggccgct   61140
gccgagggcg cgaacgcgg ccgtacggcc ggcgacgccc gggaagttct gcaccacgct    61200
gtggtgggcg agcagatgcg cggcgagcac gcgctcgtgc ggggagagca cggcgagatg   61260
ccggtccgcg gcgcgaagg aggtgcgcgg caggctcgcg cacaaggcgc cgatcgcggc    61320
cggtgggcgc tccgtccgcc agaagctgta gaggctgtcc accatgacga cgggccggcc   61380
cgccaccacg gcccgcaggg ccagctcggc gtccatgacc gagacgacct ggtcgcagga   61440
ggccagcagc ccgtcgagcg cggcggcctg gaccggttcc gaccgggaca tctcgtggat   61500
gacgtcgaag gcgtccgcgt tacgcgcgcg gaacgaggcc gccacgccgt cccccacgaa   61560
cacccggtga tgaccggaga gcagccggga gaccgcgacg agttcggccg ccggcccgaa   61620
gccgcagttc tgcgccccca tcacgatccg cacggcgccc gccccggcc ggtgggcaac    61680 gccgcgaaca cgccgaggag cagccgggcg aactccgccg gccacttcgc gtagccggag   61740
tgaccgccgg ggaactccac cagctcccgg cccagtcgtt cggcgaggac gaccgcggga   61800
cggtgcgcca cctgcgtccg cgactcccgg ccgcccgcga ccgcgatgcg ctccgccatc   61860
ggcgcgagcg ccgccacgtc gggcaggaag cgggtgaacg gccgcatcgt gtgcgccagg   61920
aagaacgcgc tgttgtcctg cgcctcgggc agcgcgggcg cggcccggcc gccgaagagg   61980
gcgctgaacc tcgccatcgc cgccccgacc ccctcccggc ggaacgccgc gtggacctcc   62040
tcgatgaacg ccagttggtc ctcggcgtcc ggcagcaggc tcagcgacgg cggctcgtgg   62100
acgaccacgg acctgaccct ctccgggtgg cggagcgtca gttcgagcgc gatgagcccg   62160
cccgagcagc ttccgaacac cgacgccgtc ccgccgggcg cggccaccgc gtccagcagc   62220
cggtacgcgt cgtccgcgtg cacctcgatc cgctgatcgg cgggcggccc gtcgagcaca   62280
ctgcgcgagt tgccgcgcgg atcgtaggag acgacacggt gaccggcggc gagcacggcg   62340
gccagcccgc cgaacacgtc cgcgtccgag ttgccgccgg ctatgaggag cagcggcggc   62400
ccctcgccgc gcacttcgta gtggagcctg gctcccggta cggccagggt gccgctgccg   62460
ctctcccgtg ggtccatcac actccagccc ctcacgatgt gtgtacgtca ggtagctacc   62520
cgtgcgcgcg gccggtcacc ggcttcggcc gacctcgtac gggtgatggt cggggtggac   62580
ggcgcagcgg gcggcccgcg aagtgcggca tgctctgcgg gacgagtgga acggacccgg   62640
cacgggcact gcccggagcg gatccgtcat ggcagaagg accggaacca gatgacagac    62700
cacaacgctg gactgatggc gttcgtgcgg gcacgcctcg acgaggaaga gcggatcgcg   62760
```

```
cgcgaagccg gcggtgattc ctggcggtgc ccgcccgagc agcccggtga gatccacgac   62820
cgcaccggca gtatcgcgtt cagcctgcgc acccacgggt acgacggcca catcgcgcgt   62880
caggatccgg cgtacacgct ccggcgtatc gagacgagcc gggtgctgct cgacgagtac   62940
gcggaggtcg cggccctgga cgtggaccgc cccgacgacg gcttcgcctc cggccgcgcg   63000
gtggggctgg gcttcgtcgt ccgccagatg gcgcgcgagc acgccaccac cgcggactac   63060
caggtgaagt ggctgccccg gttctcccac tagggacgtt ccccaccagg ggagttcccg   63120
gcggaccgga ccggtgccgg tccggtccgc cggggaaggc cacggagcgc gcggcggcta   63180
cgggacgcgt gcgacgcccg cgtagaaccc gctcagctcg ggctccgggg ccggcccgtc   63240
cttgtaccag tgggcggccg tcaccagccc gggttccacc aggtcgagac cgtcgaagaa   63300
gcgcgcgacc tccgcacggt cccgcatccg cagcgggatc tcgccctcct tgtacgccgt   63360
cgtcacgacg tccttgtact gcgggtgttc gtcgaaggtg gtgtgcgaga agatcagata   63420
gctgccgagg ggcagggcgt ccaccagggt gcggtgatc ccgtacgggt cgtcctcgtc   63480
ggggacgaag tgcagcagcg cgatgaggca gagcgcgacg ggccggtcga agtccagcag   63540
ggtgcgggcg tggtcgagga tggtctccgg ccgccggacg tccgcctgga tgtagtcggt   63600
ggcgccctcc ggtgtgctgg tgagccgggc ctcggcgtga cgcagcacga tggggtcgtt   63660
gtcggcgtac acgatccggg ccgtcgggat gatctcctgc acgacctgat ggagattcgg   63720
ctcggtgggg atccccgtac cgatgtcgag gtactggtcg atgccctgcc gcgccgtcca   63780
ggcgacggcc cgccgcatgt acgcccggtt ccgtaaggcg ttgcccttgg cctccggggg   63840
tattcgctcc ccgaccacct ggtcgaccgc gtagttgtcc ttgccgccga ggtgcttccg   63900
caaaacatag atgcggagtg cagtgggaat gatcaagaac gtggggacca tcgggcagga   63960
cagcgacctg atcactaccc cgtacgacgg gtgcgggcag tgcatggtcg ccgtacgtcg   64020
tttgtcgagg aagactgaga agaccaacag ccccggcaag caggcggccc agacgatcga   64080
agctgtgact gcgttcggtg gccatgtcat tgcttgggcc gacgacatgg aagtgtccgg   64140
cgcaaccgac cctcgcactc gccccggttt cggtccgtgg ctgcgtgatg aaatgggccc   64200
gtacgacggt atcgcgggcg ctgctgtcga tcggatcggt cgcaacgtac gggacatcct   64260
caacacggct tatgcgaatc acgagtctgg gcgggtcctg atcacagccg atcacgtcgg   64320
tgtgtgggac ctcgatgatc ccaaccagga aaacgagctg acgctgaagg cgatgggtgc   64380
gcagatggag caccgatcga ttcggacgcg gaaccgagac gaagcgaagc gggcacggaa   64440
cgccggtcag agccataacc agcctgccta tggattcgag tacgtacgtc tcacgcccat   64500
gggacggatc gaccaccaga ggttgaacgc ggtatcggca gcaaacgctc gtgacatcgc   64560
gcaccgtgtt ctgacggaca acacgggcac ggtaactcct gctactgagg cagcgcggct   64620 caccccgtgcc ggaatcctgt cccccacgga ccaccggcga gtgctgtacg gcaagacgcc   64680 caagggggggg ccgtggaccg ctaagtcggt cgaacacgtt ctgacgagct atgcgagtct   64740
gggactgctc acgcacggcg gaaagccagt gatcgggccg gacggacacc cgatcaggct   64800
ctccgagggg ctgtggtcgc gcgagacccg tgacgccttg gttgcaaaga ccgcgccgag   64860
ccgcaagcgg aagaacgtcc gggcgccgaa gagtgactat cgactgagcg gcattgcggt   64920
ctgcggtcag tgcaaagagc gtctgtactt cgccggtact gccgccgcgc cgaggtgggg   64980
ctgtactgcc cgcgtgcgag ggatcgtaaa gtcgcagcac tgcgcgccag ccccgtcgat   65040
cttcatgagt cttctagacg ctcatgtgga ggagtggttc ctttcacggc acggcagtgc   65100
ccaagtaatg cacaagcagt tcgtaccggg caccggctac ggtgctcgga tcaaggagtt   65160
```

```
ggaagccgac cgcaagcgtc tgcgcgagga ccgcaaagcc ggtctgtaca cggagtcgga    65220
cgatgcagag tggtaccgga cggagtacct acgtatggga aacgagatca aggagttgcg    65280
tcagcttcca gagcgcccgg ctggcatgcg cttggtaccg accggcgaga ccgtcgcgca    65340
gcagtggcat tccgccccag                                                65360
```

<210> SEQ ID NO 2
<211> LENGTH: 6459
<212> TYPE: PRT
<213> ORGANISM: Streptomyces sp.Mer-16208

<400> SEQUENCE: 2

```
Val Thr Asp Ser Thr Ile Glu Gly His Gly His Lys Gly Pro Val Ala
1               5                   10                  15

Ile Val Gly Leu Ser Cys Arg Leu Pro Lys Ala Ala Asp Arg His Ala
            20                  25                  30

Phe Trp Thr Met Leu Ala Asp Gly Ala His Gly Val Thr Asp Val Pro
        35                  40                  45

Ala Asp Arg Trp Asp His Ala Glu Tyr Phe Asp Glu Asp Pro Gly Ala
    50                  55                  60

Pro Gly Lys Val Asn Thr Arg Arg Gly Ala Phe Leu Asp Gln Val Asp
65                  70                  75                  80

Arg Phe Asp Pro Ala Phe Phe Gly Ile Ser Pro Arg Glu Ala Thr Ala
                85                  90                  95

Met Asp Pro Gln Gln Arg Leu Ala Leu Glu Leu Ser Trp Glu Ala Ile
            100                 105                 110

Glu Asp Ala Arg Ile Val Pro Gly Ser Leu Ala Ser Thr Arg Thr Gly
        115                 120                 125

Val Phe Met Gly Ala Met Asn Asp Glu Tyr Ala Thr Leu Thr Arg Arg
    130                 135                 140

Ala Gly Leu Arg Gln Val Asp Gln His Thr Phe Thr Gly Val Gln Arg
145                 150                 155                 160

Ser Leu Ile Ala Asn Arg Val Ser Tyr Phe Leu Gly Val Arg Gly Pro
                165                 170                 175

Ser Val Thr Met Asp Thr Gly Gln Ser Ser Ser Leu Val Ala Val His
            180                 185                 190

Leu Ala Val Gln Ser Leu Arg Thr Gly Glu Ala Asp Ile Ala Leu Ala
        195                 200                 205

Gly Gly Val Asn Leu Thr Leu Thr Pro Glu Gly Ala Val Gly Ala Ala
    210                 215                 220

Lys Leu Gly Ala Leu Ser Pro Asp Gly Arg Cys Tyr Thr Phe Asp Ala
225                 230                 235                 240

Arg Ala Asn Gly Phe Val Arg Gly Glu Gly Gly Val Val Val Leu
                245                 250                 255

Lys Pro Leu Ala Ala Ala Leu Ala Asp Gly Asp Arg Val His Cys Val
            260                 265                 270

Ile Asn Gly Ser Ala Val Asn Asn Asp Gly Gly Gly Asp Gly Leu Thr
        275                 280                 285

Val Pro Ser Gly Pro Ala Gln Glu Glu Val Leu Arg Leu Ala Tyr Glu
    290                 295                 300

Arg Ala Gly Val Asp Pro Ala Ser Val Gln Tyr Val Glu Leu His Gly
305                 310                 315                 320

Thr Gly Thr Arg Leu Gly Asp Pro Ile Glu Ala Ala Leu Gly Ala
                325                 330                 335
```

```
Val Leu Gly Ala Ala Arg Gly Thr Ala Ala Pro Leu Gln Val Gly Ser
            340                 345                 350

Val Lys Thr Asn Val Gly His Leu Glu Ser Ala Ala Gly Val Thr Gly
            355                 360                 365

Leu Ile Lys Thr Ala Leu Ala Ile Arg His Arg Leu Leu Pro Pro Ser
            370                 375                 380

Leu Gly Phe Thr Thr Pro Asn Pro Arg Ile Pro Leu Ala Asp Leu Asn
385                 390                 395                 400

Leu Asp Val Arg Val Thr His Gly Glu Trp Pro Ala Pro Asp Arg Pro
            405                 410                 415

Leu Val Ala Gly Val Ser Ser Phe Gly Val Gly Gly Thr Asn Cys His
            420                 425                 430

Val Val Leu Ser Glu Val Ser Ala Ala Ala Asp Val Ala Val Glu Asp
            435                 440                 445

Ala Cys Glu Pro Ser Ala Gly Pro Gly Gly Gly Ala Pro Trp Val
            450                 455                 460

Val Ser Gly Arg Thr Val Ala Ala Val Arg Glu Gln Ala Ala Arg Leu
465                 470                 475                 480

Arg Ala Gln Val Ala Asp His Pro Glu Thr Asp Leu Ser Asp Leu Gly
            485                 490                 495

Arg Ser Leu Ala Thr Thr Arg Thr Ala Phe Arg His Arg Ala Ala Val
            500                 505                 510

Thr Ala Thr Asp Arg Ala Gly Tyr Leu Ala Gly Leu Asp Ala Leu Ala
            515                 520                 525

Ser Gly Asp Ala Ala Pro Gly Leu Val Gln Gly Thr Ala Asp Ala Pro
            530                 535                 540

Gly Gly Thr Val Phe Val Phe Pro Gly Gln Gly Ser Gln Trp Val Gly
545                 550                 555                 560

Met Ala Val Glu Leu Met Gly Ser Ser Gly Val Phe Ala Ala Arg Met
            565                 570                 575

Gly Glu Cys Ala Gln Ala Leu Ser Pro Tyr Val Asp Trp Ser Leu Ser
            580                 585                 590

Glu Val Leu Asp Asp Gly Glu Ala Leu Gly Arg Val Asp Val Val Gln
            595                 600                 605

Pro Ala Leu Trp Ala Val Met Val Ser Leu Ala Glu Val Trp Arg Ser
610                 615                 620

Tyr Gly Val Glu Pro Val Ala Val Gly His Ser Gln Gly Glu Ile
625                 630                 635                 640

Ala Ala Ala Cys Val Ala Gly Ala Leu Ser Leu Glu Asp Gly Ala Arg
            645                 650                 655

Val Val Ala Leu Arg Ser Gln Ala Leu Val Ser Leu Ser Gly Arg Gly
            660                 665                 670

Thr Met Ala Ser Val Ala Leu Pro Ala Gly Glu Leu Thr Leu Gly Ala
            675                 680                 685

Ser Leu Ser Val Ala Ala Val Asn Gly Pro Arg Ser Thr Val Val Ala
            690                 695                 700

Gly Asp Glu Ser Ala Ile Asp Ala Leu Val Ala Glu Leu Thr Asp Arg
705                 710                 715                 720

Gly Val Arg Ala Arg Arg Ile Ala Val Asp Tyr Ala Ser His Ser Ala
            725                 730                 735

His Val Glu Ala Ile Arg Asp Arg Leu His Thr Ala Leu Ala Pro Ile
            740                 745                 750

Thr Pro Arg Thr Ala Ser Val Pro Phe Phe Ser Thr Leu Thr Gly Gln
            755                 760                 765
```

-continued

```
Trp Leu Asp Ala Gly Ala Thr Asp Ala Asp Tyr Trp Tyr Arg Asn Leu
    770                 775                 780
Arg Gly Thr Val Arg Phe Glu Glu Ala Val Arg Gly Leu Leu Ala Ala
785                 790                 795                 800
Gly His Arg Ala Phe Ile Glu Val Ser Pro His Pro Val Leu Val Met
                    805                 810                 815
Gly Val Gln Glu Thr Ala Glu Ala Met Gly Val Pro Val Val Val
                820                 825                 830
Pro Ser Ser Arg Arg Asp Asp Gly Thr Arg Ala Arg Val Met Ala Ser
            835                 840                 845
Leu Ala Glu Leu Ser Val His Gly Ala Gly Ile Asp Trp Thr Ala Val
            850                 855                 860
Phe Pro Gly Gly Arg Arg Val Glu Leu Pro Thr Tyr Pro Phe Gln Arg
865                 870                 875                 880
Gln Arg Tyr Trp Ile Ala Pro Ala Pro Glu Ala Ala Tyr Glu Gly
                885                 890                 895
Glu Ser Ala Asp Ala Gly Asp Pro Val Gly Ala Arg Glu Pro Thr Gly
            900                 905                 910
Ala Gly Ala Leu Ala Asp Asn Gly Ala Gly Val Pro Val Asp Asp Gly
            915                 920                 925
Arg Pro Ala Tyr Glu Asp Thr Pro Val Gly Ala Asp Val Leu Asp Ala
        930                 935                 940
Gly Arg Val Arg Gln Leu Val Arg Ala His Ala Ala Val Leu Gly
945                 950                 955                 960
His Thr Thr Pro Ala Ala Val Glu Thr Asp Leu Pro Phe Lys Asp Leu
                965                 970                 975
Gly Phe Asp Ser Gln Met Thr Val Ala Leu Arg Asp Arg Leu Ser Gly
            980                 985                 990
Ala Leu Gly Arg Arg Leu Pro Ser Ala Leu Leu Phe Asp His Pro Thr
        995                 1000                1005
Pro Asp Ala Leu Ile Ala His Leu Ser Gly Gly Pro Ala Ser Arg Pro
    1010                1015                1020
Ala Ala Arg Asn Asp Gly Ser Ala Thr Gly Gly Asp Pro Ile Ala Ile
1025                1030                1035                1040
Val Gly Met Ser Cys Arg Phe Pro Gly Gly Val Arg Ser Pro Glu Asp
                    1045                1050                1055
Leu Trp Asp Leu Val Val Ser Gly Ala Asp Ala Ile Ser Ala Phe Pro
                1060                1065                1070
Ala Asp Arg Gly Trp Asp Leu Asp Ala Leu Ala Ala Thr Ser His Thr
            1075                1080                1085
Arg His Gly Gly Phe Leu His Asp Ala Ala Glu Phe Asp Ala Ala Phe
        1090                1095                1100
Phe Gly Ile Ser Pro Arg Glu Ala Leu Ala Thr Asp Pro Gln Gln Arg
1105                1110                1115                1120
Leu Leu Leu Glu Ile Ser Trp Glu Ala Leu Glu Arg Ala Gly Leu Asp
                1125                1130                1135
Pro Ala Thr Leu Arg Asp Ser Asp Thr Gly Val Phe Val Gly Ala Met
                1140                1145                1150
Ala Gln Asp Tyr Val Pro Arg Leu His Glu Ala Pro Asp Gly Phe Ala
            1155                1160                1165
Gly Tyr Gly Leu Thr Gly Ser Thr Gly Ser Ala Ser Gly Arg Ile
        1170                1175                1180
Ser Tyr Val Leu Gly Leu Arg Gly Pro Ala Leu Thr Val Asp Thr Ala
```

-continued

```
1185                1190                1195                1200
Cys Ser Ser Ser Leu Val Ala Gln His Leu Ala Ala Gln Ala Leu Arg
                1205                1210                1215
Arg Gly Glu Cys Ser Leu Val Leu Ala Gly Gly Val Thr Val Met Ala
                1220                1225                1230
Asn Pro Gly Met Phe Val Glu Phe Ser Arg Gln Gly Gly Leu Ala Pro
                1235                1240                1245
Asp Gly Arg Cys Lys Ala Phe Gly Ala Gly Ala Asp Gly Thr Gly Trp
                1250                1255                1260
Ala Glu Gly Ala Gly Met Leu Val Leu Glu Arg Leu Ser Asp Ala Arg
1265                1270                1275                1280
Arg Asn Gly His Pro Val Leu Ala Leu Leu Arg Gly Ser Ala Val Asn
                1285                1290                1295
Gln Asp Gly Ala Ser Asn Gly Leu Thr Ala Pro Asn Gly Pro Ser Gln
                1300                1305                1310
Gln Glu Val Ile Arg Arg Ala Leu Ala Asp Ala Gly Leu Ala Pro Ser
                1315                1320                1325
Asp Val Asp Ala Val Glu Ala His Gly Thr Gly Thr Thr Leu Gly Asp
                1330                1335                1340
Pro Ile Glu Ala Glu Ala Leu Leu Ala Thr Tyr Gly Gln Asp Arg Glu
1345                1350                1355                1360
His Pro Leu Trp Leu Gly Ser Leu Lys Ser Asn Ile Gly His Thr Gln
                1365                1370                1375
Ala Ala Ala Gly Val Gly Gly Val Ile Lys Thr Val Leu Ala Leu His
                1380                1385                1390
His Gly Ile Val Pro Arg Thr Leu His Ala Asp Glu Val Ser Pro Gln
                1395                1400                1405
Val Asp Trp Ser Ala Gly Gln Val Ala Pro Val Thr Ala Asn Val Ala
                1410                1415                1420
Trp Pro Glu Thr Gly Arg Pro Arg Arg Ala Ala Val Ser Ser Phe Gly
1425                1430                1435                1440
Val Ser Gly Thr Asn Ala His Thr Ile Ile Glu Gln Ala Pro Pro Glu
                1445                1450                1455
Asp Glu Leu Ala Pro Glu Leu Leu Pro Gly Ser Ser Pro Ala Ala Ala
                1460                1465                1470
Val Gly Gln Gly Pro Leu Pro Trp Gln Leu Ser Gly Arg Thr Pro Gln
                1475                1480                1485
Ala Leu Gln Ala Gln Ala Arg Arg Leu Ala Ile His Leu Asp Ala Arg
                1490                1495                1500
Pro Gly Leu Gly Ala Ala Asp Ile Gly Arg Ser Leu Ala Ala Thr Arg
1505                1510                1515                1520
Ser Ala Phe Glu His Arg Ala Val Leu Leu Gly Arg Asp Arg Asp Glu
                1525                1530                1535
Leu Arg Gly Leu Leu Thr Ala Leu Ala Asp Gly Arg Thr Asp Pro Arg
                1540                1545                1550
Leu Ala Arg Gly Ser Ala Asp Thr Thr Gly Arg Val Val Phe Val Phe
                1555                1560                1565
Pro Gly Gln Gly Ser Gln Trp Ala Gly Met Ala Val Glu Leu Leu Ala
                1570                1575                1580
Thr Glu Pro Val Phe Ala Ala Arg Met Ala Asp Cys Ala Arg Ala Leu
1585                1590                1595                1600
Ala Pro His Val Thr Trp Ser Leu Ser Glu Val Leu Ser Asp Ala Glu
                1605                1610                1615
```

-continued

Ala Leu Glu Arg Val Asp Val Val Gln Pro Ala Leu Phe Ala Val Leu
             1620                1625                1630

Val Ser Leu Ala Ala Leu Trp Arg Ser Tyr Gly Val Glu Pro Ala Ala
             1635                1640                1645

Val Leu Gly His Ser Gln Gly Glu Ile Ala Ala Ala Cys Val Ala Gly
             1650                1655                1660

Ala Leu Thr Leu Glu Asp Ala Ala Arg Val Ser Ala Leu Arg Ala Lys
1665                1670                1675                1680

Leu Ile Leu Ala Glu Leu Ala Gly Pro Gly Gly Met Ala Ser Val Ala
             1685                1690                1695

Leu Ala Pro Gln Glu Leu Leu Pro Arg Leu Glu Ala Trp Asp Gly Arg
             1700                1705                1710

Leu Ser Leu Ala Ala Ser Asn Gly Pro Thr Ala Ser Val Val Ser Gly
             1715                1720                1725

Thr Pro Glu Ala Leu Asp Glu Leu Leu Ala Ala Leu Asp Ala Glu Gln
             1730                1735                1740

Val Arg Val Arg Arg Ile Pro Val Asp Tyr Ala Ser His Ser Pro Gln
1745                1750                1755                1760

Val Glu Glu Val Arg Asp Ala Leu Leu Asp Ala Leu Ala Thr Val Arg
             1765                1770                1775

Pro Arg Thr Ala Pro Gly Thr Ala Pro Val Arg Phe Phe Ser Thr Val
             1780                1785                1790

Thr Gly Gly Pro Leu Asp Thr Ala Ala Leu Asp Ala Ala Tyr Trp Tyr
             1795                1800                1805

Thr Asn Leu Arg Thr Thr Val Arg Phe Glu Gln Ala Thr Arg Ala Ala
             1810                1815                1820

Leu Asp Gln Gly Tyr Asp Leu Phe Ile Glu Val Ser Pro His Pro Val
1825                1830                1835                1840

Thr Val Pro Ser Leu Gln Glu Thr Ile Glu Ala Thr Glu Ala His Ala
             1845                1850                1855

Val Ala Leu Gly Ser Leu Arg Arg Asp Asp Gly Gly Gln Glu Arg Phe
             1860                1865                1870

Leu Thr Ser Val Ala Thr Ala His Thr Gln Gly Gly Thr Pro Asp Trp
             1875                1880                1885

Thr Gly Leu Leu Gly Thr Gly Pro Arg Val Glu Leu Pro Thr Tyr Ala
             1890                1895                1900

Phe Gln Arg Glu Arg Tyr Trp Leu Leu Pro Glu Pro Val Ser Arg Ala
1905                1910                1915                1920

Val Ser Gly Pro Asp Asp Trp Arg Tyr Arg Val Thr Trp Arg Pro Val
             1925                1930                1935

Thr Pro Arg Pro Ala Pro Pro Leu Ala Gly Gln Trp Leu Leu Leu Ala
             1940                1945                1950

Pro Ala Glu Gly Ile Gly Ala Pro Leu Val Ala Arg Cys Glu Arg Ala
             1955                1960                1965

Leu Ala Glu Ala Gly Ala Glu Val Val Arg Pro Ala Ala Gly Asp Pro
             1970                1975                1980

Ala Ala Leu Thr Asp Leu Leu Thr Ala Gly Lys Thr Pro Ala Gly Val
1985                1990                1995                2000

Leu Ser Leu Leu Ala Leu Asp Glu Arg Arg Ala Pro Asp Gly Ser Ala
             2005                2010                2015

Pro His Gly Leu Leu Asp Thr Val Ala Leu Ala Gln Ala Leu Ser Gly
             2020                2025                2030

Arg Glu Ile Pro Leu Trp Leu Ala Thr Arg Gly Ala Val Ala Val Asp
             2035                2040                2045

```
Pro Asp Asp Arg Leu Asp Asp Pro Glu Gln Ala Ala Val Trp Gly Leu
    2050                2055                2060
Gly Arg Ala Leu Ala Leu Glu Ser Pro Arg Asp Arg Gly Gly Leu Val
2065                2070                2075                2080
Asp Leu Pro Ala His Leu Asp Asp Thr Ala Ala Ala Leu Leu Ala Ala
            2085                2090                2095
Ala Leu Thr Gly Asp Ser Asp Glu Asp Gln Val Ala Val Arg Pro Ala
        2100                2105                2110
Gly Leu Phe Val Arg Arg Leu Val Arg Ala Ala Leu Pro Pro Ala Thr
    2115                2120                2125
Ala Ala Pro Trp Arg Pro Arg Asp Thr Ala Leu Ile Thr Gly Gly Thr
2130                2135                2140
Gly Ala Leu Gly Ala Arg Val Ala Arg Trp Leu Ala Ala Ala Gly Ala
2145                2150                2155                2160
Gly His Leu Val Leu Ala Ser Arg Ser Gly Pro Glu Ala Pro Gly Ala
            2165                2170                2175
Ala Ala Leu Arg Ala Glu Leu Thr Ala Leu Gly Ala Ser Val Glu Ile
        2180                2185                2190
Val Ala Cys Asp Thr Ala Arg Arg Glu Glu Leu Ala Ala Leu Leu Asp
    2195                2200                2205
Ser Val Pro Glu Asp Arg Pro Leu Arg Thr Val His Thr Ala Gly
2210                2215                2220
Val Leu Val Glu Ser Thr Val Arg Thr Leu Thr Thr Glu Glu Leu Glu
2225                2230                2235                2240
Gln Thr Leu Arg Ala Lys Thr Glu Thr Ala Arg His Leu His Glu Leu
            2245                2250                2255
Thr Gly Glu Leu Asp Ala Phe Val Leu Phe Ser Ser Gly Ala Gly Val
        2260                2265                2270
Trp Gly Ser Gly Gly Gln Gly Ala Tyr Gly Ala Ala Asn Ala Tyr Leu
    2275                2280                2285
Asp Ala Leu Ala Arg His Arg Arg Asp His Gly Leu Pro Ala Thr Ala
    2290                2295                2300
Val Ser Trp Gly Ala Trp Gly Gly Gly Gly Met Gly Ala Val Asp Gly
2305                2310                2315                2320
Ala Glu Asp Val Trp Arg Arg Leu Gly Val Leu Pro Met Asp Pro Arg
            2325                2330                2335
Ser Ala Val Thr Ala Leu Gln Arg Ala Leu Asp Ala Gly Glu Asn Thr
        2340                2345                2350
Leu Thr Val Ala Asp Ile Asp Trp Arg Arg Phe Ala Pro Ala Phe Ala
    2355                2360                2365
Ser Ala Gly Pro Arg Pro Leu Leu Ala Asp Leu Pro Glu Ala Arg Arg
    2370                2375                2380
Ala Leu Asn Gly Pro Ala Asp Asp Thr Thr Asp Pro Ala Ala Ala
2385                2390                2395                2400
Thr Pro Arg Arg Pro Glu Arg Ile Arg Lys Leu Glu Gly Leu Pro Glu
            2405                2410                2415
Ala Arg Arg Ala Asp Ala Leu Leu Glu Leu Val Arg Ala Glu Ala Ala
        2420                2425                2430
Ala Val Leu Gly His Pro Asp Pro Arg Ala Val Arg Pro Gly Arg Pro
    2435                2440                2445
Phe Lys Glu Ser Gly Phe Asp Ser Leu Thr Ser Val Glu Leu Arg Asp
    2450                2455                2460
Arg Leu Val Ala Ala Val Gly His Arg Leu Pro Thr Ser Leu Val Phe
```

```
            2465                2470                2475                2480

Asp Arg Pro Thr Pro Thr Ala Leu Ala Arg His Leu Asp Thr Leu Leu
                2485                2490                2495

Phe Gly Ala Ala Thr Thr Gly Thr Gly Thr Thr Gly Ala Ser Asp Glu
            2500                2505                2510

Pro Val Ala Ile Ile Ala Met Ala Cys Arg Tyr Pro Gly Gly Val Ser
            2515                2520                2525

Ser Pro Glu Glu Leu Trp Glu Leu Val Ala Ala Gly Thr Asp Ala Val
            2530                2535                2540

Ser Glu Phe Pro Ala Asp Arg Gly Trp Asn Val Glu Ser Leu Tyr Asp
2545                2550                2555                2560

Ala Asp Pro Asp Arg Pro Gly Thr Ser His Val Arg His Gly Gly Phe
                2565                2570                2575

Leu Tyr Asp Ala Ala Glu Phe Asp Ala Glu Leu Phe Gly Met Ser Pro
            2580                2585                2590

Arg Glu Ala Arg Ala Thr Asp Pro Gln Gln Arg Leu Leu Leu Glu Thr
            2595                2600                2605

Ala Trp Glu Thr Phe Glu Arg Ala Gly Ile Asp Pro Arg Ser Leu Ala
            2610                2615                2620

Gly Ser Pro Thr Gly Val Phe Val Gly Ala Met Ser Gln Asp Tyr Gly
2625                2630                2635                2640

Pro Arg Met His Glu Ala Pro Gln Glu Leu Glu Gly Tyr Leu Leu Thr
            2645                2650                2655

Gly Asn Ile Gly Ser Val Ala Ser Gly Arg Val Ser Tyr Thr Phe Gly
            2660                2665                2670

Leu Glu Gly Pro Ala Met Thr Val Asp Thr Gly Cys Ser Ala Ser Leu
            2675                2680                2685

Val Ala Leu His Leu Ala Ala Gln Ser Leu Arg Arg Gly Glu Ser Ser
            2690                2695                2700

Met Ala Leu Ala Gly Gly Val Thr Val Met Ser Thr Pro Gly Val Phe
2705                2710                2715                2720

Ile Glu Phe Ser Arg Gln Arg Gly Leu Ala Leu Asp Gly Arg Cys Lys
            2725                2730                2735

Ala Phe Gly Ala Gly Ala Asp Gly Thr Gly Trp Ser Glu Gly Val Gly
            2740                2745                2750

Leu Leu Leu Leu Glu Arg Leu Ser Asp Ala Glu Arg Asn Gly His Glu
            2755                2760                2765

Ile Leu Ala Val Val Arg Gly Ser Ala Val Asn Gln Asp Gly Ala Ser
            2770                2775                2780

Asn Gly Leu Thr Ala Pro Asn Gly Pro Ser Gln Glu Arg Val Ile Arg
2785                2790                2795                2800

Arg Ala Leu Ala Asp Ala Gly Leu Thr Pro Ala Glu Val Asp Ala Val
                2805                2810                2815

Glu Gly His Gly Thr Gly Thr Thr Leu Gly Asp Pro Ile Glu Ala Glu
            2820                2825                2830

Ala Leu Leu Ala Thr Tyr Gly Gln Asn Arg Glu Arg Pro Leu Trp Leu
            2835                2840                2845

Gly Ser Leu Lys Ser Asn Ile Gly His Thr Gln Thr Ala Ala Gly Val
            2850                2855                2860

Gly Gly Val Ile Lys Met Val Gln Ala Met Arg His Gly Val Leu Pro
2865                2870                2875                2880

Arg Thr Leu His Ala Asp Glu Pro Ser Pro Arg Ile Asp Trp Ser Ala
                2885                2890                2895
```

-continued

```
Gly Ala Val Ser Leu Leu Thr Glu Glu Arg Ala Trp Pro Asp Glu Gly
            2900                2905                2910

Arg Pro Arg Arg Ala Gly Val Ser Gly Phe Gly Val Gly Gly Thr Asn
            2915                2920                2925

Ala His Val Ile Val Glu Gln Gly Pro Pro Ala Pro Val Thr Leu
            2930                2935                2940

Ser Ala Pro Val Thr Pro Pro Ala Asp Ala Pro Gly Ala Leu Pro Trp
2945                2950                2955                2960

Leu Leu Ser Gly Arg Thr Glu Gln Ala Leu Arg Asp Gln Ala Arg Lys
            2965                2970                2975

Leu Ser Ala His Leu Ala Ala His Pro Asp Thr Thr Pro Leu Asp Val
            2980                2985                2990

Ala Tyr Thr Leu Ala Thr Gly Arg Thr Ala Leu Asp His Arg Ala Val
            2995                3000                3005

Val Val Ala Ala Asp Arg Ala Gly Phe Ala Ala Ala Leu Asp Ala Leu
            3010                3015                3020

Ala Thr Gly Asp Asp Val Cys Ala Arg Gly Ile Ala Asp Glu Asp Pro
3025                3030                3035                3040

Gly Thr Val Phe Val Phe Pro Gly Gln Gly Ser Gln Trp Val Gly Met
            3045                3050                3055

Ala Val Glu Leu Met Gly Ser Ser Gly Val Phe Ala Ala Arg Met Gly
            3060                3065                3070

Glu Cys Ala Gln Ala Leu Ser Pro Tyr Val Asp Trp Ser Leu Ser Glu
            3075                3080                3085

Val Leu Asp Asp Gly Glu Ala Leu Gly Arg Val Asp Val Val Gln Pro
            3090                3095                3100

Ala Leu Trp Ala Val Met Val Ser Leu Ala Glu Val Trp Arg Ser Tyr
3105                3110                3115                3120

Gly Val Glu Pro Val Ala Val Val Gly His Ser Gln Gly Glu Ile Ala
            3125                3130                3135

Ala Ala Cys Val Ala Gly Ala Leu Ser Leu Glu Asp Gly Ala Arg Val
            3140                3145                3150

Val Ala Leu Arg Ser Gln Ala Leu Arg Glu Leu Ser Gly Gly Gly Ala
            3155                3160                3165

Met Ala Ala Leu Leu Leu Ala Pro Asp Glu Val Ala Arg Leu Ile Glu
            3170                3175                3180

Pro Trp Asp Gly Arg Leu Thr Ile Ala Ala Tyr Asn Gly Pro Asn Ser
3185                3190                3195                3200

Thr Thr Val Ala Gly Asp Pro Glu Ala Val Glu Ala Leu His Ala His
            3205                3210                3215

Cys Glu Arg Glu Arg Ile Gln Ser Arg Arg Val Ala Val Asp Tyr Ala
            3220                3225                3230

Ser His Ser Pro Gln Val Glu Glu Ile Arg Asp Arg Leu Leu Ala Asp
            3235                3240                3245

Leu Ala Pro Ile Thr Pro Arg Pro Ala Gly Ile Pro Phe His Ser Thr
            3250                3255                3260

Val Thr Gly Ala Pro Leu Asp Thr Thr Gly Leu Asp Ala Ala Tyr Trp
3265                3270                3275                3280

Tyr Thr Asn Leu Arg Arg Pro Val Leu Phe Glu Pro Thr Val Arg Ala
            3285                3290                3295

Leu Ile Asp Ala Gly His Gly Ile Phe Ile Glu Pro Ser Ala His Pro
            3300                3305                3310

Val Leu Thr Thr Ala Val Gln Asp Thr Ala Glu Arg Ala Gly Arg Pro
            3315                3320                3325
```

```
Val Ala Ala Phe Gly Thr Leu Arg Arg Glu Gly Gly Ala Gly Arg
        3330                3335                3340

Trp Leu Ala Ser Leu Ala Glu Ala His Val His Gly Ala Pro Val Asp
3345                3350                3355                3360

Trp Ser Gly Leu Leu Thr Gly Gly Arg Arg Thr Asp Leu Pro Thr Tyr
            3365                3370                3375

Ala Phe Gln Arg Glu Arg Tyr Trp Leu Asp Pro Val Thr Ala Ser Gly
        3380                3385                3390

Arg Ala Val Ala Glu Gly Ala Ala Gly Leu Gly Leu Ser Ser Ala Ala
        3395                3400                3405

His Pro Leu Leu Gly Ala Ala Val Glu Leu Ala Gly Thr Asp Glu Tyr
        3410                3415                3420

Val Leu Thr Gly Arg Val Ser Leu Arg Thr His Pro Trp Leu Ala Asp
3425                3430                3435                3440

His Ala Val Ser Gly Thr Val Leu Leu Pro Gly Thr Ala Phe Val Glu
            3445                3450                3455

Leu Ala Leu Arg Ala Gly Asp Glu Val Arg Cys Asp Arg Ile Asp Glu
        3460                3465                3470

Leu Thr Leu Ser Ala Pro Leu Leu Ile Asp Gly Glu Val Thr Leu Gln
        3475                3480                3485

Val Leu Val Gly Ala Ala Asp Ala Asp Gly Arg Arg Thr Val Ala Val
        3490                3495                3500

His Ser Arg Thr Ser Gln Gly Ala Ser Trp Thr Arg His Ala Asp Gly
3505                3510                3515                3520

Ala Leu Tyr Ala Gly Gly Ala Pro Gly Pro Ser Pro Thr Gly Glu Glu
            3525                3530                3535

Met Ala Trp Pro Pro Gly Ala Arg Pro Val Ala Gln Ala Gly Leu
        3540                3545                3550

Tyr Pro Ala Leu Ala Ala Thr Gly Tyr Asp Tyr Gly Pro Ala Phe Gln
        3555                3560                3565

Gly Leu Arg Ala Val Trp Gln Asp Gly Asp Asp Leu Leu Ala Glu Val
        3570                3575                3580

Ala Leu Pro Asp Gly Glu Ser Ala Asp Gly Phe Ala Leu His Pro Ala
3585                3590                3595                3600

Leu Leu Asp Ala Cys Leu His Pro Leu Gly Leu Gly Lys Gly Pro Gly
            3605                3610                3615

Ser Gly Leu Gly Thr Gly Leu Gly Ser Glu Pro Gly Asp Gly Asp Gly
        3620                3625                3630

Thr Arg Leu Pro Phe Ala Trp Thr Gly Val Arg Leu His Ala Val Gly
        3635                3640                3645

Ala Thr Ser Val Arg Val Arg Ile Ser Pro Ser Gly Gly Asp Ala Val
        3650                3655                3660

Ser Val Thr Val Ser Asp Pro Ala Gly Ala Pro Val Ala Thr Val Glu
3665                3670                3675                3680

Gly Leu Val Leu Arg Pro Leu Ala Ala Gly Gln Leu Thr Ala Ala Arg
            3685                3690                3695

His Asp Asp His Asp Ala Leu Phe Arg Leu Val Trp Asn Pro Leu Thr
        3700                3705                3710

Asp Pro Ala Pro Val Pro Ser Pro Ile Pro Ala Gly Pro Ala Gln Gly
        3715                3720                3725

Ile Pro Leu Met Gly Thr Ala Ala Leu Asp Thr Ala Leu Ala Glu Gly
        3730                3735                3740

Val Pro Leu Pro Ala Val Val Ala Val Arg Pro Asp Ala Pro Ala Gly
```

-continued

```
              3745                3750                3755                3760
Asp Asp Leu Ala Ala Arg Val His Gly Ala Thr Ala Arg Leu Leu Glu
              3765                3770                3775
Leu Leu Arg Ala Trp Leu Ala Asp Glu Arg Arg Ala Ala Thr Arg Leu
              3780                3785                3790
Val Ile Leu Thr Arg Gly Ala Val Ala Val Arg Ala Asp Glu Glu Ile
              3795                3800                3805
Leu Asp Leu Ala Gln Ala Pro Leu Trp Gly Leu Val Arg Ala Ala Gln
              3810                3815                3820
Thr Glu Asn Pro Asp Arg Phe Leu Leu Leu Asp Thr Asp Thr Gly Ser
3825                3830                3835                3840
Asp Thr Asp Thr Ala Pro Gly Gly Ala Gly Asp Val Asp Thr Asp Pro
              3845                3850                3855
Gly Val Asp Ala Ala Val Ala Ala Val Leu Ala Ala Gly Glu Pro Gln
              3860                3865                3870
Ala Ala Leu Arg Gly Gly Ala Val Leu Val Pro Arg Leu Ala Arg Pro
              3875                3880                3885
Ala Ala Thr Arg Leu Pro Val Pro Ala Leu Asp Pro Asp Gly Ala Val
              3890                3895                3900
Leu Ile Thr Gly Gly Thr Gly Thr Leu Gly Gly Leu Val Ala Arg His
3905                3910                3915                3920
Leu Val Thr Thr His Gly Val Ala His Leu Val Leu Ile Gly Arg Arg
              3925                3930                3935
Gly Pro Asp Ala Pro Gly Ala Ala Glu Leu Ser Ala Glu Leu Thr Ala
              3940                3945                3950
Leu Gly Ala Glu Val Thr Val Ala Ala Cys Asp Ala Ala Asp Arg Asp
              3955                3960                3965
Ala Leu Ala Ala Leu Leu Ala Asp Leu Pro Val Arg Leu Thr Ala Val
              3970                3975                3980
Val His Thr Ala Gly Ala Val Asp Asp Gly Val Leu Glu Ser Leu Thr
3985                3990                3995                4000
Pro Asp Arg Leu Ala Pro Val Leu Arg Pro Lys Val Asp Ala Ala Leu
              4005                4010                4015
Asn Leu His Glu Leu Thr Asp Gly Leu Asp Ala Phe Ile Leu Phe Ser
              4020                4025                4030
Ser Ala Ser Ala Thr Phe Gly Thr Ala Gly Gln Ala Thr Tyr Cys Ala
              4035                4040                4045
Ala Asn Ala Phe Leu Asp Ala Leu Ala His His Arg Arg Thr Ala Gly
              4050                4055                4060
Leu Pro Ala Val Ser Leu Ala Trp Gly Tyr Trp Glu Gln Thr Ser Glu
4065                4070                4075                4080
Leu Thr Arg Gly Leu Gly Ala Gly Asp Ile Ala Arg Leu Glu Arg Ser
              4085                4090                4095
Gly Val Leu Pro Leu Thr Thr Gly Arg Gly Leu Ala Leu Phe Asp Ala
              4100                4105                4110
Ala Arg Gly Leu Ala Glu Pro Phe Ala Val Thr Ala Arg Leu Asp Thr
              4115                4120                4125
Ala Pro Arg Ala Gln Val Pro Ala Leu Leu Arg Asp Leu Val Arg Ala
              4130                4135                4140
Pro Ala Arg Arg Ala Ala Glu Gly Pro Ala Val Thr Pro Gly Gly Thr
4145                4150                4155                4160
Ala Leu Ser Asp Arg Leu Thr Gly Leu Ser Val Pro Glu Arg Ala Gln
              4165                4170                4175
```

```
Leu Leu Leu Ala Glu Val Leu Arg His Ala Ala Val Leu Gly Arg
                4180                4185                4190

Thr Gly Ser Thr Gly Leu Leu Pro Gly Arg Pro Phe Arg Asp Asn Gly
        4195                4200                4205

Phe Asp Ser Leu Thr Ala Val Glu Leu Arg Asn Arg Leu Thr Thr Leu
4210                4215                4220

Thr Gly Leu Arg Leu Pro Ala Thr Leu Val Phe Asp His Pro Thr Pro
4225                4230                4235                4240

Leu Ala Leu Ala Asp Asp Leu Ala Arg Arg Leu Thr Val Thr Thr Thr
                4245                4250                4255

Thr Gly Ala Ala Ala Pro Pro Ala Pro Ala Pro Val Pro Gly Asp
                4260                4265                4270

Glu Pro Ile Ala Ile Val Ala Met Ala Cys Arg Tyr Pro Gly Gly Val
                4275                4280                4285

Thr Ser Pro Glu Glu Leu Trp Glu Leu Val Ala Ala Gly Thr Asp Ala
        4290                4295                4300

Val Ser Asp Phe Pro Ala Asp Arg Gly Trp Asp Val Glu Ala Leu Tyr
4305                4310                4315                4320

Asp Pro Asp Pro Ala Thr Thr Gly Thr Ser Tyr Thr Arg Ser Gly Ala
                4325                4330                4335

Phe Leu His Asp Ala Ala Asp Phe Asp His Glu Leu Phe Gly Met Ser
                4340                4345                4350

Pro Arg Glu Ser Leu Ala Thr Asp Pro Gln Gln Arg Leu Leu Leu Glu
        4355                4360                4365

Thr Thr Trp Glu Val Phe Glu Arg Ala Gly Ile Asp Pro Leu Ser Val
        4370                4375                4380

Lys Gly Ser Ser Thr Gly Val Phe Val Gly Ala Met Tyr Asn Asp Tyr
4385                4390                4395                4400

Ala Ser Arg Ile His Gln Ala Pro Ala Thr Val Glu Gly Gln Leu Leu
                4405                4410                4415

Thr Gly Ser Ala Gly Ser Val Ala Ser Gly Arg Leu Ala Tyr Val Phe
                4420                4425                4430

Gly Leu Glu Gly Pro Ala Ile Thr Val Asp Thr Ala Cys Ser Ser Ser
                4435                4440                4445

Leu Val Ala Leu His Leu Ala Ala Arg Ser Leu Arg Gln Gly Glu Ser
        4450                4455                4460

Ser Leu Ala Val Ala Gly Gly Val Thr Leu Met Ala Gly Pro Thr Leu
4465                4470                4475                4480

Phe Val Glu Phe Ser Arg Gln Arg Gly Leu Ser Ala Asp Gly Arg Cys
                4485                4490                4495

Lys Ala Phe Gly Ala Gly Ala Asp Gly Thr Gly Trp Gly Glu Gly Val
                4500                4505                4510

Gly Val Leu Leu Leu Glu Arg Leu Ser Asp Ala Glu Arg Asn Gly His
                4515                4520                4525

Glu Val Leu Ala Leu Leu Arg Gly Thr Ala Val Asn Gln Asp Gly Ala
        4530                4535                4540

Ser Asn Gly Leu Thr Ala Pro Asn Gly Pro Ala Gln Gln Arg Val Ile
4545                4550                4555                4560

Arg Gly Ala Leu Asp Asp Ala Gly Leu Thr Ala Gln Asp Ile Asp Val
                4565                4570                4575

Val Glu Gly His Gly Thr Gly Thr Thr Leu Gly Asp Pro Ile Glu Ala
                4580                4585                4590

Gln Ala Val Leu Ala Thr Tyr Gly Gln Asp Arg Glu Arg Pro Val Trp
                4595                4600                4605
```

```
Leu Gly Ser Leu Lys Ser Asn Ile Gly His Thr Gln Ala Ala Gly
    4610            4615                4620

Val Gly Gly Val Ile Lys Met Val Glu Ala Met Arg His Gly Thr Leu
4625            4630                4635                4640

Pro Arg Thr Leu His Ala Asp Glu Pro Ser Pro Glu Val Asp Trp Glu
                4645                4650                4655

Arg Gly Ala Val Glu Leu Leu Thr Glu Ala Arg Pro Trp Pro Gly Gly
            4660                4665                4670

Thr Pro Arg Arg Ala Gly Val Ser Ser Phe Gly Ala Gly Gly Thr Asn
        4675                4680                4685

Ala His Val Ile Ile Glu Gln Gly Pro Ile Ala Glu Gln Gly Pro Ile
    4690                4695                4700

Ile Glu Gln Gly Pro Ala Thr Glu Gln Gly Pro Ile Thr Glu Pro Gly
4705                4710                4715                4720

Pro Ala Thr Glu Gln Gly Pro Ala Thr Glu Gln Gly Pro Ala Thr Val
                4725                4730                4735

Gln Gly Pro Ala Thr Glu Gln Asp Pro Ile Thr Glu Arg Asp Pro Ile
            4740                4745                4750

Ala Glu Gln Asp Pro Pro Ala Glu Ala Pro Ala Val Pro Ala Ala Thr
        4755                4760                4765

Thr Ser Ala Gly Glu Thr Ala Pro Leu Pro Trp Val Leu Ser Ala Arg
    4770                4775                4780

Ser Glu Pro Ala Leu Arg Ala Gln Ala Ala Arg Leu Leu Ser Phe Leu
4785                4790                4795                4800

Ala Ser His Asp Asp Leu Gly Pro Ala Glu Val Gly His Ser Leu Val
                4805                4810                4815

Thr Thr Arg Ala Ser Leu Asp His Arg Ala Val Leu Val Ala Ala Asp
            4820                4825                4830

Arg Pro Glu Phe Leu Ala His Leu Thr Ala Leu Ala Glu Gly Gly Gly
        4835                4840                4845

Pro Ala Val Val Gly Ser Ala Gly Gly His Gly Arg Thr Val Phe Val
    4850                4855                4860

Phe Pro Gly Gln Gly Ser Gln Trp Ala Gly Met Ala Leu Gly Leu Met
4865                4870                4875                4880

Glu Ser Ser Pro Val Phe Ala Ala Arg Met Ala Glu Cys Glu Asp Ala
                4885                4890                4895

Leu Ser Pro Tyr Thr Asp Trp Ser Leu Ser Glu Val Leu Gly Asp Gly
            4900                4905                4910

Glu Ala Leu Glu Arg Val Asp Val Val Gln Pro Ala Leu Phe Ala Val
        4915                4920                4925

Met Val Ser Leu Ala Ala Leu Trp Arg Ser Tyr Gly Val Glu Pro Ala
    4930                4935                4940

Ala Val Leu Gly His Ser Gln Gly Glu Ile Ala Ala Ala Cys Val Ala
4945                4950                4955                4960

Gly Ala Leu Ser Leu Ala Asp Ala Ala Arg Val Val Val Leu Arg Ser
                4965                4970                4975

Gln Ala Leu Thr Glu Leu Ser Gly Arg Gly Ala Met Ala Ser Val Ala
            4980                4985                4990

Leu Gly Arg Asp Ala Leu Gly Pro Arg Leu Ser Glu Arg Leu Ser Val
        4995                5000                5005

Ala Ala Val Asn Gly Pro Ala Ser Thr Val Val Ser Gly Asp Pro Leu
    5010                5015                5020

Ala Leu Asp Ala Leu Leu Asp Thr Leu Thr Ala Glu Gly Val Arg Thr
```

```
                5025               5030                5035                5040
Arg Arg Ile Ala Val Asp Tyr Ala Ser His Ser Gly His Val Glu Ala
                    5045               5050                5055

Val Gln Ala Arg Leu Leu Asp Asp Leu Ala Pro Ile Thr Pro Arg Thr
                5060               5065                5070

Pro Arg Ile Pro Phe Phe Ser Thr Val Ser Ala Ser Trp Leu Thr Glu
                5075               5080                5085

Pro Val Asp Ala Gly Tyr Trp Tyr Arg Asn Leu Arg Gly Thr Val Glu
                5090               5095                5100

Phe Glu Ala Ala Thr Arg Ala Leu Val Ala Glu Gly Tyr Gly Val Phe
5105                5110               5115                5120

Val Glu Ala Ser Pro His Pro Val Leu Thr Val Ala Ile Gln Glu Ser
                    5125               5130                5135

Ala Glu Asp Ala Val Val Val Gly Ser Leu Arg Arg Asp Glu Asp Gly
                5140               5145                5150

Pro Arg Arg Phe Leu Thr Ser Leu Ala Glu Ala His Val Arg Gly Val
                    5155               5160                5165

Asp Val Thr Trp Thr Pro Ala Phe Pro Gly Thr His Arg Arg Val Gly
                5170               5175                5180

Leu Pro Thr Tyr Ala Phe Gln Arg Glu Arg Phe Trp Leu Glu Gln Ser
5185                5190               5195                5200

Pro Gly Gly Pro Ala Asp Val Thr Ser Ala Gly Leu His Pro Ala Glu
                    5205               5210                5215

His Pro Leu Leu Gly Ala Thr Val Ala Leu Pro Gly Ser Gly Gly His
                    5220               5225                5230

Leu Ala Thr Gly Arg Leu Ser Arg Asp Asp His Pro Trp Leu Ala Asp
                    5235               5240                5245

His Gly Val Leu Gly Thr Val Leu Leu Pro Gly Ala Ala Leu Ala Glu
                5250               5255                5260

Leu Ala Val Arg Ala Gly Asp Gln Ile Gly Cys Pro His Leu Glu Glu
5265                5270               5275                5280

Leu Val Leu His Ala Pro Leu Ala Leu Pro Ala Ser Gly Gly Val Pro
                    5285               5290                5295

Val Gln Leu Glu Leu Gly Gly Pro Asp Ala Ser Gly Arg Arg Thr Leu
                5300               5305                5310

Ser Val His Ala Tyr Gly Pro Asp Gly Gln Asp Thr Trp Thr Arg His
                    5315               5320                5325

Ala Thr Gly Val Leu Ala Pro Ala Pro Glu Gln Ala Gly Glu Ala Leu
                5330               5335                5340

Thr Ala Trp Pro Pro Thr Gly Ala Thr Pro Leu Asp Leu Gly Ala Phe
5345                5350               5355                5360

Tyr Pro Gly Leu Ala Ala Arg Gly Tyr Gly Tyr Gly Pro Ala Phe Gln
                    5365               5370                5375

Gly Leu Arg Ala Ala Trp Arg Asp Gly Glu Asp Ile Val Ala Glu Val
                5380               5385                5390

Ala Leu Pro Glu Glu His His Ala Gln Ala Ala Leu Phe Gly Leu His
                    5395               5400                5405

Pro Ala Leu Phe Asp Ala Ala Leu His Thr Val Gly Leu Gly Lys Ala
                    5410               5415                5420

Leu Asp Gly His Asp Arg Pro Leu Leu Pro Phe Ser Trp Gln Gly Val
5425                5430               5435                5440

Ser Leu His Ala Val Gly Ala Ala Ala Leu Arg Val Arg Thr Arg Phe
                    5445               5450                5455
```

-continued

Thr Gly Pro Asp Thr Val Ser Leu Thr Leu Ala Gly Pro Asp Gly Ala
            5460                5465                5470

Pro Val Ala Thr Val Ala Ser Leu Thr Val Arg Pro Leu Ala Pro Glu
        5475                5480                5485

Arg Pro Ala Ala Pro Ala Val Arg Asp Ala Leu Phe His Val Ala
        5490            5495                5500

Trp Arg Glu Gln Pro Arg Thr Ala Pro His Gly Ala Val Gly Pro
5505            5510            5515                5520

Leu Leu Val Leu Gly Ala Asp Gly Leu Gly Met Arg Ala Ala Leu Glu
                5525            5530                5535

Thr Ala Gly Val Ser Val Ala Val Cys Gln Asp Val Ala Asp Trp Asn
            5540                5545                5550

Pro Ala Gly Asp Ala Pro Val Pro Leu Ser Val Val Thr Gly Asp Leu
        5555                5560                5565

Pro Gly Arg Thr Pro Arg Glu Ala Val Arg Arg Ala Leu Ala Leu Val
        5570            5575                5580

Arg Ser Trp Leu Ala Asp Asp Arg Phe Ala Ala Ser Arg Leu Val Leu
5585            5590            5595                5600

Val Thr Arg Gly Ala Val Ala Thr His His Asp Glu Asp Ile Thr Ser
                5605            5610                5615

Leu Ala Gln Ala Ala Val Trp Gly Phe Val Arg Thr Ala Gln Ala Glu
            5620                5625                5630

His Pro Gly Arg Phe Ala Leu Leu Asp Leu Gly Ala Gly Glu Pro Pro
            5635                5640                5645

Leu Ala Gly Leu Pro Ala Leu Ala Ser Gly Glu Pro Gln Leu Ala
        5650            5655                5660

Leu Arg Ser Gly Gly Phe Leu Val Pro Arg Leu Asp Arg Leu Asp Arg
5665            5670            5675                5680

Ser Gly Thr Leu Leu Pro Pro Leu Asp Gly Ala Trp Arg Leu Asp Val
            5685                5690                5695

Thr Ser Pro Gly Thr Leu Glu Asn Leu Ala Phe Leu Pro Ala Pro Glu
            5700                5705                5710

Ala Glu Ala Pro Leu Gly Glu Gly Glu Ile Arg Val Ala Val Arg Ala
            5715                5720                5725

Ala Gly Leu Asn Phe Arg Asp Val Leu Ile Ala Leu Gly Met Tyr Pro
            5730                5735                5740

Gly Ala Gly Ile Met Gly Ser Glu Gly Ala Gly Thr Val Leu Glu Thr
5745            5750            5755                5760

Gly Pro Gly Val Thr Gly Leu Ala Val Gly Asp Ala Val Phe Gly Leu
            5765                5770                5775

Phe Leu Ala Gly Ser Phe Gly Pro Arg Val Val Ala Asp Arg Arg Leu
            5780                5785                5790

Val Ala Lys Val Pro Ala Gly Trp Ser Leu Thr Asp Ala Ala Ser Val
            5795                5800                5805

Pro Val Thr Phe Leu Thr Ala Tyr His Ala Leu Val Asp Leu Ala Gly
        5810                5815                5820

Leu Arg Pro Gly Glu Ser Val Leu Val His Ala Ala Thr Gly Gly Val
5825            5830            5835                5840

Gly Thr Ala Ala Val Gln Leu Ala Arg His Leu Gly Ala Glu Val Phe
                5845            5850                5855

Ala Thr Ala Gly Pro Gly Lys Trp His Ala Leu Arg Ala Leu Gly Leu
            5860                5865                5870

Asp Glu Asp His Ile Ala Ser Ser Arg Asp Leu Asp Phe Glu Glu Arg
            5875                5880                5885

```
Phe Arg Asp Ala Thr Gly Gly Arg Gly Val Asp Val Leu Asn Ser
            5890                5895                5900

Leu Ala Arg Ala Phe Thr Asp Ala Ser Leu Arg Leu Leu Ala Glu Gly
5905                5910                5915                5920

Gly Arg Phe Ala Glu Met Gly Lys Thr Asp Leu Arg Asp Pro Asp Glu
            5925                5930                5935

Val Ala Ala Arg Tyr Pro Gly Val Thr Tyr Arg Ala Phe Glu Leu Met
            5940                5945                5950

Asp Ala Gly Pro Asp Arg Val Arg Ala Ile Leu Ala Glu Leu Leu Thr
            5955                5960                5965

Leu Phe Glu Arg Gly Val Leu Ala Pro Ala Pro Val Thr Thr Trp Asp
            5970                5975                5980

Ile Arg Arg Ala Pro Asp Ala Val Arg Phe Leu Ser Gln Ala Lys His
5985                5990                5995                6000

Leu Gly Lys Leu Val Leu Thr Leu Pro Ala Pro Leu Asp Pro Asp Gly
            6005                6010                6015

Thr Val Leu Val Thr Gly Ala Ser Gly Thr Leu Gly Gly Ala Val Ala
            6020                6025                6030

Arg His Leu Val Thr Arg His Gly Val Arg His Leu Val Leu Ala Ser
            6035                6040                6045

Arg Ser Gly Pro Ser Ala Glu Leu Cys Ala Glu Leu Thr Ala His Gly
            6050                6055                6060

Ala Thr Val Thr Ala Ala Ala Cys Asp Ile Ala Asp Arg Thr Ala Leu
6065                6070                6075                6080

Ala Arg Leu Leu Asp Ala Val Pro Gly Pro His Pro Leu Thr Gly Val
            6085                6090                6095

Val His Ala Ala Gly Val Leu Asp Asp Gly Val Val Asp Ser Leu Thr
            6100                6105                6110

Pro Glu Arg Ile Asp Thr Val Leu Arg Pro Lys Val Asp Gly Ala Ala
            6115                6120                6125

His Leu His Glu Leu Thr Arg His Leu Asp Leu Ser Ala Phe Val Leu
            6130                6135                6140

Phe Ser Ser Ala Ala Ala Thr Leu Gly Ser Ala Gly Gln Ala Ala Tyr
6145                6150                6155                6160

Ala Ala Ala Asn Ala Tyr Leu Asp Ala Leu Ala Gln His Arg Arg Ala
            6165                6170                6175

Thr Gly Leu Pro Ala Thr Ser Leu Ala Trp Gly Leu Trp Ala Glu Arg
            6180                6185                6190

Ser Ala Met Thr Gly His Leu Asp Asp Asn Asp Leu Ala Arg Met Gly
            6195                6200                6205

Arg Ser Gly Ile Ala Pro Leu Thr Thr Glu Asp Gly Leu Ala Leu Phe
            6210                6215                6220

Asp Ala Gly Arg Ser Ala Ala Glu Ala Ala Val Val Pro Leu Arg Leu
6225                6230                6235                6240

Asp Leu Ala Ala Leu Arg Ser His Ala Gly Asp Pro Ala Phe Pro Pro
            6245                6250                6255

Leu Phe His Gly Leu Val Arg Ala Pro Ala Pro Arg Ala Ala Glu Ala
            6260                6265                6270

Pro Pro Ala Ser Glu Gly Val Arg Asp Arg Phe Ala Ala Leu Arg Gly
            6275                6280                6285

Ala Asp Arg Glu Arg Ala Leu Arg Glu Leu Val Cys Asp His Ala Ala
            6290                6295                6300

Thr Val Leu Gly His Gly Asp Ser Ala Ser Val Thr Pro Gly Arg Pro
```

```
                        6305                6310                6315                6320
Phe Lys Glu Leu Gly Phe Asp Ser Leu Thr Ala Val Glu Leu Arg Asn
                        6325                6330                6335

Arg Leu Gly Gly Ala Thr Gly Leu Arg Leu Ser Ala Thr Leu Val Phe
                        6340                6345                6350

Asp His Pro Thr Pro Leu Ala Leu Ala Glu His Leu Arg Ala Glu Leu
                        6355                6360                6365

Phe Ala Asp Glu Glu Pro Ala Gly Ala Ser Pro Ala Ala Glu Leu Glu
                        6370                6375                6380

Arg Leu Glu Ala Ala Leu Ala Leu Ala Ala Pro Asp Thr Phe Asp Arg
6385                    6390                6395                6400

Thr Gln Val Thr Thr Arg Leu Arg Ala Leu Leu Lys Arg Val Glu Arg
                        6405                6410                6415

Ala Glu Arg Ala Glu Arg Ala Glu Arg Ala Glu Pro Asn Gly Gln Ala
                        6420                6425                6430

Gly Pro Asp Gly Ala Leu Asp Leu Ser Ser Ala Thr His Asp Glu Ile
                        6435                6440                6445

Phe Ala Leu Ile Asp Gly Gln His Asp Val
                        6450                6455

<210> SEQ ID NO 3
<211> LENGTH: 7189
<212> TYPE: PRT
<213> ORGANISM: Streptomyces sp.Mer-16208

<400> SEQUENCE: 3

Val Ala Thr Glu Gln Glu Leu Phe Ala Tyr Leu Lys Lys Ala Thr Ser
1               5                   10                  15

Asp Leu Gln Gln Ala Arg Arg Val Arg Leu Glu Ser Pro Glu
                20                  25                  30

Pro Val Ala Ile Val Ala Met Ala Cys Arg Tyr Pro Gly Ala Val Arg
                35                  40                  45

Ser Pro Glu Asp Leu Trp Glu Leu Val Ala Ser Gly Thr Asp Ala Val
            50                  55                  60

Thr Pro Phe Pro Asp Asp Arg Gly Trp Asp Leu Asp Gly Leu Tyr Asp
65              70                  75                  80

Pro Asp Pro Asp Val Pro Gly Thr Ser Tyr Gly Arg Glu Gly Gly Phe
                85                  90                  95

Val Ala Gly Ala Ala Asp Phe Asp Ala Pro Phe Phe Gly Ile Ser Pro
                100                 105                 110

Arg Glu Ala Leu Ala Met Asp Pro Gln Gln Arg Leu Leu Leu Glu Thr
            115                 120                 125

Ser Trp Glu Val Leu Glu Arg Ala Gly Ile Asn Pro Ala Thr Leu Arg
        130                 135                 140

Ala Gly Arg Thr Gly Val Phe Thr Gly Ile Ser His Gln Asp Tyr Ala
145             150                 155                 160

Leu Gly Leu Ser Thr Ser Ala Glu Val Ser Glu Gly His Leu Met Thr
                165                 170                 175

Gly Asn Ala Val Ser Val Met Ser Gly Arg Val Ala Tyr Thr Phe Gly
            180                 185                 190

Phe Glu Gly Pro Ala Val Thr Val Asp Thr Ala Cys Ser Ser Ser Leu
        195                 200                 205

Val Ala Leu His Leu Ala Val Gln Ser Leu Arg Thr Gly Glu Cys Thr
    210                 215                 220

Leu Ala Leu Ala Gly Gly Ala Thr Val Met Ala Thr Pro Asn Ala Phe
```

```
            225                 230                 235                 240
Thr Arg Phe Ser Arg Glu Arg Gly Leu Ala Pro Asp Gly Arg Cys Lys
                245                 250                 255
Ala Phe Gly Ala Gly Ala Asp Gly Thr Gly Phe Ser Asp Gly Val Gly
            260                 265                 270
Val Leu Leu Leu Glu Arg Leu Ser Asp Ala Glu Arg Asn Gly His Arg
        275                 280                 285
Ile Leu Ala Val Val Arg Gly Ser Ala Val Asn Gln Asp Gly Ala Ser
    290                 295                 300
Asn Gly Leu Thr Ala Pro Asn Gly Pro Ala Gln Gln Arg Val Ile Arg
305                 310                 315                 320
Glu Ala Leu Ala Ala Gly Leu Asp Pro Ser Glu Val Asp Ala Val
                325                 330                 335
Glu Ala His Gly Thr Gly Thr Thr Leu Gly Asp Pro Ile Glu Ala Gln
            340                 345                 350
Ala Leu Leu Ala Thr Tyr Gly Gln Asn Arg Asp Arg Pro Leu Trp Leu
        355                 360                 365
Gly Ser Leu Lys Ser Asn Ile Gly His Thr Gln Ala Ala Gly Val
    370                 375                 380
Gly Gly Val Ile Lys Met Val Glu Ala Met Arg His Gly Thr Leu Pro
385                 390                 395                 400
Arg Thr Leu His Ala Asp Glu Pro Ser Pro Arg Val Asp Trp Ser Ala
                405                 410                 415
Gly Ala Val Glu Pro Leu Thr Glu Ala Arg Pro Trp Glu Pro Gly Ala
            420                 425                 430
Gly Gly Val Arg Arg Ala Gly Val Ser Ser Phe Gly Ile Ser Gly Thr
        435                 440                 445
Asn Ala His Val Val Leu Glu Glu Pro Pro Ala Arg Gln Glu Thr Pro
    450                 455                 460
Arg Ala Pro Gly Arg Ala Pro Ala Ala Thr Pro Trp Val Leu Ser Ala
465                 470                 475                 480
Arg Ser Ala Pro Ala Leu Arg Ala Gln Ala Glu Ala Leu Leu Ala Phe
                485                 490                 495
Leu Asp Pro Arg Arg Asp His His Ala Asp Ile Gly Ala Ala Val Thr
            500                 505                 510
Asp Thr Asp Leu Ala Phe Ser Leu Ala Thr Thr Arg Ala Ala Leu Glu
        515                 520                 525
His Arg Ala Thr Ala Val Ala Gly Asp Arg Glu Gly Leu Leu Ala Thr
    530                 535                 540
Val Arg Thr Ile Ala Asp Gly Ser Ala Ala Thr Thr Val Ala Gly Ala
545                 550                 555                 560
Asp Pro Lys Val Ala Phe Leu Phe Ala Gly Gln Gly Ser Gln Arg Val
                565                 570                 575
Gly Met Gly Arg Glu Leu Ala Ala Arg Phe Pro Val Phe Ala Ala Ala
            580                 585                 590
Leu Asp Thr Val Cys Gly Ala Leu Asp Pro Tyr Leu Asp Arg Ala Leu
        595                 600                 605
Arg Asp Val Ile Asp Gly Asp Ala Pro Thr Leu Asp Ser Thr Asp His
    610                 615                 620
Ala Gln Pro Ala Leu Phe Ala Leu Glu Val Ala Leu His Arg Leu Leu
625                 630                 635                 640
Glu Ser Trp Gly Val Arg Pro Asp Ala Val Ala Gly His Ser Val Gly
                645                 650                 655
```

-continued

Glu Ile Ala Ala Ala His Ile Ala Gly Val Leu Thr Leu Asp Asp Ala
            660                 665                 670

Ala Leu Leu Val Ser Ala Arg Gly Arg Leu Met Arg Leu Pro Glu
        675                 680                 685

Gly Gly Ala Met Val Ala Ile Glu Ala Pro Glu Ala Glu Val Leu Pro
690                 695                 700

Leu Val Ala Pro Phe Thr Gly Pro Phe Thr Gly Ala Gly Ala Ser Val
705                 710                 715                 720

Ala Ala Val Asn Thr Ala Thr Ser Thr Val Val Ser Gly Asp Glu Ser
                725                 730                 735

Ala Val Arg Glu Ile Ala Ala His Phe Glu Arg Gly Val Arg Thr
            740                 745                 750

Lys Arg Leu Arg Val Ser His Ala Phe His Ser Pro Leu Met Glu Pro
        755                 760                 765

Met Leu Ala Glu Phe Ala Ala Val Glu Gly Leu Ser Phe Ala Pro
        770                 775                 780

Pro Glu Leu Thr Phe Val Ser Thr Val Thr Gly Arg Ala Met Thr Asp
785                 790                 795                 800

Glu Val Ala Thr Pro Ala Tyr Trp Val Arg His Ala Arg Asp Ala Val
                805                 810                 815

Arg Phe Ala Asp Ala Val Thr Glu Leu Ala Ser Leu Gly Val Thr Ala
            820                 825                 830

Leu Val Glu Leu Gly Pro Asp Ala Thr Leu Ser Ala Leu Ala Ala Gly
        835                 840                 845

Ala Ala Pro Val Val Leu Pro Val Leu Arg Lys Asp Arg Asp Glu Glu
        850                 855                 860

Arg Ser Ala Ala Ala Leu Thr Gly Leu Trp Ala His Gly Val Pro
865                 870                 875                 880

Val Ala Trp Pro Ala Tyr Phe Thr Gly Thr Asp Pro Arg Pro Ala Asp
                885                 890                 895

Leu Pro Thr Tyr Ala Phe Gln Arg Glu Arg Tyr Trp Leu Asp Pro Val
            900                 905                 910

Thr Ser Ala Pro Gly Arg Ala Ser Ala Leu Gly Leu Gly Ala Ala Asp
        915                 920                 925

His Pro Leu Leu Gly Ala Val Thr Thr Leu Ala Ala Gly Asp Gly Leu
        930                 935                 940

Leu Phe Thr Gly Arg Leu Ala Thr Ala Thr His Arg Trp Leu Ala Asp
945                 950                 955                 960

His Ala Val Asp Gly Thr Val Leu Leu Pro Gly Thr Ala Phe Val Glu
                965                 970                 975

Leu Ala Val Arg Ala Gly Asp Glu Ala Gly Cys Asp Arg Val Asp Glu
            980                 985                 990

Leu Thr Leu Leu Ala Pro Leu Val Leu Pro Thr His Asp Gly Val Arg
        995                 1000                1005

Leu Gln Ile Ala Val Gly Ala Pro Asp Pro Ala Gly Arg Arg Ala Val
        1010                1015                1020

Thr Leu His Ser Arg Pro Glu Ala Tyr Gly Ala Asp Glu Pro Trp Thr
1025                1030                1035                1040

Leu His Ala Ser Gly Leu Leu Ala Pro Ser Thr Thr Pro Pro Asp
            1045                1050                1055

Asp Leu Ala Val Trp Pro Pro Glu Gly Ala Thr Ala Leu Pro Val Asp
            1060                1065                1070

Gly Val Tyr Ala Arg Leu Ala Glu Arg Gly Tyr Gly Tyr Gly Pro Ala
            1075                1080                1085

```
Phe Gln Gly Leu Arg Ala Ala Trp Thr Arg Gly Asp Glu Val Phe Ser
    1090                1095                1100

Glu Val Ala Leu Asp Pro Val Gly Gln Arg Asp Ala Ala Phe Gly
1105                1110                1115                1120

Leu His Pro Ala Leu Leu Asp Ala Ala Leu His Ala Thr Ala Val Arg
                1125                1130                1135

Thr Leu Gly Asp Gly Gly Ala Arg Leu Leu Pro Phe Ser Trp Asn Gly
                1140                1145                1150

Val Ser Leu Tyr Ala Ser Gly Ala Thr Ala Leu Arg Val Arg Val Ala
                1155                1160                1165

Pro Ala Asp Asp Gly Ala Leu Ser Val Leu Val Thr Asp Asp Glu Gly
                1170                1175                1180

Arg Pro Val Ala Ser Val Asp Ala Leu Thr Val Arg Ala Ala Gly Ala
1185                1190                1195                1200

Asp Asp Val Thr Ala Ala Gly Gly Asp Asp Ala Leu Phe Arg Leu
                1205                1210                1215

Asp Trp Thr Glu Leu Pro Pro Ala Asp Ala Pro Glu Arg Gly Pro Gly
                1220                1225                1230

Ser Leu Val Val Leu Gly Gly Asp Gly Leu Gly Leu Asp Leu Asp Pro
                1235                1240                1245

Gly Ala Gly Pro Ala Val Arg Val His Ala Ala Leu Ala Gly Leu Asp
1250                1255                1260

Thr Val Pro Asp Thr Val Leu Ala Pro Phe Leu Thr Pro Gly Ala Gly
1265                1270                1275                1280

Gly Thr Asp Leu Ala Gly Ala Ala His Thr Ala Thr Arg Arg Ala Leu
                1285                1290                1295

Ala Leu Val Arg Glu Trp Leu Ala Asp Glu Arg Phe Ala Ala Ser Arg
                1300                1305                1310

Leu Val Phe Leu Thr Arg Gly Ala Leu Thr Ala Asp Leu Ala Asn Ala
                1315                1320                1325

Pro Val Trp Gly Leu Val Arg Ala Ala Gln Ser Glu His Pro Gly Arg
                1330                1335                1340

Phe Thr Leu Leu Asp Leu Asp Glu Ile Thr Pro Glu Gly Val Arg Ala
1345                1350                1355                1360

Gly Leu Ala Ala Asp His Ser Gln Leu Arg Val Thr Glu Gly Arg Leu
                1365                1370                1375

Arg Val Pro Arg Leu Ala Arg Val Gly Ala Ala Ala Gly Gly Ala Glu
                1380                1385                1390

Arg Pro Ala Pro Trp Ser Pro Ser Gly Thr Val Leu Ile Thr Gly Gly
                1395                1400                1405

Thr Gly Gly Leu Gly Ser Leu Val Ala Arg His Leu Val Thr Glu His
                1410                1415                1420

Gly Val Arg Arg Leu Val Leu Ala Gly Arg Arg Gly Pro Glu Ala Pro
1425                1430                1435                1440

Gly Ala Ala Glu Leu Ser Ala Glu Leu Gly Ala Leu Gly Ala Glu Val
                1445                1450                1455

Thr Val Val Ala Cys Asp Ala Ala Asp Arg Asp Ala Leu Ala Ala Leu
                1460                1465                1470

Leu Ala Ala His Pro Pro Asn Ala Val Val His Thr Ala Gly Val Leu
                1475                1480                1485

Asp Asp Gly Val Ile Ala Ser Leu Thr Pro Glu Arg Leu Asp Ala Val
                1490                1495                1500

Leu Arg Pro Lys Val Asp Ala Ala Val Asn Leu His Glu Leu Thr Ser
```

```
             1505                1510                1515                1520

Glu Leu Glu Ala Phe Val Leu Phe Ser Ser Ala Ser Gly Leu Leu Gly
                1525                1530                1535

Gly Ala Gly Gln Ala Asn Tyr Ala Ala Ala Asn Ala Phe Leu Asp Ala
            1540                1545                1550

Leu Ala Thr Ala Arg Thr Ala Gln Gly Leu Pro Ala Leu Ser Leu Ala
        1555                1560                1565

Trp Gly Ala Trp Ala Gly Asp His Gly Met Thr Gly Thr Leu Asp Glu
    1570                1575                1580

Ala Asp Thr Arg Arg Met Ala Arg Gly Val Leu Pro Leu Gly Ala
1585                1590                1595                1600

Glu Arg Gly Leu Gly Leu Phe Asp Arg Ala Leu Ala Ala Asp Arg Pro
                1605                1610                1615

Leu Leu Val Pro Met Leu Leu Asp Thr Ala Ala Val Arg Asn Ser Gly
                1620                1625                1630

Glu Pro Val Pro Glu Leu Leu Arg Gly Leu Ile Arg Pro Pro Arg Arg
            1635                1640                1645

Arg Gly Ala Ala Gly Gly Ala Gly Asp Gly Gly Gly Thr Ala Leu Ala
        1650                1655                1660

Arg Arg Leu Ala Ala Leu Asp Pro Ala Asp Arg Ala Ala Glu Leu Leu
1665                1670                1675                1680

Thr Leu Val Arg Thr Glu Val Ala Leu Ala Leu Gly Tyr Ala Asp Pro
                1685                1690                1695

Gly Thr Ile Glu Ala Asp Lys Ala Phe Lys Asp Leu Gly Phe Asp Ser
                1700                1705                1710

Leu Thr Ala Val Glu Leu Arg Asn Ala Leu His Thr Arg Thr Gly Leu
            1715                1720                1725

Arg Leu Pro Ala Thr Leu Leu Phe Asp Ala Pro Thr Pro Leu Val Leu
        1730                1735                1740

Ala Gly Arg Leu Ala Ala Glu Leu Ala Gly Thr Gly Pro Gly Ala
1745                1750                1755                1760

Ala Ala Pro Ala Ala Gln Ala Arg Ala Arg Thr Asp Gln Glu Pro Ile
                1765                1770                1775

Ala Ile Val Ala Met Gly Cys His Phe Pro Gly Gly Val Arg Ser Pro
                1780                1785                1790

Glu Glu Leu Trp Ser Leu Val Thr Gly Gly Val Asp Ala Val Ser Ala
            1795                1800                1805

Phe Pro Asp Asp Arg Gly Trp Asp Val Asp Ala Leu Tyr Asp Thr Asp
        1810                1815                1820

Pro Asp Arg Pro Gly Thr Ser Tyr Thr Arg His Gly Gly Phe Leu Arg
1825                1830                1835                1840

Asp Ala Ser Leu Phe Asp Pro Ala Phe Phe Gly Met Ser Pro Arg Glu
                1845                1850                1855

Ala Leu Ala Thr Asp Pro Gln Gln Arg Leu Leu Leu Glu Thr Thr Trp
            1860                1865                1870

Glu Val Phe Glu Arg Ala Gly Ile Asp Pro Ala Thr Val Lys Gly Thr
        1875                1880                1885

Pro Thr Gly Val Phe Val Gly Val Met Tyr Asn Asp Tyr Ala Gln Cys
    1890                1895                1900

Leu Ala Glu Ser Leu Glu Gly His Ile Ala Gly Gly Ser Ala Ala Ser
1905                1910                1915                1920

Val Ala Ser Gly Arg Leu Ser Tyr Thr Phe Gly Leu Glu Gly Pro Ala
                1925                1930                1935
```

-continued

```
Val Thr Val Asp Thr Ala Cys Ser Ser Ser Leu Val Ala Val His Leu
            1940                1945                1950

Ala Ala Gln Ser Leu Arg Gln Gly Glu Cys Thr Leu Ala Leu Ala Gly
            1955                1960                1965

Gly Val Thr Val Met Ser Thr Pro Thr Thr Phe Val Glu Phe Ser Arg
            1970                1975                1980

Gln Arg Gly Leu Ser Pro Asp Gly Arg Cys Lys Ala Tyr Gly Ala Asp
1985                1990                1995                2000

Ala Asp Gly Thr Gly Trp Ser Glu Gly Val Gly Leu Leu Leu Leu Glu
            2005                2010                2015

Arg Leu Ser Asp Ala Glu Arg Asn Gly His Glu Ile Leu Ala Val Val
            2020                2025                2030

Arg Gly Ser Ala Val Asn Gln Asp Gly Ala Ser Asn Gly Leu Thr Ala
            2035                2040                2045

Pro Asn Gly Pro Ala Gln Gln Arg Val Ile Arg Gln Ala Leu Ala Asn
            2050                2055                2060

Ala Gly Leu Gly Ala Ala Asp Ile Glu Ala Val Glu Gly His Gly Thr
2065                2070                2075                2080

Gly Thr Thr Leu Gly Asp Pro Ile Glu Ala Gln Ala Leu Leu Ala Thr
            2085                2090                2095

Tyr Gly Gln Asp Arg Asp Arg Pro Leu Trp Leu Gly Ser Leu Lys Ser
            2100                2105                2110

Asn Ile Gly His Thr Gln Ala Ala Ala Gly Val Gly Gly Ile Ile Lys
            2115                2120                2125

Met Val Gln Ala Ile Arg His Gly Val Leu Pro Arg Thr Leu His Ala
            2130                2135                2140

Asp Glu Pro Ser Pro His Val Asp Trp Ser Ala Gly Ala Val Ser Leu
2145                2150                2155                2160

Leu His Glu Asn Leu Pro Trp Pro Gly Thr Gly Arg Pro Arg Arg Ala
            2165                2170                2175

Gly Val Ser Ser Phe Gly Val Ser Gly Thr Asn Ala His Thr Leu Leu
            2180                2185                2190

Glu Glu Ala Pro Arg Pro Ala Ala Pro Pro Arg Pro Arg Glu Val Pro
            2195                2200                2205

Pro Pro Pro Thr Glu Pro Val Pro Trp Val Leu Ser Ala Lys Thr Pro
            2210                2215                2220

Gln Ala Leu Arg Ala Gln Ala Ala Arg Leu Ala Arg His Leu Asp Asp
2225                2230                2235                2240

Asp Pro Glu Val Ser Gly Ala Thr Ala Ala Asp Val Gly Leu Ser Leu
            2245                2250                2255

Ala Thr Thr Arg Ser Ala Phe Asp His Arg Ala Val Leu Val Gly His
            2260                2265                2270

Asp Pro Gly Glu Phe Arg Ala Leu Leu Ala Glu Leu Ala Thr Asp Thr
            2275                2280                2285

Val Ser Ala Arg Ile Val Arg Gly Thr Ala Arg Pro Pro Gly Lys Thr
            2290                2295                2300

Val Phe Val Phe Pro Gly Gln Gly Ser Gln Trp Pro Gly Met Ala Val
2305                2310                2315                2320

Asp Leu Leu Ala His Pro Val Phe Arg Ala Arg Met Glu Glu Cys Ala
            2325                2330                2335

Ala Ala Leu Ala Pro His Val Glu Trp Ser Leu Trp Asp Val Leu Gly
            2340                2345                2350

Asp Ala Glu Ala Leu Arg Arg Val Asp Val Val Gln Pro Ala Leu Phe
            2355                2360                2365
```

Ala Val Met Val Ser Leu Ala Ala Leu Trp Arg Ser Tyr Gly Val Glu
        2370                2375                2380

Pro Ala Val Val Gly His Ser Gln Gly Glu Ile Ala Ala Cys
2385                2390                2395                2400

Val Ala Gly Gly Leu Thr Leu Pro Asp Ala Ala Lys Val Val Ala Leu
            2405                2410                2415

Arg Ser Arg Ala Ile Leu Glu Leu Ala Gly Arg Gly Met Val Ser
        2420                2425                2430

Leu Pro Leu Ser Ala Ala Glu Ala Ala Gly Arg Leu Asp Gly Arg Asp
            2435                2440                2445

Gly Leu Ser Val Ala Ala Val Asn Gly Pro Arg Ser Val Val Val Ala
        2450                2455                2460

Gly Asp Asp Gln Ala Leu Asp Ala Leu Leu Ala Ser Cys Glu Ala Asp
2465                2470                2475                2480

Gly Ile Arg Ala Arg Arg Val Pro Val Asp Tyr Ala Ser His Ser Ala
            2485                2490                2495

His Val Glu Ala Val Gln Glu Glu Leu Arg Thr Ile Leu Asp Gly Ile
        2500                2505                2510

Thr Pro Arg Pro Gly Pro Val Ala Phe Tyr Ser Ala Val Thr Gly Ala
        2515                2520                2525

Leu Leu Asp Thr Thr Ala Leu Asp Pro Ala Tyr Trp Tyr Arg Asn Leu
        2530                2535                2540

Arg Glu Thr Val Arg Phe Asp Glu Ala Thr Arg Ala Leu Ala Gly Ser
2545                2550                2555                2560

Gly His His Arg Phe Ile Glu Met Gly Pro His Pro Val Leu Ala Val
        2565                2570                2575

Gly Ile Arg Glu Thr Leu Glu Glu Phe Gly Ala Asp Gly Gln Val Leu
        2580                2585                2590

Gly Ser Leu Arg Arg Asp Asp Gly Gly Pro Glu Arg Leu Leu Leu Ser
        2595                2600                2605

Leu Ala Glu Ala His Ala Gly Gly Gln Arg Leu Asp Trp Gln Ala Val
        2610                2615                2620

Phe Ala Gly Leu Gly Ala Arg Arg Val Pro Leu Pro Thr Tyr Pro Phe
2625                2630                2635                2640

Gln Ala Glu Arg Tyr Trp Pro Ala Pro Arg Ala Gly Arg Arg Gly Asp
            2645                2650                2655

Leu Thr Ala Leu Gly Leu Ser Ala Ser Gly His Pro Leu Phe Gly Ala
        2660                2665                2670

Gly Val Pro Met Ala Glu Gly Asp Gly Val Leu Leu Val Gly Ala Leu
        2675                2680                2685

Ser Leu Ala Thr His Pro Trp Leu Ala Asp His Ala Val Gly Asp Thr
        2690                2695                2700

Val Leu Leu Pro Gly Thr Ala Phe Val Glu Leu Ala Leu Arg Ala Gly
2705                2710                2715                2720

Asp His Ile Gly Cys Ala Gly Leu Ala Glu Leu Thr Leu Gln Ala Pro
            2725                2730                2735

Leu Ile Leu Pro Ala Arg Gly Thr Val Arg Leu Gln Leu Thr Val Gly
        2740                2745                2750

Glu Pro Asp Glu Gln Gly Arg Arg Pro Ile Thr Ala Gly Ser Arg Gln
        2755                2760                2765

Asn Asp Asp Gly Pro Trp Thr Arg His Ala Thr Gly Val Leu Glu Pro
        2770                2775                2780

Thr Ala Ala Ala Pro Gly Thr Gly Pro Asp Ala Thr Asp Phe Thr Ala

-continued

```
            2785                2790                2795                2800
Trp Pro Pro Pro Gly Ala Thr Pro Val Ala Val Asp Asp Leu Tyr Asp
                2805                2810                2815
Arg Leu Pro Gly Ile Gly Leu Arg Tyr Gly Pro Ala Phe Gln Gly Val
                2820                2825                2830
Arg Ala Leu Trp Arg Arg Gly Asp Asp Leu Phe Ala Glu Val Arg Leu
                2835                2840                2845
Ala Pro Glu Gln Arg Asp Glu Ala Gly Leu Phe Gly Val His Pro Ala
                2850                2855                2860
Leu Leu Asp Ala Ala Leu His Pro Phe Leu Thr Gly Val Leu Asp Ala
2865                2870                2875                2880
Asp Thr His Asp Gly Gln Val Ala Leu Pro Phe Ala Trp Thr Gly Val
                2885                2890                2895
Ala Leu His Ala Thr Gly Ala Ser Ala Leu Arg Val Arg Leu Ala Pro
                2900                2905                2910
Gly Gly Arg Val Glu Ala Ala Asp Glu Arg Gly Ala Pro Val Ala Thr
                2915                2920                2925
Val Gly Ala Leu Ser Ser Arg Pro Val Pro Val Ala Gly Leu Ala Ala
                2930                2935                2940
His Gly Pro Leu Tyr Arg Ile Val Trp Gln Pro Leu Ala Pro Asp Pro
2945                2950                2955                2960
Ala Gly Asp Ala Gly Gly Thr Gly Gly Val Ile Leu Gly Glu Asp Ile
                2965                2970                2975
Leu Gly Leu Gly Leu Pro Ala Tyr Pro Asp Leu Asp Thr Leu Ala Ala
                2980                2985                2990
Ala Arg Pro Ala Ala Gly Pro Val Phe Ala Thr Leu Ser Gly Gly Pro
                2995                3000                3005
Gly Ala Asp Ala Val His Thr Ala Thr His Glu Ala Leu Ala Leu Ala
                3010                3015                3020
Arg Ala Trp Thr Gly Asp Glu Arg Phe Asp Gly Ser Arg Leu Val Val
3025                3030                3035                3040
Val Gly Arg Gly Ala Val Ala Thr Ala Gly Asp Glu Asp Val Pro Asp
                3045                3050                3055
Leu Ala Ala Ala Ala Ala His Gly Leu Leu Arg Ser Thr Gln Ser Glu
                3060                3065                3070
His Pro Asp Arg Ile Val Leu Val Asp Ile Gly His Ala Gly Asp Ser
                3075                3080                3085
Thr Ala Leu Leu Tyr Ala Ala Ala Ser Cys Asp Glu Pro Asn Val Ala
                3090                3095                3100
Val Arg Asp Gly Glu Leu Arg Val Pro Arg Leu Glu Arg Val Pro Ala
3105                3110                3115                3120
Asp Ala Asp Glu Pro Thr Gly Ser Trp Asp Pro Asp Gly Thr Val Leu
                3125                3130                3135
Ile Thr Gly Gly Thr Gly Val Leu Gly Gly Leu Val Ala Arg His Leu
                3140                3145                3150
Ala Ala Thr His Gly Val Arg Arg Leu Leu Leu Thr Ser Arg Arg Gly
                3155                3160                3165
Ser Asp Ser Pro Gly Ala Thr Glu Leu Ala Ala Glu Leu Ala Ala Leu
                3170                3175                3180
Gly Ala Glu Val Thr Val Ala Ala Cys Asp Ala Ala Asp Arg Asp Ala
3185                3190                3195                3200
Leu Ala Ala Leu Leu Ala Gly His Arg Ile Thr Ser Val Val His Thr
                3205                3210                3215
```

-continued

Ala Gly Val Leu Asp Asp Gly Val Ile Gly Ala Leu Thr Pro Glu Arg
            3220                3225                3230

Val Asp Thr Val Leu Arg Pro Lys Ala Asp Ala Ala Leu His Leu His
            3235                3240                3245

Glu Leu Thr His Asp Leu Asp Ala Phe Val Leu Phe Ser Ser Ala Ala
            3250                3255                3260

Ala Ala Phe Gly Ala Pro Gly Gln Gly Asn Tyr Ala Ala Gly Asn Ala
3265                3270                3275                3280

Phe Leu Asp Ala Leu Ala Gln His Arg Arg Ala Arg Gly Leu Pro Ala
            3285                3290                3295

Val Ser Leu Ala Trp Gly Leu Trp Glu Gln Ser Ser Ala Met Thr Gly
            3300                3305                3310

His Leu Gly Ala Asp Asp Leu Ala Arg Gln Arg Ala Thr Gly Ala Leu
            3315                3320                3325

Ala Leu Pro Ser Ala Glu Gly Leu Arg Leu Pro Phe Asp Ala Ala Thr Ala
            3330                3335                3340

Thr Arg Gly Ala Asp Pro Val Thr Gly Ala Gly Ser Thr Ala Val Gln
3345                3350                3355                3360

Gly Ala Ala Leu Leu Leu Pro Leu Arg Leu Asp Leu Ala Arg Leu Arg
            3365                3370                3375

Ala Ser Ala Ala Pro Val Pro Ala Leu Leu Arg Gly Leu Val Arg Thr
            3380                3385                3390

Ala Ala Arg Pro Thr Ala Gly Thr Ala Thr Thr Asp Gly Ser Gly Leu
            3395                3400                3405

Ala His Arg Leu Thr Ala Leu Pro Val Glu Gln Gln His Arg Glu Leu
            3410                3415                3420

Leu Asp Leu Val Arg Gly His Ala Ala Ala Val Leu Gly His Pro Gly
3425                3430                3435                3440

Pro Glu Ala Ile Asp Pro Asp Thr Ala Thr Arg Asp Leu Gly Phe Asp
            3445                3450                3455

Ser Leu Thr Ala Val Ala Leu Arg Asn Gln Leu Ala Glu Ala Thr Gly
            3460                3465                3470

Leu Arg Leu Pro Ala Thr Leu Val Phe Asp His Pro Thr Pro Ala Ala
            3475                3480                3485

Leu Ala Thr Thr Leu Arg Thr Arg Leu Thr Gly Ile Ser Glu Ala Pro
            3490                3495                3500

Ala Ala Pro Val Ala Gly Thr Val Val Pro Ser Asp Pro Ile Ala
3505                3510                3515                3520

Val Val Gly Met Ala Cys Arg Tyr Pro Gly Gly Val Arg Ser Pro Glu
            3525                3530                3535

Asp Leu Trp Glu Leu Val Ala Ala Gly Gly Asp Ala Ile Ala Ala Met
            3540                3545                3550

Pro Gly Asp Arg Gly Trp Asp Ile Asp Gly Leu Tyr Asp Pro Asp Gln
            3555                3560                3565

Asp Arg Thr Gly Thr Phe Ala Thr Arg Glu Gly Gly Phe Leu Tyr Asp
            3570                3575                3580

Ala Ala Glu Phe Asp Pro Ala Phe Phe Gly Ile Ser Pro Arg Glu Ala
3585                3590                3595                3600

Leu Ala Met Asp Pro Gln Gln Arg Leu Leu Leu Glu Thr Ser Trp Gln
            3605                3610                3615

Ala Phe Glu Arg Ala Gly Ile Asp Pro Ala Thr Ala Arg Gly Ser Arg
            3620                3625                3630

Thr Gly Val Phe Val Gly Val Met Tyr His Asp Tyr Gly Ala Gly Ala
            3635                3640                3645

```
Asp Ala Val Pro Glu Asp Val Glu Gly Tyr Leu Gly Gly Thr Ala
    3650                3655                3660

Gly Ser Val Ala Ser Gly Arg Val Ser Tyr Thr Leu Gly Leu Glu Gly
3665                3670                3675                3680

Pro Ala Val Thr Val Asp Thr Ala Cys Ser Ser Leu Val Thr Leu
        3685                3690                3695

His Leu Ala Ala Gln Ala Leu Arg Ala Gly Asp Cys Thr Met Ala Leu
        3700                3705                3710

Ala Gly Gly Ala Thr Val Met Ser Thr Pro Gly Thr Phe Val Glu Phe
        3715                3720                3725

Ser Arg Gln Arg Gly Leu Ala Ala Asp Gly Arg Cys Lys Ser Phe Ala
        3730                3735                3740

Ala Gly Ala Asp Gly Thr Gly Trp Gly Glu Gly Ala Gly Met Leu Leu
3745                3750                3755                3760

Leu Glu Arg Leu Ser Asp Ala Glu Arg Asn Gly His Asp Val Leu Ala
                3765                3770                3775

Val Val Arg Ser Thr Ala Ile Asn Gln Asp Gly Ala Ser Asn Gly Leu
        3780                3785                3790

Ser Ala Pro Asn Gly Pro Ala Gln Gln Arg Val Ile Arg Gln Ala Leu
        3795                3800                3805

Ala Asn Ala Arg Leu Ser Ser Ala Asp Val Asp Val Val Glu Gly His
        3810                3815                3820

Gly Thr Gly Thr Thr Leu Gly Asp Pro Ile Glu Ala Asp Ala Leu Leu
3825                3830                3835                3840

Ala Thr Tyr Gly Gln Asp Arg Glu His Pro Leu Trp Leu Gly Ser Leu
        3845                3850                3855

Lys Ser Asn Ile Gly His Thr Gln Ala Ala Ala Gly Val Ala Gly Val
        3860                3865                3870

Ile Lys Met Val Gln Ala Leu Arg His Gly Leu Leu Pro Arg Thr Leu
        3875                3880                3885

His Val Asp Gln Pro Ser Pro His Ile Asp Trp Thr Ala Gly Ala Val
        3890                3895                3900

Arg Leu Leu Thr Asp Ala Arg Pro Trp Pro Asp Thr Gly Arg Pro Arg
3905                3910                3915                3920

Arg Ala Gly Val Ser Ser Phe Gly Val Ser Gly Thr Asn Ala His Ala
                3925                3930                3935

Ile Leu Glu Gln Ala Pro Glu Ala Pro Val Pro Asp His Arg Asp Ser
        3940                3945                3950

Pro Ala Pro Gly Ala Val Pro Trp Val Leu Ser Ala Lys Thr Ala Glu
        3955                3960                3965

Ala Leu Arg Ala Gln Ala Gly Arg Leu Ala Ala Arg Ala Thr Asp Arg
        3970                3975                3980

Pro Pro Gly Asp Val Gly Leu Ser Leu Ala Thr Thr Arg Thr Arg Phe
3985                3990                3995                4000

Glu Arg Arg Ala Val Val Ile Gly Ala Asp Gly Ala Ala Leu Leu Ala
                4005                4010                4015

Gly Thr Asp Ala Leu Ala His Gly Glu Pro Arg Ala Asp Val Val Glu
        4020                4025                4030

Gly Val Ala Asp Leu Arg Gly Arg Thr Val Phe Val Phe Pro Gly Gln
        4035                4040                4045

Gly Ser Gln Trp Val Gly Met Ala Gly Glu Leu Met Glu Ser Ser Pro
        4050                4055                4060

Val Phe Ala Ala Arg Met Ala Glu Cys Ala Glu Ala Leu Ala Pro Tyr
```

-continued

```
            4065                4070                4075                4080
Thr Asp Trp Ser Leu Ser Asp Val Leu Gly Asp Gly Ala Ala Leu Gly
                    4085                4090                4095
Arg Val Glu Val Val Gln Pro Ala Leu Phe Ala Val Met Val Ser Leu
                4100                4105                4110
Ala Ala Leu Trp Arg Ser Tyr Gly Val Glu Pro Ala Ala Val Val Gly
                4115                4120                4125
His Ser Gln Gly Glu Ile Ala Ala Cys Val Ala Gly Ala Leu Ser
                4130                4135                4140
Leu Ala Asp Ala Ala Arg Ile Val Ala Leu Arg Ser Arg Ala Ile Ala
4145                4150                4155                4160
Ala Thr Leu Ala Gly His Gly Gly Met Met Ser Leu Ala Leu Ser Val
                    4165                4170                4175
Ala Glu Ala Glu Ser Gln Leu Ala His Arg Asp Gly Arg Ile Thr Leu
                4180                4185                4190
Ala Ala Val Asn Gly Pro Arg Ser Val Val Ala Gly Glu Pro Ala
                4195                4200                4205
Ala Leu Glu Glu Leu Arg Ala Ala Val Glu Glu Ser Gly Arg Arg Ala
                4210                4215                4220
Arg Arg Ile Pro Val Asp Tyr Ala Ser His Thr Ala His Val Glu Ala
4225                4230                4235                4240
Val Glu Ala Glu Leu Leu Ala Thr Leu Ala Asp Val Ala Pro Arg Ser
                    4245                4250                4255
Ala Thr Val Pro Phe Phe Ser Thr Val Thr Ala Gly Trp Leu Asp Gly
                4260                4265                4270
Thr Arg Leu Asp Ala Ala Tyr Trp Tyr Arg Asn Leu Arg Glu Pro Val
                4275                4280                4285
Arg Phe Glu Glu Ala Val Arg Glu Leu Ala Thr His Gly Phe Asp Phe
                4290                4295                4300
Phe Val Glu Thr Ser Gly His Pro Val Leu Thr Val Gly Val Arg Glu
4305                4310                4315                4320
Thr Leu Asp Ala Leu Asp Ser Pro Ala Val Thr Leu Gly Ser Leu Arg
                    4325                4330                4335
Arg Asp Asp Gly Gly Pro Asp Arg Phe Leu Arg Ser Leu Ala Glu Gly
                4340                4345                4350
His Val Arg Gly Leu Ser Val Asp Trp Thr Pro Ala Phe Pro Gly Ala
                4355                4360                4365
Arg Arg Thr Ala Leu Pro Thr Tyr Ala Phe Gln Arg Glu Arg Tyr Trp
                4370                4375                4380
Leu Glu Ser Gly Arg Gln Arg Ala Thr Ala Pro Arg Asp Ala Thr Asp
4385                4390                4395                4400
Arg Ala Phe Trp Ala Ala Val Glu Arg Ala Asp Leu Ala Glu Leu Thr
                    4405                4410                4415
Gly Thr Leu Ala Leu Thr Gly Asp Glu Pro Leu Ser Ala Val Leu Pro
                4420                4425                4430
Ala Leu Ser Ser Trp Arg Arg Arg His Arg Glu Arg Ser Arg Thr Asp
                4435                4440                4445
Gly Trp Arg Tyr Arg Ile Thr Trp Gln Pro Val Ala Ala Thr Arg Arg
                4450                4455                4460
Pro Ala Ala Gly Thr Arg Leu Val Leu Leu Pro Ala Thr Gly Asp Gly
4465                4470                4475                4480
Ala Ala Trp Ala Asp Ala Leu Gly Asp Pro Thr Val Arg Ile Val Val
                    4485                4490                4495
```

-continued

```
Asp Ala Asp Asp Arg Ala Thr Leu Ala Ala Arg Leu Arg Ala Val Arg
            4500                4505                4510

Asp Ala Leu Pro Asp Gly Gly Arg Ile Thr Gly Val Val Ser Leu Leu
        4515                4520                4525

Ala Leu Asp Gly Arg Ala Gly Pro Ala Gly Thr Ala Val Pro Val Gly
    4530                4535                4540

Thr Ala Ala Thr Leu Thr Leu Val Gln Ala Leu Gly Asp Ala Asp Val
4545                4550                4555                4560

Asp Ala Pro Leu Trp Leu Leu Thr Gln Gly Ala Val Ala Val Gly Pro
            4565                4570                4575

Glu Arg Leu Ala Arg Val Pro Gln Ala Gln Ile Trp Gly Leu Gly Arg
        4580                4585                4590

Val Val Ala Leu Glu His Pro Glu Arg Trp Gly Gly Leu Ile Asp Leu
    4595                4600                4605

Pro Glu Ser Pro Asp Gly Ala Ala Thr Glu Arg Leu Ala Gly Ala Leu
4610                4615                4620

Thr Arg Thr Asp Asp Glu Asp Gln Leu Ala Ile Arg Ala Ser Gly Val
4625                4630                4635                4640

Tyr Val Arg Arg Leu Thr Arg Ala Pro Glu Thr Ser Pro Thr Ser Ser
            4645                4650                4655

Ser Thr Ser Ser Pro Thr Ser Ser Ala Ala Val Pro Asp Ala Ala
        4660                4665                4670

Val Pro Asp Ala Thr Trp Arg Pro Ser Gly Thr Trp Arg Pro Ser Gly
    4675                4680                4685

Thr Trp Arg Pro Ser Gly Thr Val Leu Val Thr Gly Gly Thr Gly Ala
    4690                4695                4700

Leu Gly Ala Arg Ala Ala Arg Trp Leu Ala Ala Ser Gly Ala Gly His
4705                4710                4715                4720

Leu Val Leu Thr Ser Arg Arg Gly Pro Glu Ala Pro Gly Ala Ala Glu
            4725                4730                4735

Leu Thr Ala Glu Leu Arg Ala Leu Gly Ala Glu Val Thr Val Ala Ala
        4740                4745                4750

Cys Asp Ala Ala Asp Arg Asp Ala Met Gly Arg Leu Leu Ala Glu His
    4755                4760                4765

Pro Pro Thr Ala Val Val His Thr Ala Gly Val Leu Asp Asp Gly Val
    4770                4775                4780

Leu Asp His Leu Asp Thr Gly Arg Leu Ala Thr Val Phe Gly Pro Lys
4785                4790                4795                4800

Thr Ala Ala Ala Thr Val Leu Asp Ala Leu Thr Arg Asp Leu Gly Leu
            4805                4810                4815

Asp Leu Ser Ala Phe Val Leu Phe Ser Ser Ala Ala Gly Val Leu Gly
        4820                4825                4830

Ser Ala Gly Gln Ala Asn Tyr Ala Ala Ala Asn Ala His Leu Asp Ala
    4835                4840                4845

Leu Ala Glu Gln Arg Arg Ala Asp Gly Leu Pro Ala Thr Ser Val Ala
        4850                4855                4860

Trp Gly Ala Trp Ala Asp Ser Gly Leu Ala Met Asp Ala Gly Val Val
4865                4870                4875                4880

Glu Arg Arg Leu Gln Gln Gly Gly Val Leu Pro Met Ala Pro Asp Leu
            4885                4890                4895

Ala Leu Gly Ala Leu Gln Gln Ala Leu Asp Gln Gly Asp Thr Ala Val
        4900                4905                4910

Met Val Ala Asp Ile Asp Trp Gln Arg Phe Thr Gly Ala Gly Ala Gly
    4915                4920                4925
```

```
Arg Thr Arg Pro Trp Leu Gly Arg Leu Ala Gly Ala Pro Thr Ala Pro
        4930                4935                4940

Asp Gly Thr Ala Pro Asp Ala Ala Pro Asp Leu Leu Arg Gln Leu Arg
4945                4950                4955                4960

Gly Gln Gly Ala Ala Gln Arg Ala Arg Thr Leu Arg Thr Leu Val Arg
            4965                4970                4975

Thr Gln Ala Ala Val Val Leu Gly His Arg Gly Pro Ala Ser Val Asp
        4980                4985                4990

Ala Gly Arg Ala Phe Arg Asp Leu Gly Leu Asp Ser Leu Thr Ala Val
            4995                5000                5005

Glu Leu Arg Asn Arg Leu Gly Ala Ala Thr Gly Leu Lys Leu Pro Thr
        5010                5015                5020

Thr Leu Val Phe Asp His Pro Thr Ala Ala Leu Leu Ala Asp His Leu
5025                5030                5035                5040

Glu His Glu Leu Phe Gly Ala Asp Glu Ala Leu Ala Pro Gly Asp Glu
            5045                5050                5055

Leu Ser Pro Asp Ala Ala Pro Leu Ala Ala Thr Asp Ser Asp Pro Ile
            5060                5065                5070

Val Ile Val Ala Met Ser Cys Arg Phe Pro Gly Gly Val Arg Asn Pro
        5075                5080                5085

Asp Asp Leu Trp Glu Leu Leu Ala Ala Gly Arg Asp Ala Val Gly Ala
5090                5095                5100

Phe Pro Asp Asp Arg Gly Trp Asp Leu Asp Ala Leu His His Pro Asp
5105                5110                5115                5120

Pro Asp His Arg Gly Thr Thr Tyr Thr Arg His Gly Ala Phe Leu His
            5125                5130                5135

Asp Ala Pro Asp Phe Asp Ala Asp Leu Phe Gly Ile Ser Pro Arg Glu
            5140                5145                5150

Ala Leu Ala Met Asp Pro Gln Gln Arg Val Leu Leu Glu Thr Ala Trp
            5155                5160                5165

Glu Ala Phe Glu Gly Ala Gly Ile Asp Pro Ala Thr Leu Arg Gly Ser
        5170                5175                5180

Arg Ala Gly Val Phe Val Gly Thr Asn Gly Gln Asp Tyr Ala Gly Gly
5185                5190                5195                5200

Pro Gly Asp Ala Pro Glu Gly Thr Glu Gly Tyr Leu Leu Ala Gly Asn
            5205                5210                5215

Ala Ala Ser Val Val Ser Gly Arg Ile Ala Tyr Thr Phe Gly Leu Glu
            5220                5225                5230

Gly Pro Ala Val Thr Val Asp Thr Ala Cys Ser Ser Ala Leu Val Ala
            5235                5240                5245

Leu His Trp Ala Ala Gln Ala Leu Arg Gln Gly Glu Cys Thr Leu Ala
        5250                5255                5260

Leu Ala Gly Gly Val Ser Val Met Ser Thr Pro Ala Ala Phe Val Glu
5265                5270                5275                5280

Phe Ser Arg Gln Arg Gly Leu Ala Pro Asp Gly Arg Cys Lys Ala Phe
            5285                5290                5295

Ala Asp Ser Ala Asp Gly Thr Gly Trp Gly Glu Gly Ala Gly Leu Val
            5300                5305                5310

Val Leu Glu Arg Leu Ser Asp Ala Glu Arg His Gly His Pro Val Leu
        5315                5320                5325

Ala Leu Val Arg Gly Ser Ala Val Asn Gln Asp Gly Ala Ser Asn Gly
        5330                5335                5340

Leu Thr Ala Pro Asn Gly Pro Ala Gln Gln Arg Val Ile Arg Gln Ala
```

```
                5345                5350                5355                5360
Leu Ala His Ala Arg Leu Ala Pro Ala Asp Ile Asp Ala Val Glu Ala
                5365                5370                5375
His Gly Thr Gly Thr Thr Leu Gly Asp Pro Ile Glu Ala Gln Ala Leu
                5380                5385                5390
Leu Ala Thr Tyr Gly Gln Asp Arg Glu Arg Pro Leu Trp Leu Gly Ser
                5395                5400                5405
Val Lys Ser Asn Leu Gly His Thr Gln Ala Ala Gly Met Ala Gly
        5410                5415                5420
Val Leu Lys Met Val Gln Ala Met Arg His Ala Thr Leu Pro Arg Thr
5425                5430                5435                5440
Leu His Val Asp Ala Pro Thr Ser Gln Val Asp Trp Ser Ala Gly Ala
                5445                5450                5455
Val Ser Leu Leu Thr Glu Glu Arg Pro Trp Glu Ala Gly Glu Arg Pro
                5460                5465                5470
Arg Arg Ala Gly Val Ser Ser Phe Gly Val Ser Gly Thr Asn Ala His
                5475                5480                5485
Val Ile Leu Glu Gln Gly Pro Ala Ala Pro Ser Arg Pro Val Pro Pro
                5490                5495                5500
Ala Ala Pro Asp Pro Leu Pro Leu Pro Val Val Leu Ser Gly Arg Thr
5505                5510                5515                5520
Glu Pro Ala Leu Arg Ala Gln Ala Ser Arg Leu Arg Ala His Leu Ala
                5525                5530                5535
Ala Arg Pro Asp Asp Thr Leu Leu Asp Leu Ala Phe Ser Leu Ala Thr
                5540                5545                5550
Thr Arg Ser Ala Leu Asp Arg Arg Ala Val Val Leu Ala Gly Ser Arg
                5555                5560                5565
Asp Thr Leu Arg Ser Gly Leu Asp Ala Leu Ala Glu Gly Arg Ser Ala
                5570                5575                5580
Ala Gly Val Val Thr Gly Ala Ala Arg Thr Gly Arg Ser Val Ala Phe
5585                5590                5595                5600
Leu Phe Ser Gly Gln Gly Ser Gln Arg Ala Gly Met Gly Arg Glu Leu
                5605                5610                5615
Tyr Asp Ala Tyr Pro Val Phe Ala Arg Ala Leu Asp Glu Ile Cys Ala
                5620                5625                5630
Glu Leu Asp Pro Leu Leu Asp Pro Arg Leu Gly Gly Ser Leu Arg Thr
                5635                5640                5645
Ala Met Phe His Gly Pro Ala Gln Asp Ser Asp Pro Leu Asp Arg Thr
                5650                5655                5660
Glu Leu Thr Gln Pro Ala Leu Phe Ala Leu Glu Ile Ala Leu His Arg
5665                5670                5675                5680
Leu Leu Asp His Trp Gly Ile Thr Pro Glu Tyr Val Ala Gly His Ser
                5685                5690                5695
Val Gly Glu Ile Ala Ala Ala Gln Val Ala Gly Val Leu Ser Leu Pro
                5700                5705                5710
Asp Ala Ala Ala Leu Val Val Ala Arg Gly Arg Leu Met Gln Ala Leu
                5715                5720                5725
Pro Gly Gly Gly Ala Met Leu Ala Val Asn Ala Pro Glu Ala Ala Val
                5730                5735                5740
Leu Pro Leu Leu Ala Glu His Glu Gly Arg Val Ala Val Ala Ala Val
5745                5750                5755                5760
Asn Gly Pro Ala Ser Val Val Val Ala Gly Asp Glu Asp Pro Val Thr
                5765                5770                5775
```

-continued

```
Arg Ile Gly Glu Leu Leu Thr Ala Ser Gly Val Arg Thr Arg Arg Leu
            5780                5785                5790

Arg Val Ser His Ala Phe His Ser Pro His Met Asp Gly Met Leu Thr
            5795                5800                5805

Glu Phe Arg Arg Ile Ala Asp Gly Leu Thr Tyr Gly Thr Pro Arg Ile
            5810                5815                5820

Pro Val Val Ser Ala Leu Ala Gly Arg Ser Val Thr Asp Glu Met Gly
5825                5830                5835                5840

Thr Ala Glu Tyr Trp Thr Arg His Ala Arg Asp Ala Val Arg Phe His
                5845                5850                5855

Asp Ala Val Gly Thr Leu Arg Asp Leu Gly Val Thr Val Phe Val Glu
                5860                5865                5870

Leu Gly Pro Gly Ser Ala Leu Thr Pro Met Val Val Glu Ser Leu Gly
                5875                5880                5885

Asp Gly Ala Ser Ala Leu Pro Val Leu Arg Gly Asp Arg Thr Glu Thr
                5890                5895                5900

Asp Gly Ala Leu Asp Ala Leu Ala Arg Leu His Val Ala Gly Val Ser
5905                5910                5915                5920

Pro Asp Trp Ala Ala Phe His Ala Gly Ser Gly Ala Ala Arg Val Pro
                5925                5930                5935

Leu Pro Ser Tyr Ala Phe Gln Arg Cys Arg Tyr Trp Met Glu Arg Pro
                5940                5945                5950

Ala Pro Ala Ala Asp Leu Gly Ser Ala Gly Leu Thr Val Ser Gly His
                5955                5960                5965

Pro Leu Leu Gly Ala Gly Val Pro Leu Ala His Gly Pro Gly Ala Leu
                5970                5975                5980

Phe Thr Gly Ser Leu Ser Val Arg Thr His Pro Trp Leu Ala Asp His
5985                5990                5995                6000

Thr Val Ser Gly Val Thr Val Leu Pro Gly Thr Ala Phe Val Glu Leu
                6005                6010                6015

Ala Val His Ala Gly Asp Gln Val Gly Cys Ala Thr Val Glu Glu Leu
                6020                6025                6030

Thr Ile Glu Ala Pro Leu Val Leu Pro Glu Arg Gly Ala Val Gln Val
                6035                6040                6045

Gln Leu Trp Val Asp Gly Pro Asp Ala Ser Gly Arg Arg Ala Leu Thr
                6050                6055                6060

Leu Tyr Gly Arg Ala Gly Ser Asp Asp Pro Asp Ala Pro Ala Ala Trp
6065                6070                6075                6080

Thr Arg His Ala Gly Gly Val Leu Ala Arg Gly Ala Thr Ala Pro Gly
                6085                6090                6095

Asp Ala Leu Thr Ala Trp Pro Pro Ser Gly Ala Glu Pro Val Pro Val
                6100                6105                6110

Asp Asp Leu Tyr Arg Thr Val Ala Asp Ala Gly Phe Gly Tyr Gly Pro
                6115                6120                6125

Val Phe Arg Gly Leu Arg Ala Ala Trp Arg Arg Gly Asp Glu Val Tyr
                6130                6135                6140

Ala Glu Val Ala Leu Pro Glu Glu Asn Gly Ala Ala Asp Glu Ala Arg
6145                6150                6155                6160

Arg Phe Gly Leu His Pro Ala Leu Leu Asp Ala Ala Leu His Thr Val
                6165                6170                6175

Ala Leu Ser Arg Ala Gly Gln Asp Gly Ile Gly Arg Met Pro Phe Ala
                6180                6185                6190

Trp Ser Gly Val Ala Leu His Ala Ser Gly Ala Ala Ala Leu Arg Val
                6195                6200                6205
```

```
Arg Leu Thr Ala Thr Gly Thr Asp Thr Val Ala Leu Thr Val Ala Asp
    6210                6215                6220

Pro Ala Gly Ala Ser Val Ala Thr Val Glu Ser Leu Lys Leu Arg Pro
6225                6230                6235                6240

Val Ala Ala Gly Leu Gly Ala Ala Pro Ala Arg Thr Asp Ala Leu His
                6245                6250                6255

Thr Val Glu Trp Thr Pro Leu Glu Thr Ala Pro Val Asp Thr Pro Val
            6260                6265                6270

Asp Thr Pro Asp Asn Ser Val Ala Pro Val Pro Val Ala Pro Val
        6275                6280                6285

Val Arg Ile Ala Thr Ala Ala Asp Leu Ala Ala Leu Asp Glu Val Pro
            6290                6295                6300

Gly Leu Val Ala Val Ala Leu Pro Arg Thr Ala Gly Thr Ala Ala Asp
6305                6310                6315                6320

Gln Ala Arg Gly Ala Val His Arg Thr Val Glu Leu Leu Gln Ala Trp
                6325                6330                6335

Leu Ala Asp Pro Arg Cys Ala Gly Ser Arg Leu Ala Phe Leu Thr Ser
                6340                6345                6350

Ala Ala Ala Gly Pro Asp Ser Pro Asp Gly Pro Gly Thr Phe Gly Ala
    6355                6360                6365

Gly Ser Pro Asp Ser Pro Tyr Gly Ala Asp Thr Leu Asp Gly Leu Gly
    6370                6375                6380

Gln Ala Pro Val Trp Gly Ala Val Arg Ser Ala Arg Ala Glu His Pro
6385                6390                6395                6400

Gly Arg Phe Leu Leu Val Asp Ala Asp Pro Ala Ala Cys Leu Ala
            6405                6410                6415

Leu Leu Pro Ser Leu Ala Thr Leu Asp Glu Pro Glu Leu Ala Val Arg
                6420                6425                6430

Ala Gly Ala Val Thr Val Pro Arg Leu Thr Arg Leu Ser Ser Asp Asp
    6435                6440                6445

Ala Leu Val Pro Pro Ala Gly Thr Ala Ala Trp Arg Leu Asp Ile Pro
    6450                6455                6460

Val Gln Gly Thr Pro Asp Asn Leu Arg Leu Val Gly Glu Pro Ala Ala
6465                6470                6475                6480

Ala Ala Pro Leu Asp Asp His Glu Ile Arg Val Ala Ile Arg Ala Ala
                6485                6490                6495

Gly Val Asn Phe Arg Asp Val Leu Thr Thr Leu Gly Ala Tyr Pro Gly
                6500                6505                6510

Pro Ala Val Ile Gly Ile Glu Gly Ala Gly Ile Val Thr Gly Thr Gly
            6515                6520                6525

Ala Gly Val Ala Asp Leu Ala Pro Gly Asp Arg Val Ala Gly Ile Phe
            6530                6535                6540

Ser Gly Ala Phe Gly Pro Ile Ala Val Thr Asp His Arg Met Val Ala
6545                6550                6555                6560

Arg Leu Pro Glu Asp Trp Ser Phe Glu Gln Ala Ala Ser Val Pro Val
                6565                6570                6575

Ala Phe Leu Thr Ala Tyr Tyr Ala Leu Thr Asp Leu Ala Gly Leu Lys
            6580                6585                6590

Glu Gly Glu Ser Val Leu Val His Ala Ala Ala Gly Gly Val Gly Met
                6595                6600                6605

Ala Ala Val Gln Leu Ala Arg His Leu Gly Ala Glu Val Tyr Gly Thr
            6610                6615                6620

Ala Ser Pro Gly Lys Trp Asp Thr Leu Thr Gly Ala Gly Leu Pro Ala
```

```
                6625                6630                6635                6640
Asp Arg Val Ala Ser Ser Arg Thr Thr Asp Phe Ala Gly Gln Phe Leu
                    6645                6650                6655
Thr Ala Thr His Gly Arg Gly Val Asp Val Val Leu Asn Ala Leu Thr
            6660                6665                6670
Gly Glu Phe Ile Asp Ala Ser Leu Arg Leu Leu Pro Arg Gly Gly Arg
        6675                6680                6685
Phe Leu Glu Met Gly Lys Ala Glu Ile Arg Thr Ala Asp Ala Val Gly
        6690                6695                6700
Thr Gly His Pro Gly Val Ala Tyr Arg Ala Phe Asp Leu Met Glu Ala
6705                6710                6715                6720
Gly Pro Ala Arg Ile Arg Glu Met Leu Thr Asp Ile Leu Gly Leu Phe
                6725                6730                6735
Ala Ser Gly Ala Leu Thr Pro Leu Pro Val Arg Thr Trp Asp Val Arg
                    6740                6745                6750
Arg Ala Arg Glu Ala Phe Arg His Leu Gly Gln Ala Arg His Ile Gly
                6755                6760                6765
Lys Val Val Leu Thr Val Pro Arg Pro Leu Asp Pro Ser Gly Thr Val
            6770                6775                6780
Leu Ile Thr Gly Ala Asn Gly Ala Leu Gly Ser His Ile Ala Arg His
6785                6790                6795                6800
Leu Val Thr Ala His Gly Ala Arg Thr Leu Leu Leu Val Gly Arg Gly
            6805                6810                6815
Gly Ala Asp Asp Leu Arg Asp Glu Leu Leu Ala Leu Gly Ala Asp Ala
        6820                6825                6830
Thr Ser Ala Ala Cys Asp Val Thr Asp Arg Asp Ala Leu Ala Arg Leu
        6835                6840                6845
Leu Ser Gly Val Ser Leu Thr Ala Val Val His Cys Ala Gly Val Leu
    6850                6855                6860
Asp Asp Gly Val Val Thr Ala Leu Thr Pro Asp Arg Ile Asp Thr Val
6865                6870                6875                6880
Leu Arg Pro Lys Val Asp Ala Ala Leu His Leu His Glu Leu Thr Ala
                6885                6890                6895
His His Asp Leu Ala Ala Phe Val Leu Phe Ser Ser Ala Ala Ala Val
            6900                6905                6910
Phe Gly Ser Pro Gly Gln Ala Ala Tyr Ala Ala Gly Asn Thr Phe Leu
        6915                6920                6925
Asp Ala Leu Ala Arg Arg Arg Ala Ala Gly Leu Pro Ala Gln Ser
    6930                6935                6940
Leu Ala Trp Gly Pro Trp Ala Pro Asp Asp Gly Met Thr Ser His Leu
6945                6950                6955                6960
Thr Ser Thr Asp Leu Thr Arg Val Ala Arg Gly Gly Met Ala Ser Leu
                6965                6970                6975
Thr Pro Ala Gln Gly Leu Ala Leu Tyr Asp Ala Ala Gly Ala Ala Asp
            6980                6985                6990
Gln Ala Leu Val Val Pro Val Leu Leu Asp Leu Ala Ala Leu Arg Thr
        6995                7000                7005
Pro Ala Ala Gly Thr Glu Gly Pro Ala Ala Leu Leu Arg Gly Leu Val
        7010                7015                7020
Thr Ala Pro Ala Arg Arg Ala Ala Ser Pro Ala Gly Thr Ala Ala Ser
7025                7030                7035                7040
Ala Thr Ala Pro Glu Trp Pro Arg Arg Leu Ala Ala Leu Thr Ala Ala
            7045                7050                7055
```

-continued

```
Glu Arg Asp Gln Val Leu Gly Glu Leu Val Arg Thr Glu Ala Ala Ala
              7060                7065                7070

Val Leu Gly His Ala Thr Ala Asp Ala Ile Asp Pro Asp Arg Gly Phe
        7075                7080                7085

Leu Asp Leu Gly Phe Asp Ser Leu Thr Ala Leu Glu Leu Arg Asn Arg
    7090                7095                7100

Met Asn Ala Ala Thr Ala Leu Arg Leu Pro Ala Thr Leu Val Phe Asp
7105                7110                7115                7120

His Pro Thr Pro Leu Ala Leu Val Arg His Leu Arg Asp Ala Leu Ala
            7125                7130                7135

Pro Asp Pro Gly Thr Asp Pro Ala Gly Pro Thr Ala Thr Ala Thr Ala
                7140                7145                7150

Gly Ser Thr Asp Thr Ala Gly Pro Pro Glu Asn Pro Ile Asp Ser
            7155                7160                7165

Met Glu Leu Asp Gly Leu Leu Glu Leu Ala Tyr Glu Asn Ala Asp Ser
        7170                7175                7180

Asp Leu Glu Met Ser
7185

<210> SEQ ID NO 4
<211> LENGTH: 2030
<212> TYPE: PRT
<213> ORGANISM: Streptomyces sp.Mer-16208

<400> SEQUENCE: 4

Met Thr Gly Thr Gly Ala Pro Thr Gly Thr Glu Gln Arg Ile Val Asp
1               5                   10                  15

Ala Leu Arg Ala Ser Leu Lys Ala Asn Glu Arg Leu Arg Arg Gln Asn
            20                  25                  30

Asp Glu Leu Thr Ala Ala Ser Val Glu Pro Leu Ala Ile Val Gly Met
        35                  40                  45

Ser Cys Arg Phe Pro Gly Gly Val Ala Thr Pro Asp Ala Leu Trp Glu
    50                  55                  60

Leu Ile Ser Ala Gly Arg Asp Ala Leu Thr Pro Phe Pro Ala Asp Arg
65                  70                  75                  80

Asp Trp Asp Leu Ala Ala Leu Tyr Asp Pro Asp Pro Asp Arg Ala Gly
                85                  90                  95

Thr Ser Tyr Val Arg Val Gly Gly Phe Leu His Asp Ala Ala Glu Phe
            100                 105                 110

Asp Gly Ala Phe Phe Gly Ile Ser Pro Arg Glu Ala Ala Ala Met Asp
        115                 120                 125

Pro Gln Gln Arg Leu Ser Leu Glu Thr Ala Trp Glu Val Phe Glu His
    130                 135                 140

Ala Gly Ile Asp Pro Ala Thr Leu Arg Ser Ser Arg Thr Gly Val Phe
145                 150                 155                 160

Val Gly Ala Ala Asp Gln Gly Tyr Gly Thr Arg Leu Arg Pro Pro
                165                 170                 175

Glu Asp Leu Glu Gly Tyr Leu Leu Thr Gly Ser Ala Ala Ser Val Ile
            180                 185                 190

Ser Gly Arg Ile Ala Tyr Thr Leu Gly Leu Glu Gly Pro Ala Leu Thr
        195                 200                 205

Val Asp Thr Ala Cys Ser Ser Ser Leu Val Ala Leu His Leu Ala Gly
    210                 215                 220

Gln Ala Leu Arg Arg Gly Glu Cys Ser Leu Ala Leu Ala Gly Gly Val
225                 230                 235                 240
```

```
Ser Val Met Val Thr Pro Gly Thr Phe Val Glu Phe Ser Arg Gln Arg
                245                 250                 255

Gly Leu Ala Ala Asp Gly Arg Cys Lys Ser Phe Ala Ala Ala Ala Asp
            260                 265                 270

Gly Thr Gly Trp Gly Glu Gly Ala Val Met Val Leu Leu Glu Arg Leu
        275                 280                 285

Ser Asp Ala Glu Arg Ser Gly His Pro Val Leu Ala Val Val Arg Gly
    290                 295                 300

Ser Ala Val Asn Gln Asp Gly Ala Ser Ser Gly Leu Thr Ala Pro Asn
305                 310                 315                 320

Gly Pro Ala Gln Gln Arg Val Ile Arg Glu Ala Leu Gly Ala Ala Arg
                325                 330                 335

Leu Thr Pro Ala Asp Val Asp Ala Val Glu Ala His Gly Thr Gly Thr
            340                 345                 350

Ala Leu Gly Asp Pro Ile Glu Ala Gln Ala Leu Leu Ala Thr Tyr Gly
        355                 360                 365

Gln Asp Arg Glu His Pro Leu Trp Leu Gly Ser Val Lys Ser Asn Ile
    370                 375                 380

Gly His Thr Gln Ala Ala Ser Gly Leu Ala Gly Val Val Lys Thr Val
385                 390                 395                 400

Leu Ala Leu Arg His Gly Val Leu Pro Arg Thr Leu His Val Asp Ala
                405                 410                 415

Pro Thr Pro Arg Val Asp Trp Glu Ala Gly Ala Val Ser Leu Leu Thr
            420                 425                 430

Glu Ala Arg Pro Trp Val Arg His Gly Arg Pro Arg Ala Gly Val
        435                 440                 445

Ser Ser Phe Gly Val Ser Gly Thr Asn Ala His Val Val Leu Glu Glu
    450                 455                 460

Ala Pro Val Ala Pro Ala Val Pro Glu Thr Ala Val Pro Arg Pro Gly
465                 470                 475                 480

Val Leu Pro Trp Val Leu Ser Ala Arg Ser Glu Glu Ala Leu Arg Ala
                485                 490                 495

Gln Ala Ala Arg Leu Ala Ala His Leu Thr Thr Arg Ser Gly Asp Ser
            500                 505                 510

Leu Ala Asp Ile Gly Tyr Ser Leu Ala Thr Thr Arg Ser Ala Phe Pro
        515                 520                 525

His Arg Ala Ala Val Val Ala Ala Asp Arg Asp Ser Phe Leu Arg Gly
    530                 535                 540

Leu Asp Ala Leu Ala Thr Gly Ala Pro Gly Pro Val Arg Gly Thr Ala
545                 550                 555                 560

Arg Pro His Ser Arg Thr Ala Trp Leu Phe Ser Gly Gln Gly Ala Gln
                565                 570                 575

Arg Pro Gly Met Gly Arg Asp Leu Ala Asp Ala Phe Pro Ala Phe Ala
            580                 585                 590

Asp Ala Leu Asp Glu Val Cys Ala Gln Leu Asp Pro Arg Leu Pro Arg
        595                 600                 605

Pro Leu Arg Glu Val Met Phe Ala Ala Glu Gly Thr Pro Glu Ala Ala
    610                 615                 620

Leu Leu Asp Arg Thr Glu Phe Thr Gln Pro Ala Leu Phe Ala Phe Glu
625                 630                 635                 640

Val Ala Leu Phe Arg Leu Phe Thr Ser Trp Gly Leu Thr Pro Asp Leu
                645                 650                 655

Leu Leu Gly His Ser Ile Gly Glu Ile Ala Ala Ala His Ala Ala Gly
            660                 665                 670
```

```
Val Leu Ser Leu Pro Asp Ala Cys Ala Leu Val Ala Ala Arg Gly Arg
            675                 680                 685

Leu Met Gln Ala Leu Pro Glu Gly Gly Ala Val Val Ser Val Arg Ala
        690                 695                 700

Glu Glu Asp Glu Val Ala Ser Leu Ala Gly Arg Thr Gly Arg Leu
705                 710                 715                 720

Gly Val Ala Ala Val Asn Gly Pro Ala Ser Thr Val Ile Ala Gly Asp
                725                 730                 735

Glu Glu Ala Val Met Glu Ala Arg Tyr Trp Glu Ala Arg Gly Arg
            740                 745                 750

Arg Thr Arg Arg Leu Arg Val Ser His Ala Phe His Ser Pro Leu Met
        755                 760                 765

Glu Pro Met Leu Ala Glu Leu Arg Thr Val Val Ala Gly Leu Thr Phe
        770                 775                 780

Ser Ala Pro Arg Ile Pro Val Val Ser Thr Leu Thr Gly Glu Pro Ala
785                 790                 795                 800

Thr Pro Leu Asp Glu Pro Glu Tyr Trp Val Arg Gln Ala Arg Glu Pro
                805                 810                 815

Val Arg Phe Arg Asp Gly Val Arg Ala Leu Glu Arg Leu Gly Ala Arg
            820                 825                 830

Thr Tyr Leu Glu Ile Gly Pro Asp Ala Val Leu Thr Pro Met Ala Glu
        835                 840                 845

Thr Cys Leu Thr Gly Pro Ala Ala Leu Val Ala Ala Val Arg Arg Thr
        850                 855                 860

Gly Gly Gly Pro Leu Gly Ala His Thr Ala Leu Ala Glu Leu Phe Ala
865                 870                 875                 880

Asp Gly Ala Pro Val Asp Trp Pro Ala Val Phe Pro Gly Ala Gly Arg
                885                 890                 895

Val Asp Leu Pro Thr Tyr Ala Phe Arg Arg Arg Arg Phe Trp Ala Ser
            900                 905                 910

Ala Gly Pro Ser Ala Asp Val Gly Ala Ala Gly Leu Thr Pro Ala Gly
        915                 920                 925

His Pro Leu Leu Gly Ala Thr Leu Glu Pro Ala Ala Gly Gly Gly Pro
        930                 935                 940

Val Phe Thr Gly Arg Leu Ser Leu Arg Ser His Pro Trp Leu Ala Tyr
945                 950                 955                 960

His Ala Val Gly Gly Thr Val Leu Phe Pro Gly Thr Gly Phe Leu Glu
                965                 970                 975

Leu Ala Phe His Ala Gly Ala Tyr Val Gly Cys Gly Arg Val Asp Glu
            980                 985                 990

Leu Leu Val Glu Ala Pro Leu Val Leu Gly Ala Glu Gly Ala Ala Arg
        995                 1000                1005

Val Gln Val Thr Val Gly Glu Pro Gly Glu His Gly Thr Arg Thr Val
        1010                1015                1020

Ser Val His Ala Arg Pro Asp Gly Ala Asp Leu Pro Trp Thr Leu His
1025                1030                1035                1040

Ala Ser Gly Val Leu Ala Pro Asp Thr Glu Pro Ala Gly Phe Asp Leu
                1045                1050                1055

Thr Ala Trp Pro Pro Asp Gly Ala Thr Pro Leu Glu Val Asp Gly Leu
            1060                1065                1070

Tyr Ala Ser Val Ala Asp Leu Gly Tyr Asp Tyr Gly Ser Ala Phe Gln
        1075                1080                1085

Gly Val Arg Arg Ala Trp Arg Arg Gly Ala Glu Thr Phe Ala Glu Val
```

```
            1090            1095            1100

Arg Leu Pro Gly Glu Gln Arg Glu Thr Ala Gly Ala Phe Gly Val His
1105                1110                1115                1120

Pro Ala Leu Leu Asp Ala Cys Leu His Val Leu Gly Leu Ser Ala Gly
                1125                1130                1135

Asp Glu Asp Arg Gly Ala Ala Ser His Arg Leu Val Phe Ser Trp Asn
            1140                1145                1150

Gly Val Arg Leu His Gly Ser Gly Pro Ala Glu Leu Arg Val Arg Met
        1155                1160                1165

Thr Ser Thr Gly Pro Asp Ser Val Thr Leu Asp Ala Ala Asp Ala Thr
    1170                1175                1180

Gly Arg Pro Val Val Ser Ile Gly Ser Leu Ala Leu Arg Ser Val Ala
1185                1190                1195                1200

Ala Asp Arg Leu Arg Ala Ala Thr Gly Ala Val Arg Asp Ala Leu Phe
                1205                1210                1215

Arg Ile Thr Leu Ala Glu Leu Pro Pro Ala Gly Glu Glu Phe Arg Ala
            1220                1225                1230

Leu Arg Leu Val Ala Leu Glu Asp Gly Asp Gly Thr Ala Tyr Gly Ala
        1235                1240                1245

Pro Gly Thr Ala Ser Tyr Ala Gly Leu Glu Ala Leu Thr Lys Ala Ile
    1250                1255                1260

Asp Asp Gly Leu Arg Val Pro Asp Ala Val Val Pro Cys Leu Ser
1265                1270                1275                1280

Gly Arg Asp Ala His Gly Ala Thr His Arg Ala Leu Asp Leu Val Arg
                1285                1290                1295

Glu Trp Leu Ala Asp Asp Arg Phe Ala Pro Ser Arg Leu Val Phe Leu
            1300                1305                1310

Thr Ser Gly Ala Val Gly Glu Gly Val Thr Asp Leu Val His Ala Pro
        1315                1320                1325

Leu Trp Gly Leu Val Arg Ser Ala Ala Ser Glu His Pro Asp Arg Phe
    1330                1335                1340

Ala Leu Val Asp Leu Asp Asp Pro Ala Asp Arg His Arg Thr Leu Pro
1345                1350                1355                1360

Ala Ala Leu Ala His Gly Glu Thr Glu Val Ile Val Arg Ala Gly Thr
                1365                1370                1375

Pro Tyr Ala Pro Arg Leu Ala Arg Leu Ala Ala Ser Gly Arg Thr Val
            1380                1385                1390

Thr Thr Asp Pro Ala Gly Thr Val Leu Val Thr Gly Ala Thr Gly Ala
        1395                1400                1405

Leu Gly Gly Leu Val Ala Arg His Leu Val Arg Ala His Gly Val Arg
    1410                1415                1420

Arg Leu Leu Leu Ser Arg Ser Gly Ala Ala Ala Glu Gly Ala Asp
1425                1430                1435                1440

His Leu Leu Ala Asp Leu Arg Glu Leu Gly Ala Glu Ala Glu Phe Ala
                1445                1450                1455

Ala Cys Asp Thr Ala Asp Arg Ala Ala Leu Ala Asp Val Leu Gly Arg
            1460                1465                1470

Val Pro Ala Gly Arg Pro Leu Thr Ala Val His Thr Ala Gly Val
        1475                1480                1485

Leu Asp Asp Ser Val Val Thr Glu Leu Thr Pro Gly Arg Leu Asp Arg
    1490                1495                1500

Val Leu Arg Pro Lys Val Asp Gly Ala Leu Asn Leu His Glu Leu Thr
1505                1510                1515                1520
```

-continued

```
Ala Gly Ala Asp Leu Ser Ala Phe Val Leu Phe Ser Val Ala Gly
            1525                1530                1535

Ile Val Gly Thr Pro Gly Gln Ala Asn Tyr Ala Ala Asn Ala Phe
        1540                1545                1550

Leu Asp Ala Leu Ala Gly His Arg Arg Ala Ala Gly Leu Pro Ala Thr
    1555                1560                1565

Ser Leu Ala Trp Gly Leu Trp Ala Pro Gly Gly Met Thr Gly Thr
    1570                1575                1580

Leu Asp Asp Ser Asp Arg Ala Arg Ile Ala Arg Ser Gly Met Arg Ala
1585                1590                1595                1600

Leu Ser Ala Glu Asp Gly Leu Ala Leu Phe Asp Leu Trp Ala Gln
            1605                1610                1615

Asp Glu Ala Val Val Pro Ala Ala Phe Asp Leu Ala Gly Leu Arg
        1620                1625                1630

Gly Arg Ala Arg Thr Gly Gly Val Pro Ala Pro Leu Arg Ala Leu Val
    1635                1640                1645

Pro Pro Pro Arg Arg Ala Gly Thr Pro Ala Asp Ala Pro Ser Leu
    1650                1655                1660

Ala Arg Arg Leu Ala Gly Leu Pro Glu Asp Glu Arg Asp Gly Ala Val
1665                1670                1675                1680

Leu Glu Leu Val Arg Gly Leu Ala Ala Glu Val Leu Gly His Gly Ser
            1685                1690                1695

Pro Asp Ala Val Gly Pro Glu Gln Asp Phe Ile Glu Met Gly Phe Asp
        1700                1705                1710

Ser Leu Thr Thr Val Glu Leu Arg Asn Cys Leu Ala Glu Ala Val Gly
            1715                1720                1725

Ser Pro Leu Pro Ala Thr Leu Leu Phe Glu Cys Thr Thr Pro Arg Ala
        1730                1735                1740

Leu Ala Ala Arg Leu Arg Ser Ala Val Ala Val Pro Glu Gln Ala Ala
1745                1750                1755                1760

Gly Pro Arg Pro Ser Ala Glu Ser Gly Ala Gly Leu Ser Ala Leu Phe
            1765                1770                1775

Arg Ala Ala Cys Asp Asp Gly Arg Phe Glu Ala Phe Val His Leu Leu
        1780                1785                1790

Gly Asp Ala Ala Ser Phe Arg Pro Thr Phe Thr Asp Gly Thr Gly Pro
        1795                1800                1805

Ala Pro Arg Pro Leu Arg Leu Ala Thr Gly Glu Glu Thr Pro Gly Leu
        1810                1815                1820

Phe Cys Phe Pro Ser Phe Leu Ala Ile Ala Gly Pro Gln Gln Tyr Ala
1825                1830                1835                1840

Arg Phe Ala Ala Ala Phe Arg Gly Val Arg Glu Val Thr Val Leu Pro
            1845                1850                1855

Glu Pro Gly Phe Thr Asp Gly Gly Pro Leu Pro Ala Asp Val Gly Ala
        1860                1865                1870

Leu Val Ala Leu His Ala Glu Thr Val Arg Arg His Ala Gly Pro Ala
    1875                1880                1885

Pro Tyr Ala Leu Leu Gly His Ser Ser Gly Ala Met Ile Ala Tyr Ala
    1890                1895                1900

Val Ala Ala Arg Leu Glu Glu Leu Gly Ala Ala Pro Arg Ala Val Val
1905                1910                1915                1920

Leu Leu Asp Val Val Pro Thr Asp Val His Ala Leu Pro Gly Phe Gln
            1925                1930                1935

Ser Asp Leu Ala Ala Gly Leu Arg Glu Arg Asp Gly Asp Ala Ala Ser
        1940                1945                1950
```

-continued

Leu Asp Asp Gln Arg Leu Thr Ala Met Gly Gly Tyr Val Arg Ala Phe
            1955                1960                1965

Ala Thr Trp Glu Pro Ala Glu Ile Ser Val Pro Thr Leu Leu Val Arg
    1970                1975                1980

Ala Gly Glu Asn His Trp Ser Ser Ala Trp Pro His Pro His Thr Ala
1985                1990                1995                2000

Val Asp Ala Pro Gly Asp His Phe Thr Met Leu Glu Thr His Ala Gly
            2005                2010                2015

Glu Thr Ala Arg Leu Val Gln Glu Trp Leu Ser Gly Leu Ser
            2020                2025                2030

<210> SEQ ID NO 5
<211> LENGTH: 477
<212> TYPE: PRT
<213> ORGANISM: Streptomyces sp.Mer-16208

<400> SEQUENCE: 5

Met Ala Ala Arg Ala Thr His Ala Val Val Leu Gly Gly Gly Leu Ala
1               5                   10                  15

Gly Thr Leu Ala Ala Ala Leu Ala Gly His Ala Asp His Ile Thr
            20                  25                  30

Leu Val Glu Arg Asp Arg Met Pro Ala Gly Pro Gln Glu Arg Thr Gly
            35                  40                  45

Val Pro Gln Ala Arg His Ala His Met Leu Met Ser Ser Gly Ala Glu
    50                  55                  60

Ala Ile Asp Ala Leu Val Pro Gly Val Thr Lys Asn Leu Tyr Ala Ala
65                  70                  75                  80

Gly Ala His Arg Val Ser Val Arg Lys Gly Leu Val Ser Ser Thr Ala
                85                  90                  95

Gln Gly Trp Val Pro Arg Ser Ala Asp Leu Gln Tyr Val Ile Thr Cys
            100                 105                 110

Gly Arg Ala Leu Leu Asp Trp Thr Val Arg Glu Arg Val Leu Met Asp
            115                 120                 125

Pro Arg Val Thr Leu Leu Gln Gly Thr Asp Val Thr Gly Leu Asp Gly
    130                 135                 140

Asp Ser Arg Arg Val Thr Ala Val Arg Val Arg Asp Arg Ala Thr Gly
145                 150                 155                 160

Glu Ala Ser Leu Ile Gly Ala Asp Pro Val Val Asp Ala Thr Gly Arg
                165                 170                 175

Gly Ser Ala Ala Arg Thr Trp Leu Glu Glu Leu Gly Met Pro Arg Val
            180                 185                 190

Arg Glu Glu Thr Val Asp Thr Gly Leu Ala Tyr Ser Thr Arg Leu Phe
            195                 200                 205

Arg Val Pro Pro Gly Ala Glu Arg Asp Phe Pro Ala Val Thr Val Met
    210                 215                 220

Pro Ser Pro Ala Asp Pro Val Pro Gly Arg Ser Gly Thr Leu Leu Pro
225                 230                 235                 240

Ile Glu Asp Gly Arg Trp Leu Val Thr Leu Thr Gly Leu Arg Pro Ala
                245                 250                 255

Gln Pro Pro Thr Asp Asp Ala Gly Phe Leu Pro Phe Ala Arg Thr Leu
            260                 265                 270

Arg Thr Pro Val Ile Gly Asp Leu Ile Glu Ala Ala Gln Pro Leu Gly
            275                 280                 285

Pro Val Cys Gly Ser Arg Ser Thr Ala Asn Arg Arg Tyr Tyr Glu
    290                 295                 300

```
Glu Leu Ser Leu Trp Pro Asp Gly Phe Val Ala Leu Gly Asp Ala Leu
305                 310                 315                 320

Ala Ala Phe Asn Pro Val Tyr Gly His Gly Met Ser Val Ala Ala Lys
                325                 330                 335

Ala Ala Thr Ala Leu Arg Thr Asp Leu Glu Arg Tyr Gly Tyr Leu Pro
            340                 345                 350

Glu Arg Ser Arg His Val Gln Arg Ala Val Ala Thr Val Asn Asp
        355                 360                 365

Ala Trp Ala Leu Ala Val Gly Gln Asp Val Gln Tyr Pro Asp Val Ile
    370                 375                 380

Gly Pro Arg Pro Gly Ala Ala Lys Leu Met Arg Arg Tyr Ser Ala
385                 390                 395                 400

Arg Ala Ala Arg Ala Ser Ala Thr Arg Pro Ala Val Ala Ala Ile
                405                 410                 415

Ala Asp Ile Phe Thr Leu Ser Ala Pro Val Ser Arg Leu Leu Ala Pro
            420                 425                 430

Arg Ala Val Leu Gly Ala Leu Arg Gly Pro Gly Ala Pro Pro Leu Thr
        435                 440                 445

Ala Pro Pro Phe Thr Glu Arg Glu Arg Ala Leu Phe Ser Arg Glu Pro
450                 455                 460

Arg Glu Pro Thr Arg Lys Thr Glu Gln Asp Thr Thr Gln
465                 470                 475

<210> SEQ ID NO 6
<211> LENGTH: 287
<212> TYPE: PRT
<213> ORGANISM: Streptomyces sp.Mer-16208

<400> SEQUENCE: 6

Met Ser Arg Ser Thr Glu Glu Thr Leu Trp Thr Thr Glu Glu Val Gly
1               5                   10                  15

His Arg Tyr Asp Arg Leu Ser Arg Val Pro Glu Leu Leu Ala Phe Gly
                20                  25                  30

Glu Ser Leu His Phe Gly Tyr Trp Glu Asp Pro Glu Asp Glu Gly Gly
            35                  40                  45

Leu Ser Asp Ala Met Gly Arg Leu Thr Asp Leu Val Ile Gly Gly Leu
        50                  55                  60

Asp Ala Gly Pro Gly Ser Arg Val Leu Asp Leu Gly Cys Gly Val Gly
65                  70                  75                  80

Gly Pro Ala Val Lys Leu Ala Ser Ala Thr Gly Ala Glu Val Val Gly
                85                  90                  95

Val Thr Val Ser Arg Glu Gln Ile Thr Lys Ala Thr Gly Leu Ala Arg
                100                 105                 110

Ala Glu Gly Leu Thr Gly Gln Val Val Phe Gln Tyr Ala Asp Ala Met
            115                 120                 125

Asp Leu Pro Phe Glu Glu Gly Glu Phe Asp Ala Val Phe Gly Leu Glu
        130                 135                 140

Ser Ile Met His Met Asp Arg Pro Ala Val Leu Ala Gln Ile Ala Arg
145                 150                 155                 160

Val Leu Arg Pro Gly Gly Arg Leu Val Leu Thr Asp Glu Val Leu Arg
                165                 170                 175

Ala Pro Ile Pro Ala Asp Arg Ala Glu Asp Asp Glu Thr Val Ala Gly
            180                 185                 190

Tyr Leu Arg Ala Asn Met Ile Arg Ser Leu Ala Thr Pro Glu Ala Tyr
        195                 200                 205
```

```
Pro Glu Leu Leu Thr Gly Ala Gly Leu Asp Pro Glu Ala Ile Thr Asp
        210                 215                 220

Ile Thr Asp Arg Thr Val Arg Pro Thr Phe Arg Thr Leu Trp Arg Gln
225                 230                 235                 240

Ala Asn Asp Arg Leu Asp Thr Ile Leu Asn Asp Leu Gly Ser Pro Pro
                245                 250                 255

Ala Ala Val Ala Glu Glu Leu Arg Gly Trp Gln Arg Leu Ala Glu Ile
        260                 265                 270

Pro Glu Phe Gly Tyr Leu Leu Ile Ser Ala His Arg Pro Gly Arg
        275                 280                 285

<210> SEQ ID NO 7
<211> LENGTH: 422
<212> TYPE: PRT
<213> ORGANISM: Streptomyces sp.Mer-16208

<400> SEQUENCE: 7

Met Thr Glu Thr Cys Pro Ala His Ala Val Tyr Thr Pro Ala Tyr Phe
1               5                   10                  15

Lys Asp Pro Tyr Pro Ala Leu Thr Arg Leu Arg Asp Ala Gly Pro Val
            20                  25                  30

His Arg Val Glu Arg Pro Asp Gly Leu Val Val Trp Leu Ile Thr Arg
        35                  40                  45

Tyr Ala Glu Ala Gln Ala Ala Leu Gly Asp Pro Arg Leu Ser Met Asp
    50                  55                  60

Gly Glu Val Val Gln Lys Ala Leu Gly Ala Phe Ala Tyr Gly Tyr Leu
65                  70                  75                  80

Asp Pro Glu Asn Glu Ala Pro His Thr Leu Leu Ser Ser Asp Pro Pro
                85                  90                  95

Asp His Thr Arg Leu Arg Arg Leu Val Asn Arg Thr Phe Thr Ala Arg
            100                 105                 110

Arg Ile Gln Ala Leu Arg Pro Arg Val Gln Glu Leu Met Asp Gly Leu
        115                 120                 125

Leu Asp Ala Leu Gly Pro Asp Ala Ala His Ala Asp Leu Ile Glu Ala
    130                 135                 140

Val Ala Ala Pro Leu Pro Ile Ala Val Ile Cys Glu Leu Leu Gly Val
145                 150                 155                 160

Pro Pro Glu Asp Tyr Asp Ser Phe Lys Leu Trp Thr Thr Thr Met Phe
                165                 170                 175

Val Leu Pro Ala Asp Val Gly Asp Gly Met Ser Pro Thr Asp Ala Met
            180                 185                 190

Arg Asn Leu Arg Arg Tyr Leu Ser Asp Leu Ile Ala Ala Lys Arg Ala
        195                 200                 205

Glu Arg Pro Glu Thr Gly Gln Gly Ala Ala Gly Ala Glu Glu Ser Gly
    210                 215                 220

Asp Leu Leu Ser Ala Leu Ile Ala Val Arg Asp Thr Asp Glu Gly Arg
225                 230                 235                 240

Leu Ser Glu His Glu Leu Val Ser Met Ala Val Gln Leu Leu Ile Ala
                245                 250                 255

Gly His Glu Thr Thr Val Asn Gly Ile Gly Asn Ala Val Leu Asn Leu
            260                 265                 270

Leu Arg His Pro Glu Gln Leu Ala Ala Leu Arg Ala Glu Pro Ala Leu
        275                 280                 285

Leu Pro Arg Ala Val Asp Glu Leu Leu Arg Phe Glu Gly Pro Leu Glu
    290                 295                 300
```

```
Thr Ala Ile Leu Arg Val Ala Thr Glu Pro Ile Pro Leu Gly Asp Gln
305                 310                 315                 320

Val Val Pro Ala Gly Ala Leu Val Lys Val Leu Ala Ala Ala Asn
            325                 330                 335

Arg Asp Pro Asp Arg Phe Ala Ala Pro Asp Thr Leu Asp Ile Thr Arg
            340                 345                 350

Lys Asn Glu Gly His Leu Gln Phe Gly His Gly Ile His Asn Cys Leu
            355                 360                 365

Gly Ala Phe Leu Ala Arg Met Glu Thr Glu Ile Ala Ile Ser Ser Leu
370                 375                 380

Leu Arg Arg Tyr Pro Gly Leu Ser Leu Gly Val Pro Glu Asp Glu Ile
385                 390                 395                 400

Arg Trp Arg Glu Ile Ala Ile Met Arg Ala Leu Ala Glu Leu Pro Val
            405                 410                 415

Thr Leu Thr Gly Pro Val
            420

<210> SEQ ID NO 8
<211> LENGTH: 342
<212> TYPE: PRT
<213> ORGANISM: Streptomyces sp.Mer-16208

<400> SEQUENCE: 8

Val Pro Pro Ile Ser Ala Ala Gly Asp Arg Lys Arg Pro Thr Leu Ala
1               5                   10                  15

Asp Val Ala Ala Arg Ala Gly Val Ser Thr Ala Leu Val Ser Val Val
            20                  25                  30

Met Arg Gly Ala Lys Gly Ala Gly Ala Ala Thr Arg Glu Arg Val Leu
        35                  40                  45

Glu Ala Ala Arg Glu Ile Gly Tyr Arg Pro Asp Thr Arg Ala Arg Leu
    50                  55                  60

Leu Arg Ser Ser Arg Ser Arg Leu Leu Gly Val Gln Phe Gly Leu Gln
65                  70                  75                  80

His Pro Phe His Ala Asp Leu Val Glu Gly Val Tyr Gly Ala Ala Glu
                85                  90                  95

Ser Ala Gly Tyr Gln Val Ala Leu Ser Ala Val Ala Pro Ser Arg Gly
            100                 105                 110

Glu Gln His Ala Leu Glu Thr Leu Leu Ala Asp Arg Cys Glu Ala Leu
        115                 120                 125

Ile Leu Leu Gly Pro Glu Leu Pro Ala Ala Arg Leu Thr Glu Leu Ala
130                 135                 140

Gly Gln Met Pro Val Val Ser Val Ala Arg Arg Leu Arg Gln Pro Ser
145                 150                 155                 160

Gly Ala Val Glu Val Val Arg Thr Ala Asp Asp Glu Gly Ala Arg Gln
                165                 170                 175

Ala Val Asp His Leu Val Gly Leu Gly His Arg Ala Val Ala His Ile
            180                 185                 190

Asp Gly Gly Arg Ala Pro Gly Ala Ala Asp Arg Arg Gly Tyr Arg
        195                 200                 205

Thr Ala Met Asn Arg His Gly Leu Ala Arg His Ala Tyr Val Leu Pro
    210                 215                 220

Gly Gly Pro Thr Glu Glu Asp Gly Ala Ala Ala Arg Thr Leu Leu
225                 230                 235                 240

Ala Gly Pro Ala Arg Pro Thr Ala Val Leu Ala Phe Asn Asp Arg Cys
                245                 250                 255
```

```
Ala Thr Gly Val Leu Asp Thr Phe Leu Arg Ala Gly Val Pro Val Pro
        260                 265                 270

Gly Glu Val Ser Val Val Gly Phe Asp Asp Ser Arg Leu Ala Arg Leu
        275                 280                 285

Ala His Ile Asp Leu Thr Thr Val Gly Gln Asp Val Ala Arg Leu Thr
        290                 295                 300

Arg Glu Ala Val Ala Arg Val Val Gly Arg Leu Asp Gly Asp Pro Val
305                 310                 315                 320

Pro Asp Arg Glu Thr Val Val Ala Pro Cys Leu Val Ile Arg Thr Thr
                325                 330                 335

Thr Ala Ala Pro Pro Gly
            340

<210> SEQ ID NO 9
<211> LENGTH: 21
<212> TYPE: DNA
<213> ORGANISM: Artificial Sequence
<220> FEATURE:
<223> OTHER INFORMATION: PLDDF Primer

<400> SEQUENCE: 9
ccgatcgagg acggacgctg g                                              21

<210> SEQ ID NO 10
<211> LENGTH: 27
<212> TYPE: DNA
<213> ORGANISM: Artificial Sequence
<220> FEATURE:
<223> OTHER INFORMATION: PLDDR Primer

<400> SEQUENCE: 10
ggcggccacc gacatgccgt gcccgta                                        27

<210> SEQ ID NO 11
<211> LENGTH: 30
<212> TYPE: DNA
<213> ORGANISM: Artificial Sequence
<220> FEATURE:
<223> OTHER INFORMATION: HbdDin-1F Primer

<400> SEQUENCE: 11
gccctcgggg acgcgctggc cgcgttcaac                                     30

<210> SEQ ID NO 12
<211> LENGTH: 30
<212> TYPE: DNA
<213> ORGANISM: Artificial Sequence
<220> FEATURE:
<223> OTHER INFORMATION: HbdDin-1F Primer

<400> SEQUENCE: 12
ctgcgcgggc ctcaggcccg tcagggtgac                                     30

<210> SEQ ID NO 13
<211> LENGTH: 29
<212> TYPE: DNA
<213> ORGANISM: Artificial Sequence
<220> FEATURE:
<223> OTHER INFORMATION: HbdDin-3F Primer

<400> SEQUENCE: 13
cccgcccttc acggagcggg agcgcgcgc                                      29
```

```
<210> SEQ ID NO 14
<211> LENGTH: 30
<212> TYPE: DNA
<213> ORGANISM: Artificial Sequence
<220> FEATURE:
<223> OTHER INFORMATION: HbdEin-1R Primer

<400> SEQUENCE: 14
gagcagttcg cagatcaccg cgatgggcag                                     30

<210> SEQ ID NO 15
<211> LENGTH: 30
<212> TYPE: DNA
<213> ORGANISM: Artificial Sequence
<220> FEATURE:
<223> OTHER INFORMATION: 635-1F Primer

<400> SEQUENCE: 15
ggtcgagggg cacggtacgg ggacgacgct                                     30

<210> SEQ ID NO 16
<211> LENGTH: 29
<212> TYPE: DNA
<213> ORGANISM: Artificial Sequence
<220> FEATURE:
<223> OTHER INFORMATION: 635-1R Primer

<400> SEQUENCE: 16
ccctgcaccg tggccgggcc ctgctcggt                                      29

<210> SEQ ID NO 17
<211> LENGTH: 34
<212> TYPE: DNA
<213> ORGANISM: Artificial Sequence
<220> FEATURE:
<223> OTHER INFORMATION: NP2-SN2F Primer

<400> SEQUENCE: 17
gggcatatga ctagtctgat caagagacag gatg                                34

<210> SEQ ID NO 18
<211> LENGTH: 39
<212> TYPE: DNA
<213> ORGANISM: Artificial Sequence
<220> FEATURE:
<223> OTHER INFORMATION: CE1-NXHR Primer

<400> SEQUENCE: 18
gggcatatgt ctagaagctt ggtaactgtc agaccaagt                           39

<210> SEQ ID NO 19
<211> LENGTH: 29
<212> TYPE: DNA
<213> ORGANISM: Artificial Sequence
<220> FEATURE:
<223> OTHER INFORMATION: OT-SF Primer

<400> SEQUENCE: 19
gggcccgggc tcggtcttgc cttgctcgt                                      29

<210> SEQ ID NO 20
<211> LENGTH: 29
<212> TYPE: DNA
<213> ORGANISM: Artificial Sequence
<220> FEATURE:
<223> OTHER INFORMATION: OT-SR Primer

<400> SEQUENCE: 20
```

```
gggcccgggg cgcttttccg ctgcataac                                      29

<210> SEQ ID NO 21
<211> LENGTH: 32
<212> TYPE: DNA
<213> ORGANISM: Artificial Sequence
<220> FEATURE:
<223> OTHER INFORMATION: SCPR-AF Primer

<400> SEQUENCE: 21
gggcctaggt cgacggcctc ggtcacggcg ct                                  32

<210> SEQ ID NO 22
<211> LENGTH: 38
<212> TYPE: DNA
<213> ORGANISM: Artificial Sequence
<220> FEATURE:
<223> OTHER INFORMATION: SCPR-SR Primer

<400> SEQUENCE: 22
cccactagtc ctcgaattct tcgagcaatg gatccatc                            38

<210> SEQ ID NO 23
<211> LENGTH: 39
<212> TYPE: DNA
<213> ORGANISM: Artificial Sequence
<220> FEATURE:
<223> OTHER INFORMATION: dEU-AHEF Primer

<400> SEQUENCE: 23
cccattaata agcttgaatt cacgggaacg ggtcctcat                           39

<210> SEQ ID NO 24
<211> LENGTH: 33
<212> TYPE: DNA
<213> ORGANISM: Artificial Sequence
<220> FEATURE:
<223> OTHER INFORMATION: dEU-NXR Primer

<400> SEQUENCE: 24
ccctctagac atatggtcgt cctccgggag acg                                 33

<210> SEQ ID NO 25
<211> LENGTH: 28
<212> TYPE: DNA
<213> ORGANISM: Artificial Sequence
<220> FEATURE:
<223> OTHER INFORMATION: dED-XF Primer

<400> SEQUENCE: 25
ccctctagag cccggagtca gaggtggt                                       28

<210> SEQ ID NO 26
<211> LENGTH: 33
<212> TYPE: DNA
<213> ORGANISM: Artificial Sequence
<220> FEATURE:
<223> OTHER INFORMATION: dED-EHR Primer

<400> SEQUENCE: 26
cccaagcttg aattcgccga tggcggagcg cat                                 33

<210> SEQ ID NO 27
<211> LENGTH: 33
<212> TYPE: DNA
<213> ORGANISM: Artificial Sequence
```

```
<220> FEATURE:
<223> OTHER INFORMATION: TR-AF Primer

<400> SEQUENCE: 27
cccattaatc ggcatcgcgt ggcgggcccg att                            33

<210> SEQ ID NO 28
<211> LENGTH: 30
<212> TYPE: DNA
<213> ORGANISM: Artificial Sequence
<220> FEATURE:
<223> OTHER INFORMATION: TR-XR Primer

<400> SEQUENCE: 28
cggtctagat tatcggttgg ccgcgagatt                                30

<210> SEQ ID NO 29
<211> LENGTH: 39
<212> TYPE: DNA
<213> ORGANISM: Artificial Sequence
<220> FEATURE:
<223> OTHER INFORMATION: dFU-AHEF Primer

<400> SEQUENCE: 29
cccattaata agcttgaatt cctccacgcc gagacggta                      39

<210> SEQ ID NO 30
<211> LENGTH: 33
<212> TYPE: DNA
<213> ORGANISM: Artificial Sequence
<220> FEATURE:
<223> OTHER INFORMATION: dFU-NXR Primer

<400> SEQUENCE: 30
ccctctagac atatggctgt ccttccggtc gcc                            33

<210> SEQ ID NO 31
<211> LENGTH: 27
<212> TYPE: DNA
<213> ORGANISM: Artificial Sequence
<220> FEATURE:
<223> OTHER INFORMATION: dFD-XF Primer

<400> SEQUENCE: 31
ccctctagag tgccgctgac cgcccga                                   27

<210> SEQ ID NO 32
<211> LENGTH: 33
<212> TYPE: DNA
<213> ORGANISM: Artificial Sequence
<220> FEATURE:
<223> OTHER INFORMATION: dFD-EHR Primer

<400> SEQUENCE: 32
cccaagcttg aattccgagc ggtacgtcgc gtt                            33

<210> SEQ ID NO 33
<211> LENGTH: 39
<212> TYPE: DNA
<213> ORGANISM: Artificial Sequence
<220> FEATURE:
<223> OTHER INFORMATION: dDU-AHEF Primer

<400> SEQUENCE: 33
cccattaata agcttgaatt cccgtaccgt caccacgga                      39
```

```
<210> SEQ ID NO 34
<211> LENGTH: 33
<212> TYPE: DNA
<213> ORGANISM: Artificial Sequence
<220> FEATURE:
<223> OTHER INFORMATION: dDU-NXR Primer

<400> SEQUENCE: 34
ccctctagac atatgcgtga cgttccttcc tcg                          33

<210> SEQ ID NO 35
<211> LENGTH: 27
<212> TYPE: DNA
<213> ORGANISM: Artificial Sequence
<220> FEATURE:
<223> OTHER INFORMATION: dDD-XF Primer

<400> SEQUENCE: 35
ccctctagag cgaccggaag gacagcg                                 27

<210> SEQ ID NO 36
<211> LENGTH: 33
<212> TYPE: DNA
<213> ORGANISM: Artificial Sequence
<220> FEATURE:
<223> OTHER INFORMATION: dDD-EHR Primer

<400> SEQUENCE: 36
cccaagcttg aattcgagat ggccctcgtt ctt                          33

<210> SEQ ID NO 37
<211> LENGTH: 39
<212> TYPE: DNA
<213> ORGANISM: Artificial Sequence
<220> FEATURE:
<223> OTHER INFORMATION: dA3U-AHEF Primer

<400> SEQUENCE: 37
cccattaata agcttgaatt ccgtcaactt ccgcgatgt                    39

<210> SEQ ID NO 38
<211> LENGTH: 33
<212> TYPE: DNA
<213> ORGANISM: Artificial Sequence
<220> FEATURE:
<223> OTHER INFORMATION: dA3U-NXR Primer

<400> SEQUENCE: 38
ccctctagac atatgggtca tgacatctcc aag                          33

<210> SEQ ID NO 39
<211> LENGTH: 27
<212> TYPE: DNA
<213> ORGANISM: Artificial Sequence
<220> FEATURE:
<223> OTHER INFORMATION: dA3D-XF Primer

<400> SEQUENCE: 39
ccctctagat accgacgtac ccaccga                                 27

<210> SEQ ID NO 40
<211> LENGTH: 33
<212> TYPE: DNA
<213> ORGANISM: Artificial Sequence
<220> FEATURE:
<223> OTHER INFORMATION: dA3D-EHR Primer

<400> SEQUENCE: 40
```

```
cccaagcttg aattcccatg tgcatgatcg att                                33

<210> SEQ ID NO 41
<211> LENGTH: 39
<212> TYPE: DNA
<213> ORGANISM: Artificial Sequence
<220> FEATURE:
<223> OTHER INFORMATION: dRU-AHEF Primer

<400> SEQUENCE: 41
cccattaata agcttgaatt cggtggtgac ggactcgat                          39

<210> SEQ ID NO 42
<211> LENGTH: 33
<212> TYPE: DNA
<213> ORGANISM: Artificial Sequence
<220> FEATURE:
<223> OTHER INFORMATION: dRU-NXR Primer

<400> SEQUENCE: 42
ccctctagac atatgtggcc tcctcggtag aca                                33

<210> SEQ ID NO 43
<211> LENGTH: 27
<212> TYPE: DNA
<213> ORGANISM: Artificial Sequence
<220> FEATURE:
<223> OTHER INFORMATION: dRD-XF Primer

<400> SEQUENCE: 43
ccctctagag gacccgagct ggggcta                                       27

<210> SEQ ID NO 44
<211> LENGTH: 33
<212> TYPE: DNA
<213> ORGANISM: Artificial Sequence
<220> FEATURE:
<223> OTHER INFORMATION: dRD-EHR Primer

<400> SEQUENCE: 44
cccaagcttg aattcgttga tgacgcagtg gac                                33
```